US008476062B2

(12) United States Patent
Greenbaum et al.

(10) Patent No.: US 8,476,062 B2
(45) Date of Patent: *Jul. 2, 2013

(54) BIOSENSOR METHOD AND SYSTEM BASED ON FEATURE VECTOR EXTRACTION

(75) Inventors: Elias Greenbaum, Knoxville, TN (US); Miguel Rodriguez, Jr., Oak Ridge, TN (US); Hairong Qi, Knoxville, TN (US); Xiaoling Wang, San Jose, CA (US)

(73) Assignees: University of Tennessee Research Foundation, Knoxville, TN (US); UT-Battelle, LLC, Oak Ridge, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/431,664

(22) Filed: Mar. 27, 2012

(65) Prior Publication Data
US 2012/0238009 A1 Sep. 20, 2012

Related U.S. Application Data

(62) Division of application No. 11/216,282, filed on Aug. 31, 2005, now Pat. No. 8,158,377.

(51) Int. Cl.
C12M 1/00 (2006.01)
C12M 1/34 (2006.01)
C12M 3/00 (2006.01)

(52) U.S. Cl.
USPC ................................... 435/287.1; 435/283.1

(58) Field of Classification Search
None
See application file for complete search history.

(56) References Cited

U.S. PATENT DOCUMENTS

| | | |
|---|---|---|
| 3,790,461 A | 2/1974 | Yeh |
| 4,267,038 A | 5/1981 | Thompson |
| 4,909,919 A | 3/1990 | Morris et al. |
| 5,313,264 A | 5/1994 | Ivarsson et al. |
| 5,426,306 A | 6/1995 | Kolber et al. |
| 5,437,772 A | 8/1995 | De Castro et al. |
| 5,602,446 A | 2/1997 | Kolber et al. |
| 5,661,697 A | 8/1997 | Swan et al. |
| 5,670,031 A | 9/1997 | Hintsche et al. |
| 5,779,911 A | 7/1998 | Haug et al. |
| 5,817,954 A | 10/1998 | Kahng et al. |
| 5,876,960 A | 3/1999 | Rosen |
| 6,051,437 A | 4/2000 | Luo et al. |
| 6,198,107 B1 | 3/2001 | Seville |
| 6,486,588 B2 * | 11/2002 | Doron et al. ................. 310/322 |
| 6,511,854 B1 | 1/2003 | Asanov et al. |
| 6,569,384 B2 * | 5/2003 | Greenbaum et al. ......... 422/68.1 |
| 6,573,107 B1 | 6/2003 | Bowen et al. |
| 6,692,696 B1 | 2/2004 | Alberte |
| 6,726,881 B2 | 4/2004 | Shinoki et al. |
| 6,740,518 B1 | 5/2004 | Duong et al. |
| 6,783,647 B2 | 8/2004 | Culbertson et al. |
| 6,891,317 B2 | 5/2005 | Pei et al. |
| 6,942,765 B2 | 9/2005 | Griego et al. |
| 6,964,857 B2 | 11/2005 | Greenbaum et al. |
| 7,015,484 B2 | 3/2006 | Gillispie et al. |
| 7,081,189 B2 | 7/2006 | Squires et al. |
| 7,110,920 B2 | 9/2006 | McCarter et al. |
| 7,214,427 B2 | 5/2007 | Huang et al. |
| 7,747,391 B2 | 6/2010 | Gustafsson et al. |
| 8,198,075 B2 * | 6/2012 | Greenbaum et al. ....... 435/292.1 |
| 2002/0102629 A1 | 8/2002 | Greenbaum et al. |
| 2002/0177232 A1 | 11/2002 | Melker et al. |
| 2005/0003396 A1 | 1/2005 | Ozkan et al. |
| 2006/0219939 A1 | 10/2006 | Satyanarayana et al. |
| 2008/0032326 A1 | 2/2008 | Greenbaum et al. |

OTHER PUBLICATIONS

Bhatt, K. et al., "An AC electrokinietic technique for collection and concentration of particles and cells on patterned electrodes," Langmuir, vol. 21, 2005, pp. 6603-6612.
Chemla, Y. R. et al., "Ultrasensitive magnetic biosensor for homogenous immunoassay," PNAS, vol. 97, No. 26, 2000, pp. 14268-14272.
Collection of Abstracts of Annual Meeting of the Institute of Electrostatics Japan, Toyohashi University of Technology, Aug. 2002, 60 pages.
Florescu, M. et al., "Development and evaluation of electrochemical glucose enzyme biosensors based on carbon film electrodes," Talanta, vol. 65, 2005, pp. 306-312.
Huang, G. G. et al., "Development of infrared optical sensor for selective detection of tyrosine in biological fluids," Biosensors and Bioelectronics, vol. 21, 2005, pp. 408-418.
Oliveira, J. F. et al., "Magnetic resonance as a technique to magnetic biosensors characterization in *Neocapritermes opacus* termites," Journ. Magnetism and Magnetic Materials, vol. 294, 2005, pp. e171-e174.
Rodriguez, Jr. et al., Biosensors for Rapid Monitoring of Primary Source Drinking Water using Naturally Occuring Photosynthesis Biosensors & Bioelectronics, vol. 17, 2002, pp. 843-849.
Sanders, et al., Stand-off Tissue-based Biosensors for the Detection of Chemical Warfare Agents using Photosynthetic Fluorescence Induction, Biosensors & Bioelectronics, vol. 16, 2001, pp. 439-446.
Wang, T. et al., "Acoustic immunosensor for real-time sensing of neurotransmitter GABA," Proceedings of the 25th IEEE Annual International Conference, vol. 4, 2003, pp. 2998-3000.
Wu, J. et al., "Long-range AC electroosmotic trapping and detection of bioparticles," Ind. Eng. Chem. Res., vol. 44, 2005, pp. 2815-2822.
Wu, J. et al., "Particle detection by electrical impedance spectroscopy with asymmetric-polarization AC electroosmotic trapping," Microfluid Nanofluid, vol. 1, 2005, pp. 161-167.

* cited by examiner

*Primary Examiner* — Debbie K Ware
(74) *Attorney, Agent, or Firm* — Brinks, Hofer, Gilson & Lione

(57) ABSTRACT

A system for biosensor-based detection of toxins includes providing at least one time-dependent control signal generated by a biosensor in a gas or liquid medium, and obtaining a time-dependent biosensor signal from the biosensor in the gas or liquid medium to be monitored or analyzed for the presence of one or more toxins selected from chemical, biological or radiological agents. The time-dependent biosensor signal is processed to obtain a plurality of feature vectors using at least one of amplitude statistics and a time-frequency analysis. At least one parameter relating to toxicity of the gas or liquid medium is then determined from the feature vectors based on reference to the control signal.

5 Claims, 129 Drawing Sheets

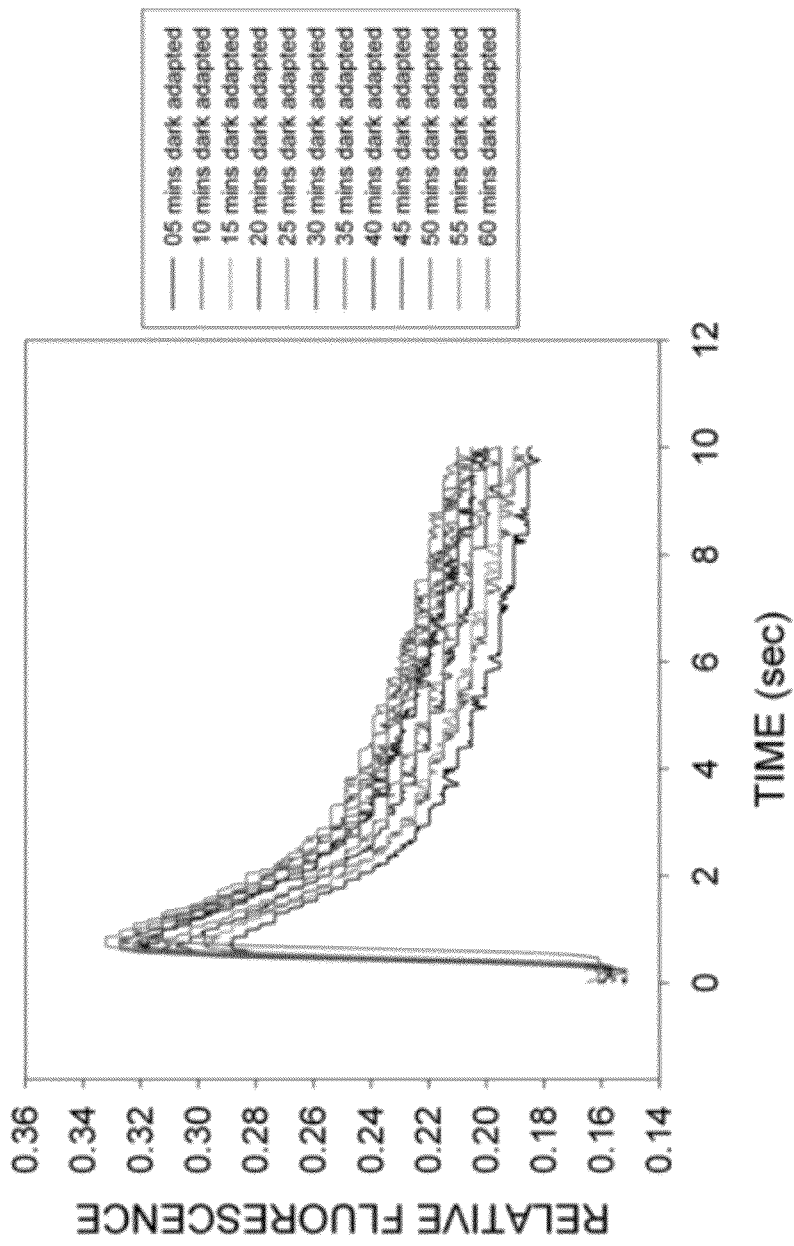
FIGURE 1 (a) KCN Control

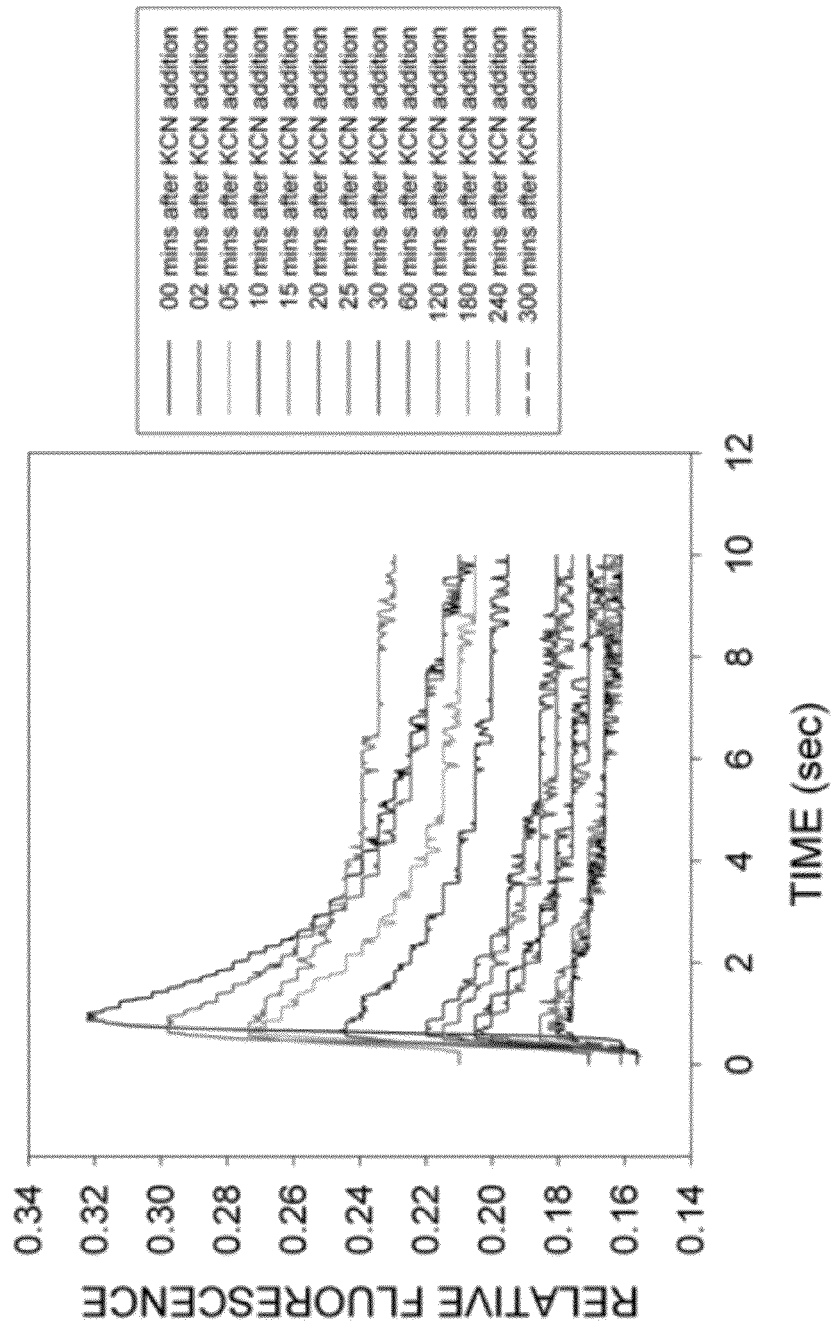

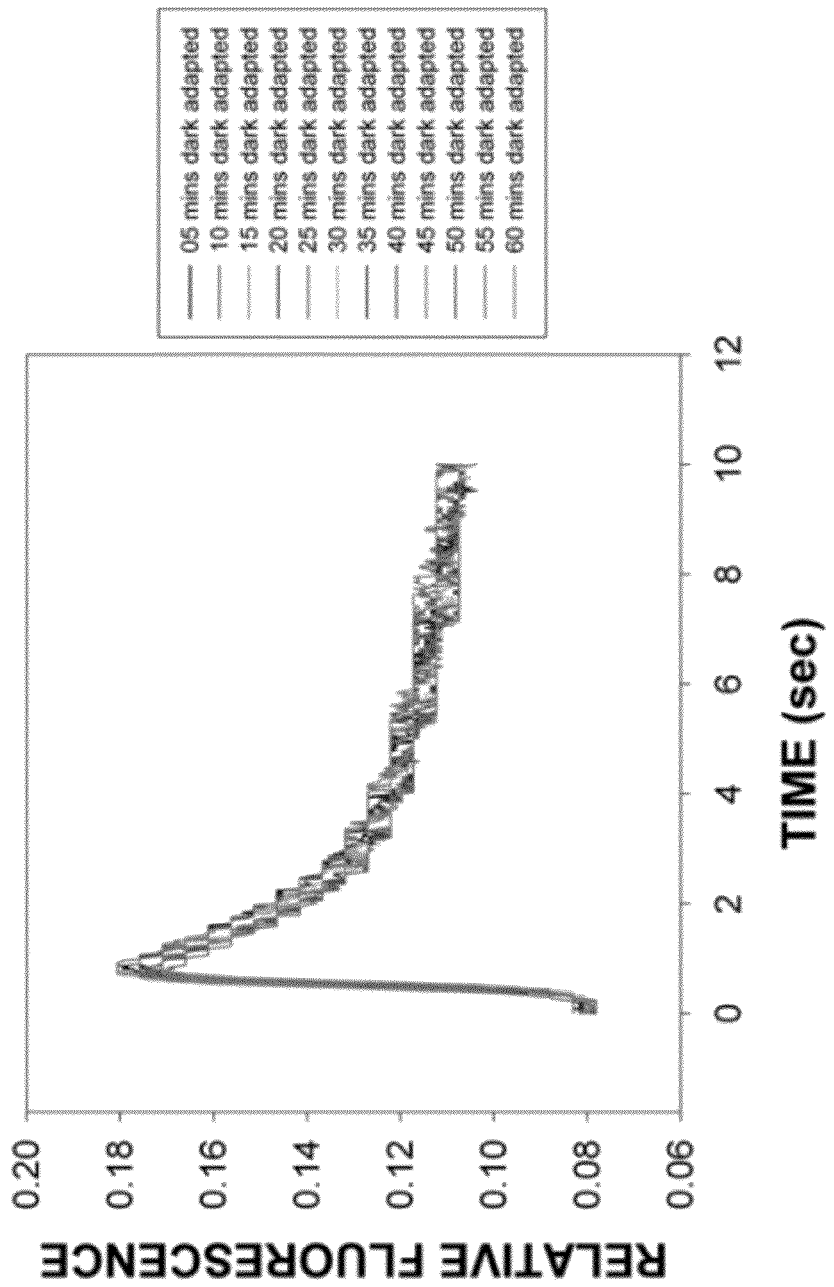
FIGURE 1 (c) MPt Control

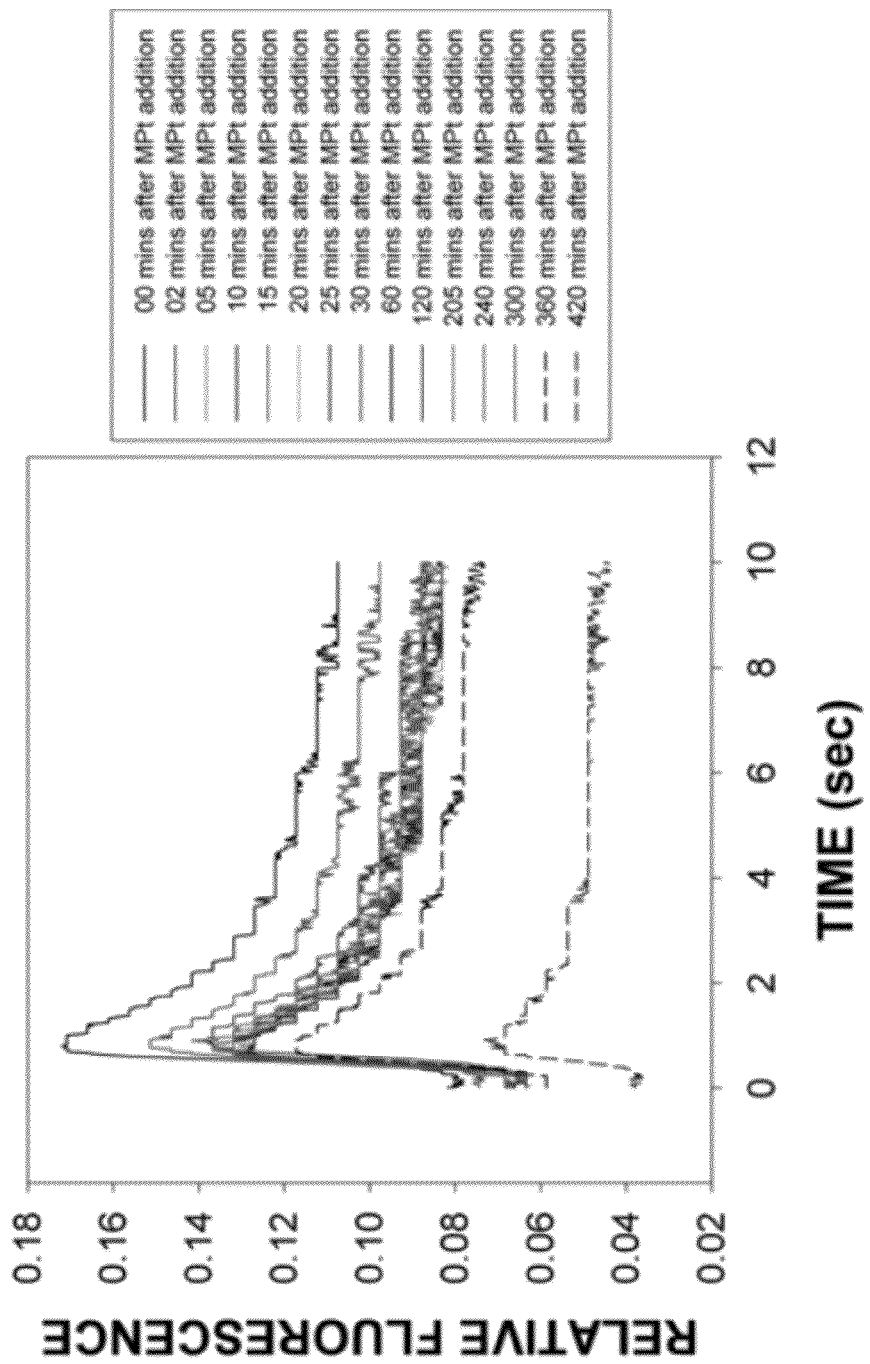

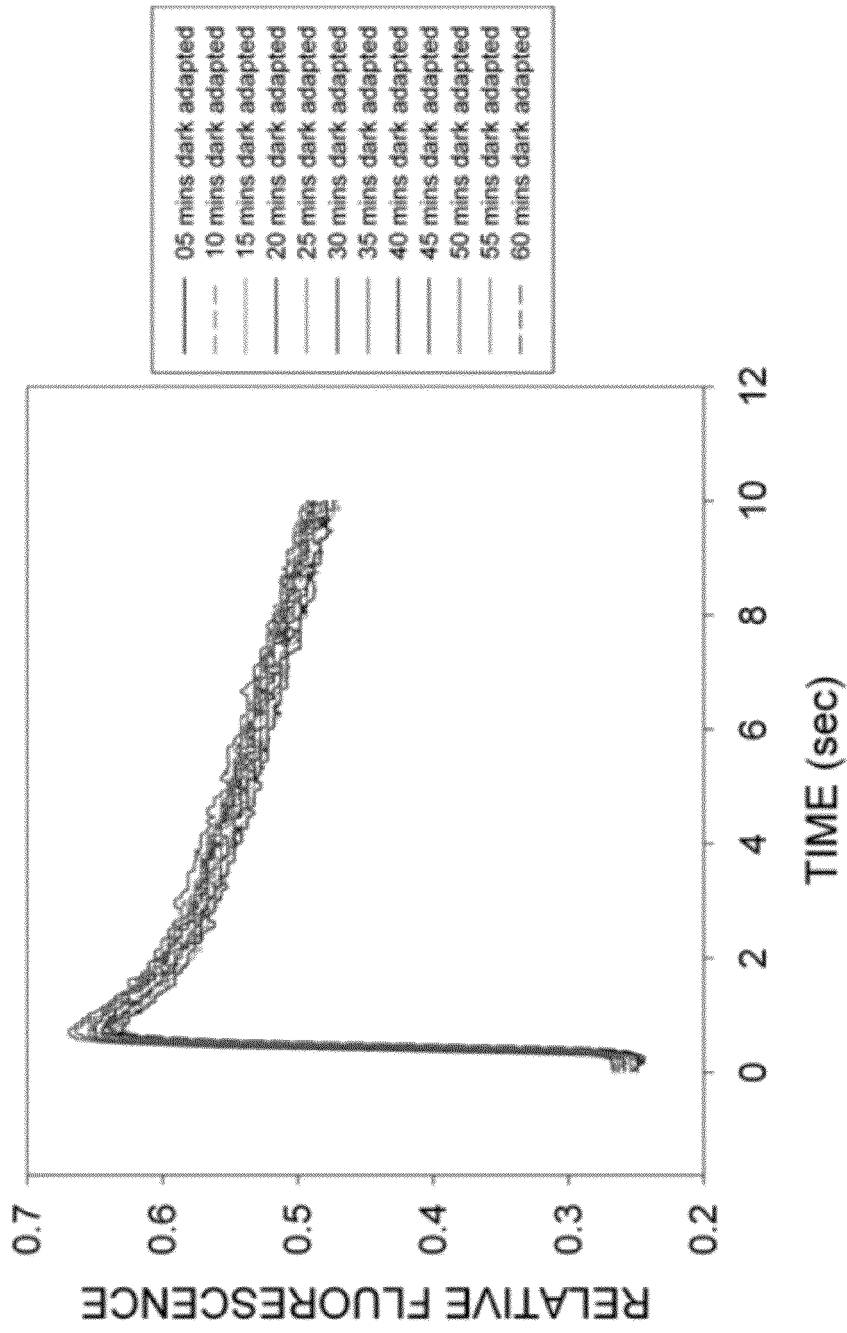
FIGURE 1 (e) DCMU Control

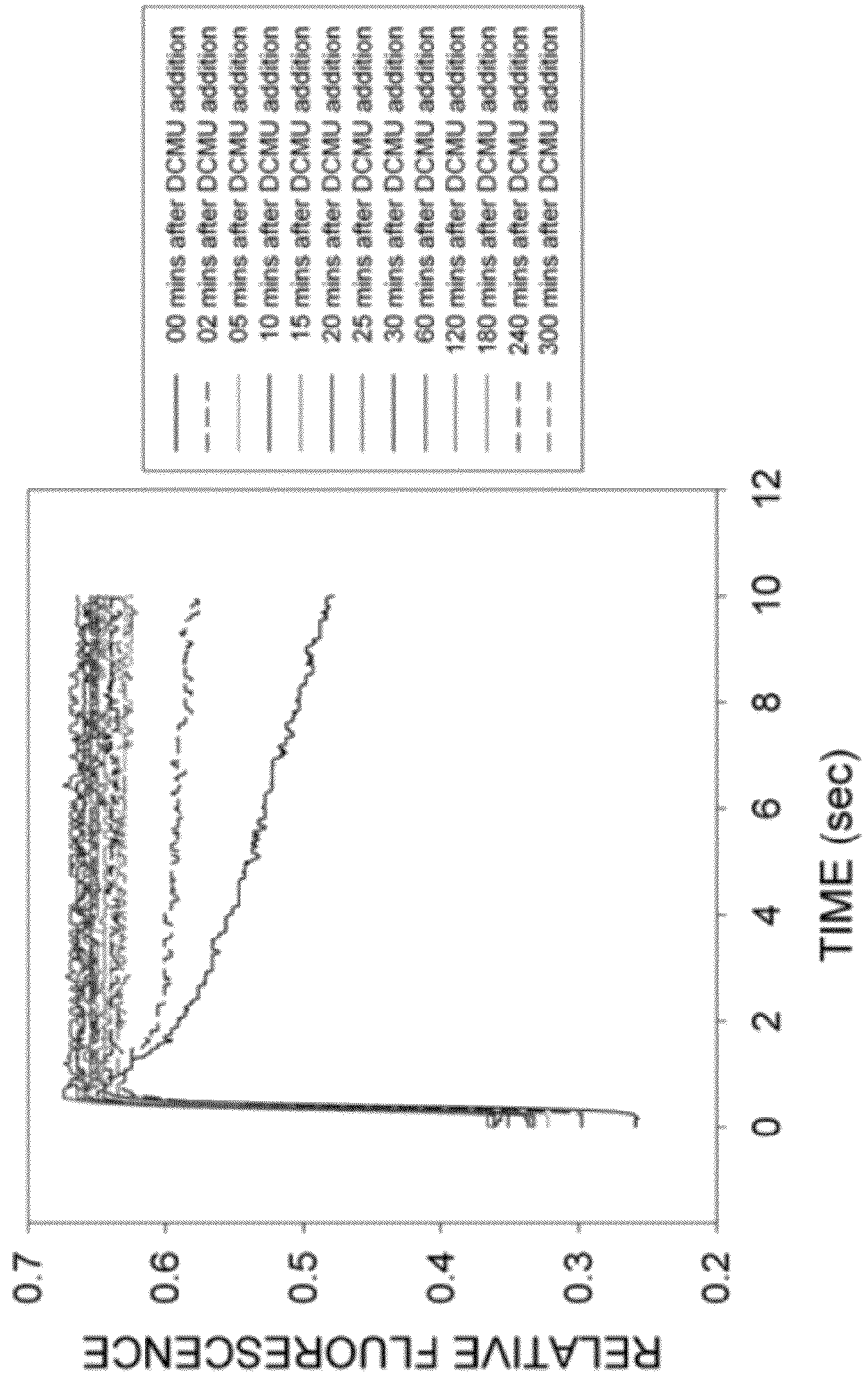
FIGURE 1 (f) DCMU-Exposure

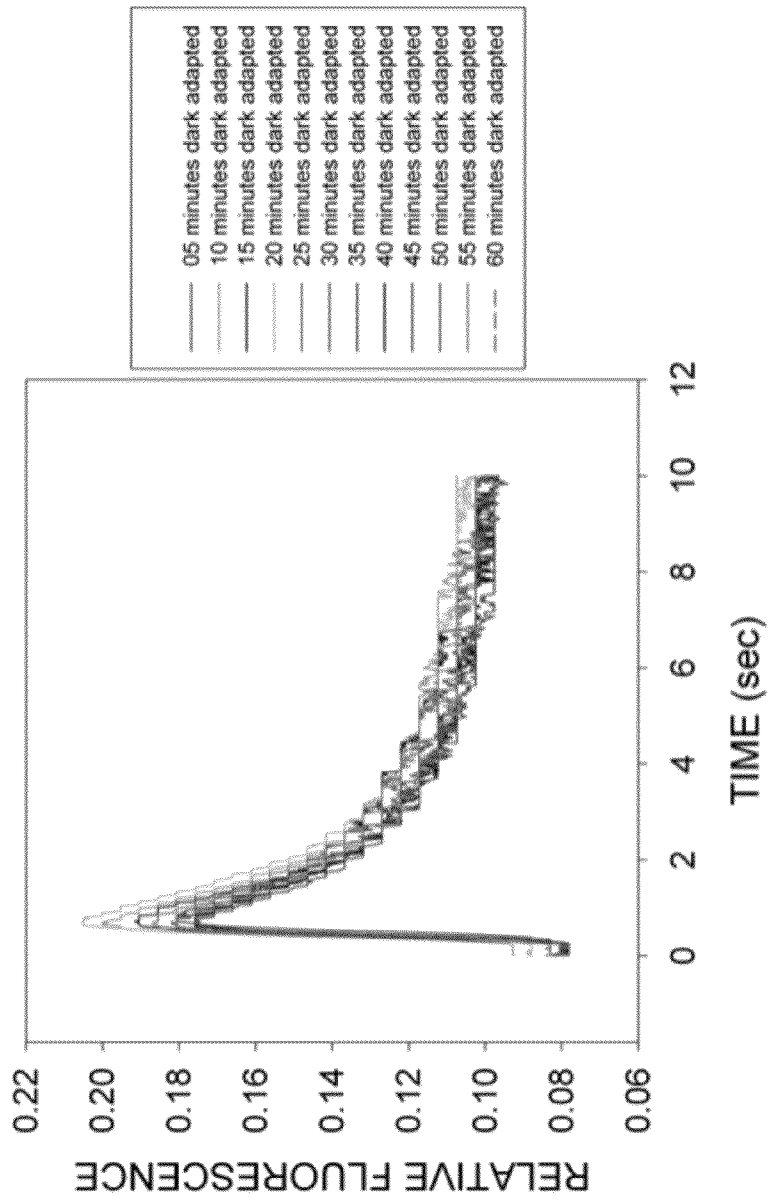
FIGURE 1 (g) Paraquat Control

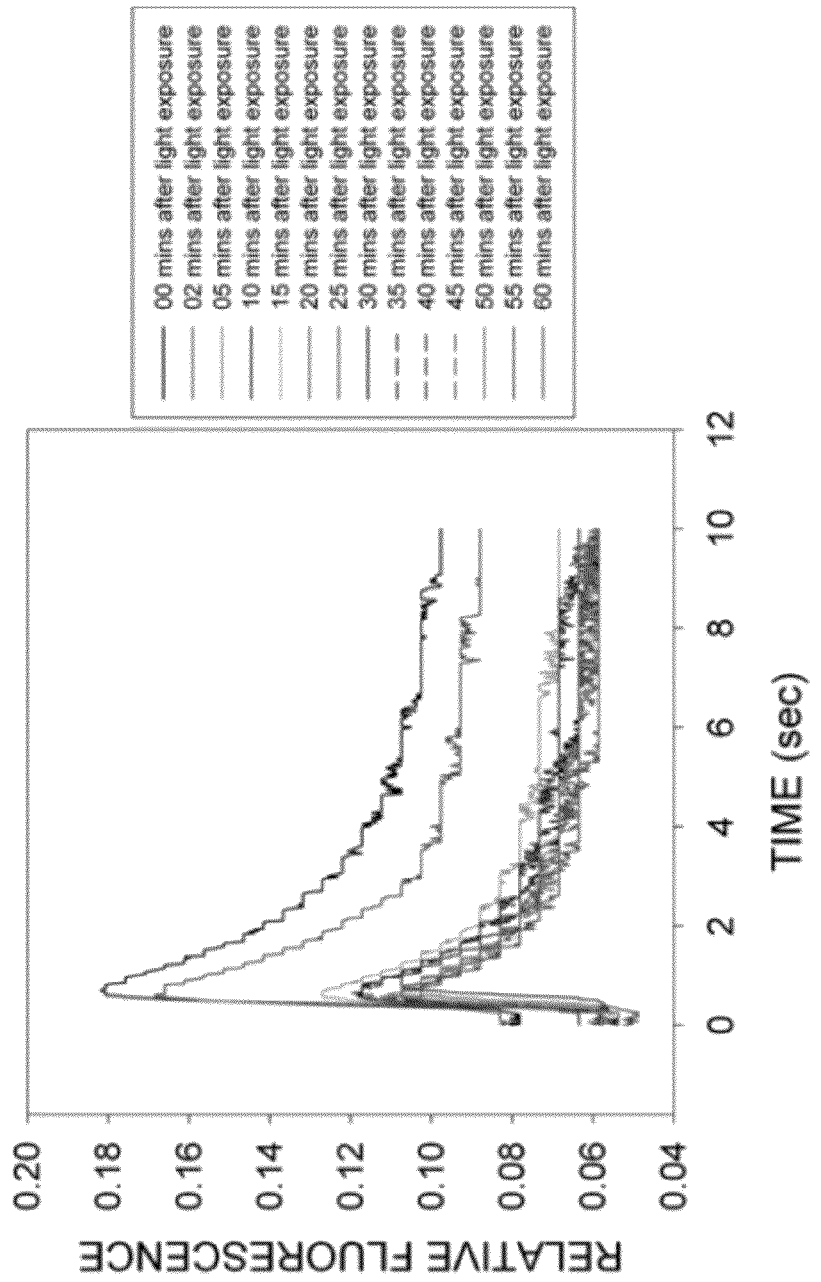
FIGURE 1 (h) Paraquat Exposure

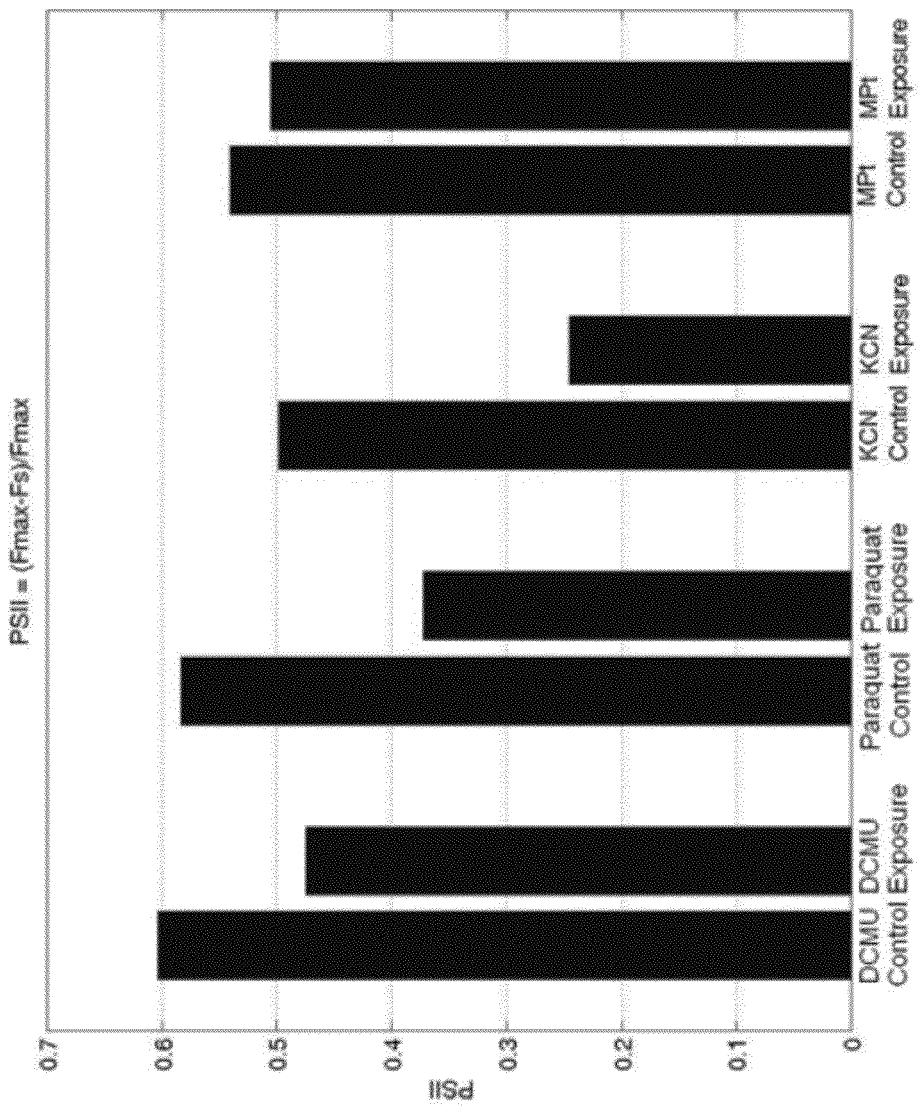
FIGURE 3 (a) PSII efficiency

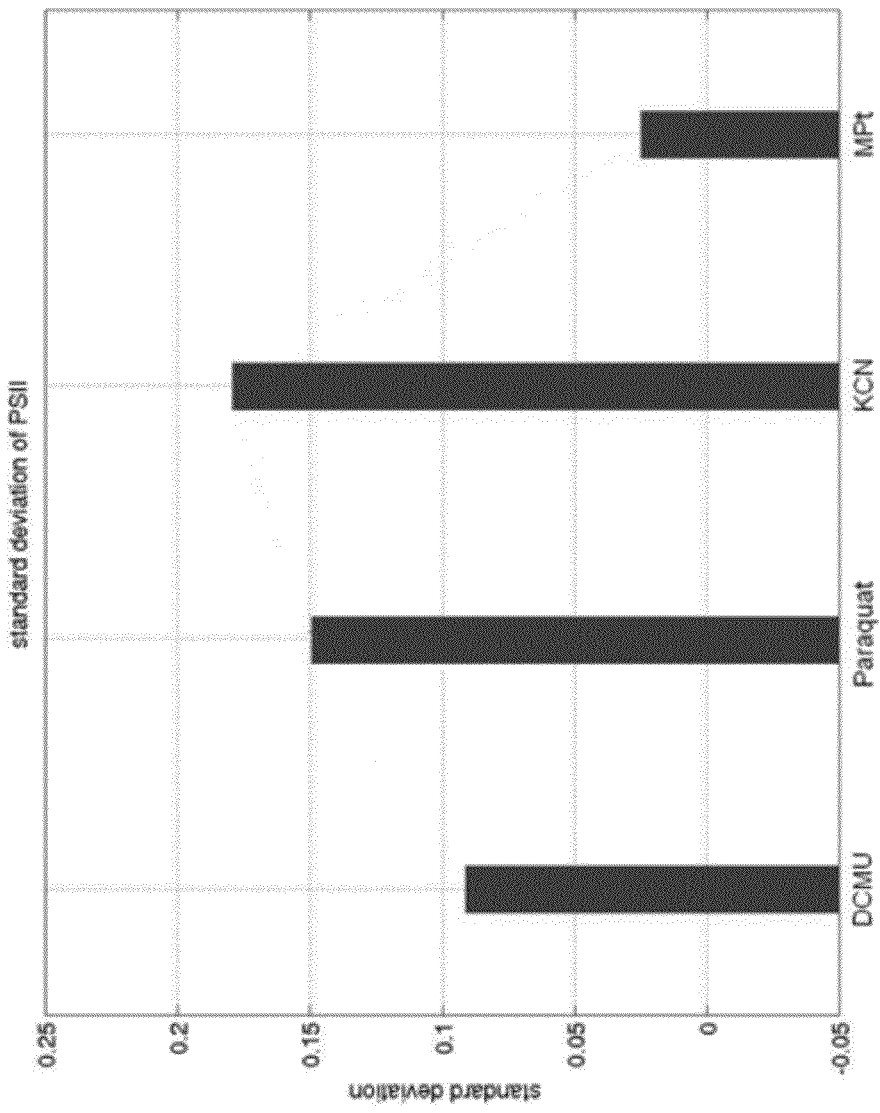
FIGURE 3 (b) Standard deviation

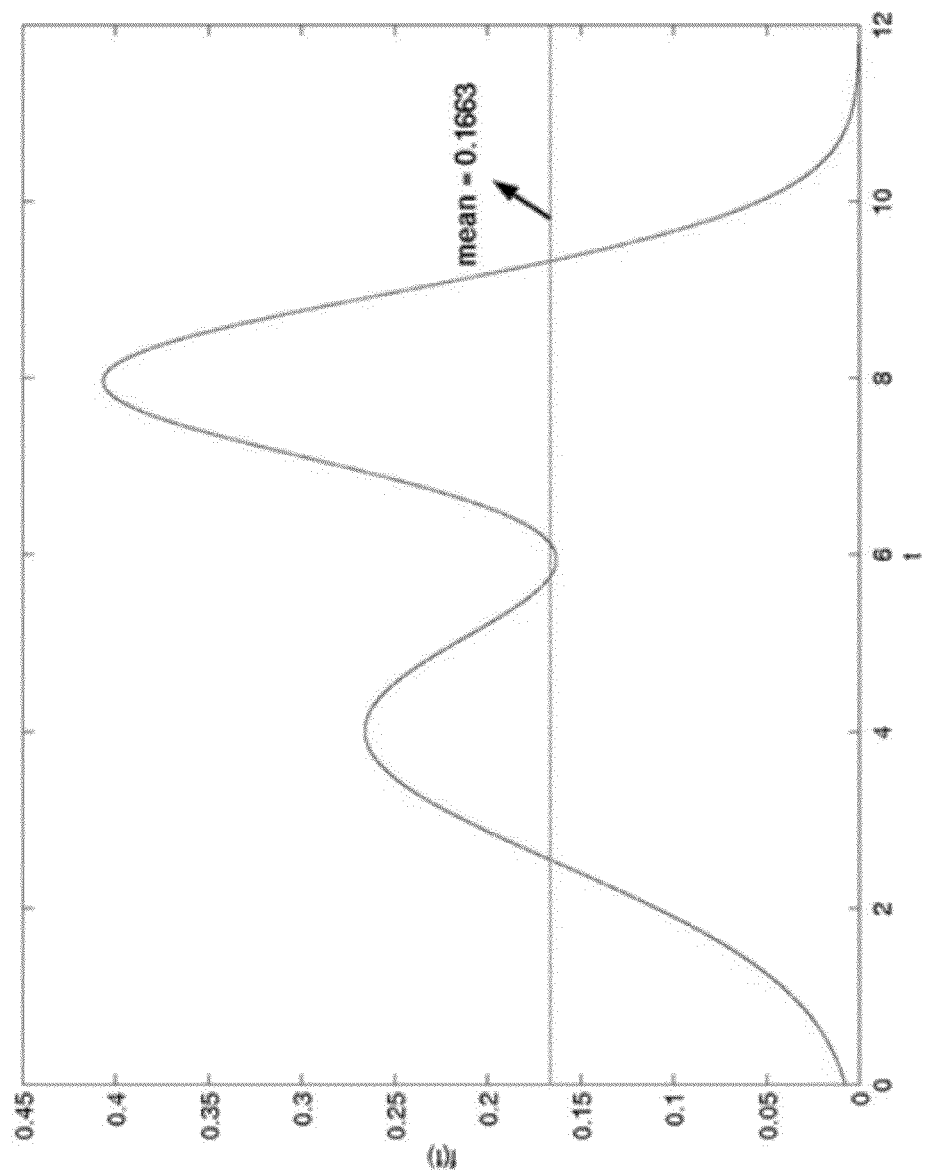
FIGURE 4 (a) Mean

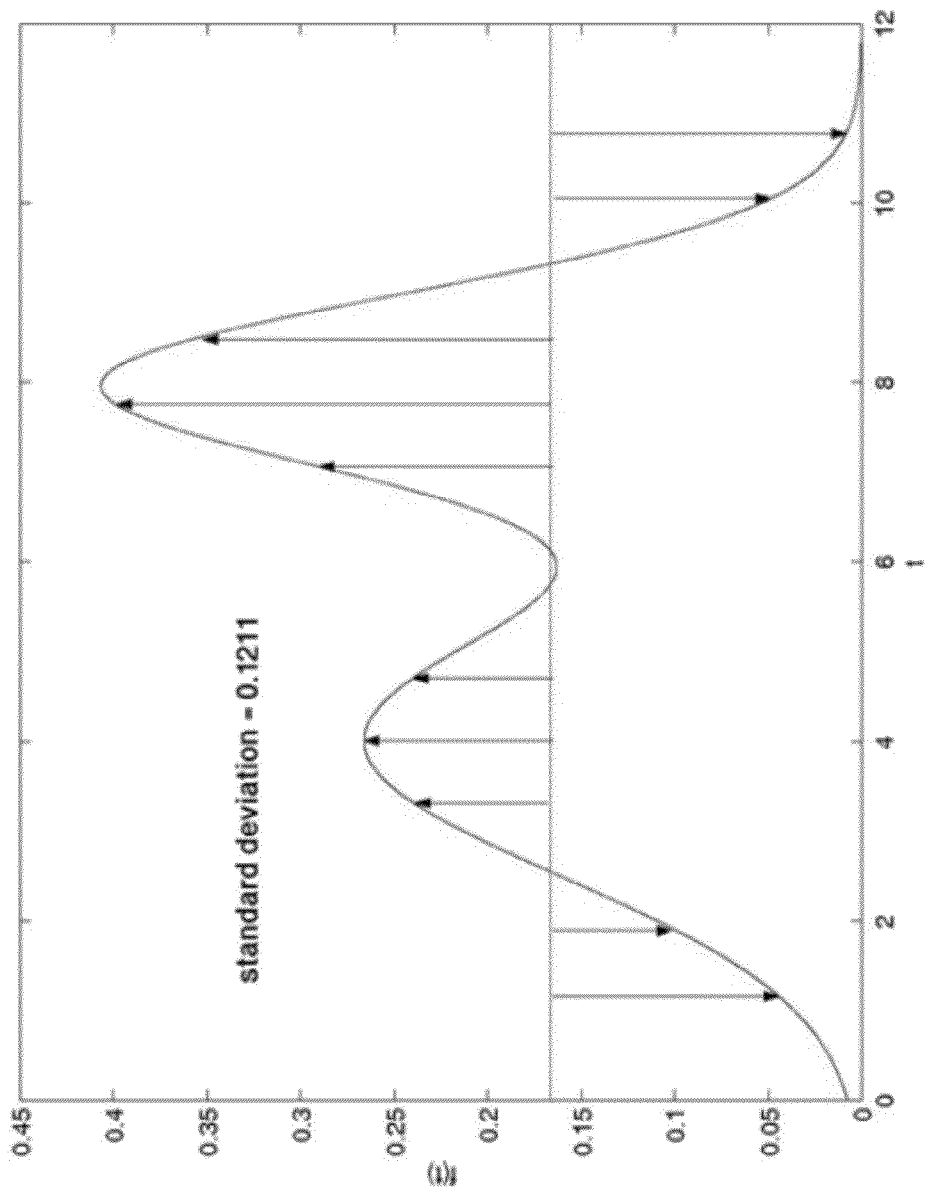
FIGURE 4 (b) Standard Deviation

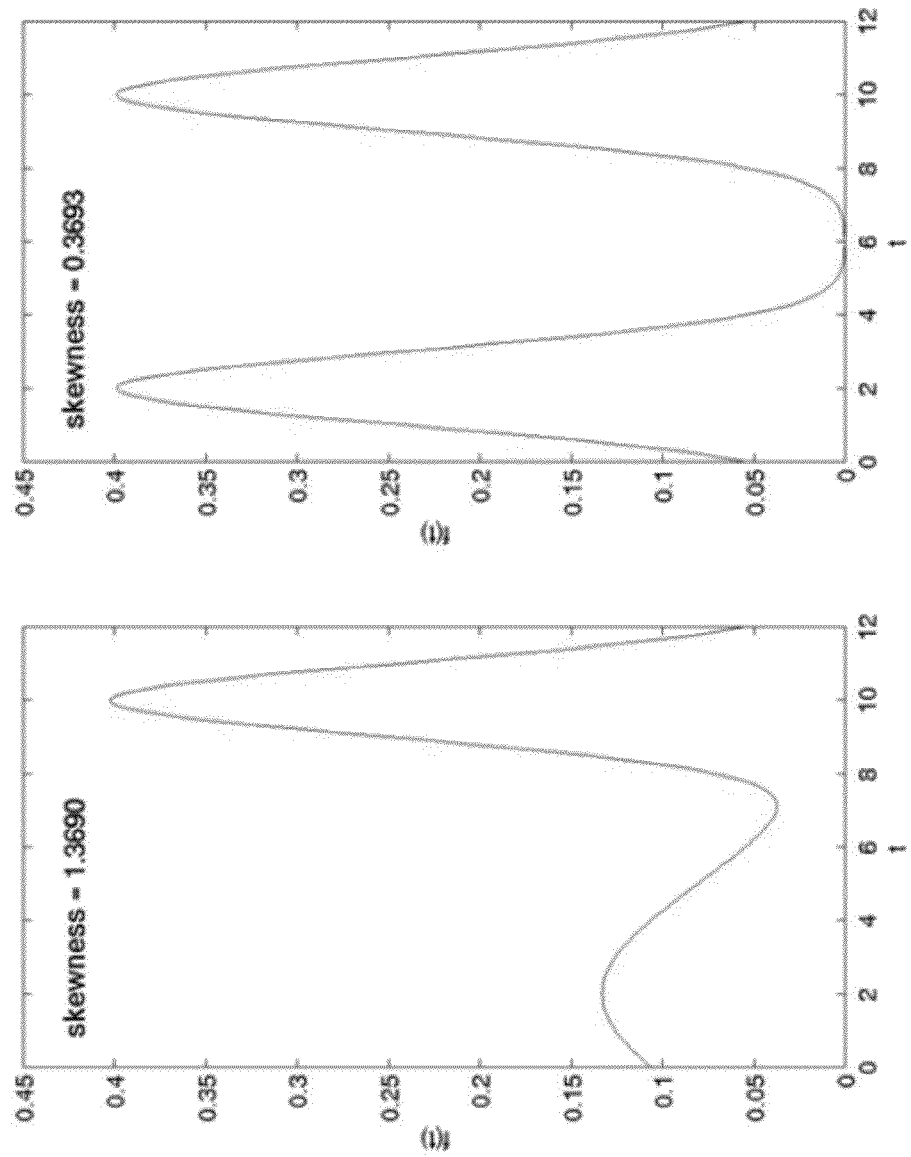
FIGURE 4 (c) Skewness comparison

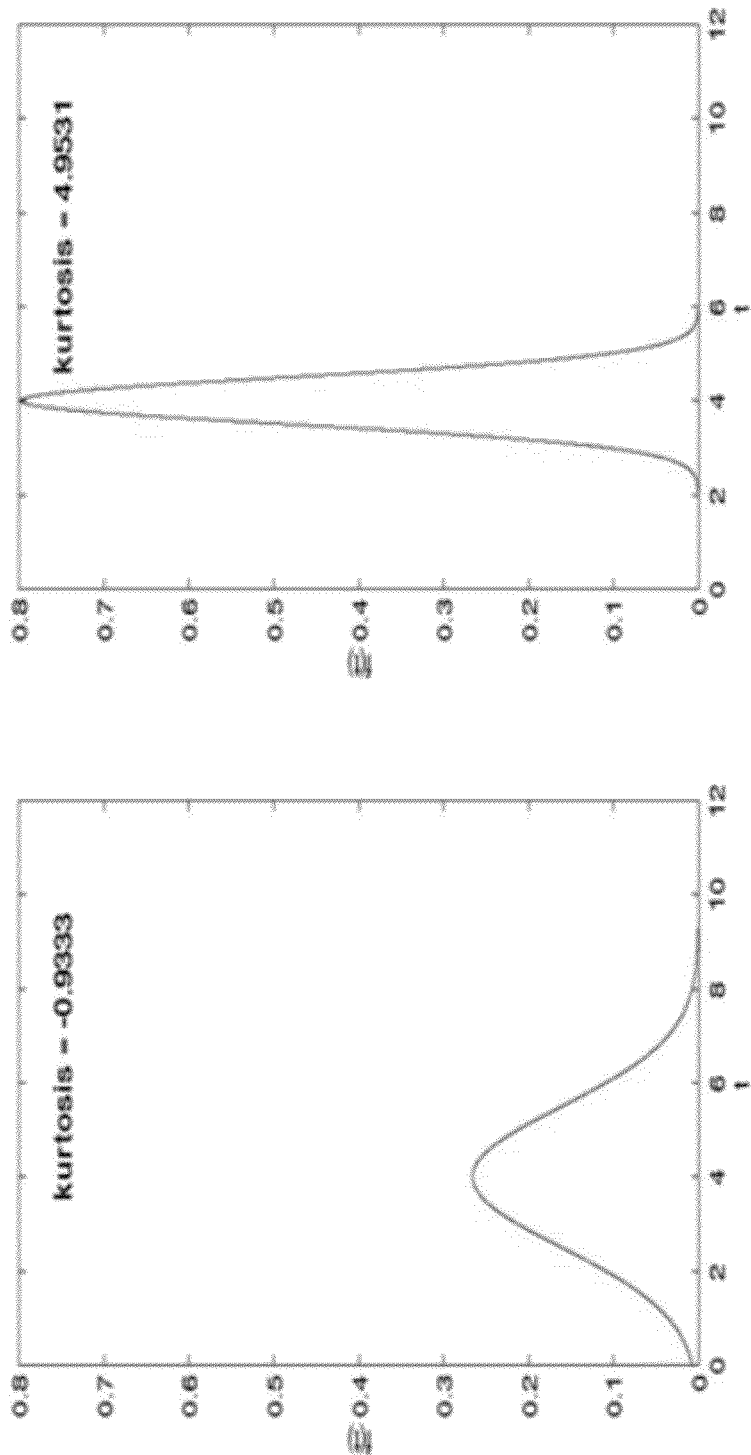
FIGURE 4 (d) Kurtosis comparison

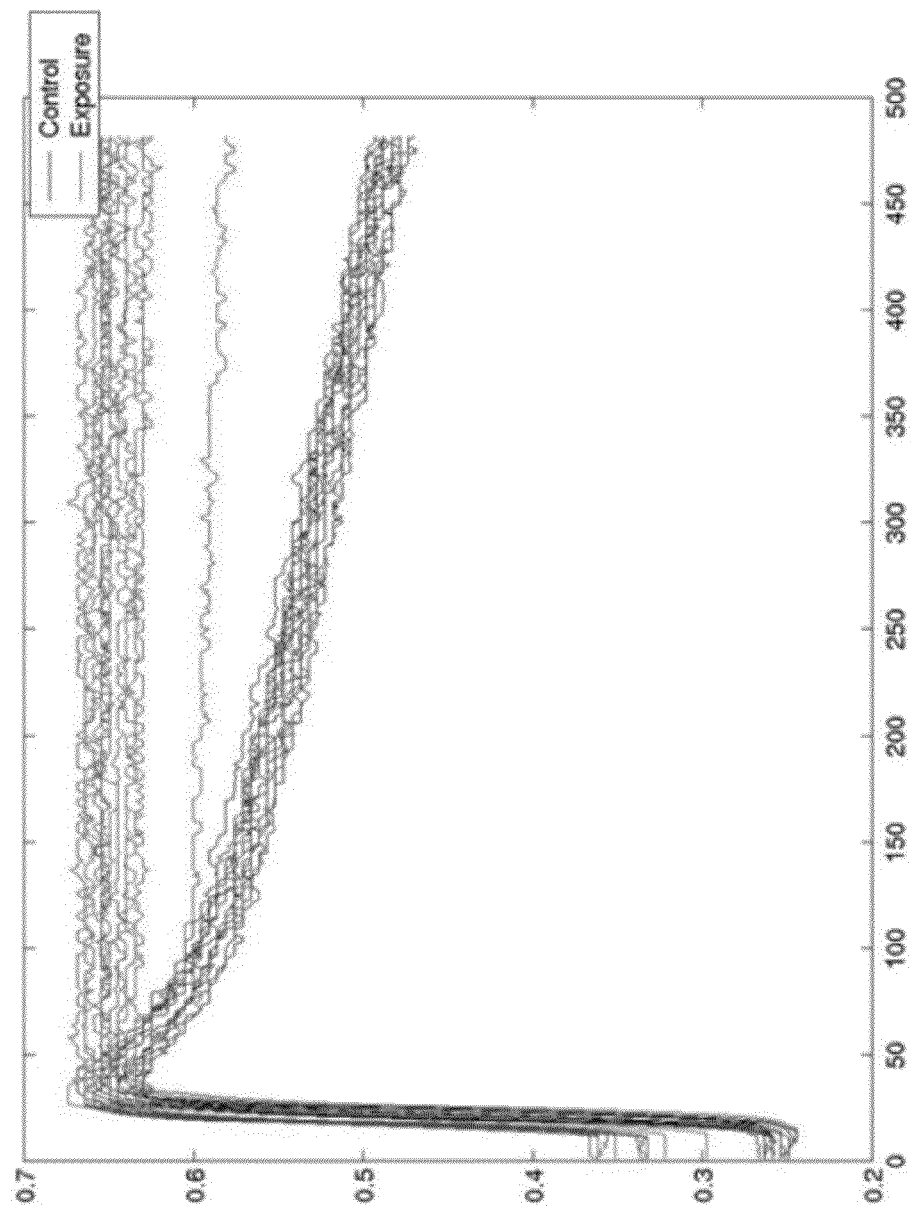
FIGURE 10 (a)(1) DCMU curves.

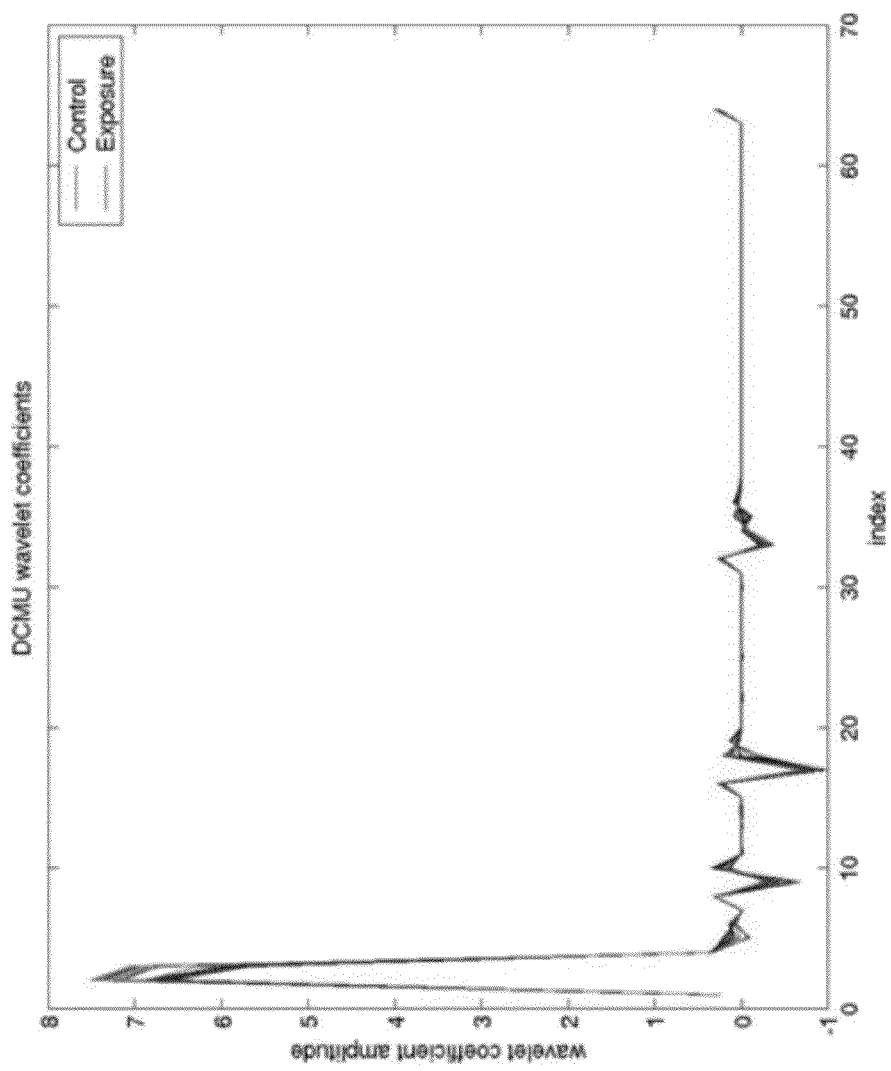
FIGURE 10 (a)(2) DCMU curves.

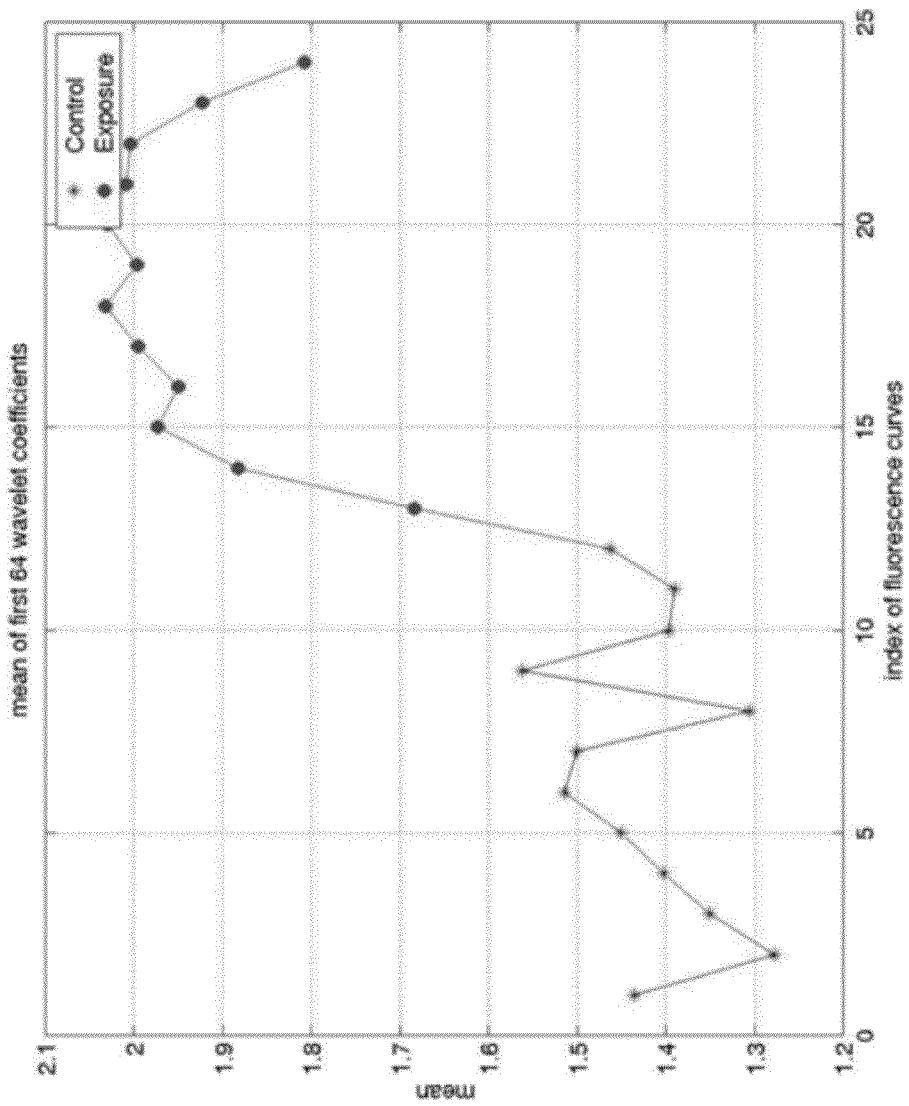
FIGURE 10 (a)(3) DCMU curves.

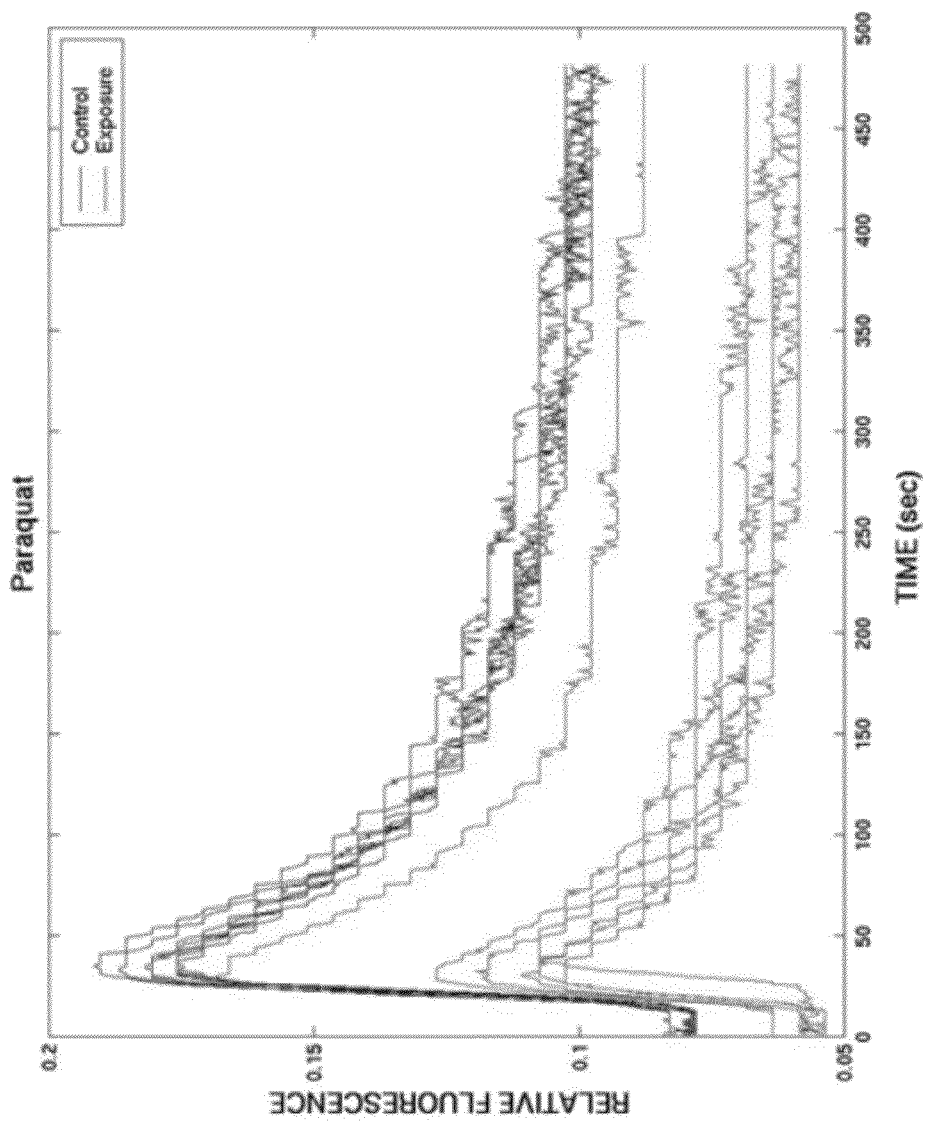
FIGURE 10 (b)(1) Paraquat curves.

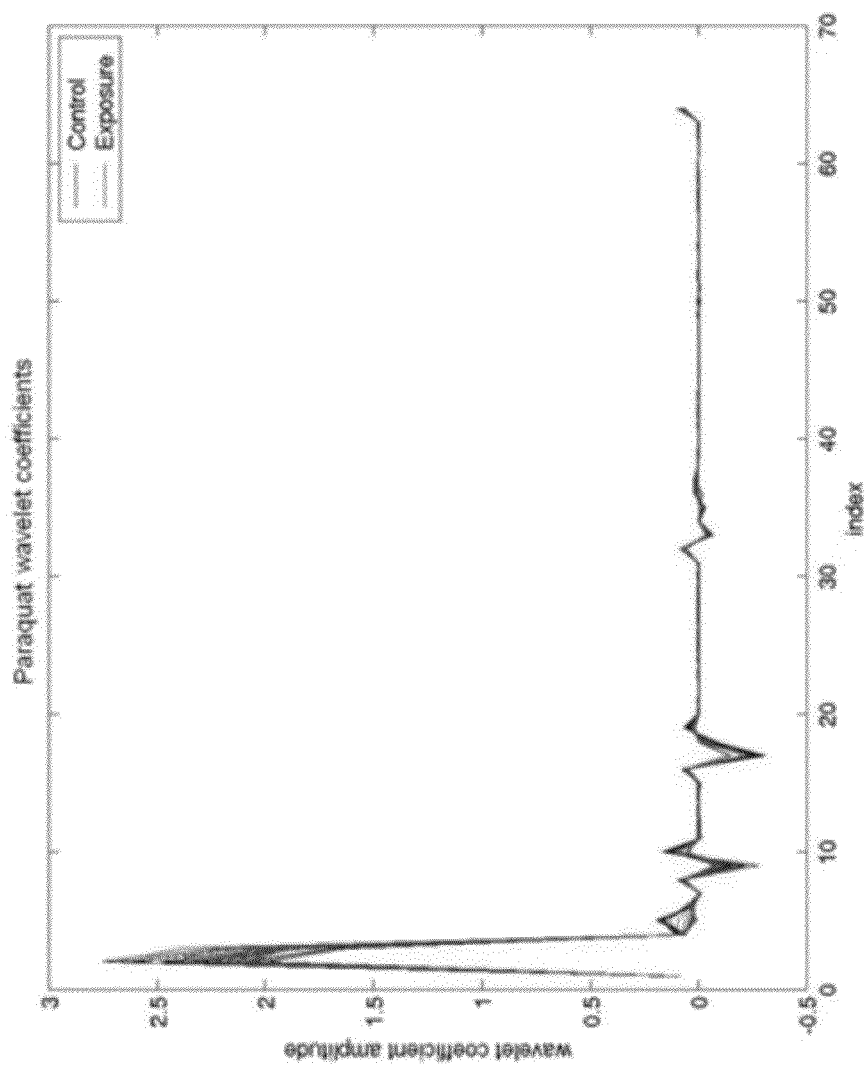
FIGURE 10 (b)(2) Paraquat curves.

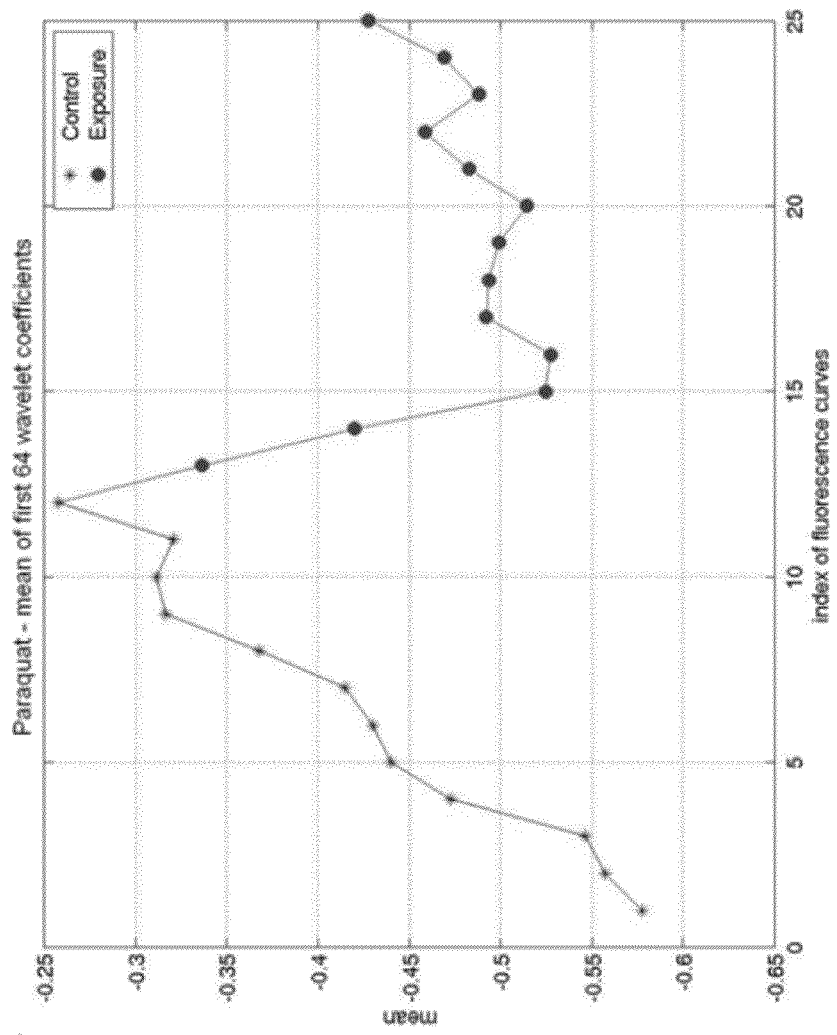
FIGURE 10 (b)(3) Paraquat curves.

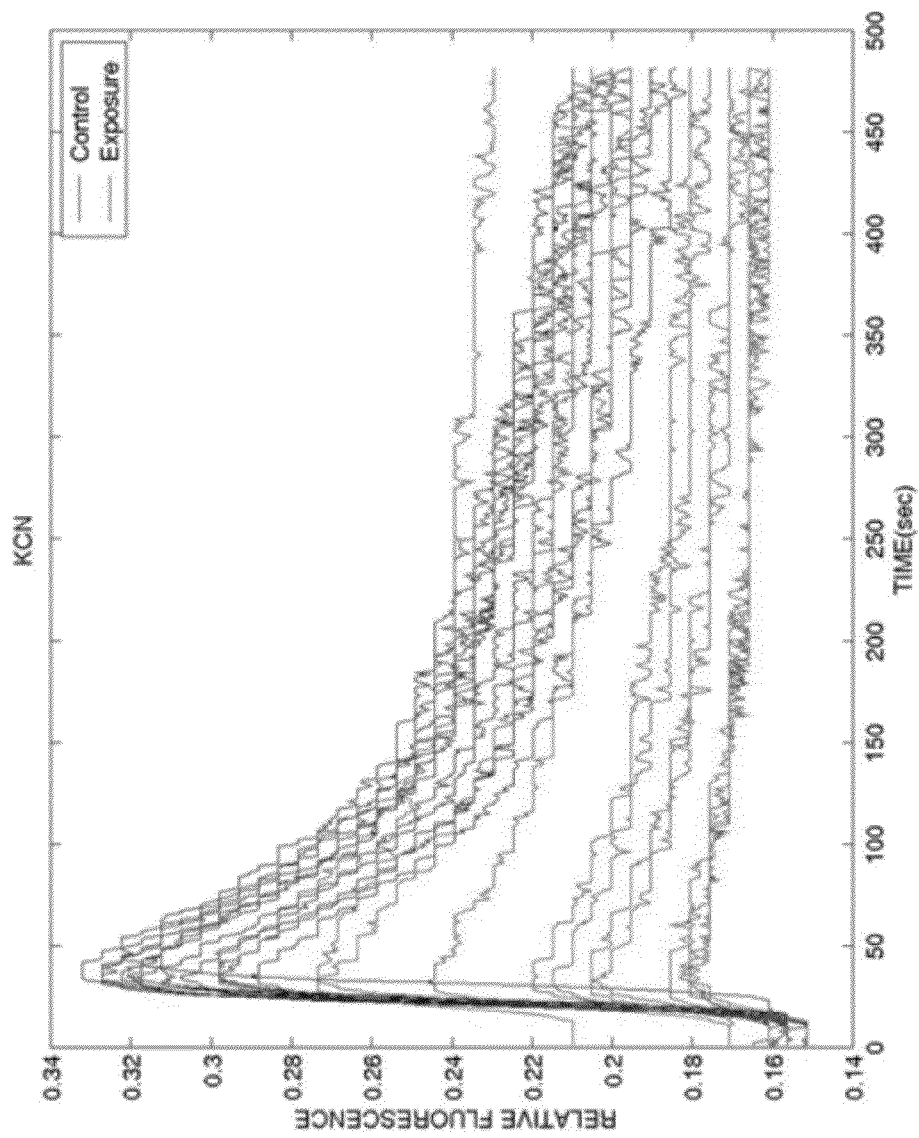
FIGURE 10 (c)(1) KCN curves.

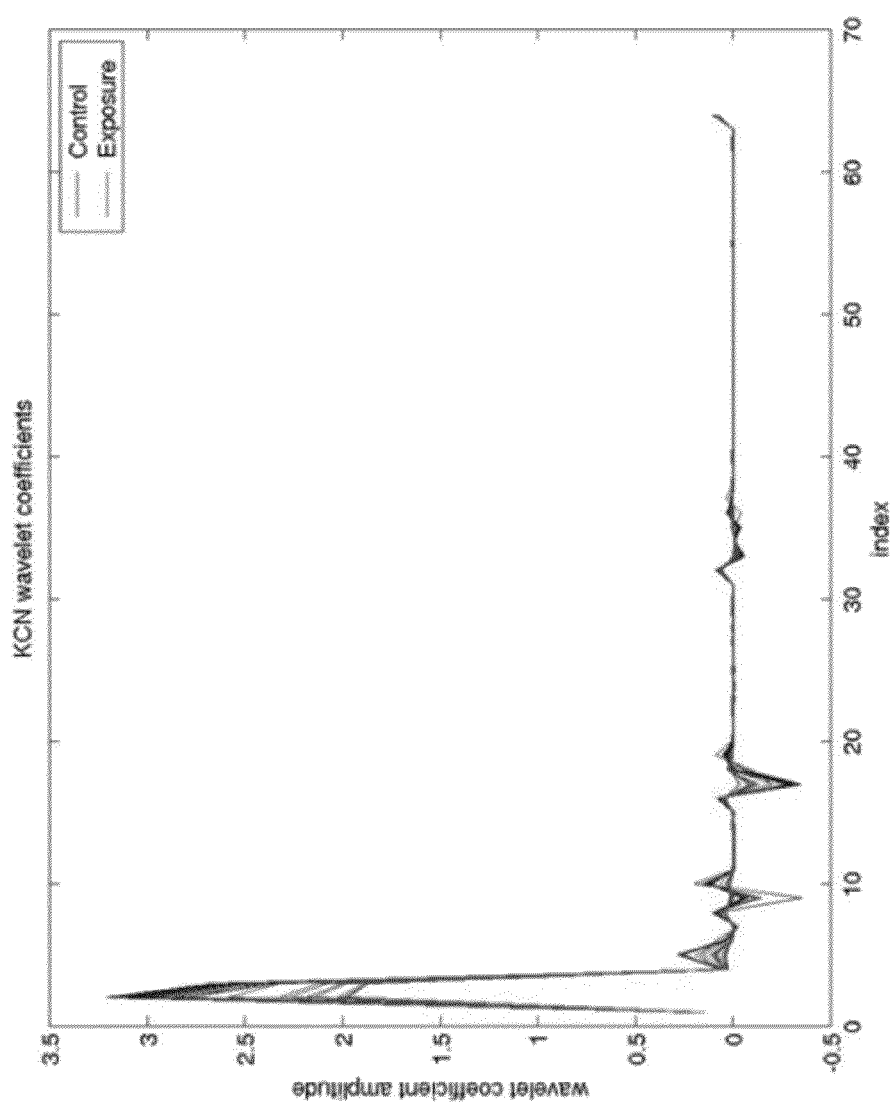
FIGURE 10 (c)(2) KCN curves.

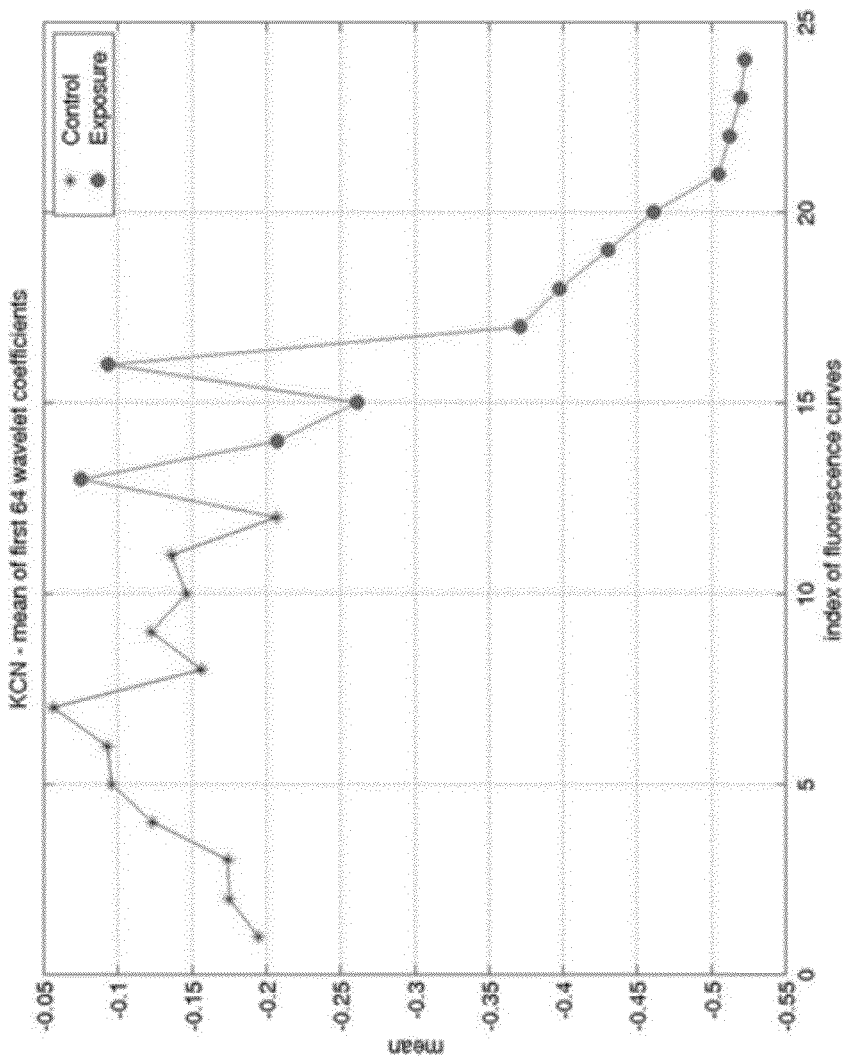
FIGURE 10 (c)(3) KCN curves.

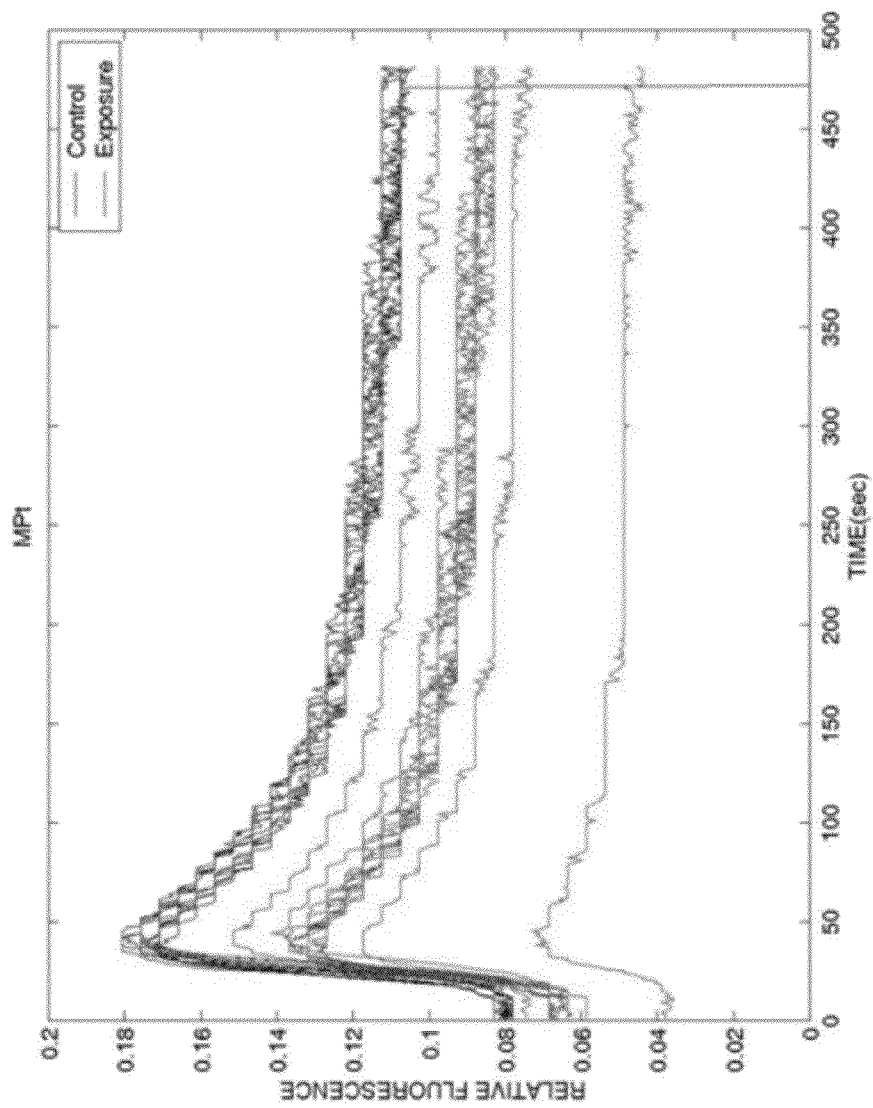
FIGURE 10 (d)(1) MPt curves.

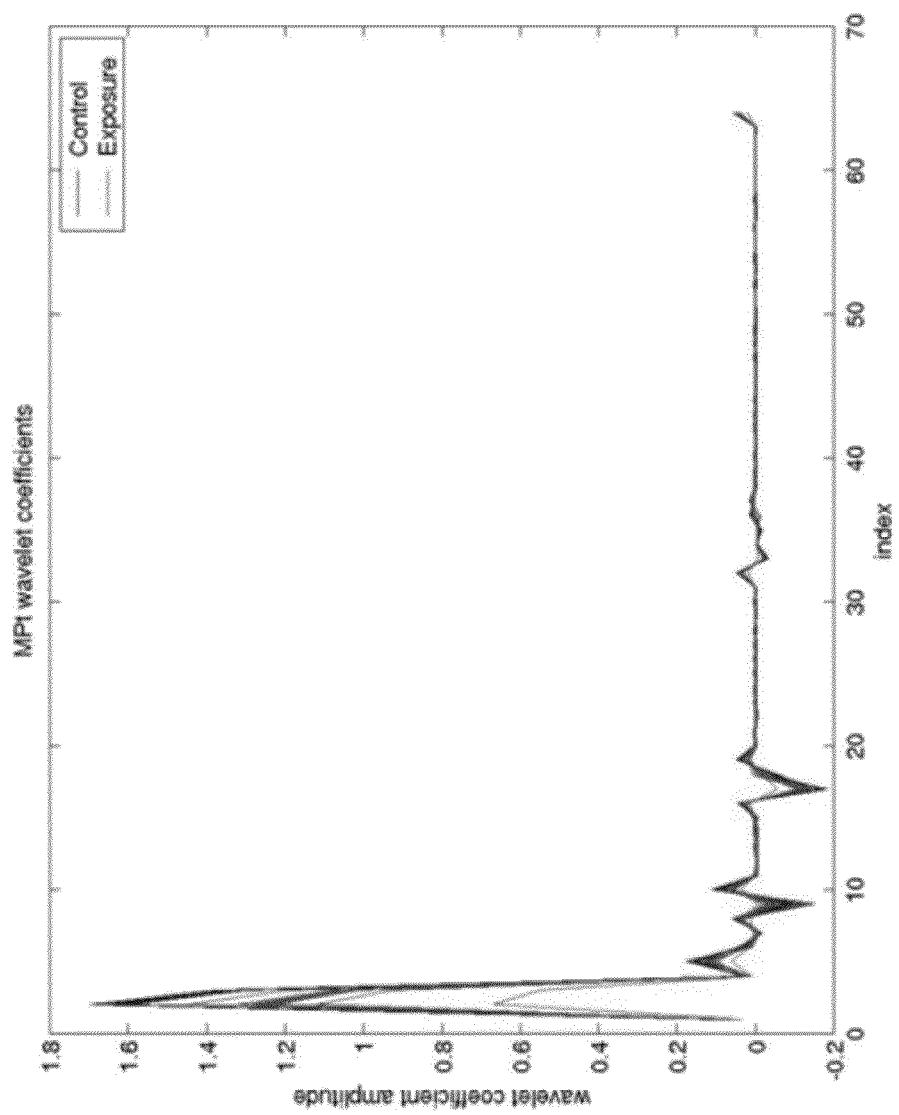
FIGURE 10 (d)(2) MPt curves.

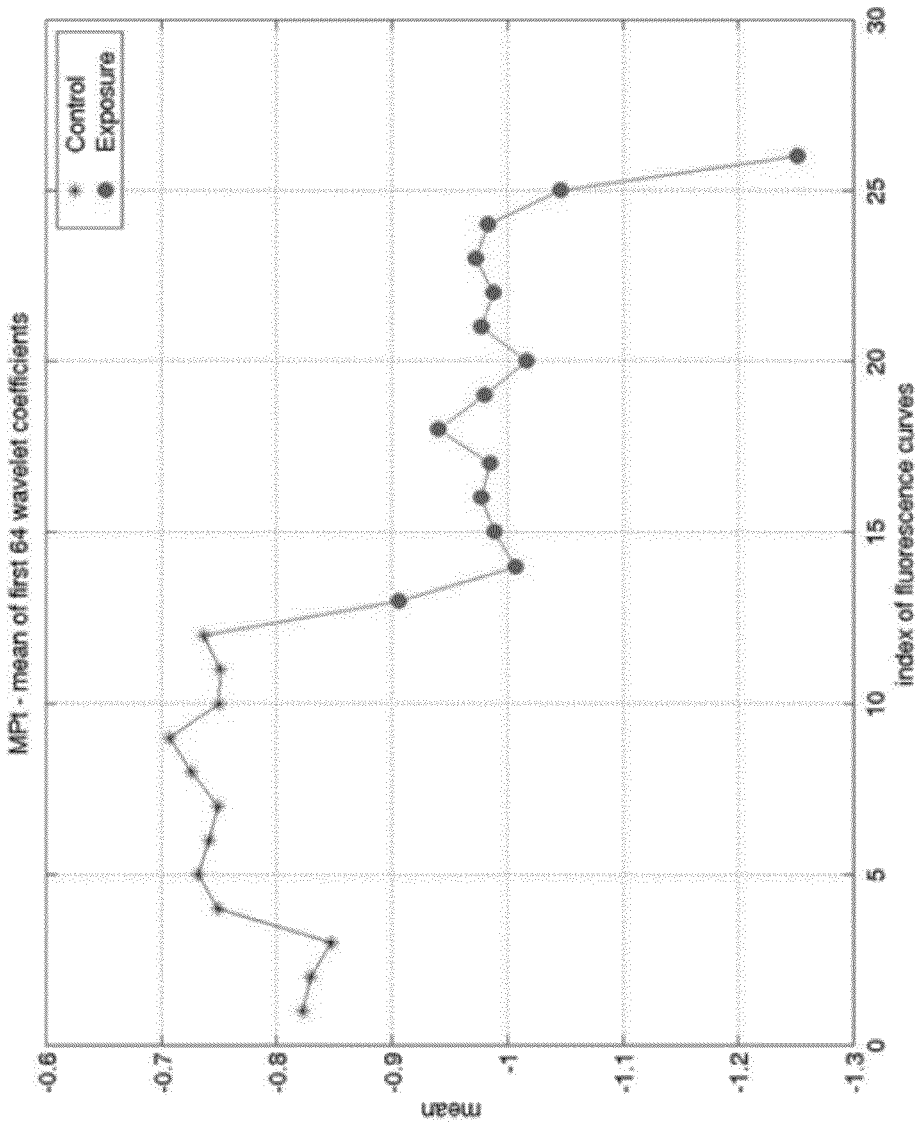
FIGURE 10 (d)(3) MPt curves.

BIOSENSOR METHOD AND SYSTEM BASED ON FEATURE VECTOR EXTRACTION

This application is a divisional application that claims priority to U.S. Pat. No. 8,158,377 entitled "BIOSENSOR METHOD AND SYSTEM BASED ON FEATURE VECTOR EXTRACTION" filed on Aug. 31, 2005, the entire disclosure of which is incorporated by reference.

STATEMENT REGARDING FEDERALLY SPONSORED RESEARCH OR DEVELOPMENT

The United States Government has rights in this invention persuant to contract no. DEAC05-00OR22725 between the United States Department of Energy and UT-Battelle, LLC.

FIELD OF THE INVENTION

The present invention relates to biosensors for detecting chemical, biological and/or radiological contaminants in water or air, and more particularly to biosensor systems and related methods for sensing of toxins based on analysis of time-dependent changes in signals provided by the biosensors responsive to the toxin.

BACKGROUND OF THE INVENTION

There is an increased awareness of the possibility of attacks on metropolitan areas using chemical, biological and radiological warfare agents. Researchers at Oak Ridge National Laboratory have developed a biosensor system to detect toxic agents in primary-source drinking water, such as disclosed in U.S. Pat. No. 6,569,384 to Greenbaum et al. through the analysis of fluorescence induction curves. FIGS. 1(b, d, f, and h) illustrate exposure fluorescence induction curves recorded every 5 minutes when exposed to different toxic agents and data collection for each curve is within 10 seconds, while FIGS. 1(a, c, e, and g) provide controls (no toxins).

In order to detect the existence of toxic agents, the traditional method is to measure the so-called "efficiency of PSII (photosystem II) photochemistry", $$PSII \text{ efficiency} = \frac{F_{max} - F_s}{F_{max}}$$

where $F_s$ is the value at the stable time and $F_{max}$ is the maximum value of the fluorescence induction curve, as shown in FIG. 2. The PSII efficiency represents a simple induction curve-based calculation of the fluorescence signal "signature", and significant deviations thereof indicate the potential presence of a toxic agent in the water.

Although PSII efficiency is generally effective in detecting the presence of toxic agents, it fails in some cases due to the non-significant photochemical yield presented by certain toxic agents. Moreover, it cannot classify between different agents or the same agent with different concentrations. In addition, using this parameter it can take as long as 60 minutes to arrive at a decision regarding detection of a contamination event. The classification of different agents with a shorter response time is of profound importance, such as to reduce response time to a contamination event. With the knowledge of the type of toxic agent, appropriate medicine and rescue strategies can be used in time to save lives as well as counter the terrorist attacks.

FIG. 3(a) compares the average PSII efficiencies of controlled induction curves and the curves obtained from water exposed to four different toxic agents, and FIG. 3(b) shows the average standard deviation of each toxic-agent-exposed signal to its corresponding control signal. It is observed that there is no deterministic pattern in the deviation of PSII efficiency between control and exposure signals to indicate the presence of a specific toxic agent.

SUMMARY

A method of biosensor-based detection of toxins comprises the steps of providing at least one time-dependent control signal generated by a biosensor in a gas or liquid medium (e.g. water), and obtaining a time-dependent biosensor signal from the biosensor in the gas or liquid medium to be monitored or analyzed for the presence of one or more toxins selected from chemical, biological or radiological agents. The time-dependent biosensor signal is processed to obtain a plurality of feature vectors using at least one of amplitude statistics and a time-frequency analysis. At least one parameter relating to toxicity of the gas or liquid medium is then determined from the feature vectors based on reference to the control signal.

The time-frequency analysis can comprises wavelet coefficient analysis. In a preferred embodiment of the invention both amplitude statistics and time-frequency analysis are used in the processing step.

The biosensors can comprise naturally-occurring, free-living, indigenous photosynthetic organisms when the liquid medium is water. In this embodiment, the time-dependent biosensor signal can comprise fluorescence induction data.

The method can also include the step of identifying which toxin(s) are present in the gas or liquid medium. In a preferred embodiment, a linear discriminant method is used for the identifying step, such as support vector machine (SVM) classification.

A water or air quality sensor system comprises a biosensor in an air or water medium to be monitored or analyzed for the presence of one or more toxins selected from chemical, biological or radiological agents, a detector proximate to the biosensor for measuring a time-dependent biosensor signal from the biosensor, and a processor for analyzing the time-dependent biosensor signal to obtain a plurality of feature vectors using at least one of amplitude statistics and time-frequency analysis. The processor then determines at least one parameter relating to toxicity of the air or water medium from the feature vectors. The system can further comprise a memory for storing at least one time-dependent control signal, wherein the processor analyzes the time-dependent biosensor signal to obtain the parameter from the feature vectors based on reference to the control signal. The system preferably includes a classifier for identifying which toxins are present in the air or water medium.

BRIEF DESCRIPTION OF THE DRAWINGS

A fuller understanding of the present invention and the features and benefits thereof will be obtained upon review of the following detailed description together with the accompanying drawings, in which:

FIGS. 1(b, d, f, and h) illustrate conventional exposure fluorescence induction curves recorded every 5 minutes when exposed to different toxic agents and data collection for each curve is within 10 seconds, while FIGS. 1(a, c, e, and g) provide controls.

FIG. 3(a) compares conventional average PSII efficiencies of controlled induction curves and the curves obtained from water exposed to four different toxic agents, while FIG. 3(b) shows the average standard deviation of each toxic-agent-exposed signal to its corresponding control signal.

FIG. 4(a)-(d) provides some examples to illustrate the effect of different curves on the amplitude statistics.

FIG. 10(a)(1)-(d)(3) show fluorescence induction curves exposed to four classes of toxic agents and the corresponding wavelet transforms of these signals.

DETAILED DESCRIPTION

Figure 2:
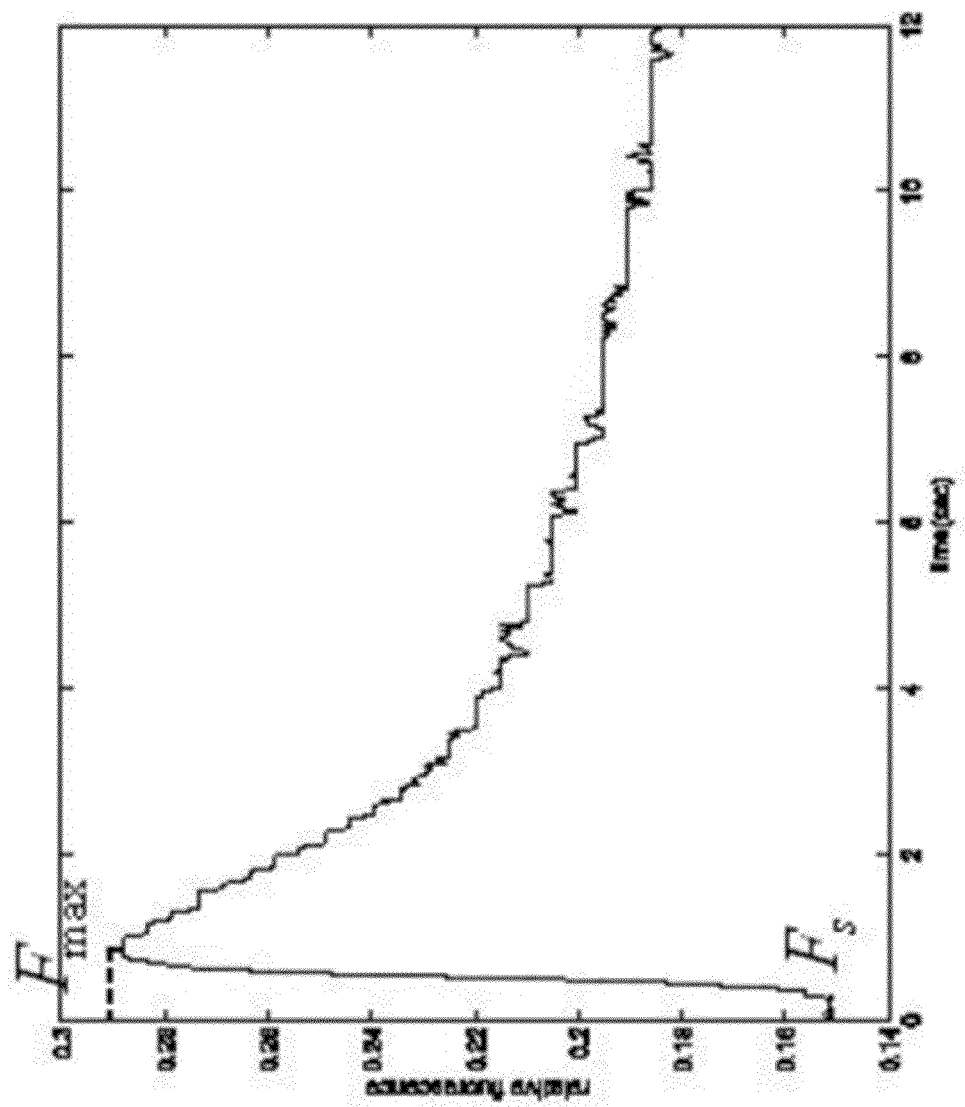
FIG. 2 shows conventional PS II efficiency parameters based on a fluorescence induction curve, $F_s$ being the value at a stable time and $F_{max}$ being the maximum value of the fluorescence induction curve.

A method of biosensor-based detection of toxins comprises the steps of providing at least one time-dependent control signal generated by a biosensor in a liquid (e.g. water) or a gas (e.g. air), and obtaining a time-dependent biosensor signal from the biosensor in a gas or liquid medium to be monitored or analyzed for the presence of one or more toxins selected from chemical, biological or radiological agents. The time-dependent biosensor signal is processed to obtain a plurality of feature vectors using at least one of amplitude statistics and a time-frequency analysis. At least one parameter relating to the toxicity of the gas or liquid medium is then determined from the feature vectors based on reference to the control signal provided. As used herein, the phrase "feature vector" is defined as (i) summation based statistical measures as described below (amplitude statistics) and (ii) coefficients (e.g. wavelet coefficients), or statistical parameters derived from the coefficients (e.g. wavelet coefficient standard deviation) generated by application of a time-frequency analysis to the time-dependent sensor signal.

As noted in the background, conventional aquatic biosensors monitor the quality of primary-source drinking water by analyzing the fluorescence signal signature from healthy algae during photosynthesis. Fluorescence emitted by healthy algae differs from that emitted by algae exposed to a toxic agent. Simple algorithms based on PSII efficiency are generally used to characterize the signature of the fluorescence signal without any time-frequency analysis or high-order statistical analysis.

In contrast, applied to fluorescence data, the invention describes algorithms which better characterize features of the fluorescence signal such that more detailed information can be obtained, such as detection of a toxic agent with a higher confidence level, the identification of different types of toxic agents, the detection of toxic agents at different concentration levels, as well as a more robust response that is less affected by the photo-inhibition effect or diurnal cycle on the algae. The invention also permits substantially more rapid assessment to permit arriving at a decision regarding detection of a contamination event in generally no more than several minutes (CHECK), as compared to up to 60 minutes using conventional fluorescence signature analysis.

A first new algorithm comprises high-order statistical analysis (referred to herein as "amplitude statistics") of the light signal in the time domain. As used herein, the phrase "amplitude statistics" is defined as summation based statistical measures derived from a plurality of (N) time points in the signal curve, such as first order (mean), second order (standard deviation), third order (skewness), and fourth order (kurtosis). PS II efficiency as described in U.S. Pat. No. 6,569,384 to Greenbaum et al. is thus clearly not amplitude statistics since the measurement therein is based on the simple difference between discrete points being the maximum value of the fluorescence induction curve ($F_{max}$) and the fluorescence value at the stable time ($F_s$).

Amplitude statistics can capture more dynamic features of the signal than PSII efficiency, including how fast the signal approaches maximum and minimum, how far samples are from the mean value, and how symmetric the signal appears. These features are generally required in the detection and identification regarding the existence of different toxic agents.

A first new algorithm comprises wavelet analysis of the light signal in the time-frequency domain referred to herein as "time-frequency analysis". Because of the nature of the light signal captured by the aquatic biosensors, time-frequency analysis can reveal when and how the frequency of the signal changes. In a preferred embodiment, only three features extracted from the wavelet coefficients are used in the algorithm instead of the entire set of coefficients for signal characterization.

Amplitude statistics and time-frequency analysis according to the invention can be used independently to provide detection results significantly improved as compared to algorithms based on the fluorescence signal signature. However, by combining amplitude statistics and time-frequency analysis, the confidence detection and identification can be improved to an even higher level.

The gas or liquid medium to be monitored or analyzed is generally air in the case of gas and water in the case of liquid. The water can be primary-source drinking water. In a preferred embodiment of the invention, algae is the biosensor used to generate time-dependent biosensor signals such as fluorescence induction curves which are analyzed through extraction of feature vectors to permit classification of different toxic agents in sunlight-exposed primary-source drinking water based on feature vectors. As described in the Examples below, agents studied included methyl parathion (MPt), potassium cyanide (KCN), Diuron (DCMU), and Paraquat in both the samples of Clinch River (Tennessee) and the samples with lab-grown *Chlamydomonas reinhardtii*. The Examples provided demonstrate superior performance of the claimed methodology through three groups of experimental results, including the capabilities of toxic agent detection, multi-type toxic agent classification, and immunity to the effect of photo-inhibition or diurnal cycle.

Biosensors are generally cell-based, and can include genetically modified cells. For example, a bacterium modified with lux genes can be used. In the case of fluorescence induction, algae can be used, either naturally-occurring or genetically modified. Naturally-occurring aquatic algae does not generally require culturing.

Every water source that is exposed to sunlight contains populations of photosynthetic microorganisms (phytoplankton and algae, for example), at concentrations ranging from 10 to as high as 100,000 organisms/ml. Although always present in sunlight-exposed water, these microorganisms are often invisible to the unaided eye. Phytoplankton emits a characteristic fluorescence signal that, if detectable in solutions with low microorganism concentrations, can be utilized as an in situ indicator of chemical and/or biological warfare agents water supplies. Biosensors provide time-dependent biosensor signal while in a gas or liquid medium to be monitored or analyzed for the presence of one or more toxins selected from chemical, biological or radiological agents. Water-soluble toxic chemical and/or biological agents, for example, can include blood agents (cyanide, for example), pesticides (methyl parathion, for example) and herbicides (DCMU, for example), or radionuclide that could pose a threat to primary-source drinking water supplies.

The time-dependent biosensor signal is modified by the toxin as compared to a control signal when the toxin is absent. A variety of signal types can be analyzed using the invention. For example, the signals can be spectroscopic (e.g. fluorescent). Regarding spectroscopic signals, see, e.g., Huang, G. G., Yang, J. 2005 "Development of infrared optical sensor for selective detection of tyrosine in biological fluids", *Biosensors and Bioelectronics*, 21(3):408-418. Regarding acoustic signals, see, e.g., U.S. Pat. No. 6,486,588 to Doron, et al. "Acoustic biosensor for monitoring physiological conditions in a body implantation site"; "Acoustic immunosensor for real-time sensing of neurotransmitter GABA", *Proceedings of the 25th IEEE Annual International Conference*, 4:2998-3000.+Khraiche, M. L., Zhou, A., Muthuswamy, J. 2003, and "Acoustic sensors for monitoring neuronal adhesion in real-time", *Proceedings of the 25th IEEE Annual International Conference*, 3:2186-2188.). Regarding electrochemical signals, see, e.g., U.S. Pat. No. 6,511,854 to Asanov, et al. "Regenerable biosensor using total internal reflection fluorescence with electrochemical control", and "Development and evaluation of electrochemical glucose enzyme biosensors based on carbon film electrodes" *Talanta*, 65(2):306-312.+Xu, J.-Z., et al. 2004.

Regarding thermal detection, see e.g.,"Calorimetric biosensors with integrated microfluidic channels. *Biosensors and Bioelectronics*", 19(12):1733-1743.+Towe, B. C., Guilbeau, E. J. 1996. Regarding magnetic based sensors, see de Oliveira, J. F., et al. 2005 "Magnetic resonance as a technique to magnetic biosensors characterization in Neocapritermes opacus termites" *Journal of Magnetism and Magnetic Materials*, 292(2):e171-e174.+Chemla, Y. R., et al. 2000, "Ultrasensitive magnetic biosensor for homogeneous immunoassay", *Proc. Natl. Acad. Sci. USA*, 97(26):14268-72. Regarding surface plasmon resonance (SPR) using enzymes or antibodies see, e.g., U.S. Pat. No. 6,726,881 to Shinoki, et al. "Measurement chip for surface resonance biosensor", U.S. Pat. No. 6,573,107 to Bowen, et al. "Immunochemical detection of an explosive substance in the gas phase through surface plasmon resonance spectroscopy", U.S. Pat. No. 5,313,264 to Ivarsson, et al. "Optical biosensor system".

In the case of air monitoring using algae-based biosensors, the algae generally requires culturing. In this embodiment, air to be analyzed can be drawn through filter paper having algae cultured thereon.

Although the invention is generally hereafter described related to fluorescence induction provided by algal biosensors in water, as noted above, the invention is in no way limited to this specific embodiment.

Feature Extraction of Fluorescence Induction Curves

Classification of different toxic agents in primary-source drinking water through the analysis of fluorescence induction curves is a challenging undertaking. It is difficult to separate different curves by simply looking at the amplitude responses of the curves. Statistical analysis according to the invention can describe, for example, how "fast" the curve reaches the maximum, how "slow" the curve decreases after reaching the maximum. These features are largely related to high-order statistics. In addition, further analyses in other transformation domains (frequency or time-frequency) as described below are also preferably performed in order to provide additional information related to the frequency change over time.

Amplitude Statistics

Amplitude statistics provide statistical measurements of the biosensor signal to be analyzed, such as average fluorescence amplitude over time. The mathematical definition of amplitude statistics up to the fourth order is as follows:

$$\text{mean: } \mu_{amp} = \frac{1}{N}\sum_{i=1}^{N} F(i)$$

$$\text{standard deviation: } \sigma_{amp} = \sqrt{\frac{1}{N}\sum_{i=1}^{N}(F(i) - \mu_{amp})^2}$$

$$\text{skewness: } \gamma_{amp} = \frac{1}{N} \sum_{i=1}^{N} \left( \frac{F(i) - \mu_{amp}}{\sigma_{amp}} \right)^2$$

$$\text{kurtosis: } \beta_{amp} = \frac{1}{N} \sum_{i=1}^{N} \left( \frac{F(i) - \mu_{amp}}{\sigma_{amp}} \right)^4$$

where, regarding fluorescence, F(i) represents the relative fluorescence at the ith time point, and N is the number of time points in the induction curve.

FIG. 4 provides some examples to illustrate the effect of different curves on the amplitude statistics. The first-order statistics, the mean, is actually the average of amplitude, as shown in FIG. 4(a). The second-order statistics, the standard deviation, reflects how different each sample is from the mean, as shown in FIG. 4(b). The third-order statistics, the skewness, depicts how symmetric the curve is. In FIG. 4(c), the skewness is compared for two different curves. It is obvious that the left curve is less symmetric than the right curve and correspondingly, the skewness of the left curve is much larger (1.369) than that of the right curve (0.369). The fourth-order statistics, the kurtosis, describes how flat the curve is. The flatter the curve, the less the kurtosis, which can be observed by the two example curves shown in FIG. 4(d).

Figure 5:
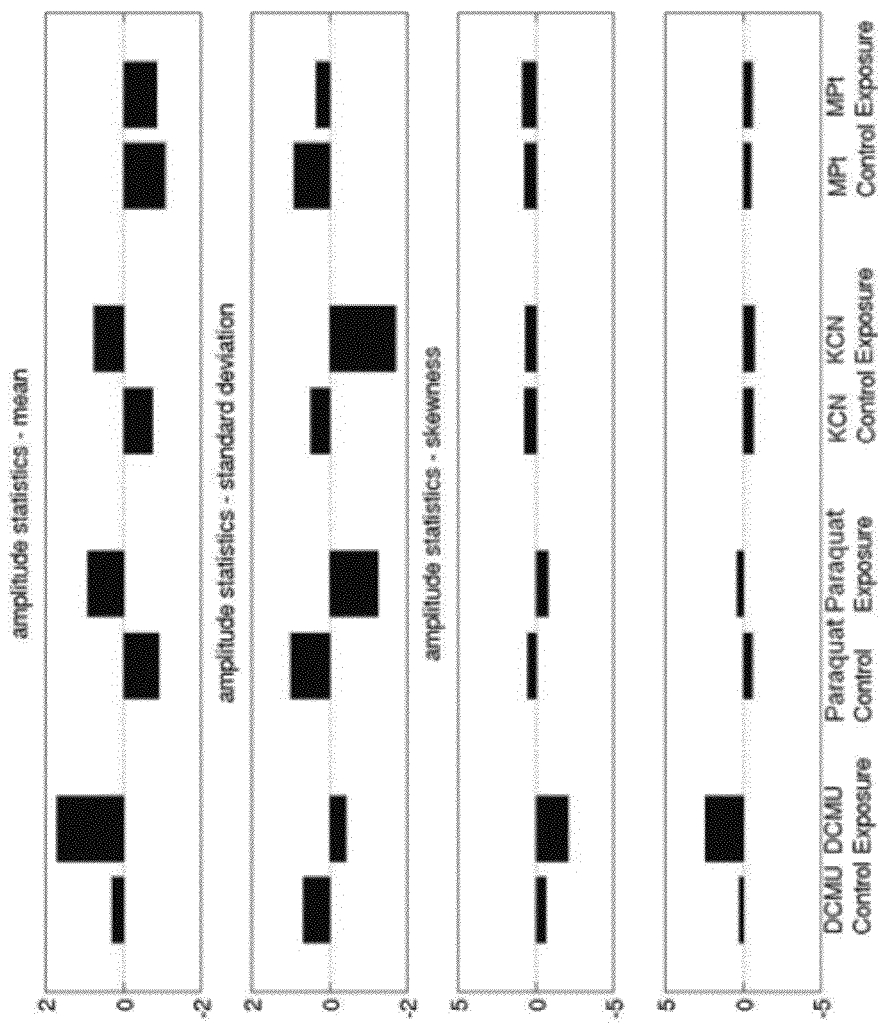
FIG. 5 compares the average amplitude statistics generated from the control and exposure signals of each toxic agent class.
Figure 6:
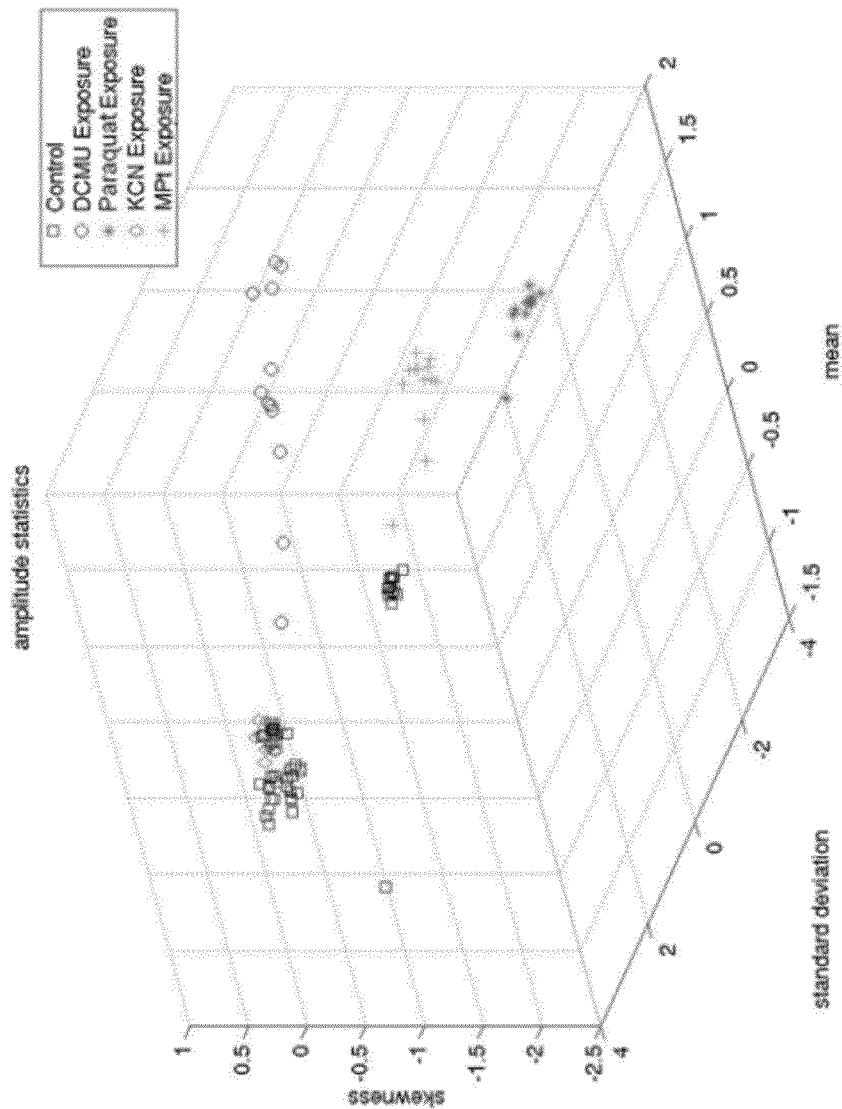
FIG. 6 shows a 3-D plot showing three amplitude statistics features (mean, standard deviation, and skewness). It can be seen from FIG. 6 that data from different classes of toxic agents cluster at different positions within the 3D feature space that can be separated relatively easily.

FIG. 5 compares the average amplitude statistics generated from the control and exposure signals of each toxic agent class. FIG. 6 shows the 3-D plot regarding to the three amplitude statistics features (mean, standard deviation, and skewness). It can be seen from FIG. 6 that data from different classes of toxic agents cluster at different positions within the 3D feature space that can be separated relatively easily. This data demonstrates the effectiveness of using amplitude statistics in feature extraction to classify among different toxic chemical agents.

Statistics in Wavelet Coefficients

The wavelet transform is a generalization of the well-known Fourier transform in signal processing. The Fourier transform represents a signal in the frequency domain by decomposing a waveform into sinusoids of different frequencies with different amplitudes (weights) which sum to the original waveform. In another word, the Fourier transform reveals the amount of each frequency component needed to form the original waveform. Although informative, the Fourier transform does not preserve any information concerning the time domain, e.g., when and how long in the time domain that a specific frequency component occurs. The lack of time-domain information in the Fourier transform presents a critical problem for the analysis of non-stationary signals which do not maintain the same frequency component throughout the duration of the signal. For example, a stationary signal with four frequency components (e.g. 10 Hz, 25 Hz, 50 Hz, and 100 Hz) at all times, and a non-stationary signal with the same four frequency components occurring at different time periods will have the same Fourier transform despite the obvious difference presented in the respective time-domain signals.

Unlike the Fourier transform, time-frequency analysis, such as provided by the wavelet transform, presents a time-frequency representation of the signal. A time-frequency representation of the signal provides time-domain information that a specific spectral component occurs. Since biosensor signals such as the fluorescence induction signals are generally non-stationary (See FIG. 1), it is beneficial to apply a time-frequency analysis such as the wavelet transform to present both the time-domain and the frequency-domain information.

Different from the Fourier transform that uses the sine and cosine functions as basis functions, wavelet transforms use basic functions that are localized in both time and frequency domains. Wavelet transforms aim at representing the time function in terms of simple, fixed models, which are called wavelets. Wavelets are derived from a single generating function that is called the mother wavelet. The mother wavelet meets the following conditions:

$$\int \psi(t)dt = 0, \psi_{a,b}(t) = \frac{1}{\sqrt{a}} \psi\left(\frac{t-b}{a}\right)$$

where a is the scaling factor and b is the translation factor. The translation and scaling of the mother wavelet will generate a family of functions. The parameter a changes the scale of the wavelet, that is, the greater |a| is, the smaller the frequency. The parameter b controls the translation of the wavelet. In other words, wavelet transforms use narrower windows when the signal frequencies are high and wider windows when the signal frequencies are low. This representation allows the wavelet transform to "enlarge" every high-frequency component, such as the transient in signals. This is one of the main advantages of the wavelet transform over the Fourier transform. The wavelet transform could be categorized into the continuous wavelet transform (CWT) and the discrete wavelet transform (DWT), defined as:

$$CWT_f(a, b) = |a|^{-1/2} \int_{-\infty}^{\infty} f(t)\psi\left(\frac{t-b}{a}\right) dt$$

$$DWT_f(m, n) = a_0^{-m/2} \int_{-\infty}^{\infty} f(t)\psi(a_0^{-m}t - nb_0) dt$$

Considering the computation complexity of CWT, given sampled signals of finite length, it is generally preferable to use the DWT with the invention. In the DWT, the family of wavelets is given as:

$$\psi_{m,n}(t) = a_0^{-m/2} \psi(a_0^{-m}t - nb_0)$$

Figure 7:
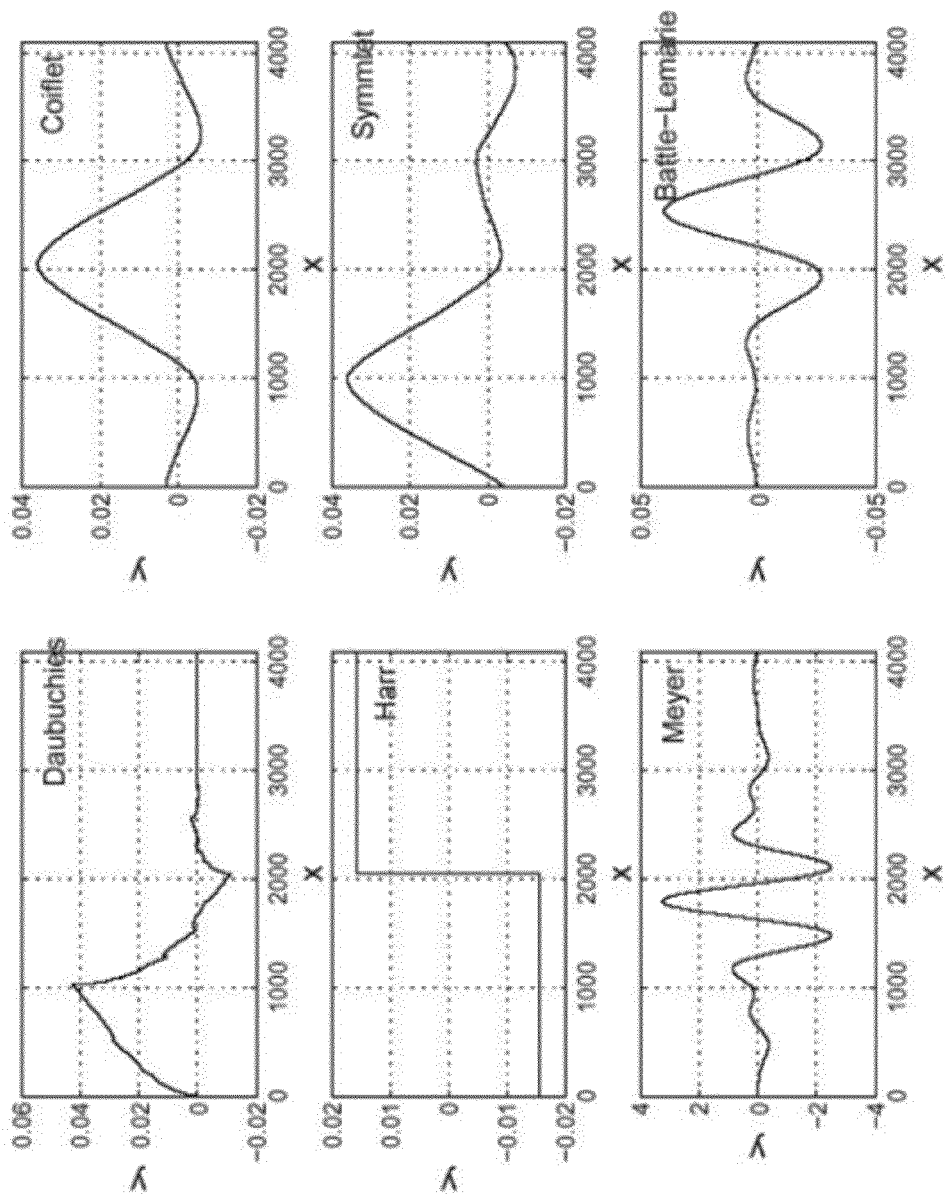
FIG. 7 shows some examples of some exemplary mother wavelets, including the Daubechies wavelet, the Coiflet wavelet, the Harr wavelet, the Symmlet wavelet, the Meyer wavelet and the Battle Lemarie wavelet.

Some examples of some exemplary mother wavelets are shown in FIG. 7, including the Daubechies wavelet, the Coiflet wavelet, the Harr wavelet, the Symmlet wavelet, the Meyer wavelet and the Battle Lemarie wavelet. Among these wavelets, the Daubechies wavelet is popularly used in the engineering field. The parameters of the corresponding Daubechies wavelets are given by sequence $(h_0, h_1, \ldots, h_N)$ that satisfies the following conditions:

$$\sum_{n=0}^{N} h_n = \sqrt{2},$$

$$\sum_{n=0}^{N} (-1)^n n^k h_n = 0, \text{ for } k = 0, 1, 2, \ldots, (N-1)/2, \text{ and}$$

$$\sum_{n=0}^{N-2k} h_n h_{n+2k} = 0, \text{ for } k = 1, 2, 3, \ldots, (N-1)/2.$$

Figure 8:
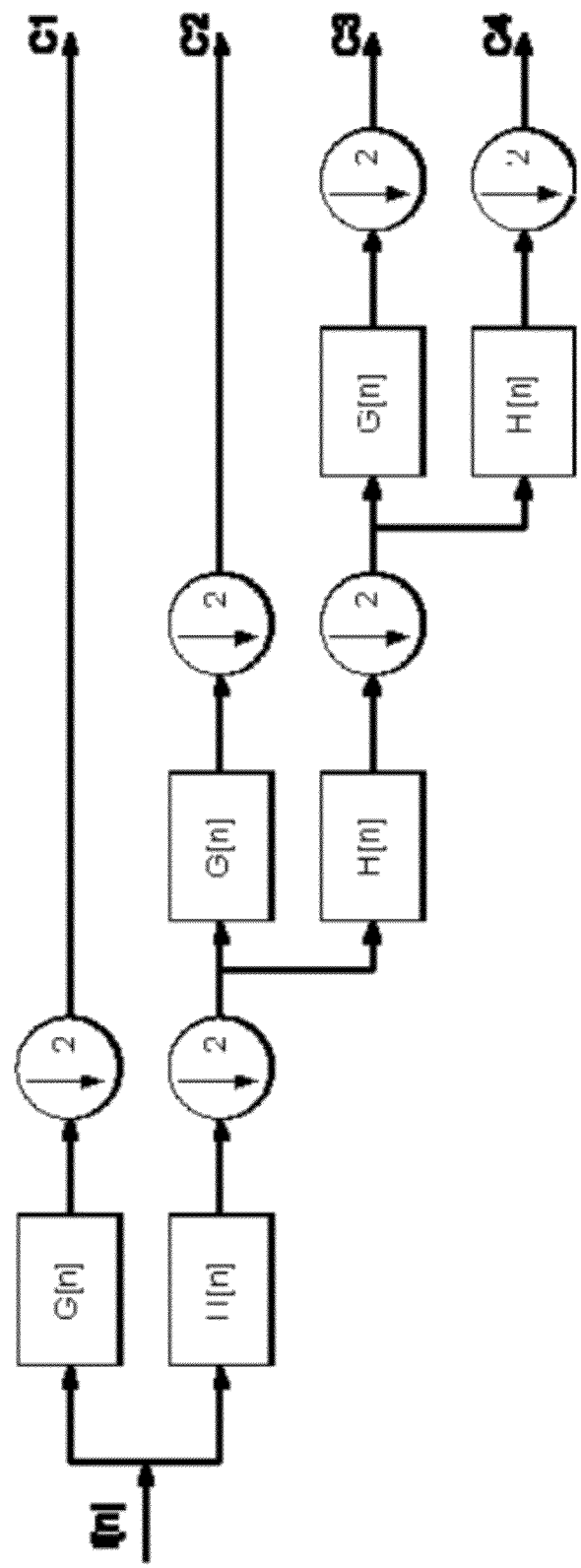
FIG. 8 shows a filter bank implementation of a discrete wavelet transform.
Figure 9:
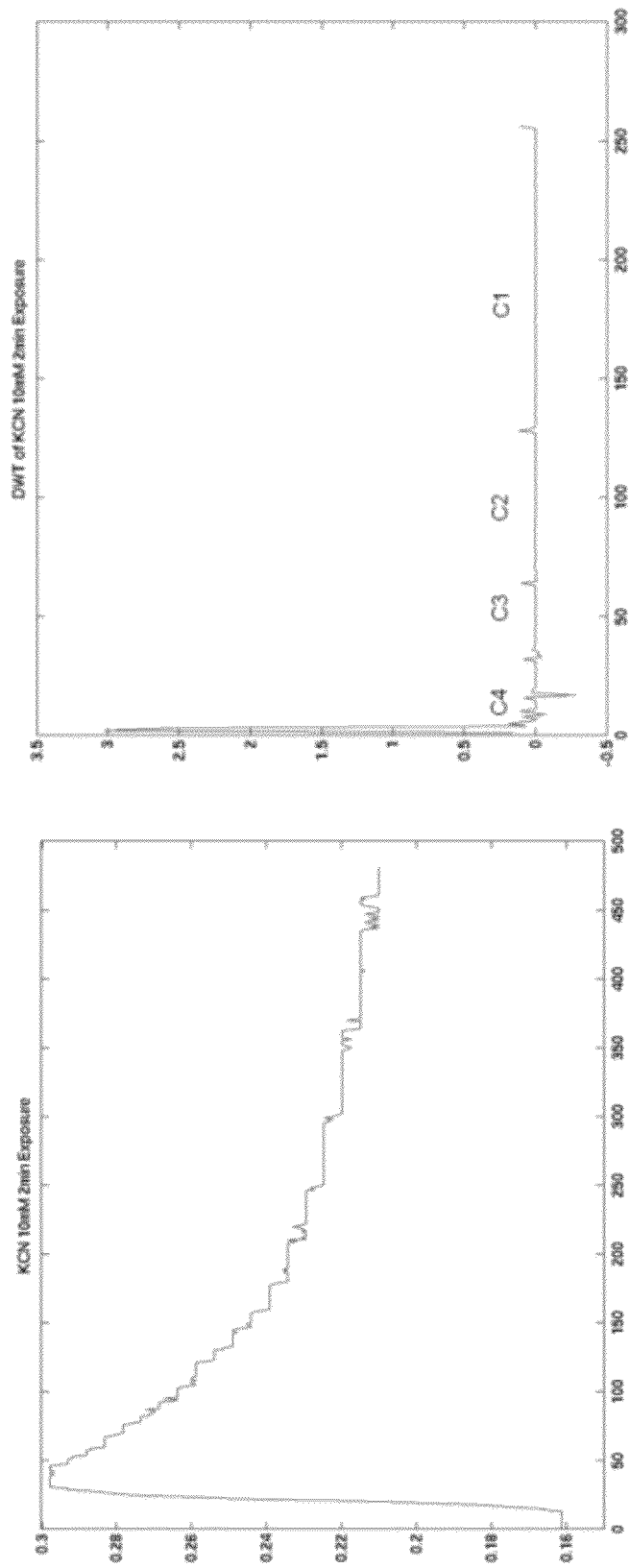
FIG. 9 shows an example of a fluorescence induction curve exposed to 10 mM KCN and the corresponding 3-level wavelet decomposition.

In practice, the forward and inverse wavelet transforms could be implemented using a set of sampling functions, called digital filter banks as shown in FIG. 8. The sampled data f[n] is first input in parallel to a low-pass filter (H[n]) and a high-pass filter (G[n]). The outputs from the two filters are down-sampled and thus kept exactly one half of the size of the input signals. After the first stage, the output of the high-pass filter becomes the first-level wavelet coefficients, C1. The second stage uses the output from the low-pass filter of the previous step as the input, which is again sent to H[n] and G[n]. The output of the down-sampled high-pass filter of this stage becomes the second-level wavelet coefficients, C2. The same process continues until only two sample points are left. In another word, the DWT uses filters of different cutoff frequencies to analyze the signal at different scales. The signal is passed through a series of high-pass and low-pass filters to analyze the high frequency and low frequency contents respectively. FIG. 8 shows a three-level wavelet transform with four series of coefficients, C1 to C4. FIG. 9 shows an example of a fluorescence induction curve exposed to 10 mM KCN and the corresponding 3-level wavelet decomposition.

FIG. 10(a)-(d) show fluorescence induction curves exposed to four classes of toxic agents and the corresponding wavelet transforms of these signals. In a preferred embodiment, each original induction curve is preprocessed by downsampling them into signals with 256 discrete samples and then apply the DWT. Suppose the highest frequency component existed in the fluorescence induction signal is $f_{max}$, then in a three-level wavelet decomposition, the C1 wavelet coefficients of 128 samples correspond to spectral components within frequency band ($f_{max}/2$, $f_{max}$), the C2 coefficients of 64 samples reflect frequency components of band ($f_{max}/4$, $f_{max}/2$), the C3 coefficients of 32 samples correspond to band ($f_{max}/8$, $f_{max}/4$), and the C4 coefficients of 32 samples are the low-pass content of band (0, $f_{max}/4$). FIG. 9 shows one example of the 3-level decomposition.

Since the fluorescence induction signals are mainly composed of very-low-frequency components, only the first 64 wavelet coefficients (C4 and C3) that correspond to low-frequency spectral components are considered and shown in FIG. 10.

Existing methods use the wavelet coefficients themselves to serve as a feature set for classification. However, not all the coefficients are necessary. In addition, the use of all generated coefficients would increase the dimensionality of the feature set and bring both computation burden and the "insufficient training sample" problem. Therefore, it is generally preferable to choose to calculate only three statistical features from the first 64 wavelet coefficients: the mean, the variance, and the energy. The mean of the first 64 wavelet coefficients is plotted in FIG. 10 as an example to show the distinction between control and exposure data of different toxic agent classes.

The use of the wavelet transform in pattern recognition has been a hot research area. Many new algorithms are used to develop robust feature vectors from the wavelet transform. These algorithms normally require more complex computation. Since algorithms according to the invention aims at real-time signal processing, these simplified feature extraction could save computation cost and facilitate real-time response.

Classifier Design

A supervised classifier is preferably used to differentiate among different toxic agents. Among all existing supervised classification algorithms, a linear discriminant method is preferred, such as the support vector machine (SVM) technique (Duda, R. O., Hart, P. E., Stork, D. G. 2001, Pattern classification; John Wiley & Sons, 2nd edition). The SVM classifier relies on transforming the data to represent patterns in a much higher dimension than the original feature space. With an appropriate nonlinear mapping (which is application specific) to a sufficiently high dimension, data from different categories can be separated by hyperplanes. The optimal hyperplane between each pair of classes is decided by the support vectors that are the most informative training samples for the classification task. Compared to other classification methods, SVM solves the problem of overfitting since the complexity of the classifier is characterized by the number of support vectors instead of the dimensionality of the transformed space. Before applying the classifier, a normalization phase is preferably conducted based on the features extracted from the raw data using algorithms described above.

Figure 11:
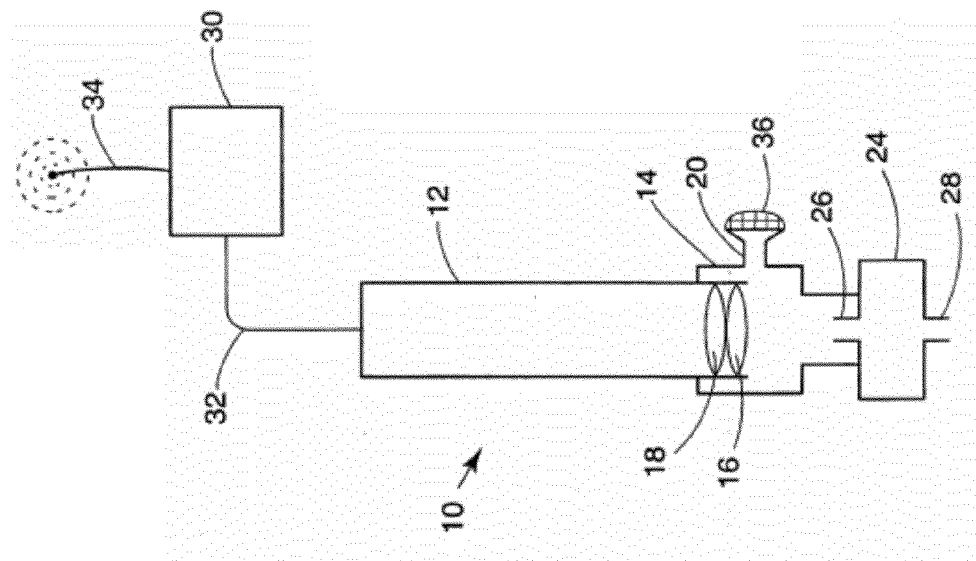
FIG. 11 is a schematic of an exemplary biosensor system for carrying out the method of present invention.
Figure 12:
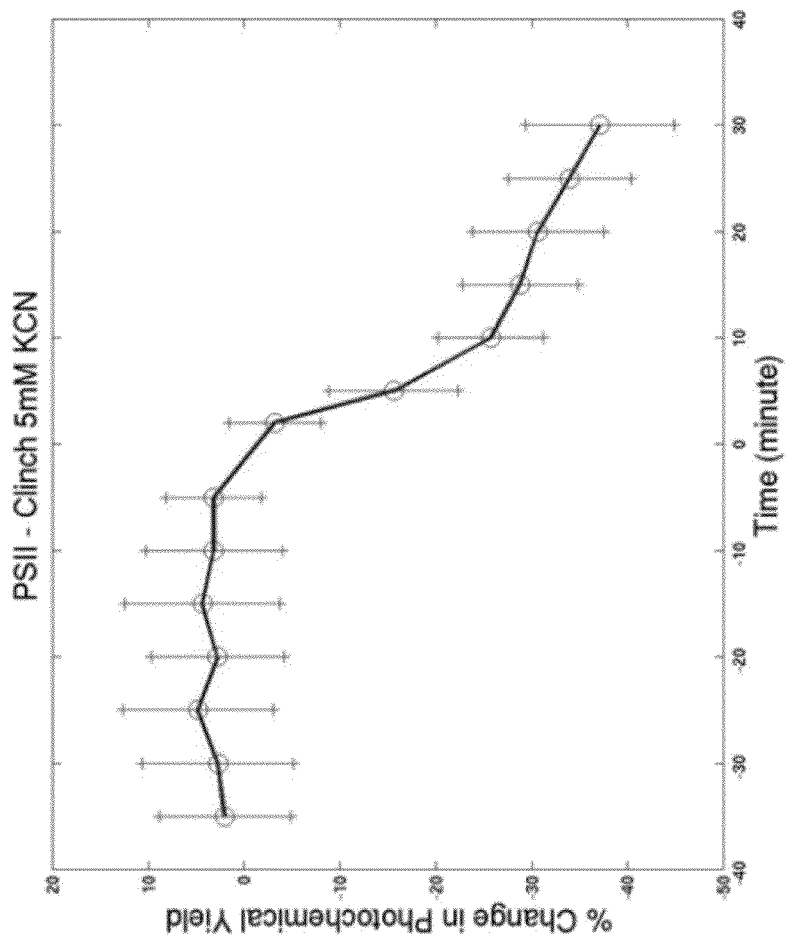
FIG. 12(a)-(h) shows the extracted features of 5 mM potassium cyanide (KCN) in the Clinch River samples as functions of time. The toxic agent is added into the sample at time 0.
Figure 12:
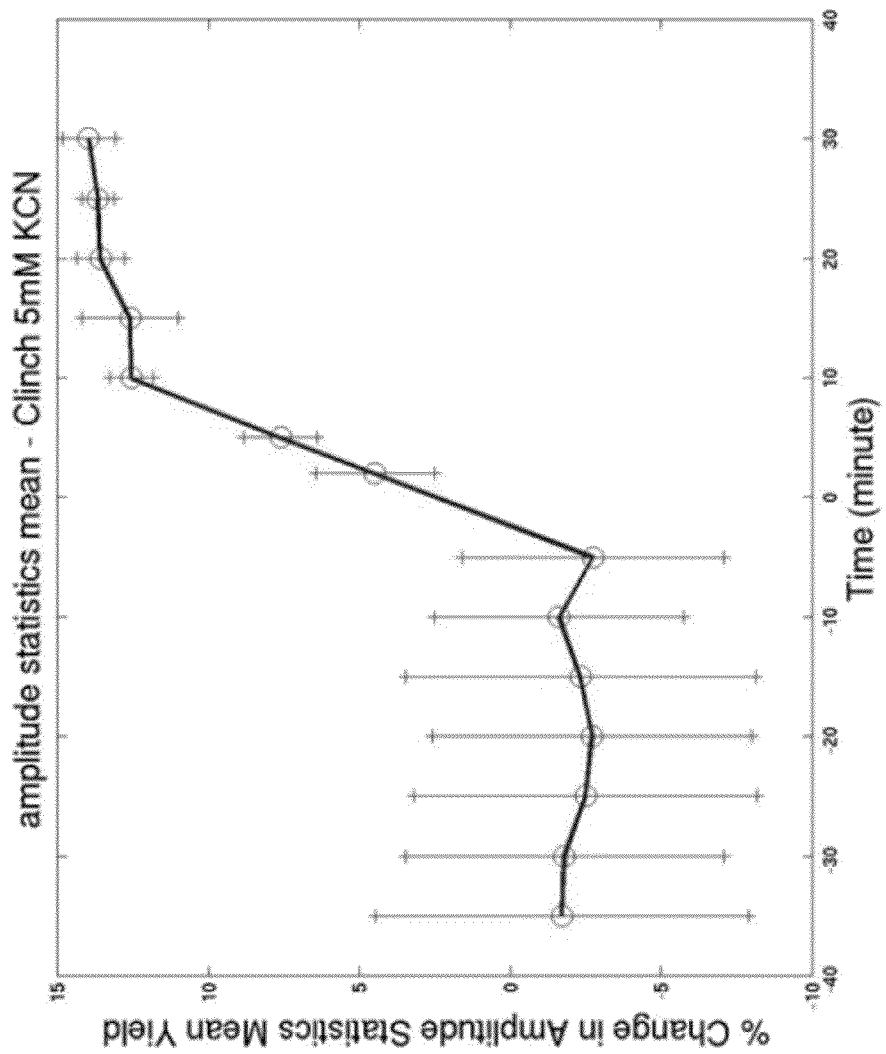
Figure 12:
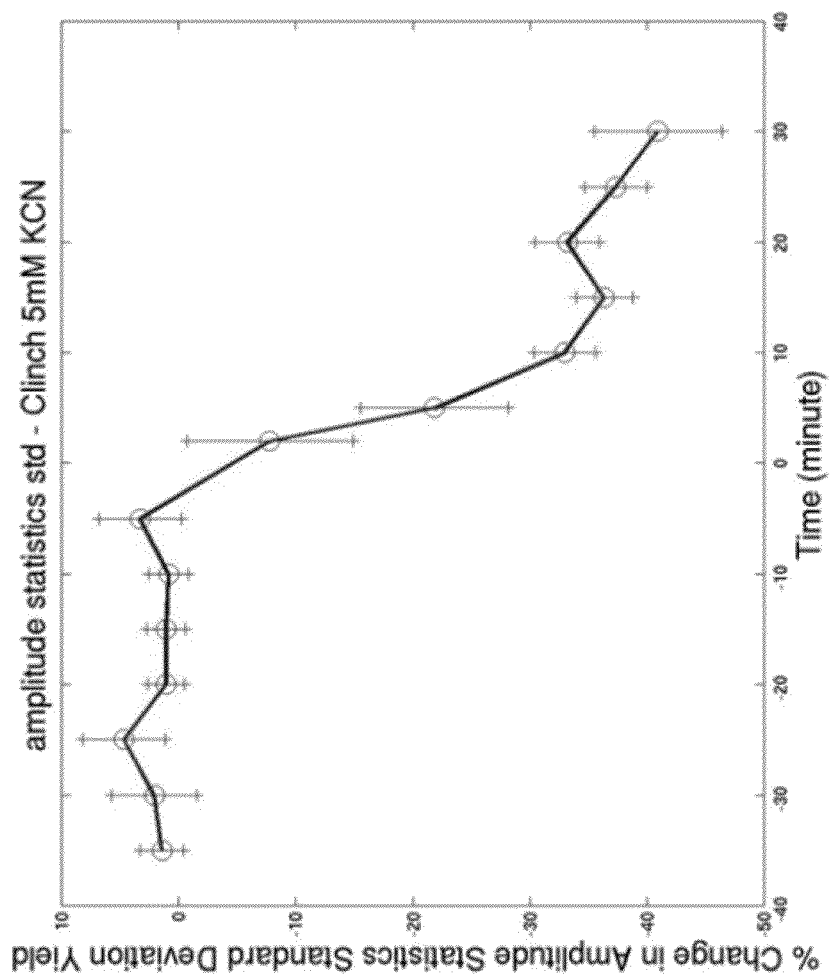
Figure 12:
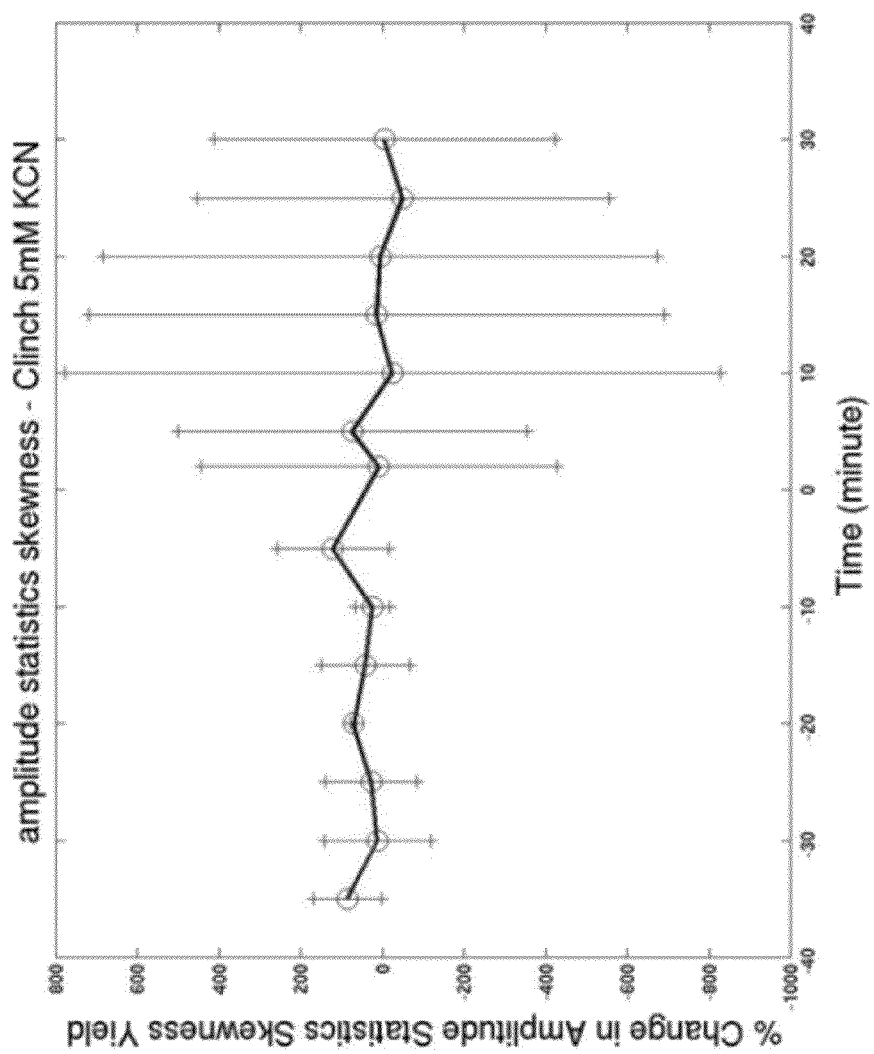
Figure 12:
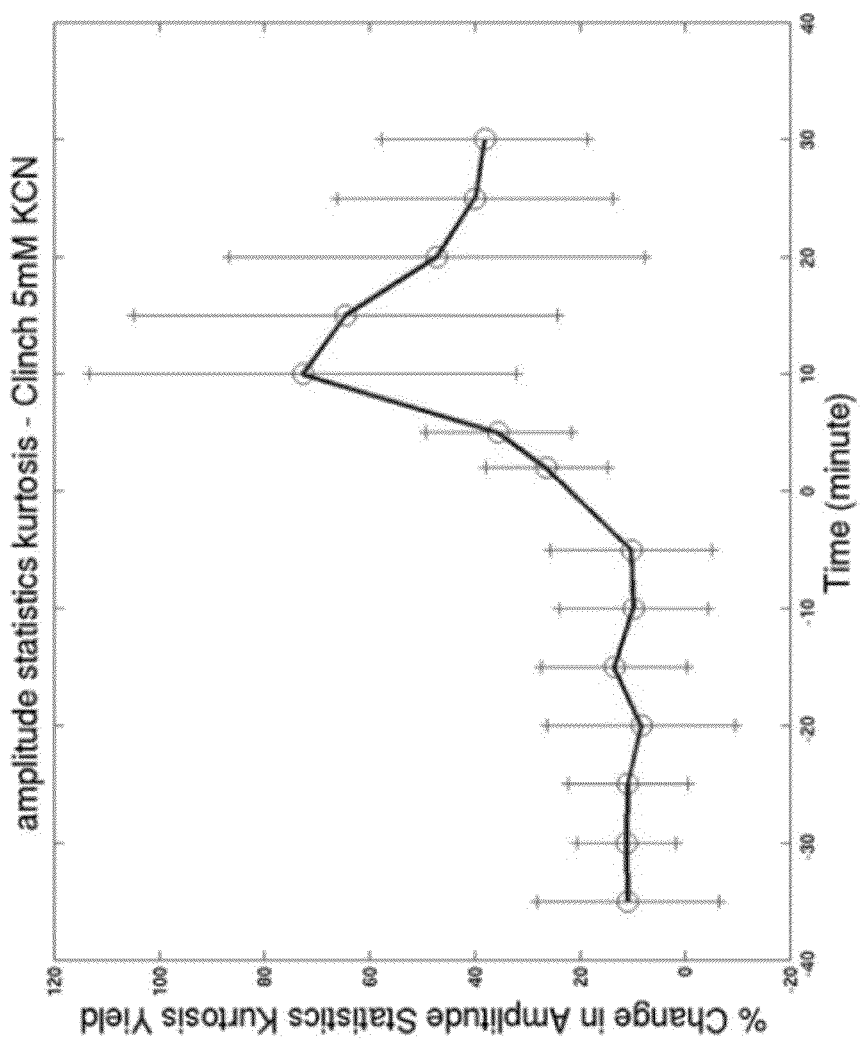
Figure 12:
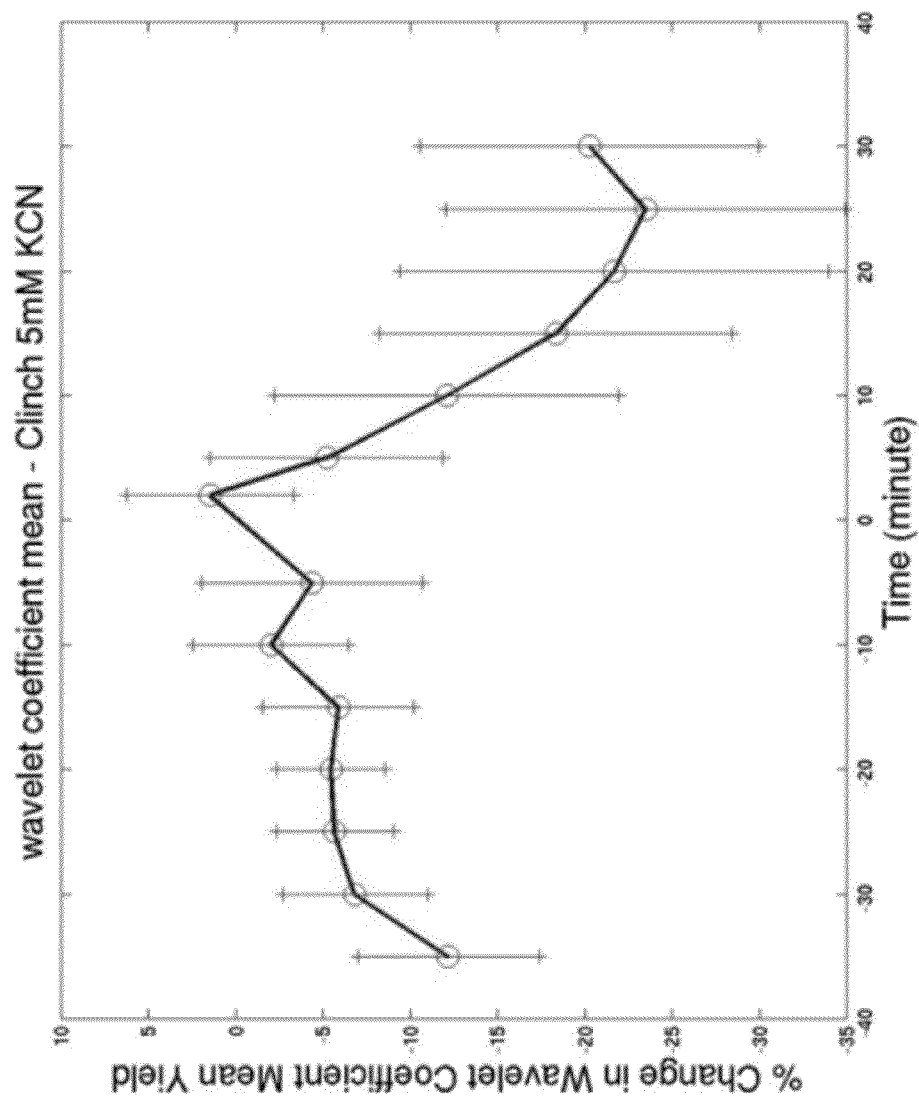
Figure 12:
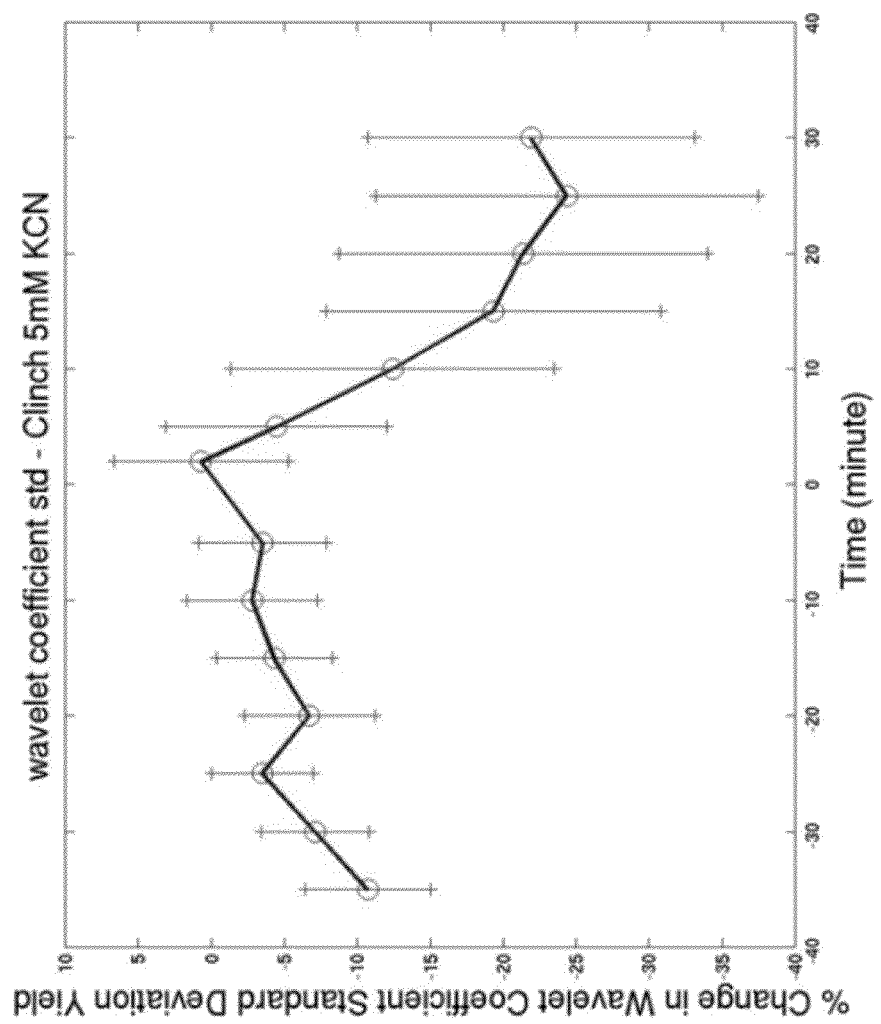
Figure 12:
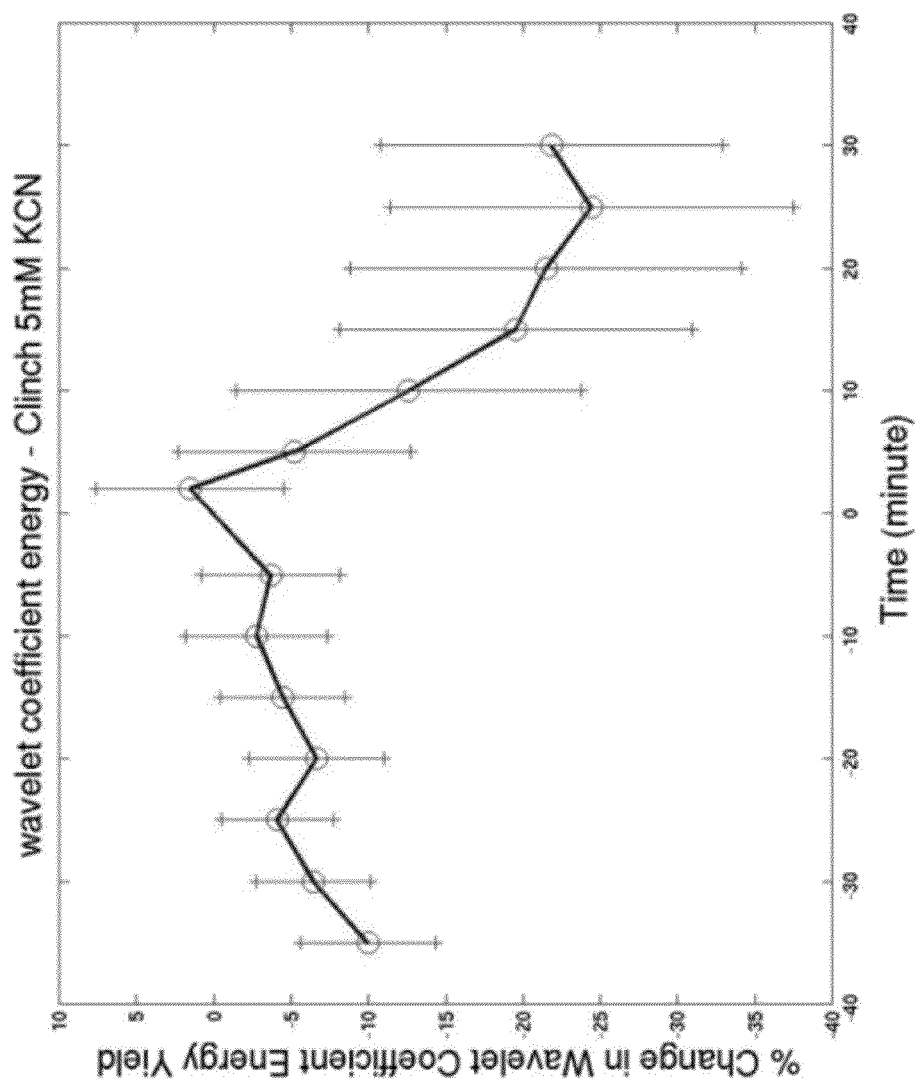
Figure 13:
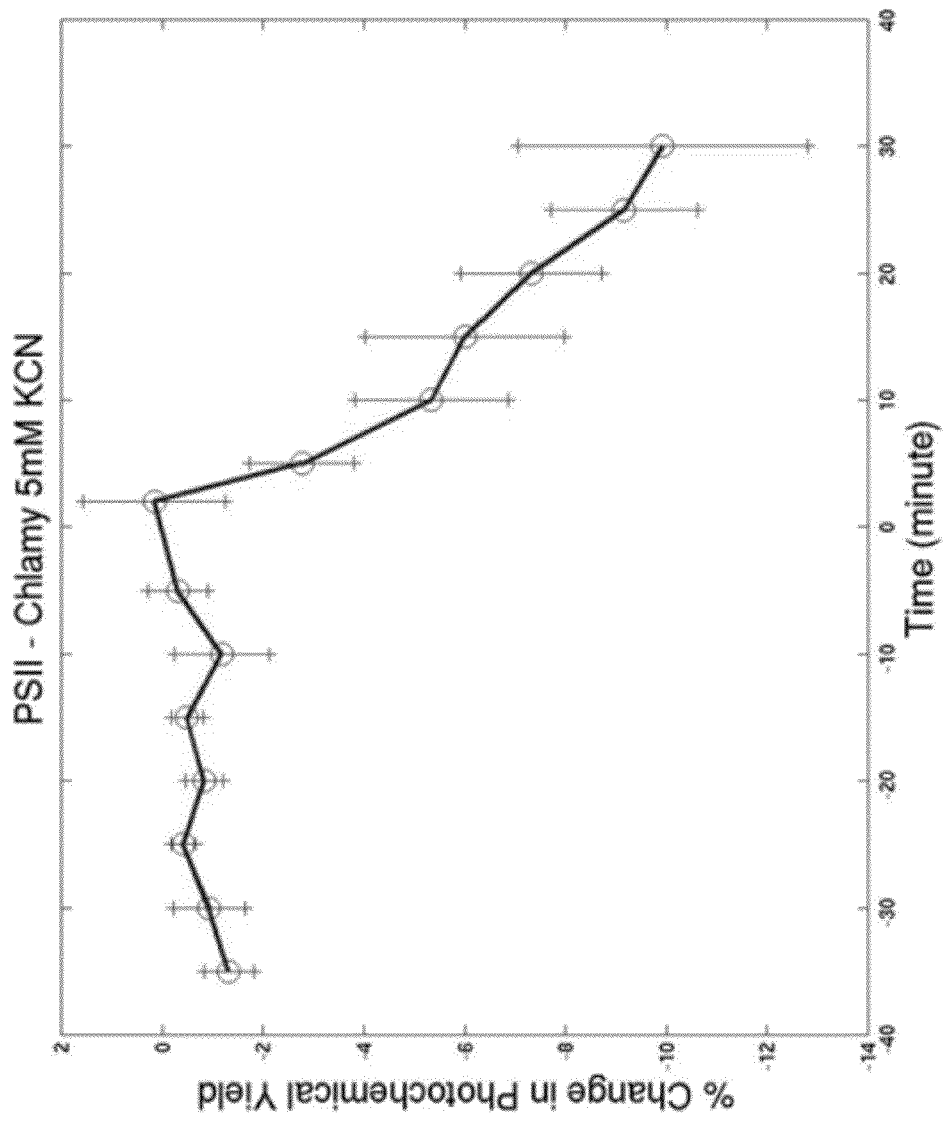
FIG. 13(a)-(h) shows the extracted features of 5 mM KCN in the *Chlamydomonas* samples as function of time. The toxic agent is added into the samples at time 0.
Figure 13:
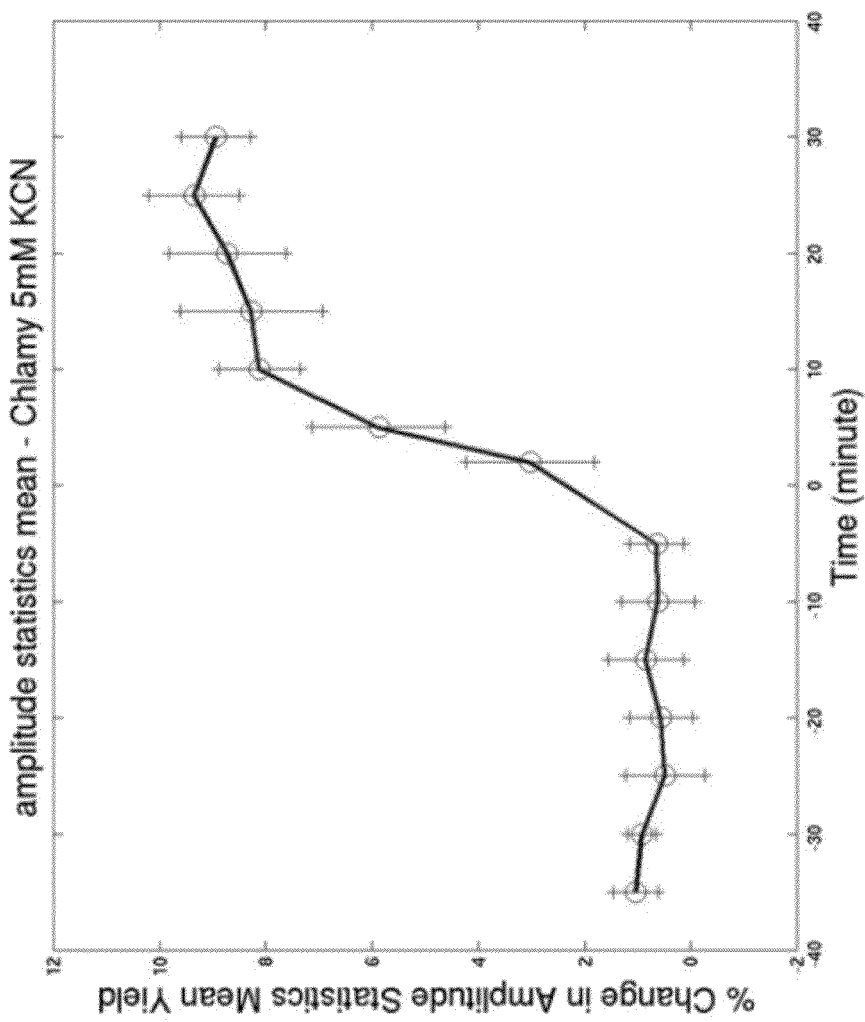
Figure 13:
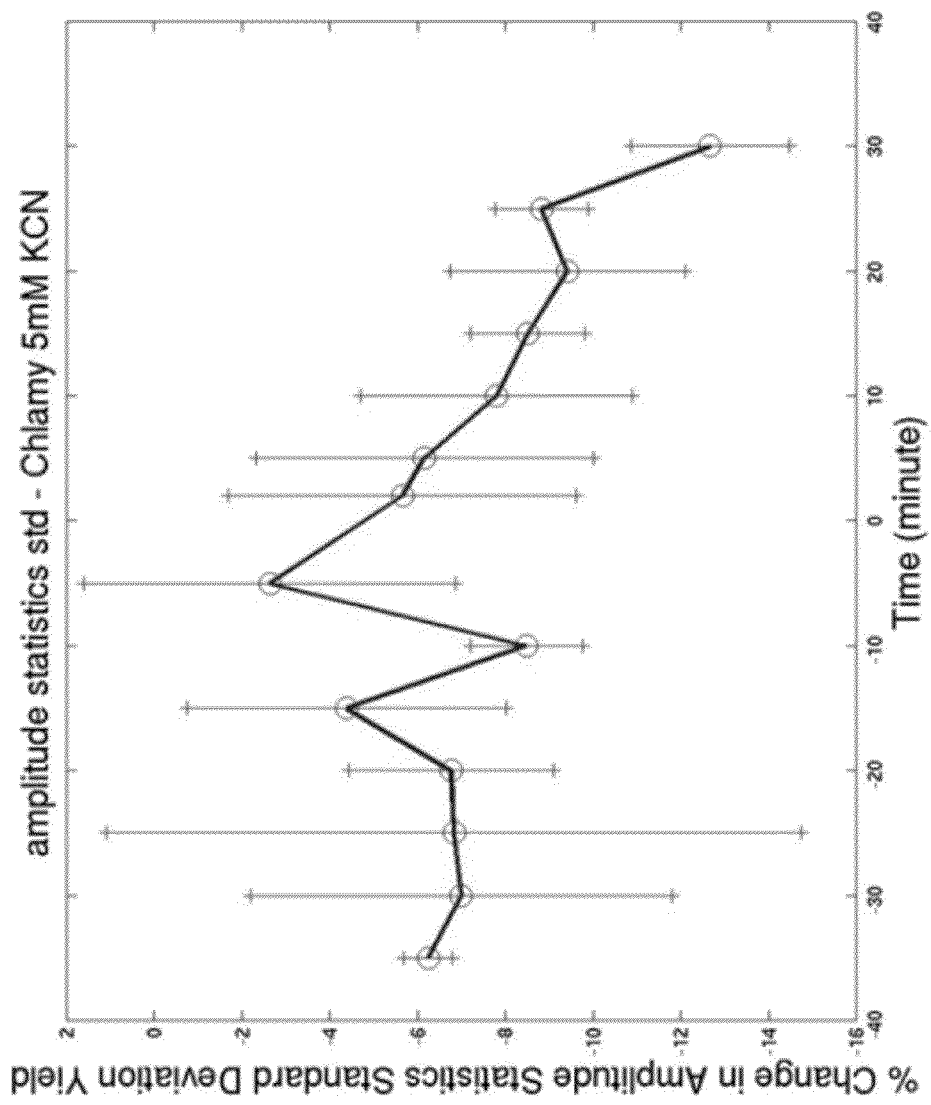
Figure 13:
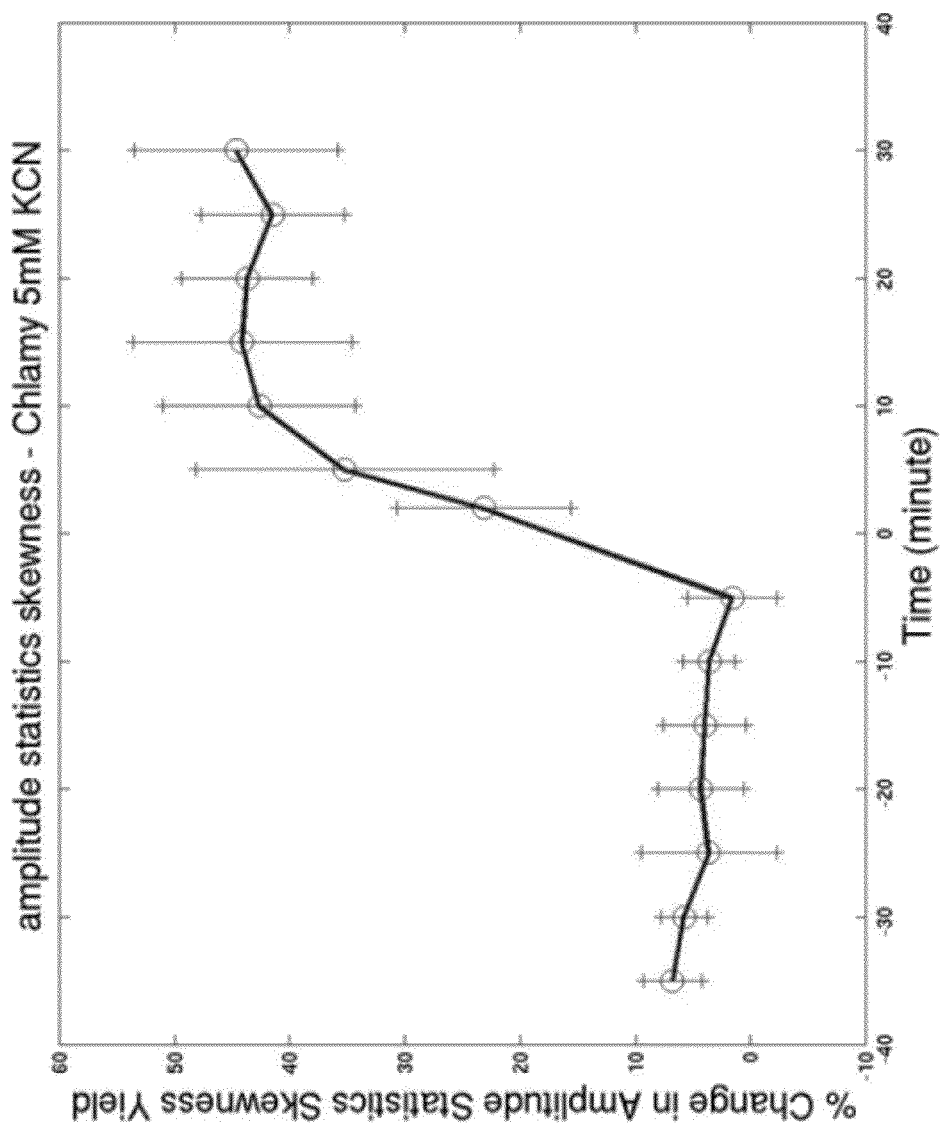
Figure 13:
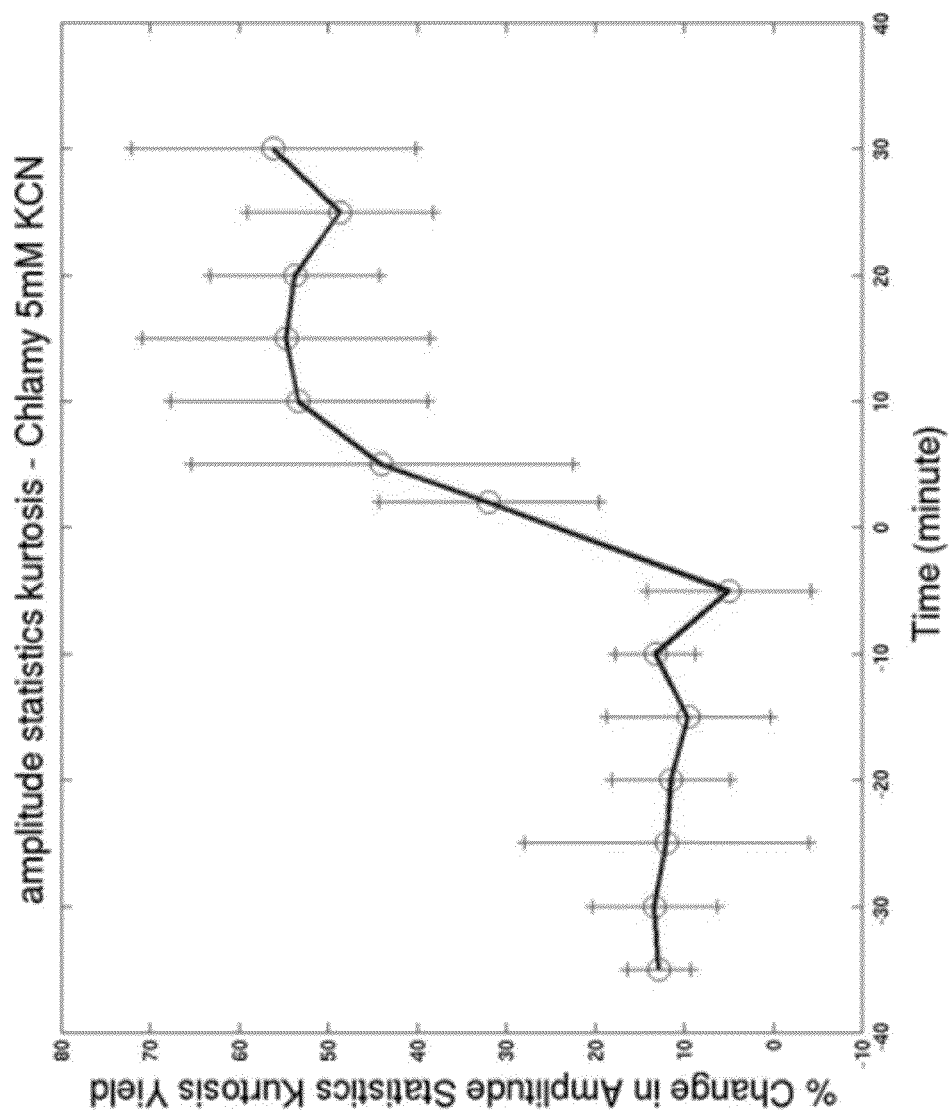
Figure 13:
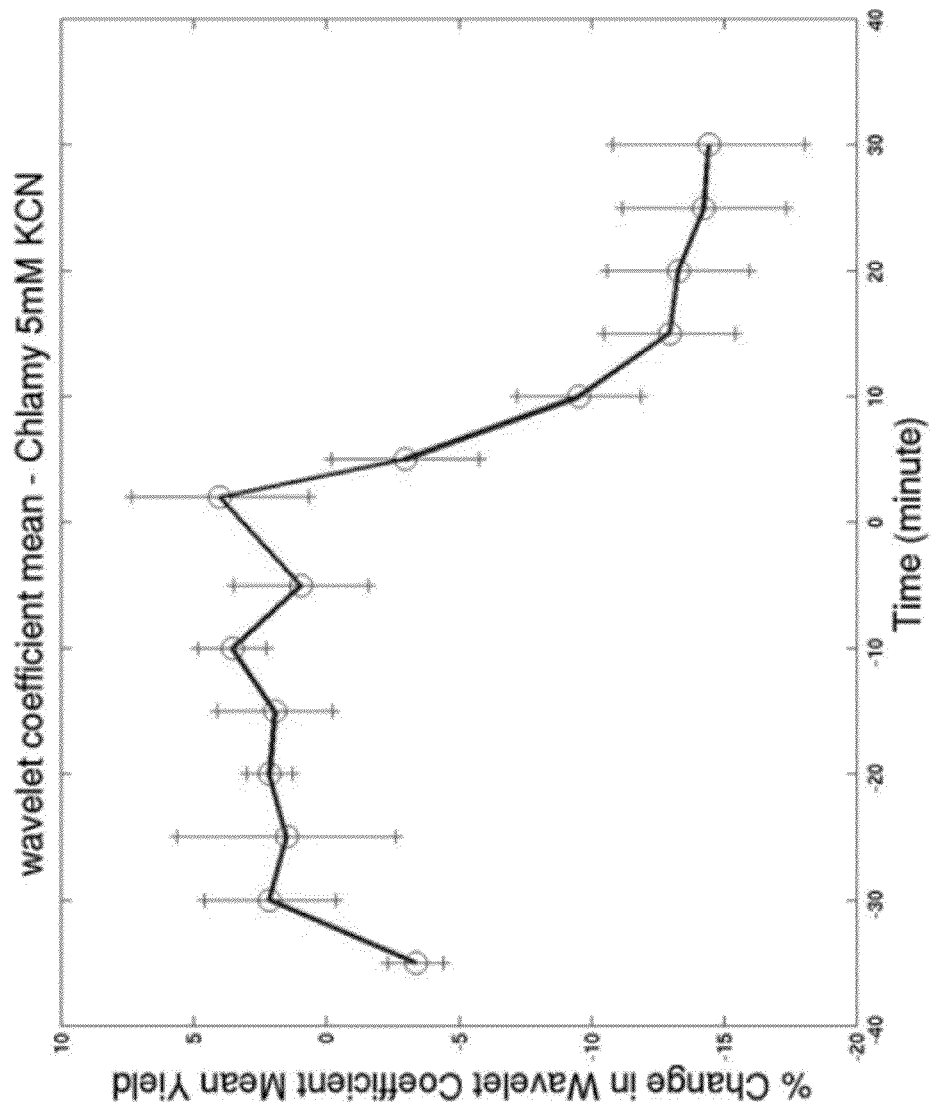
Figure 13:
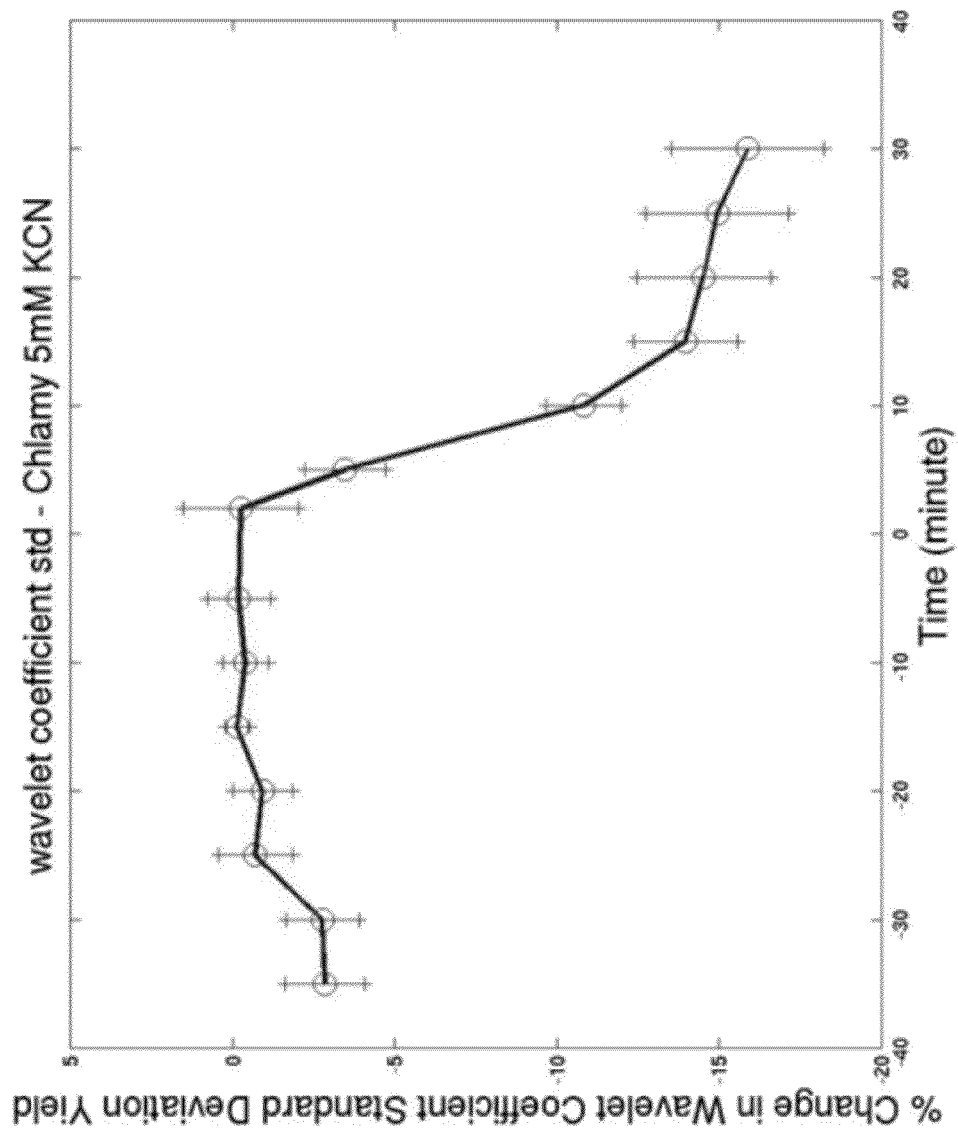
Figure 13:
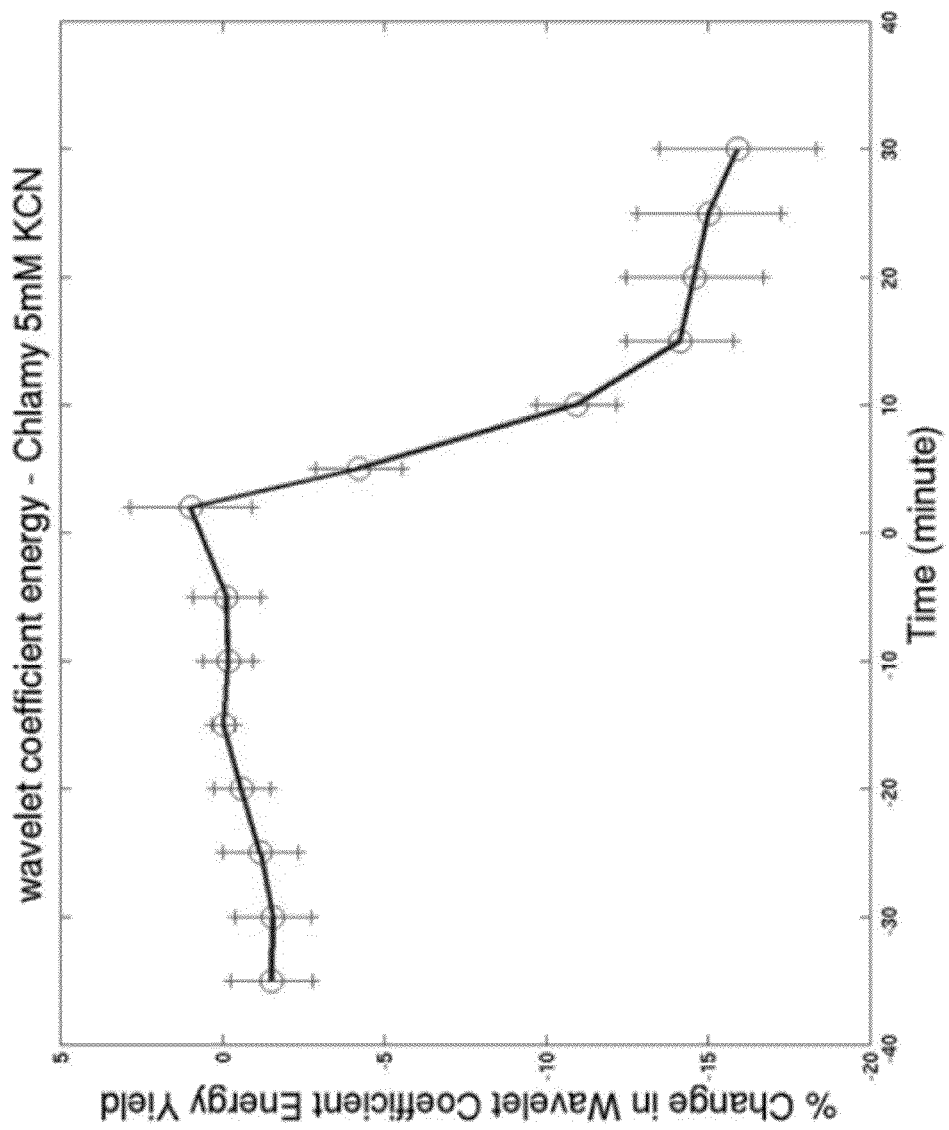
Figure 14:
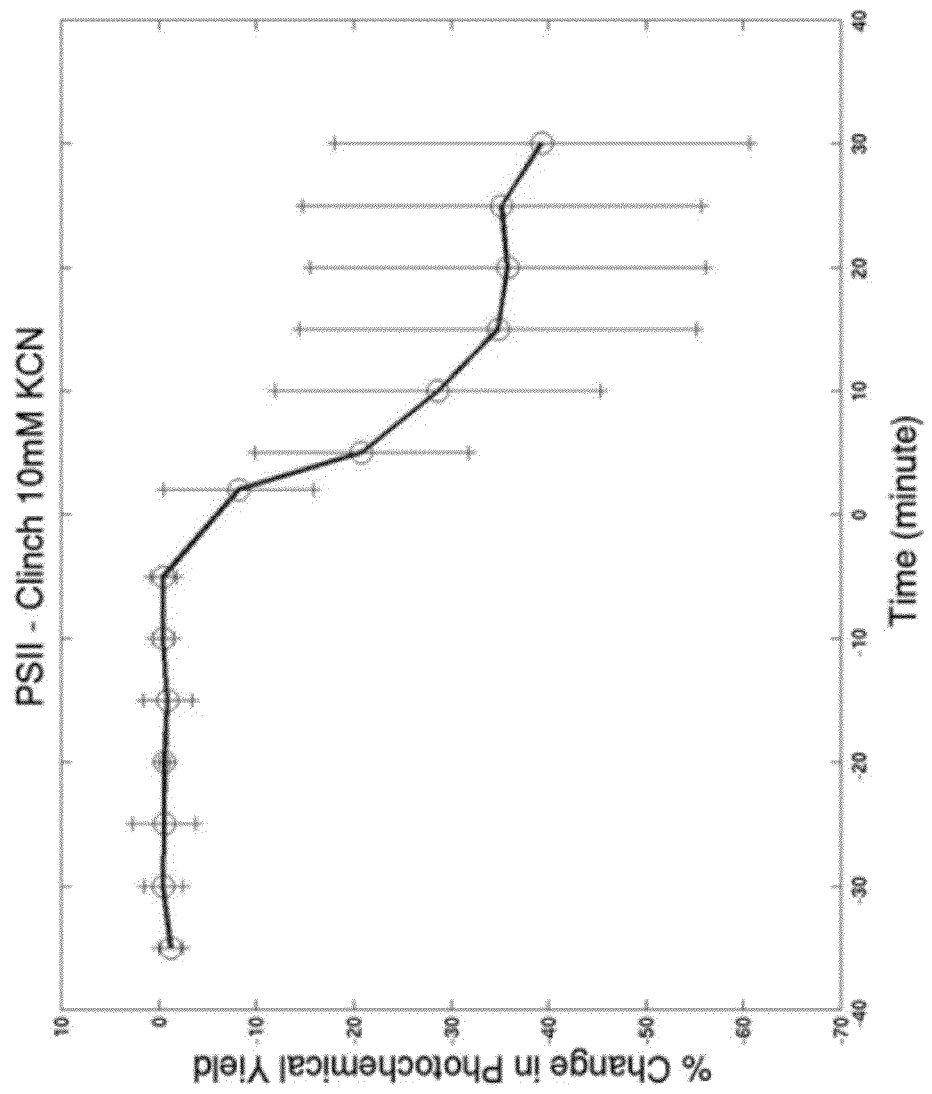
FIG. 14(a)-(h) shows the extracted features of 10 mM KCN in the Clinch River samples as functions of time. The toxic agent is added into the samples at time 0.
Figure 14:
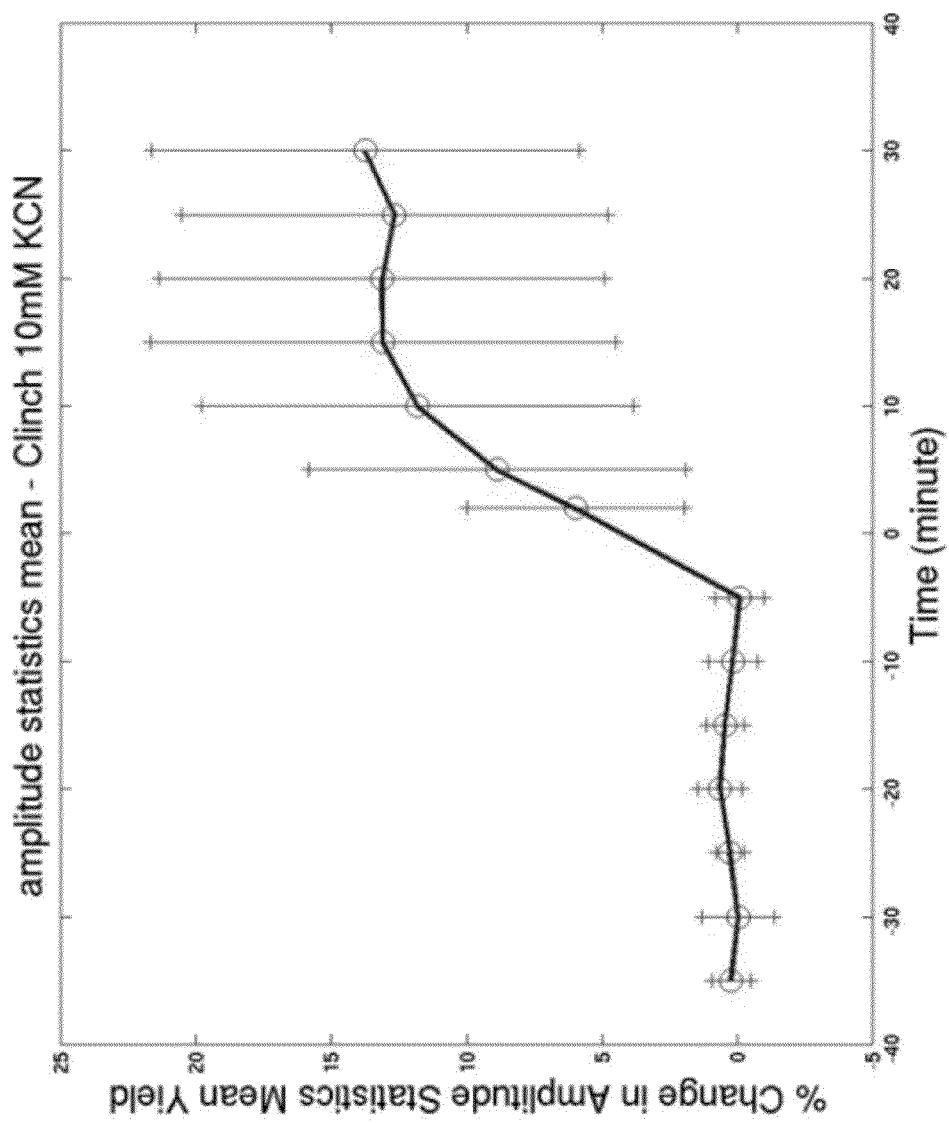
Figure 14:
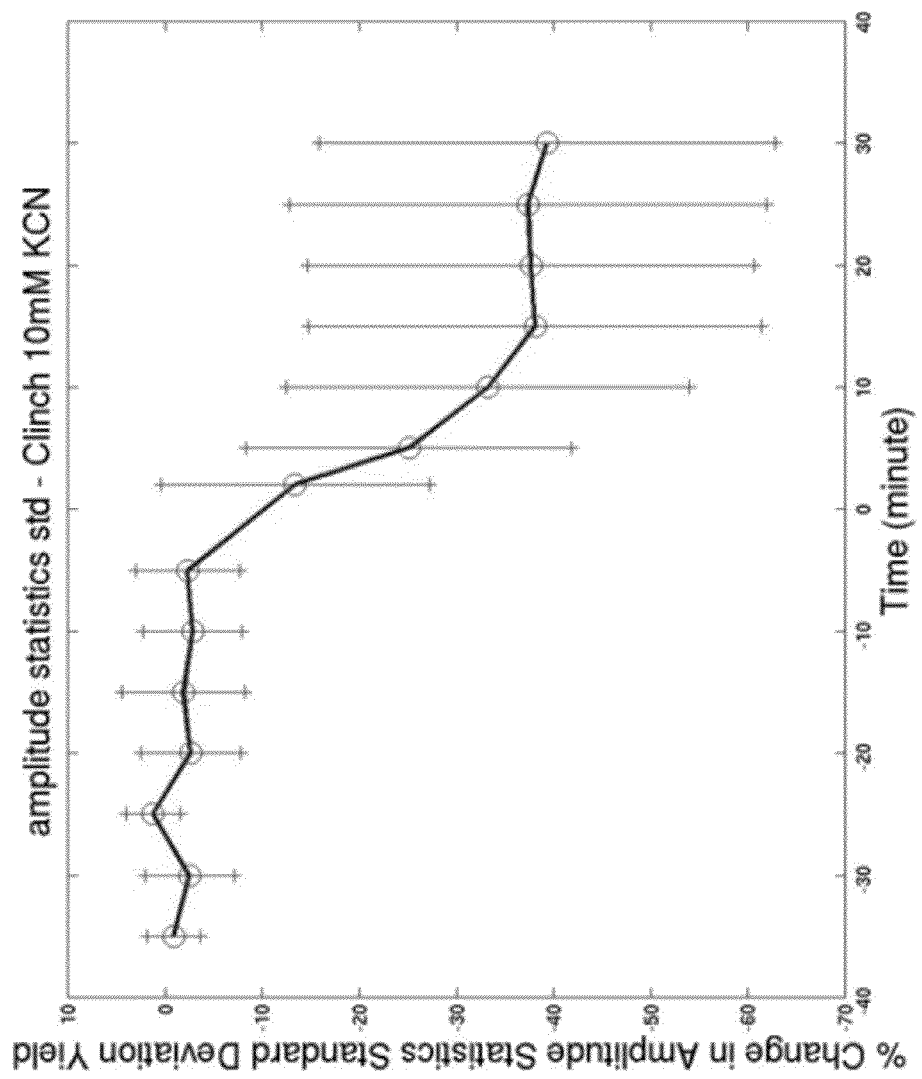
Figure 14:
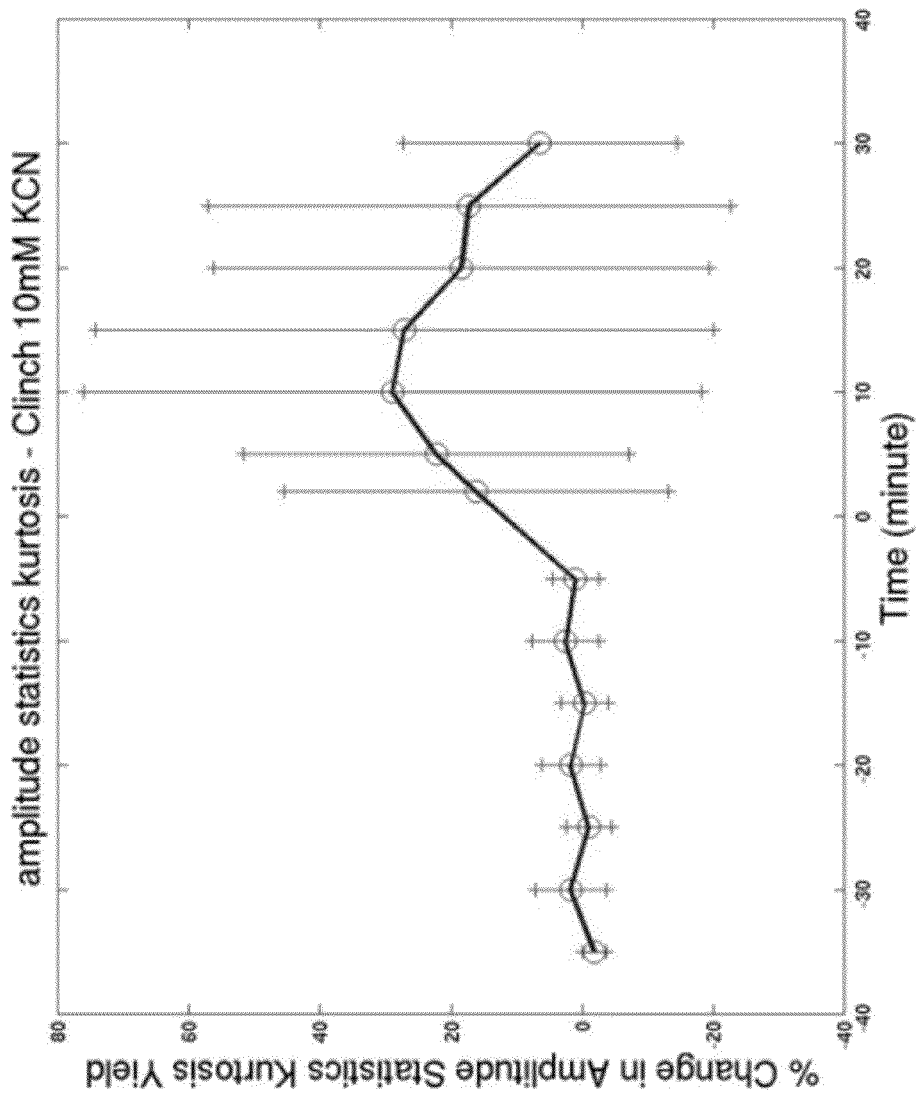
Figure 14:
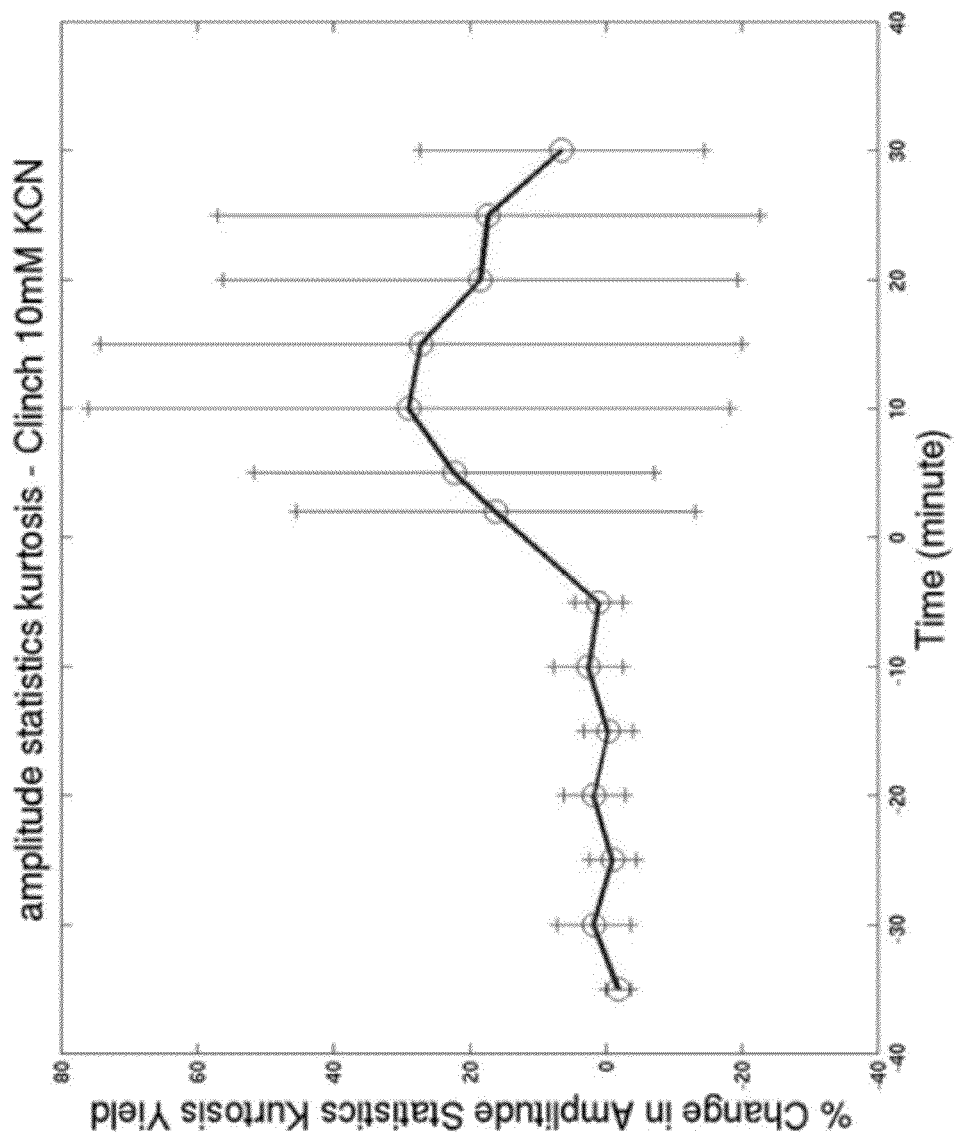
Figure 14:
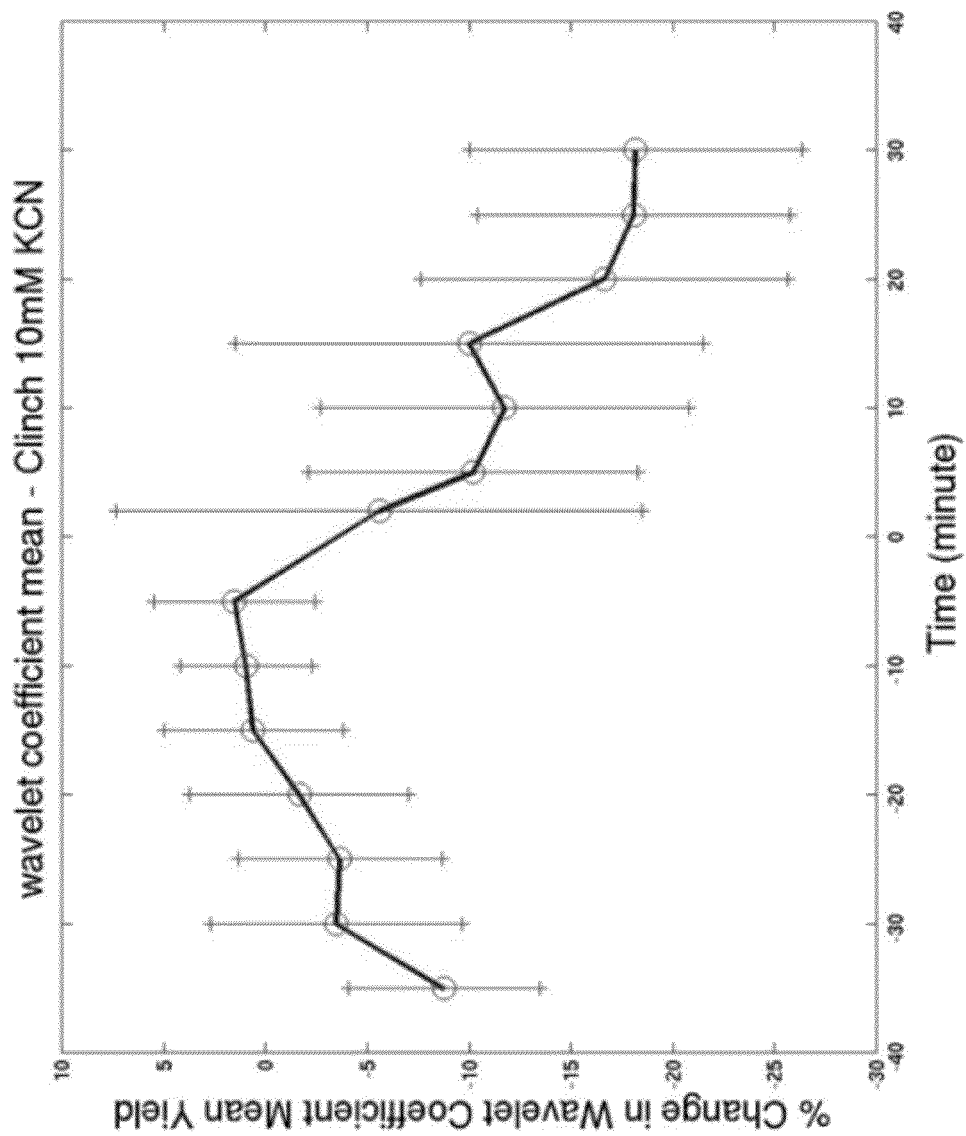
Figure 14:
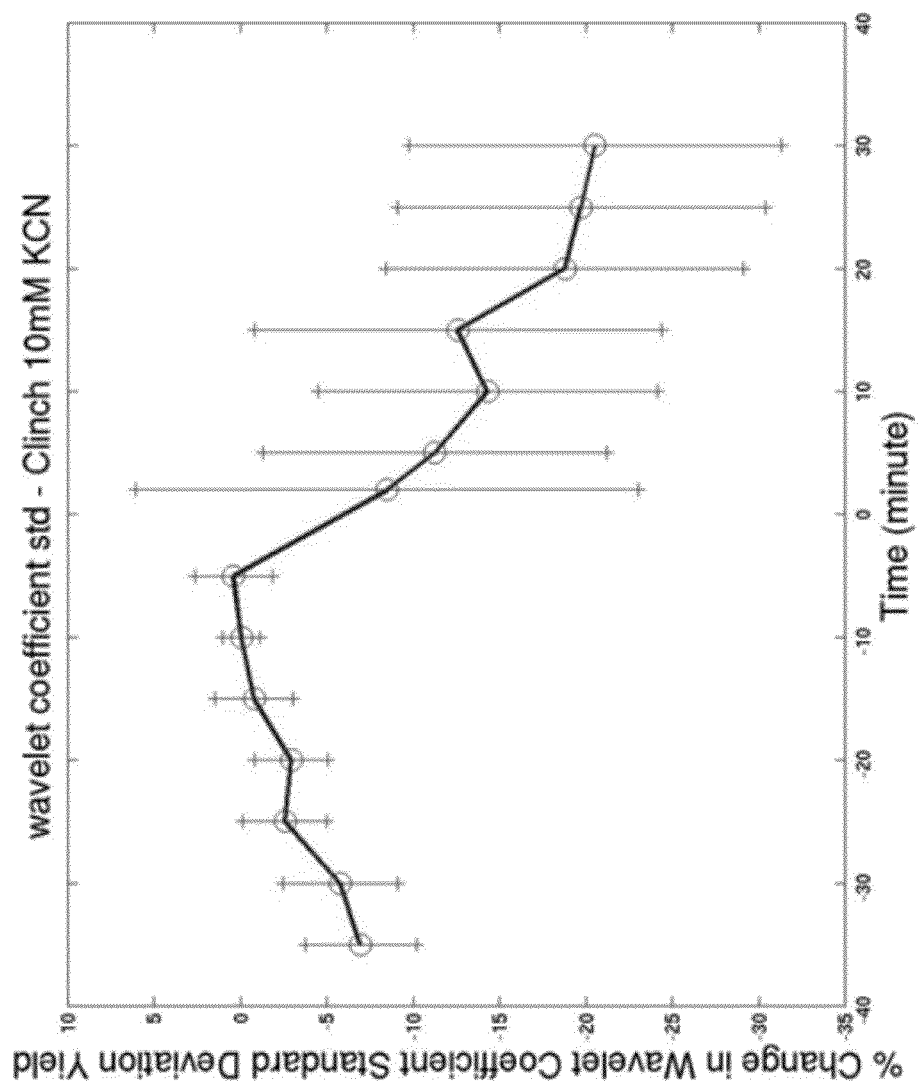
Figure 14:
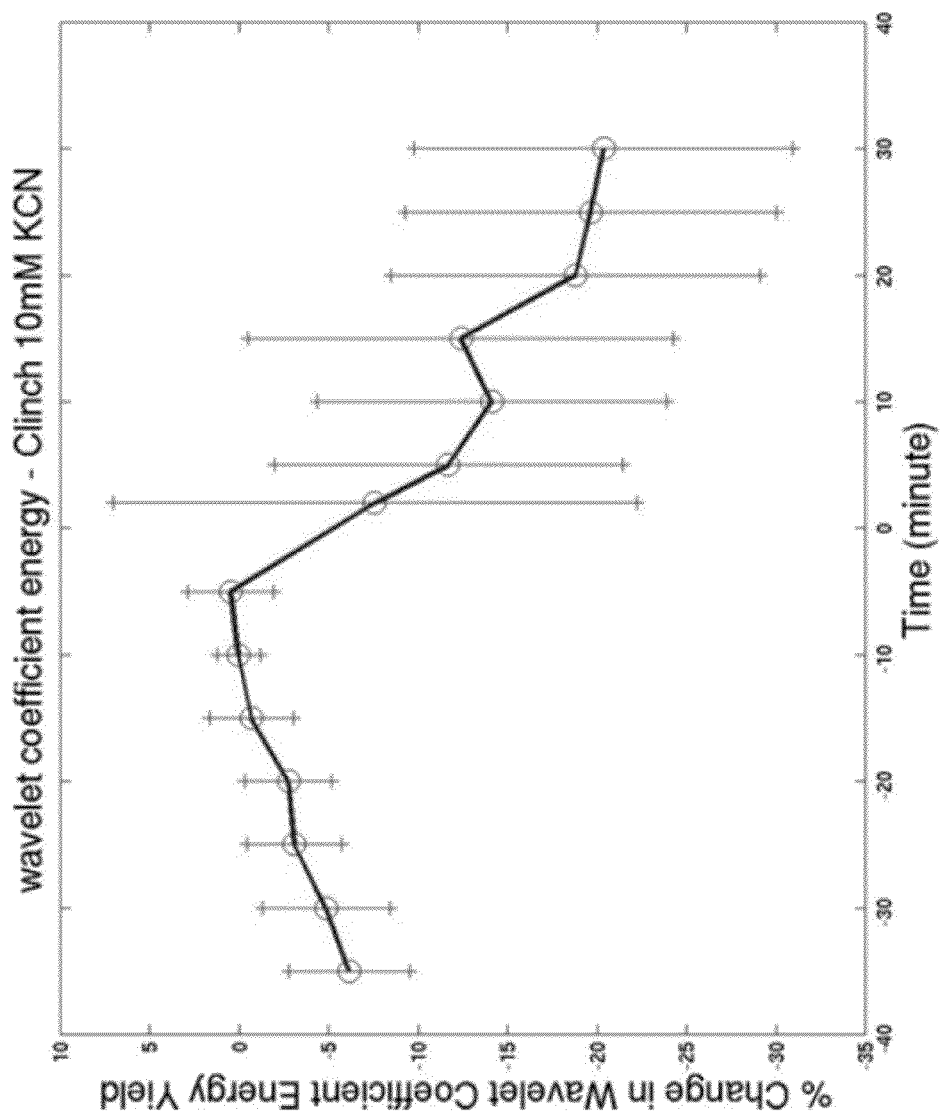
Figure 15:
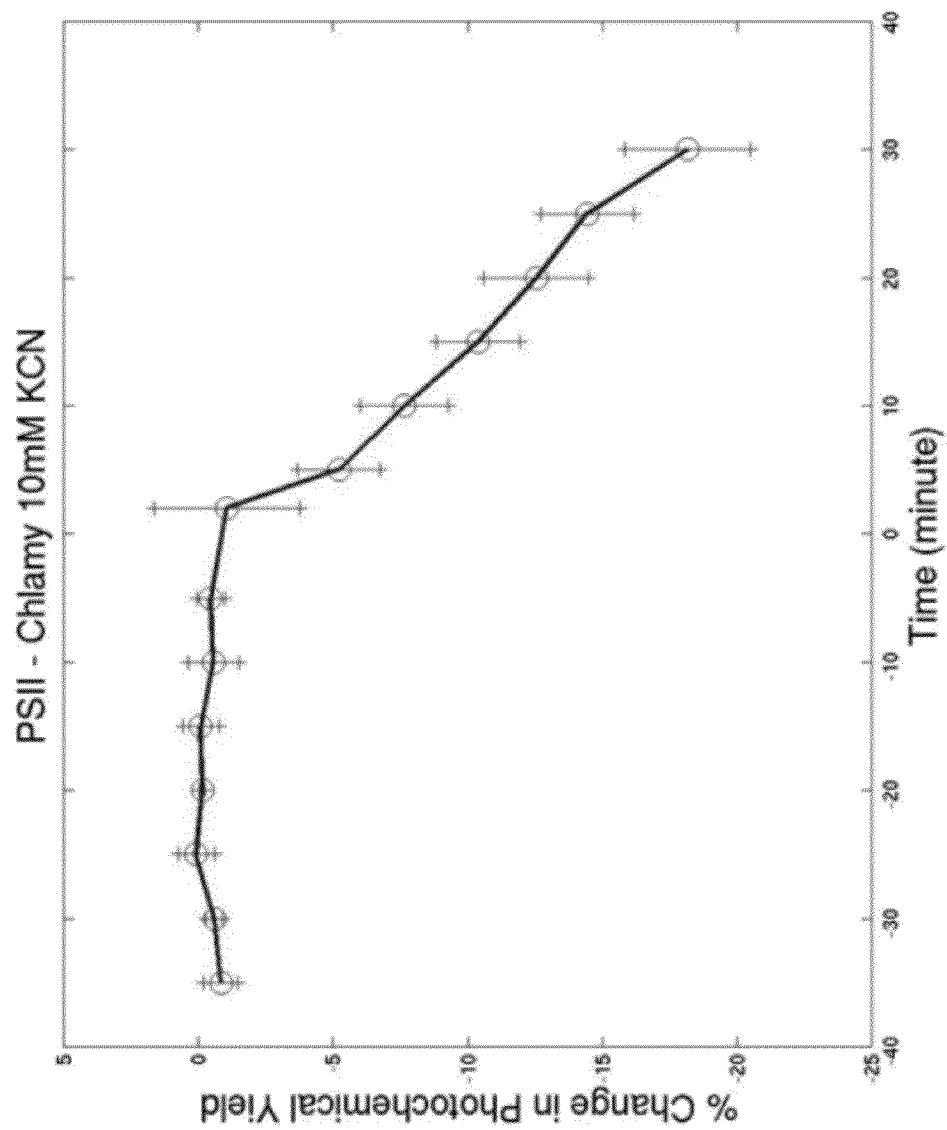
FIG. 15(a)-(h) shows the extracted features of 10 mM KCN in the *Chlamydomonas* samples as functions of time. The toxic agent is added into the samples at time 0.
Figure 15:
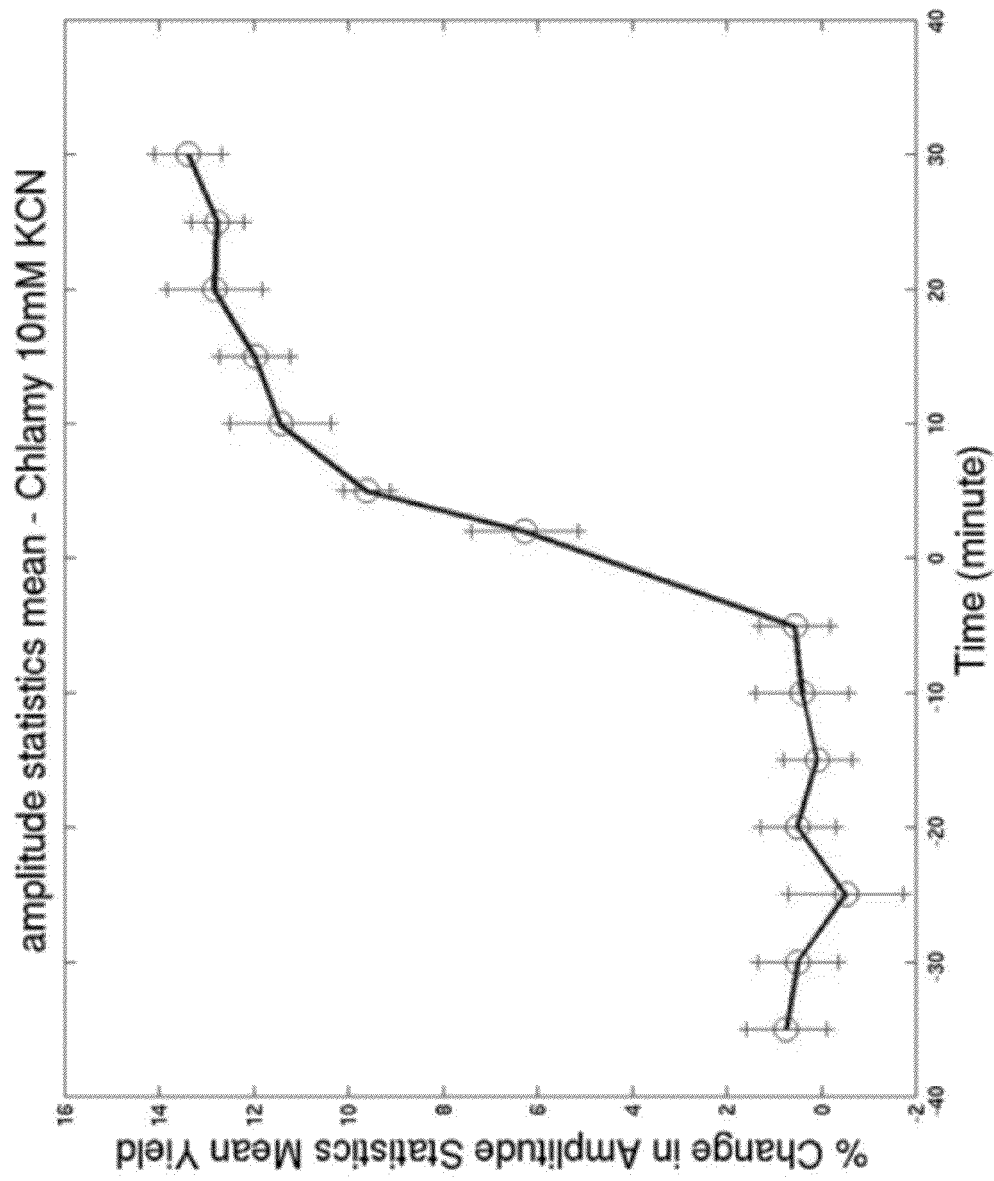
Figure 15:
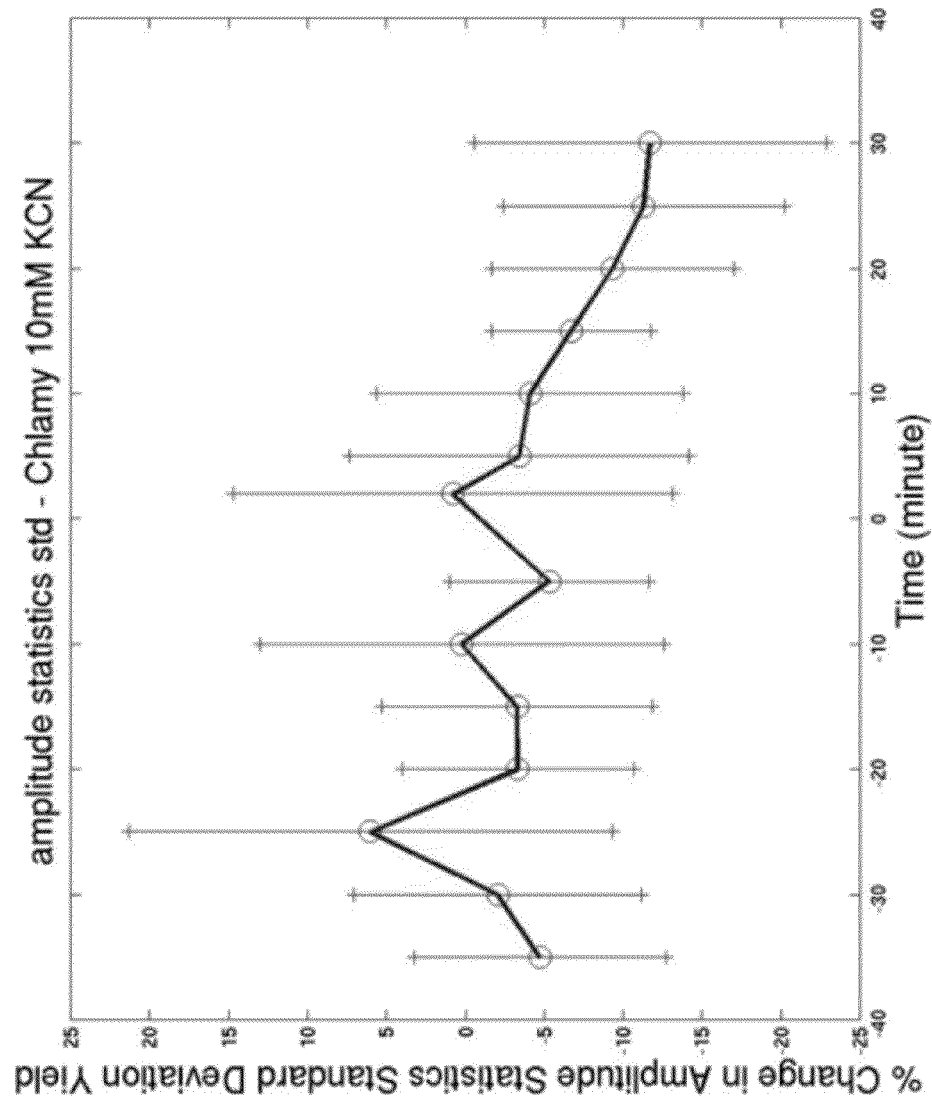
Figure 15:
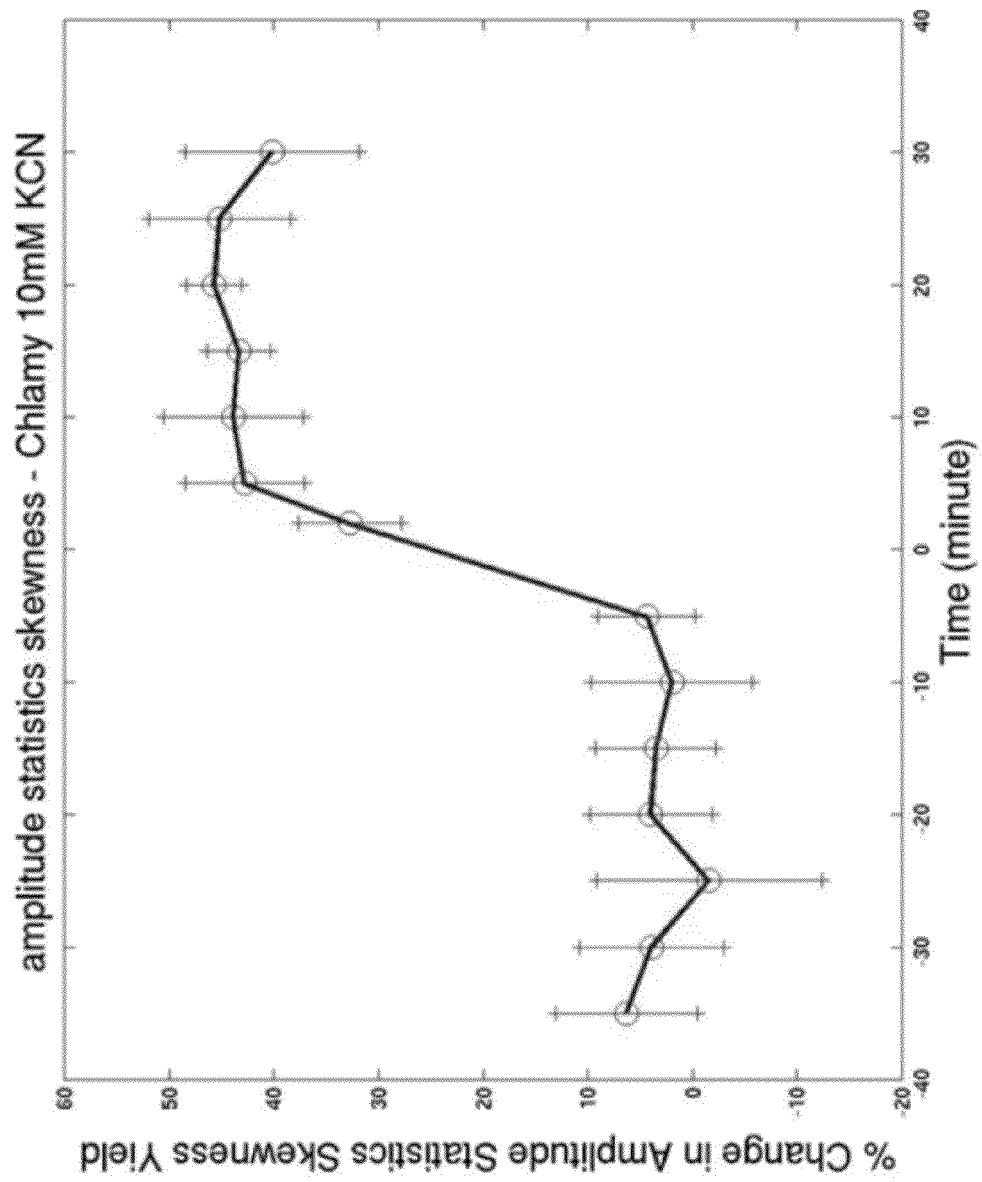
Figure 15:
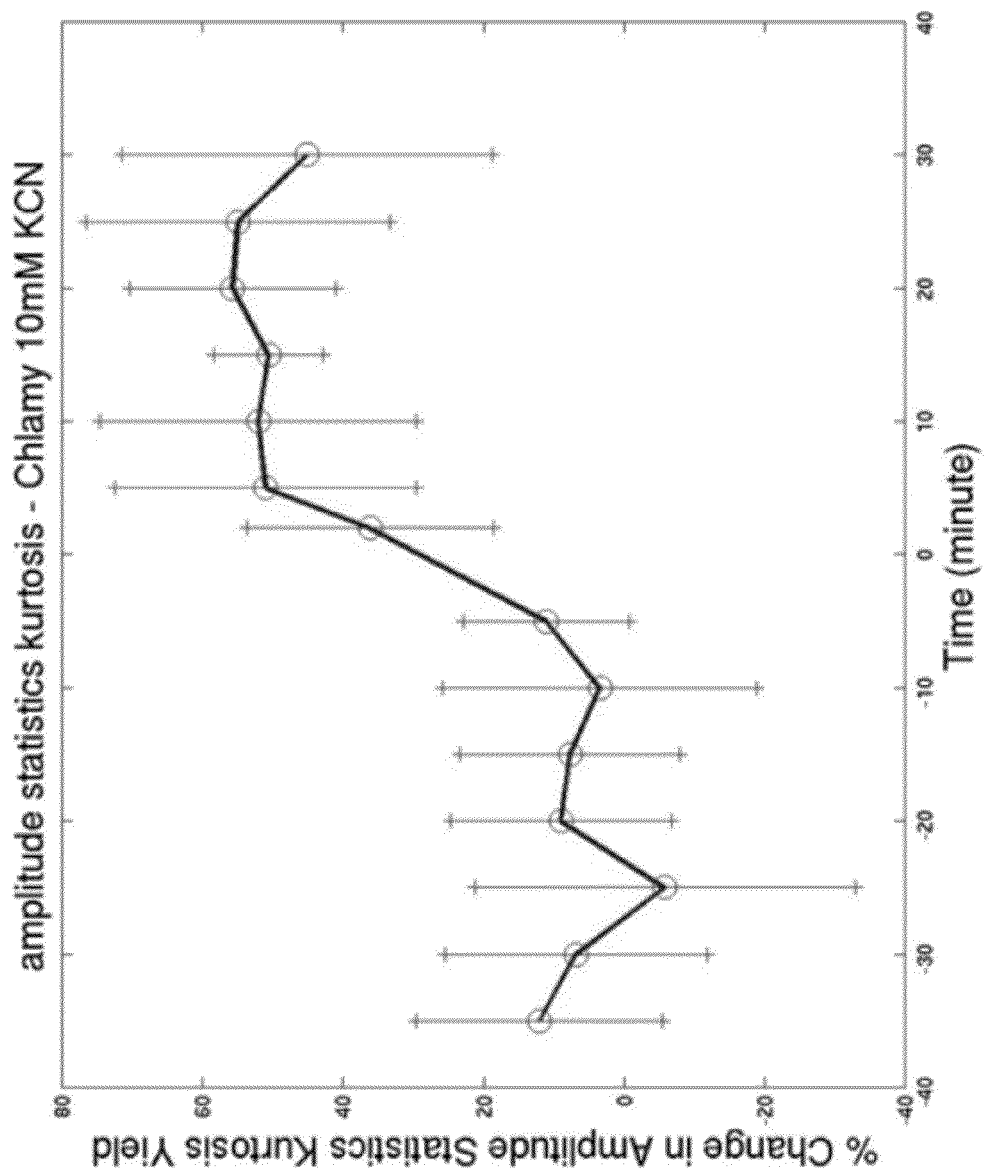
Figure 15:
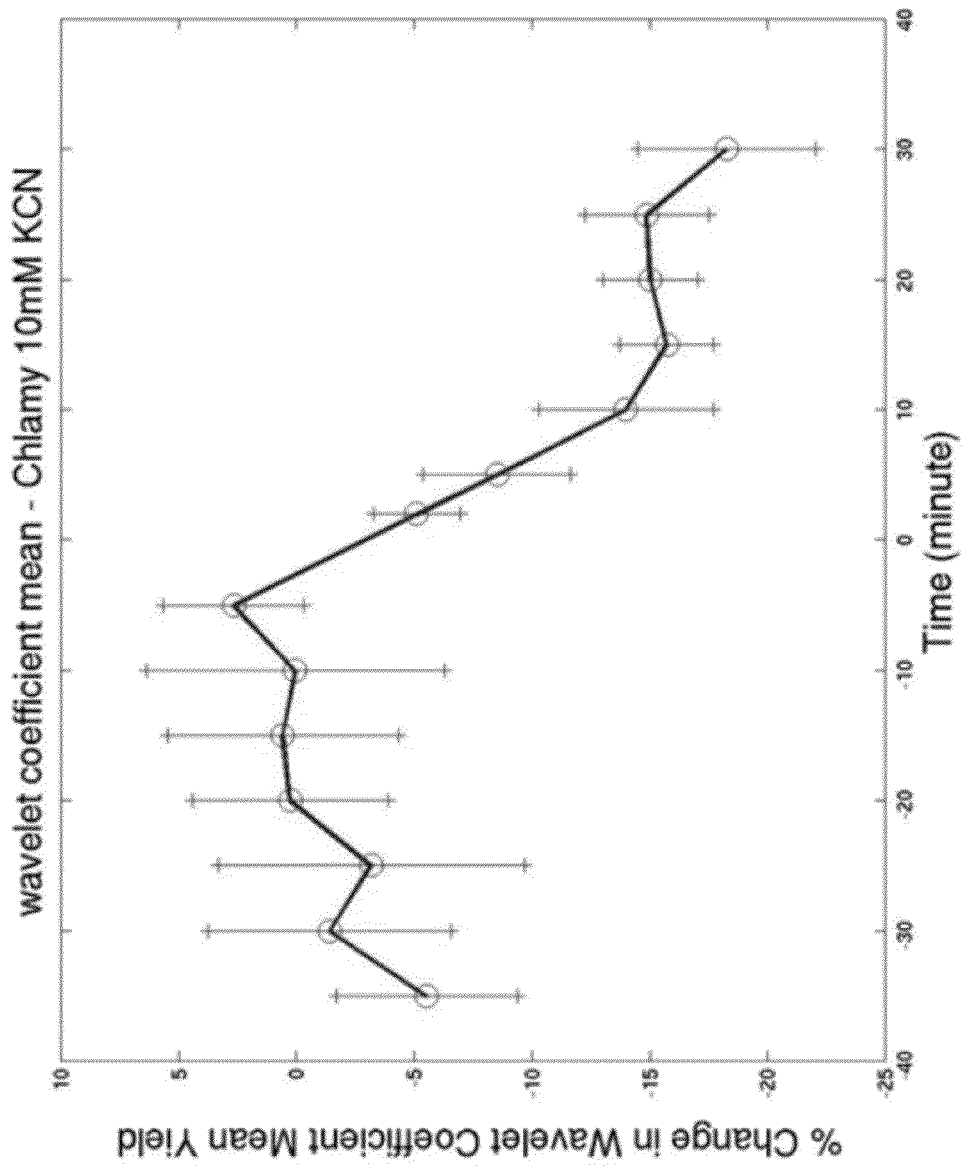
Figure 15:
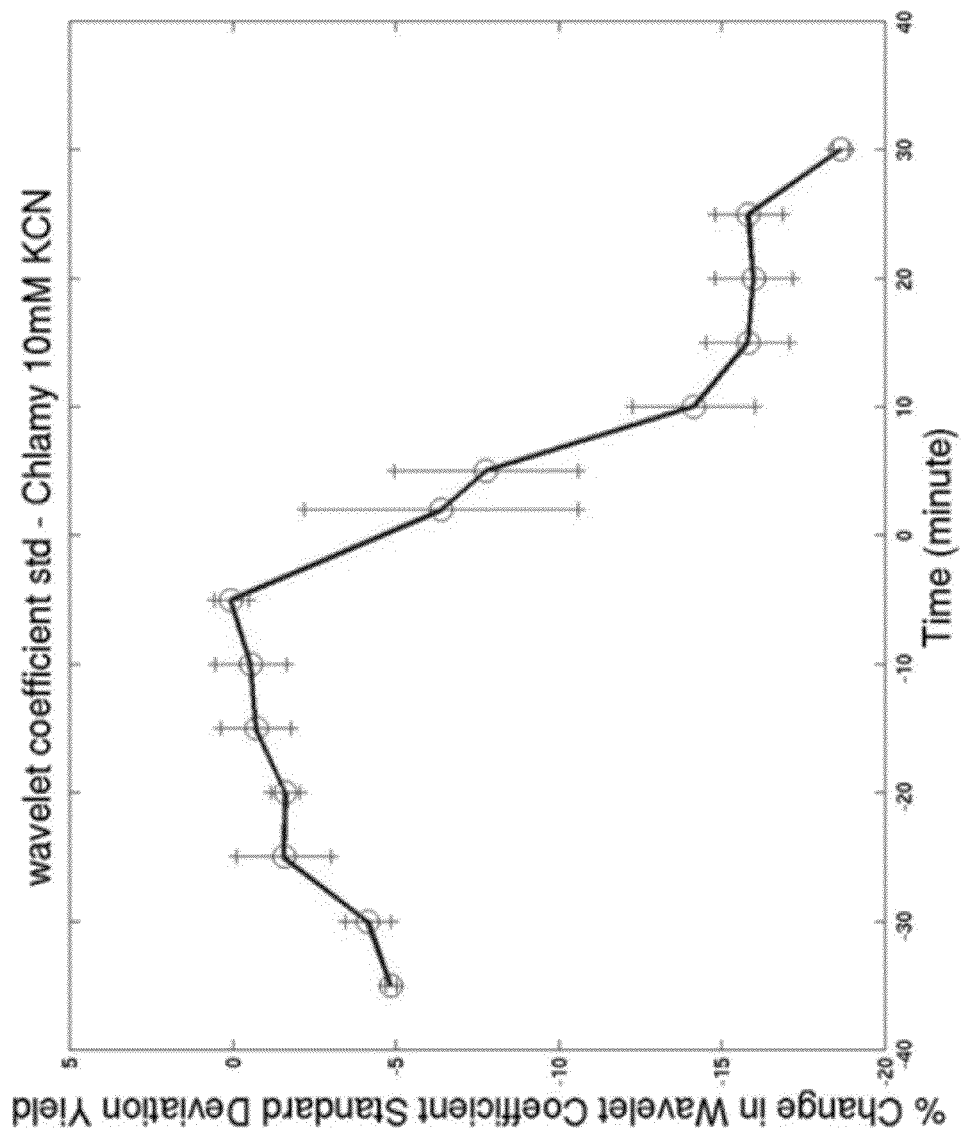
Figure 15:
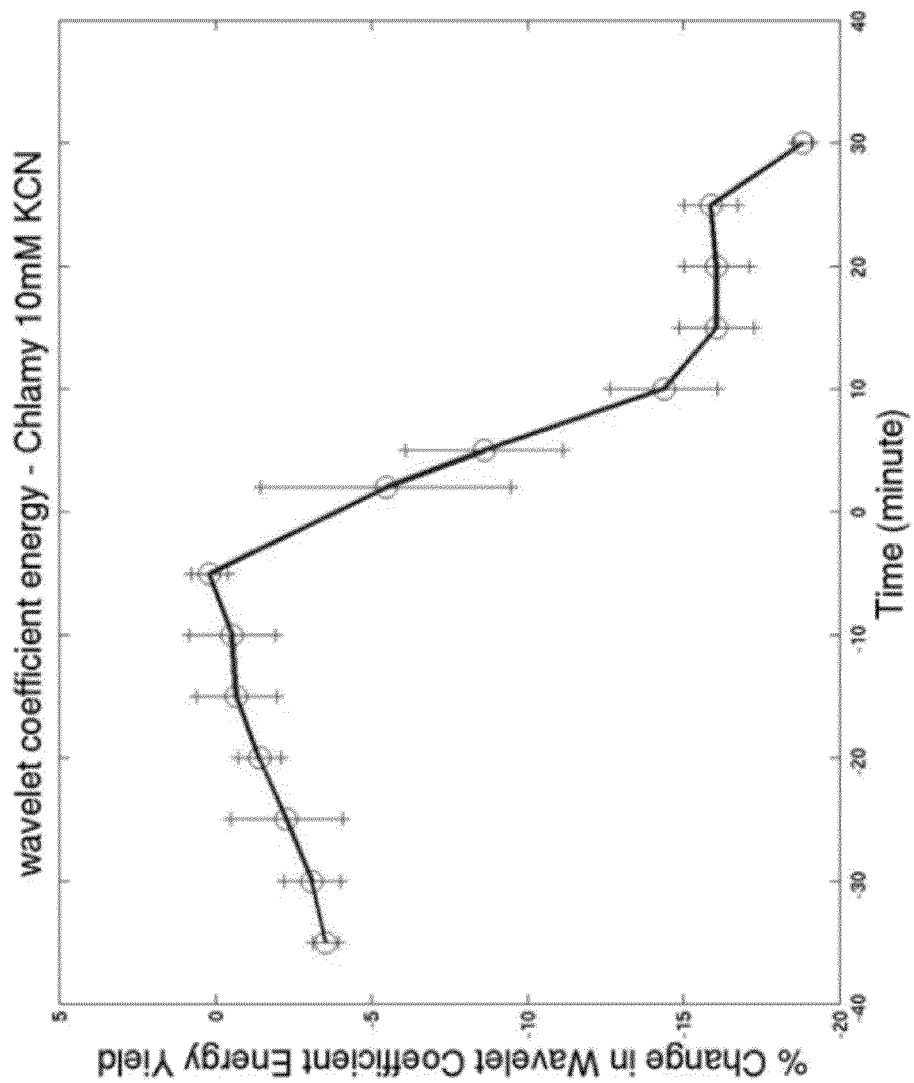
Figure 16:
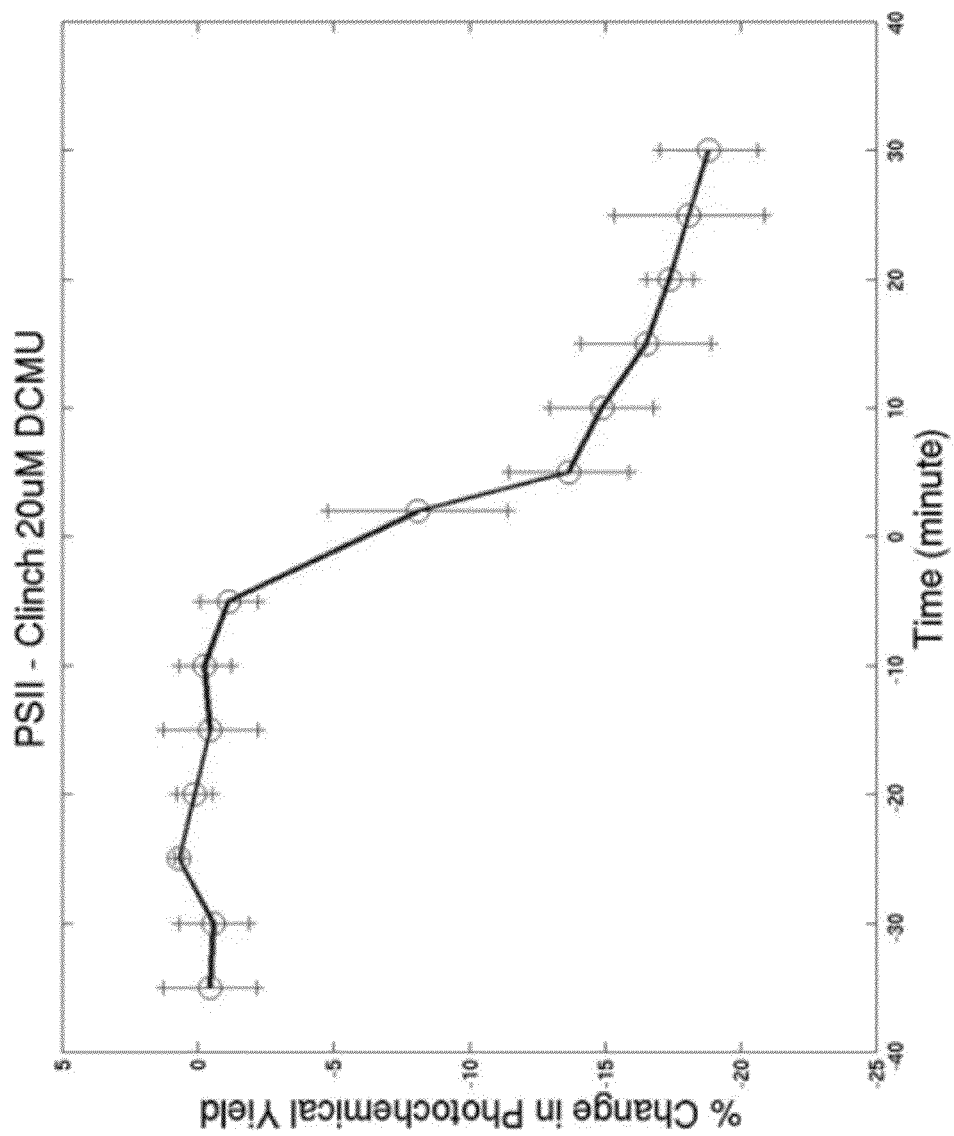
FIG. 16(a)-(h) shows the extracted features of 20 μM Diuron (DCMU) in the Clinch River samples as functions of time. The toxic agent is added into the samples at time 0.
Figure 16:
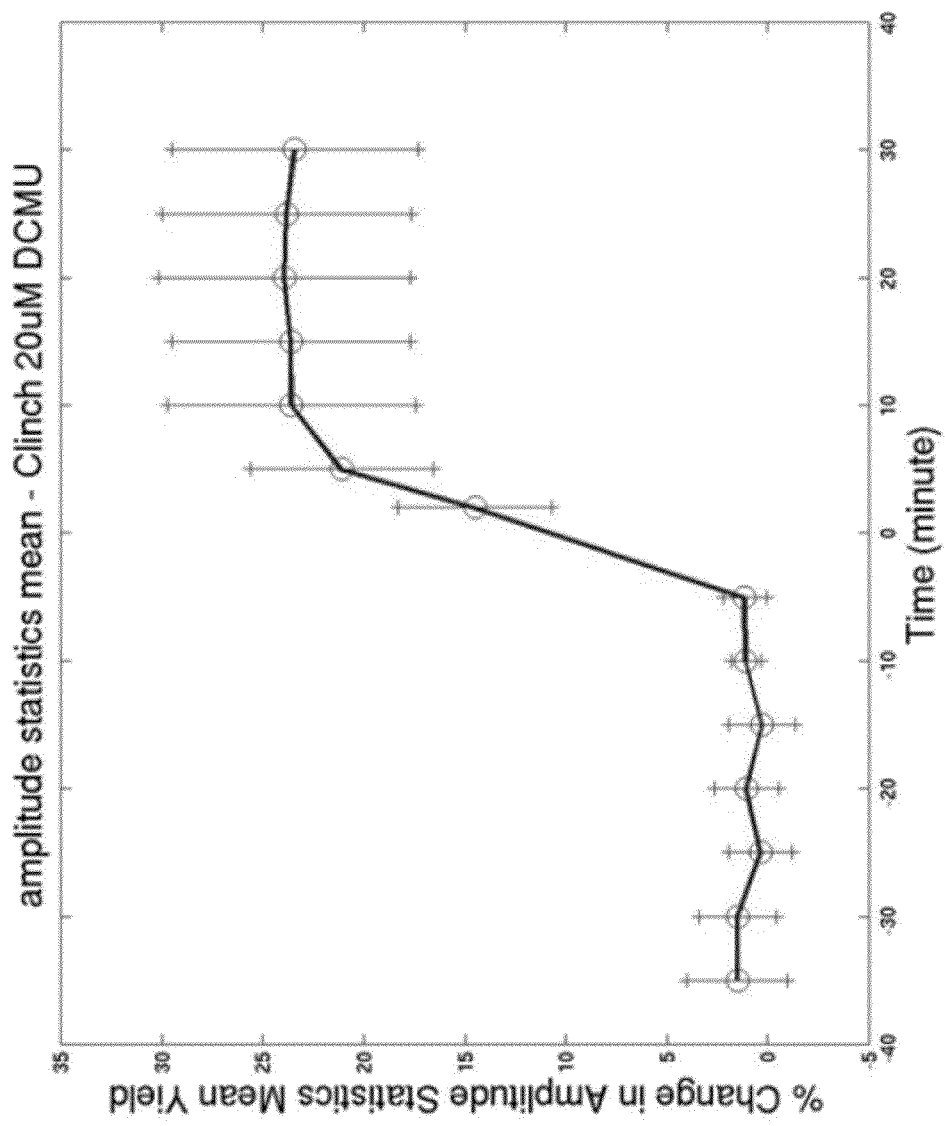
Figure 16:
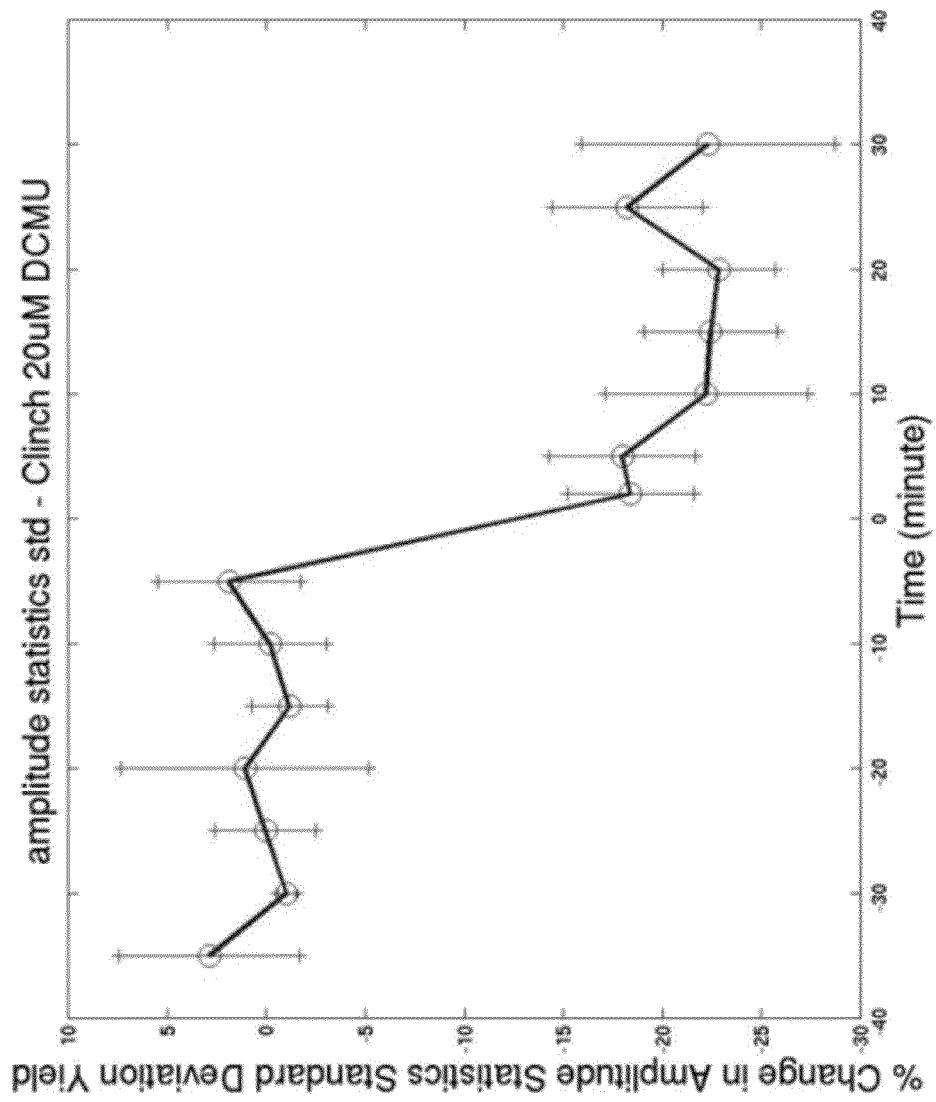
Figure 16:
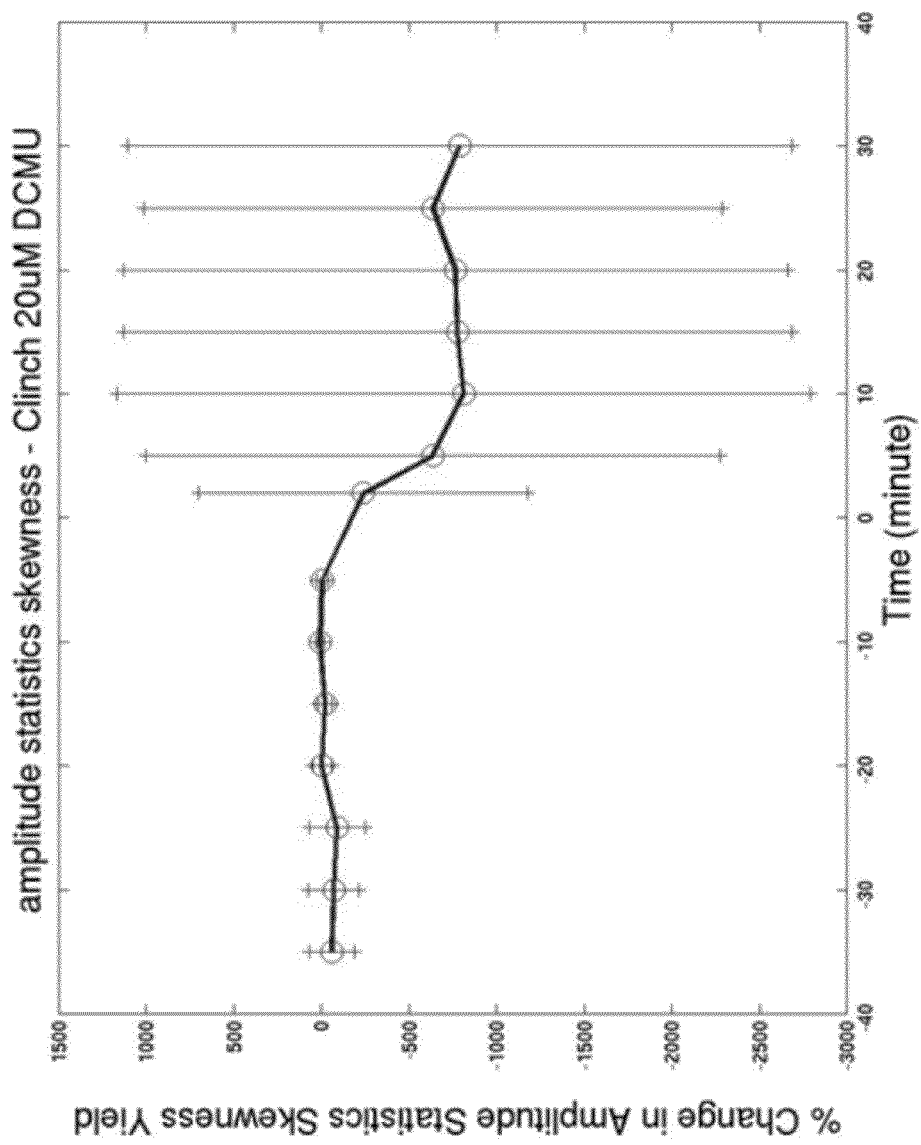
Figure 16:
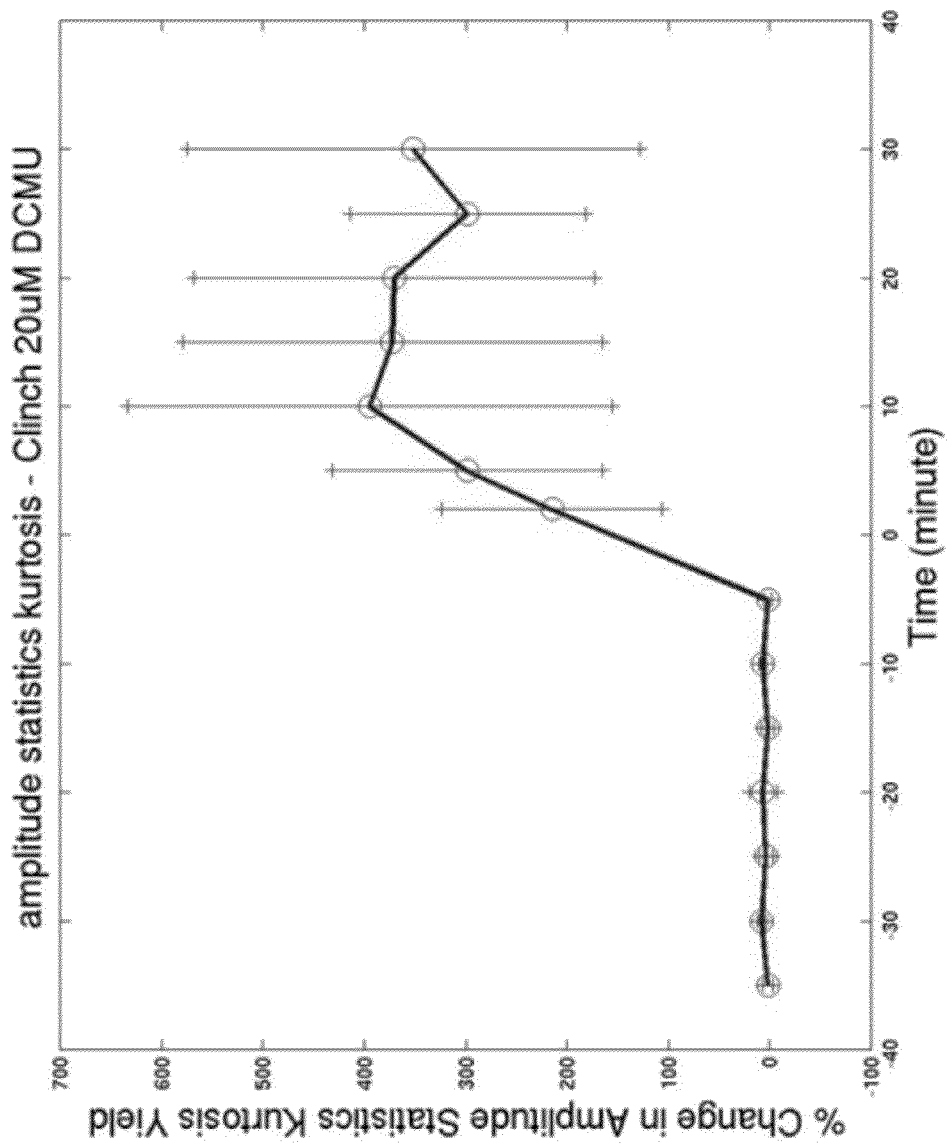
Figure 16:
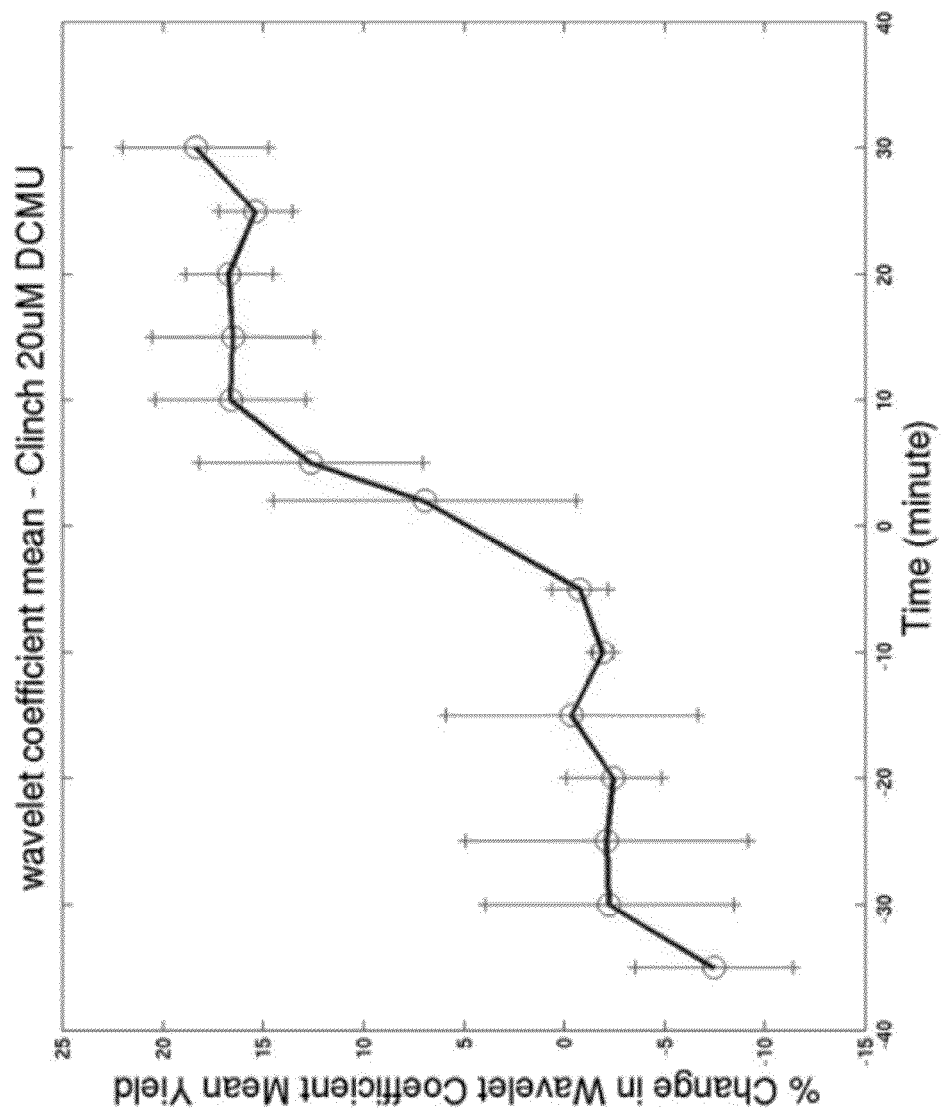
Figure 16:
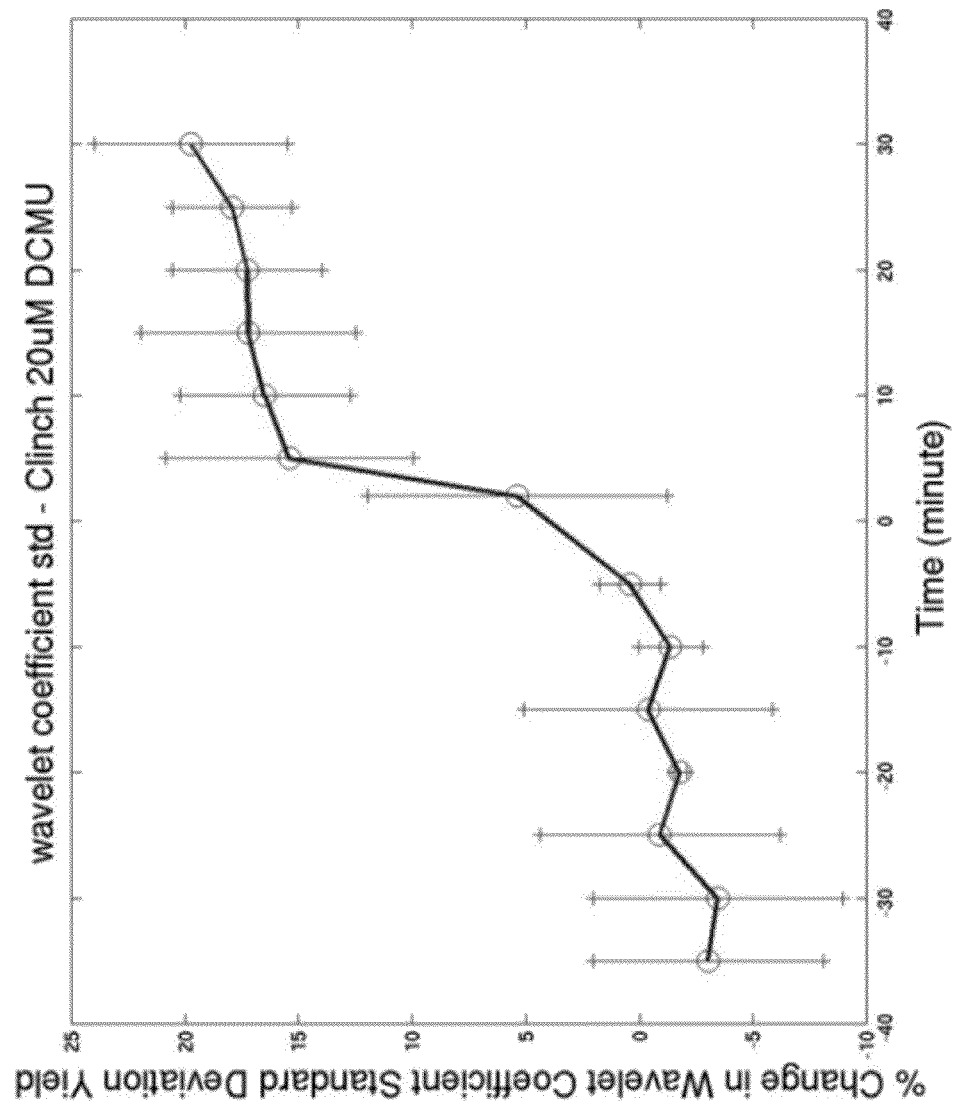
Figure 16:
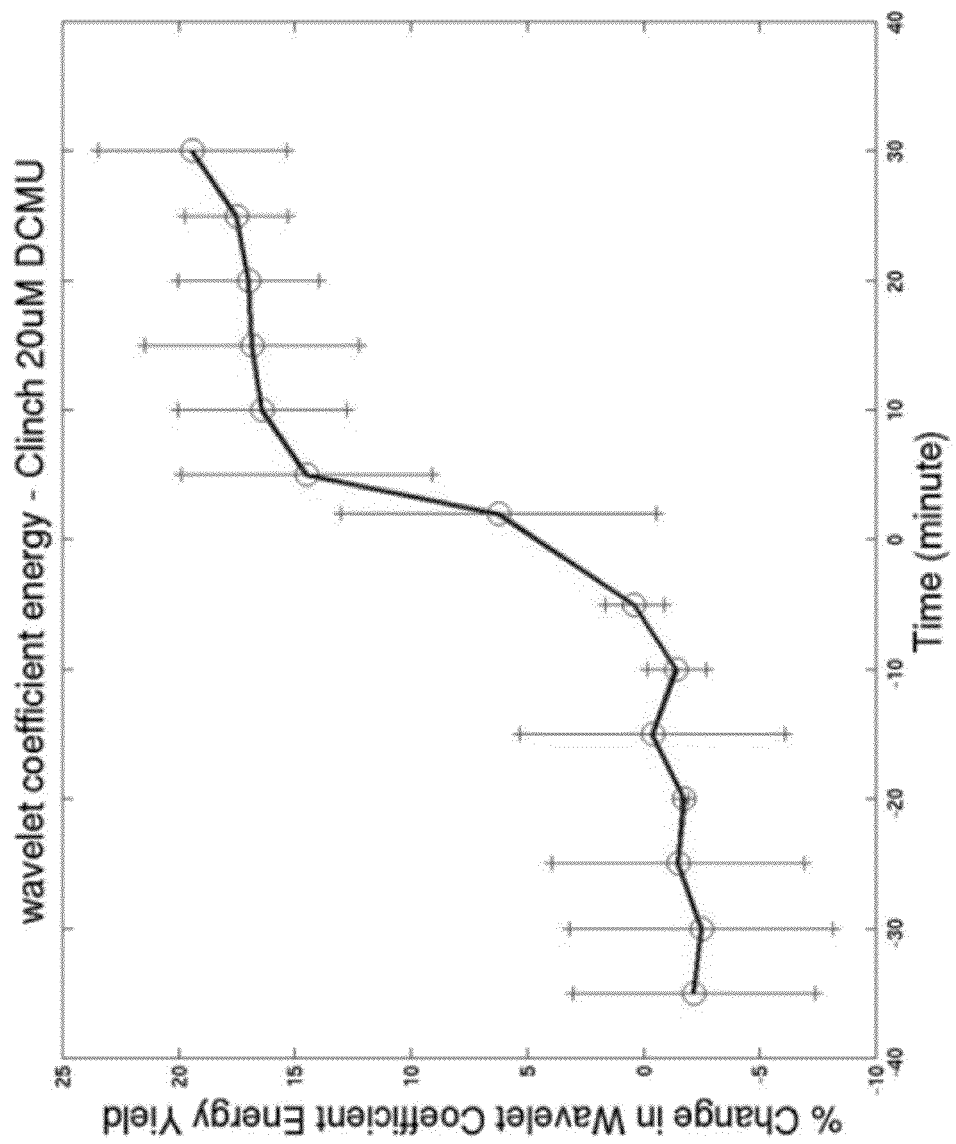
Figure 17:
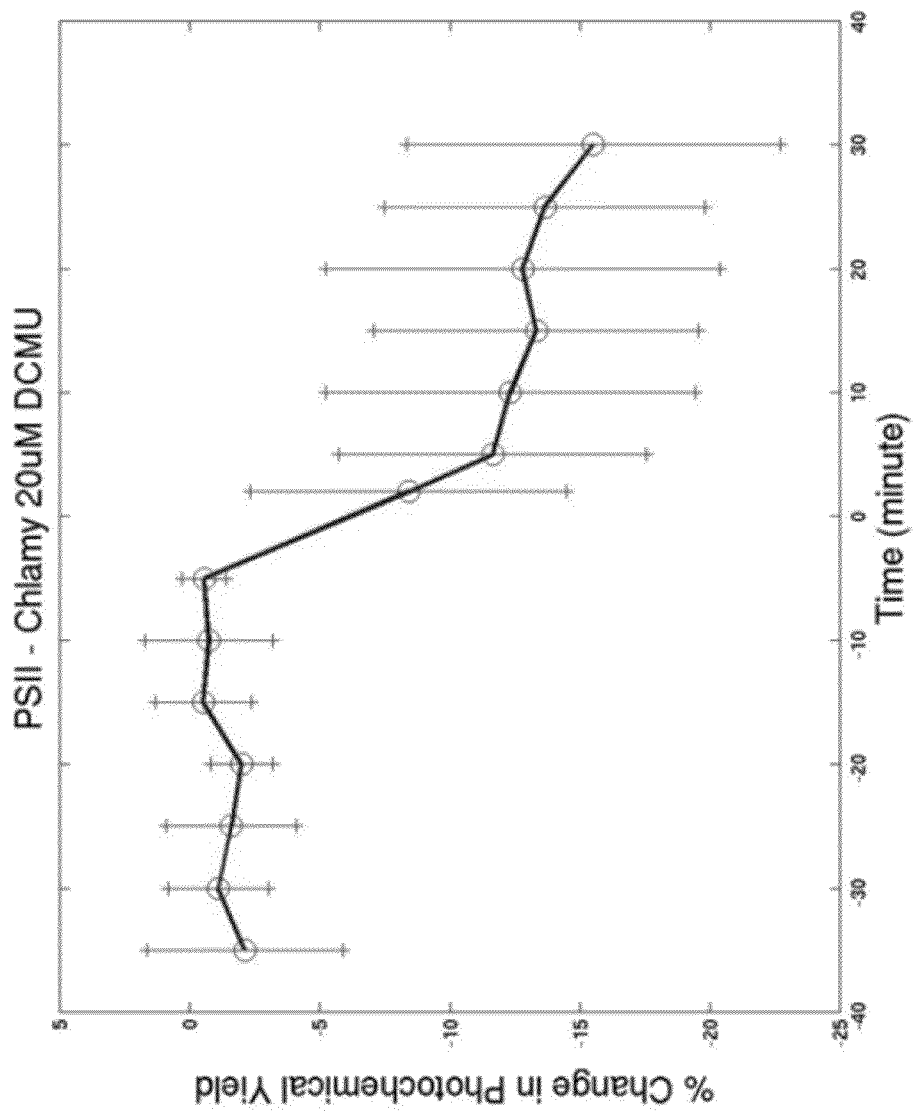
FIG. 17(a)-(h) shows the extracted features of 20 μM DCMU in the *Chlamydomonas* samples as functions of time. The toxic agent is added into the samples at time 0.
Figure 17:
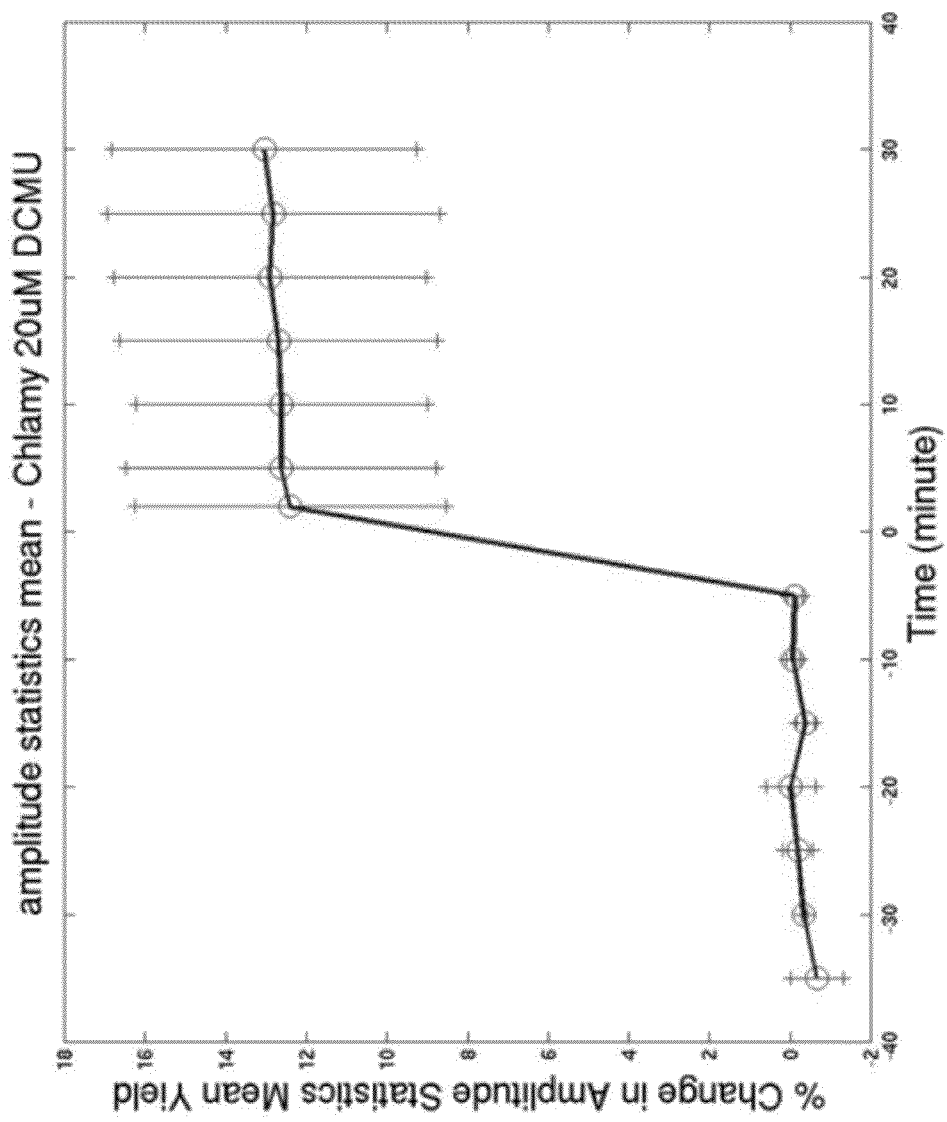
Figure 17:
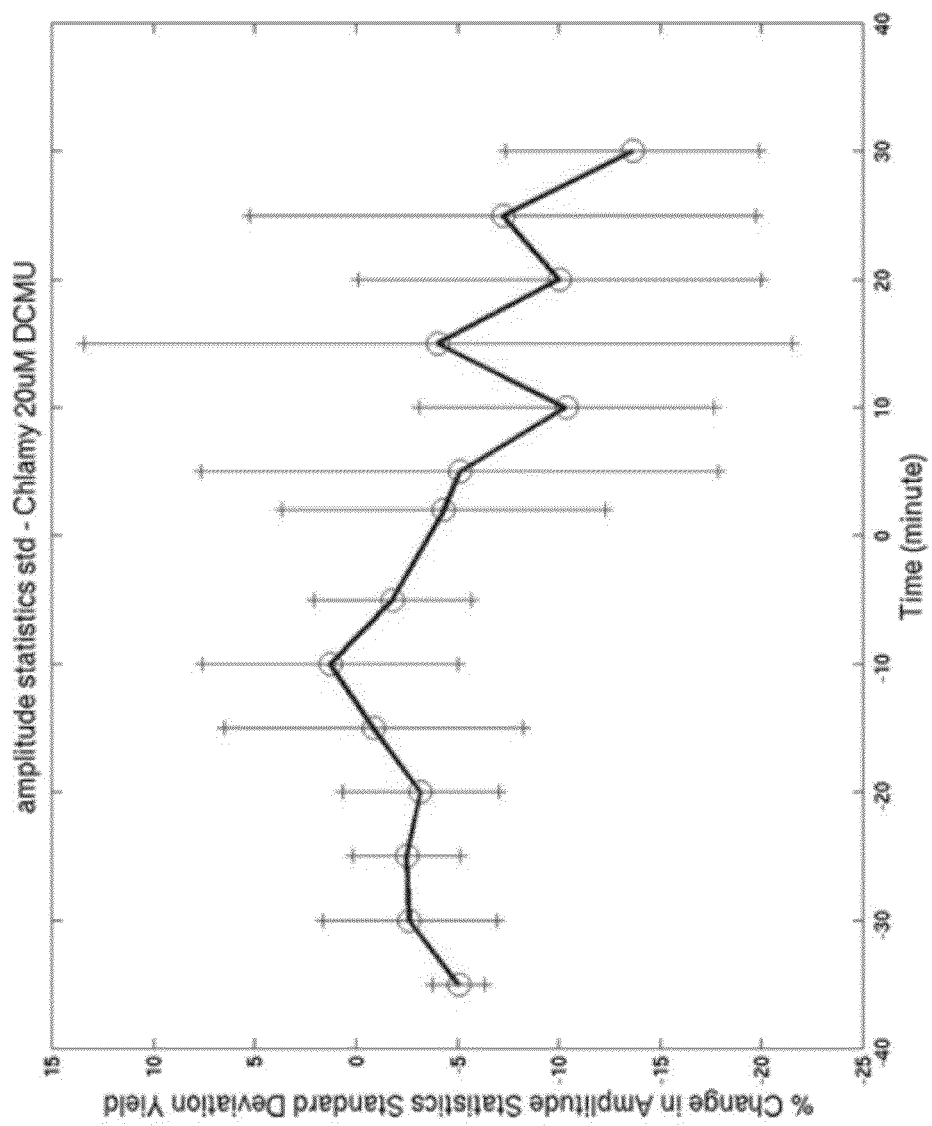
Figure 17:
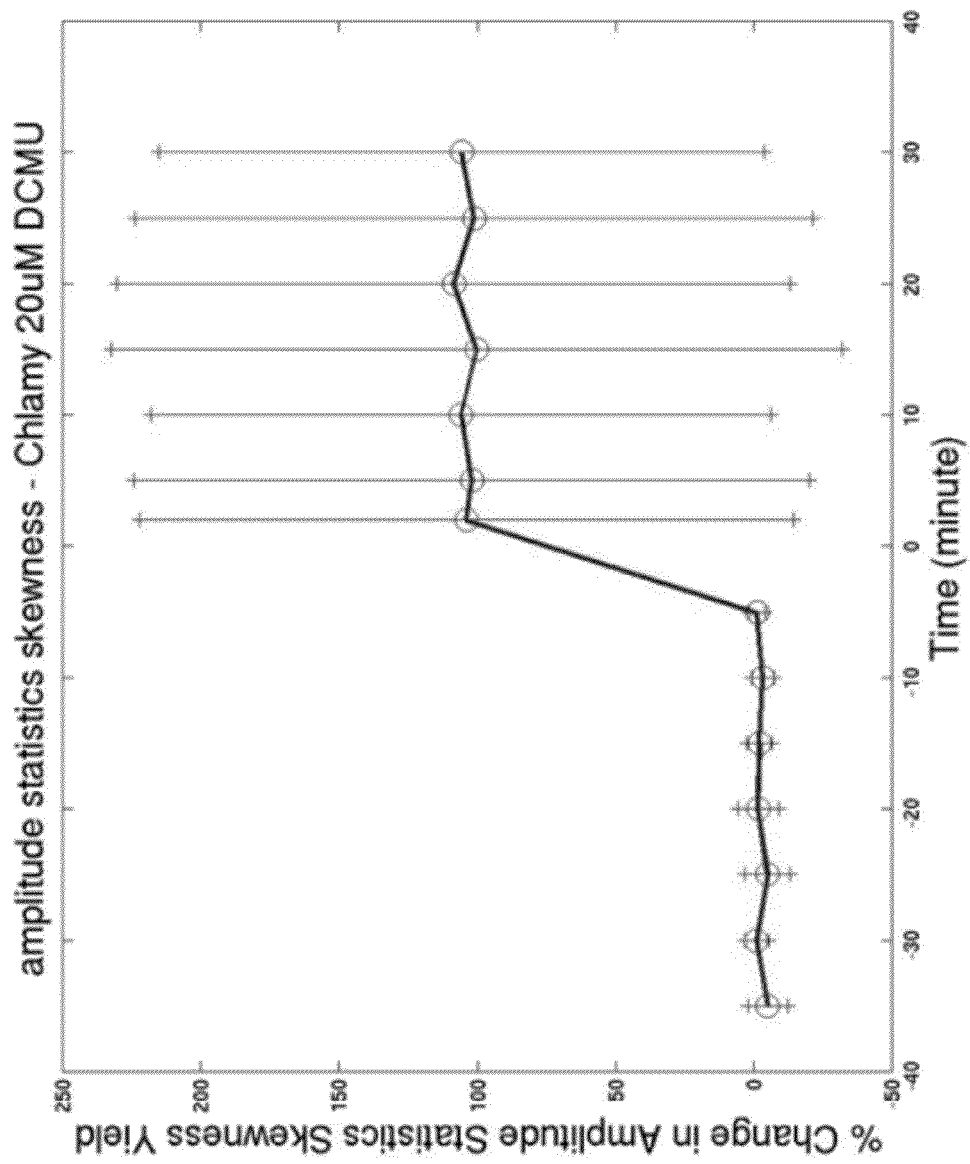
Figure 17:
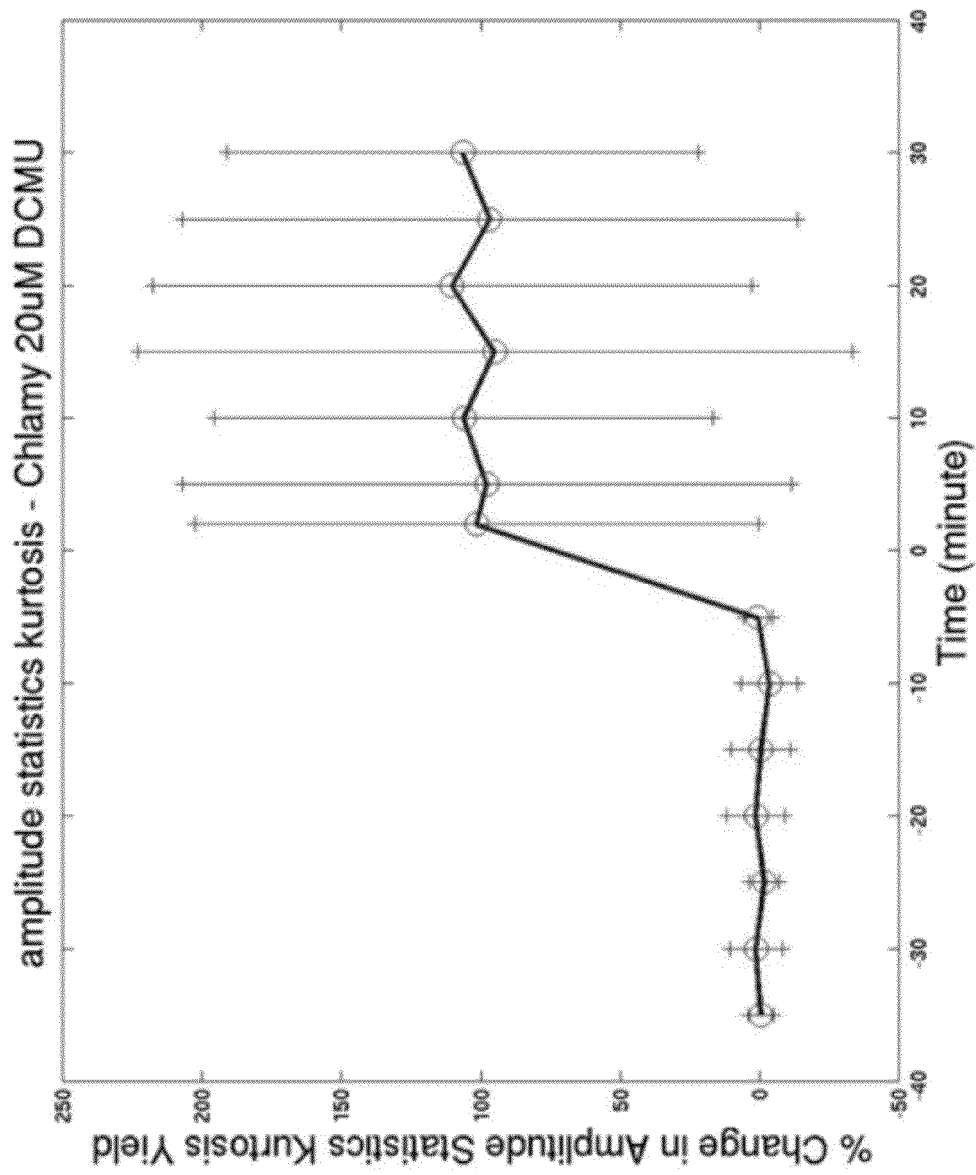
Figure 17:
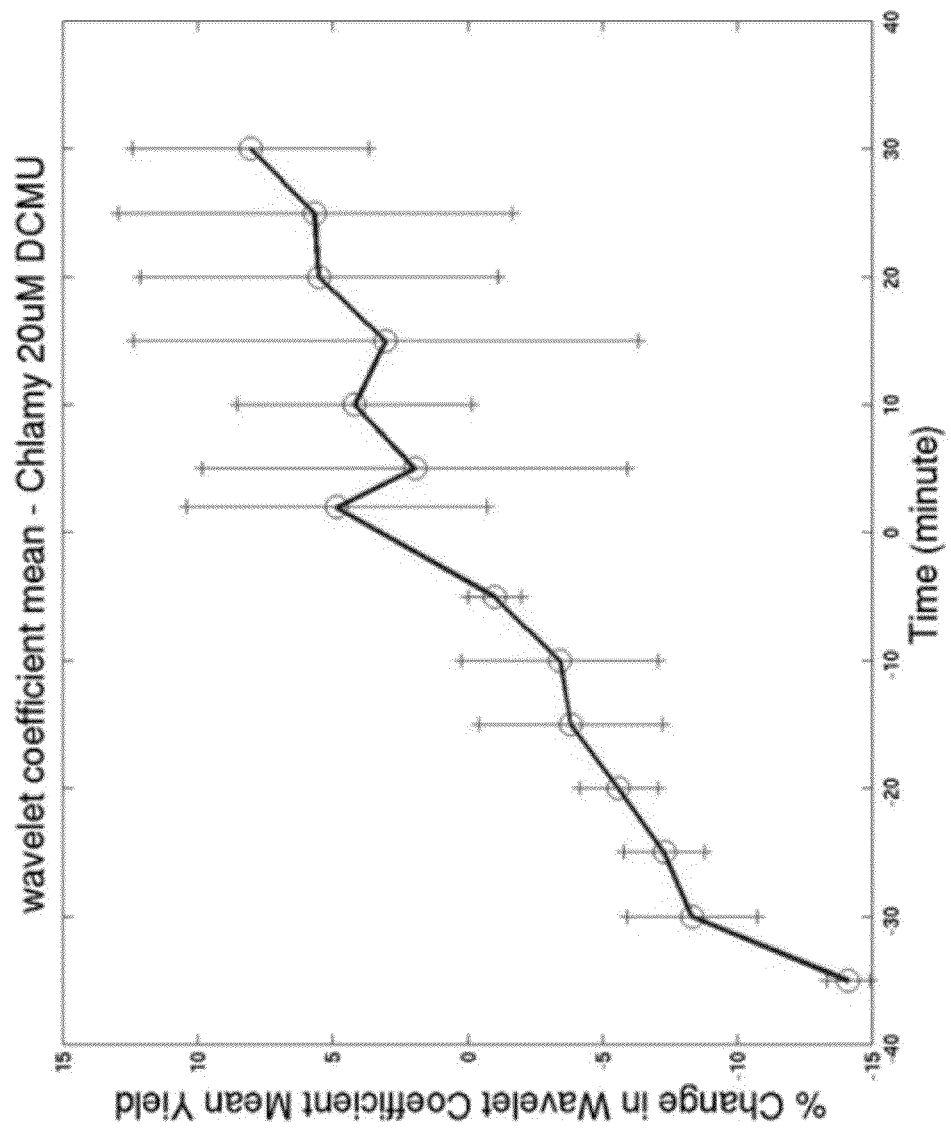
Figure 17:
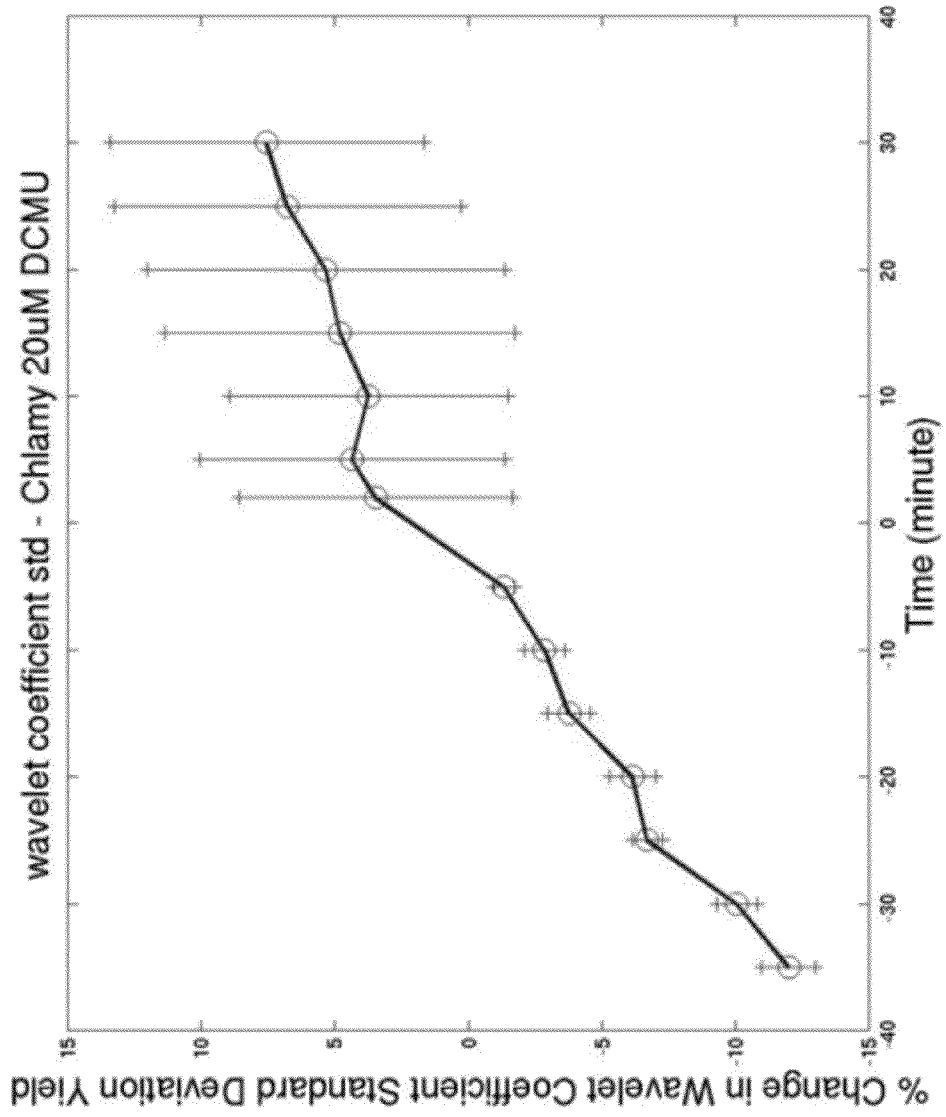
Figure 17:
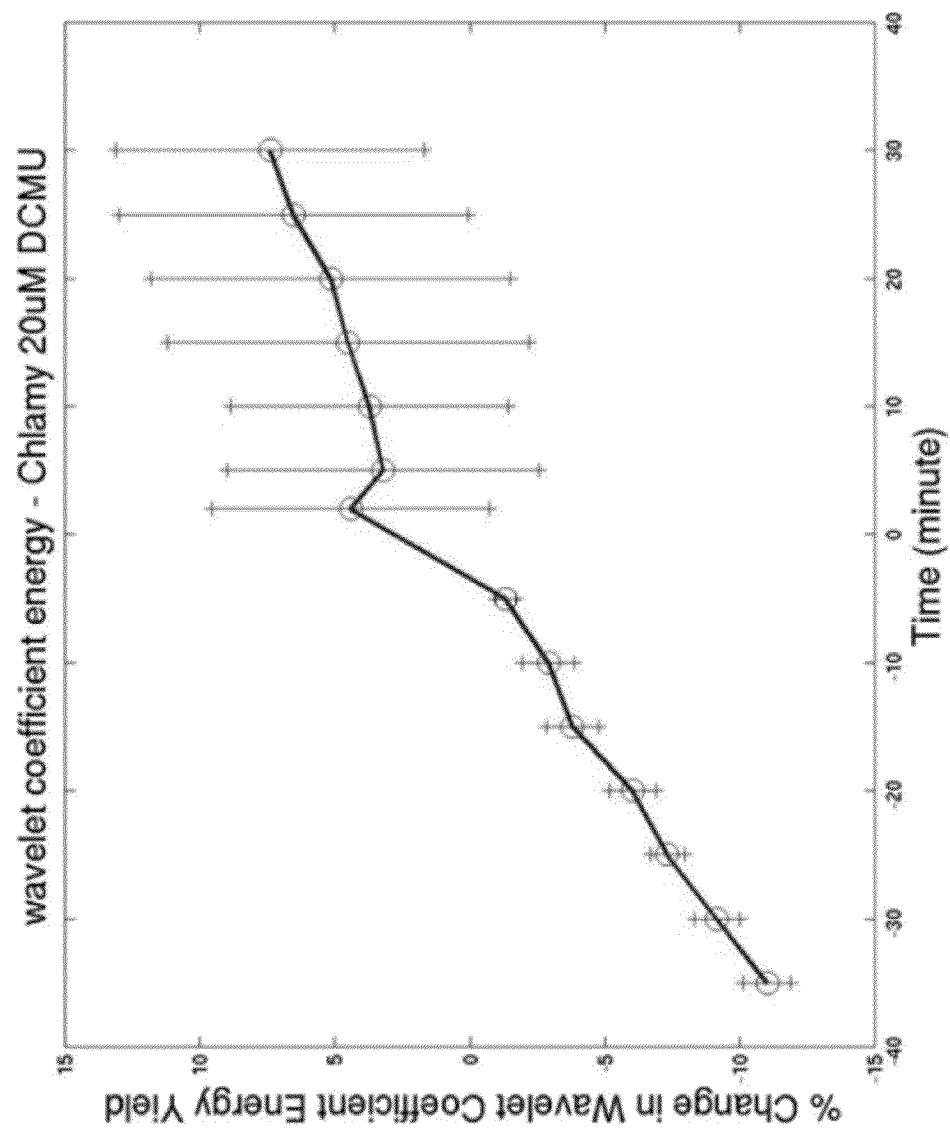
Figure 18:
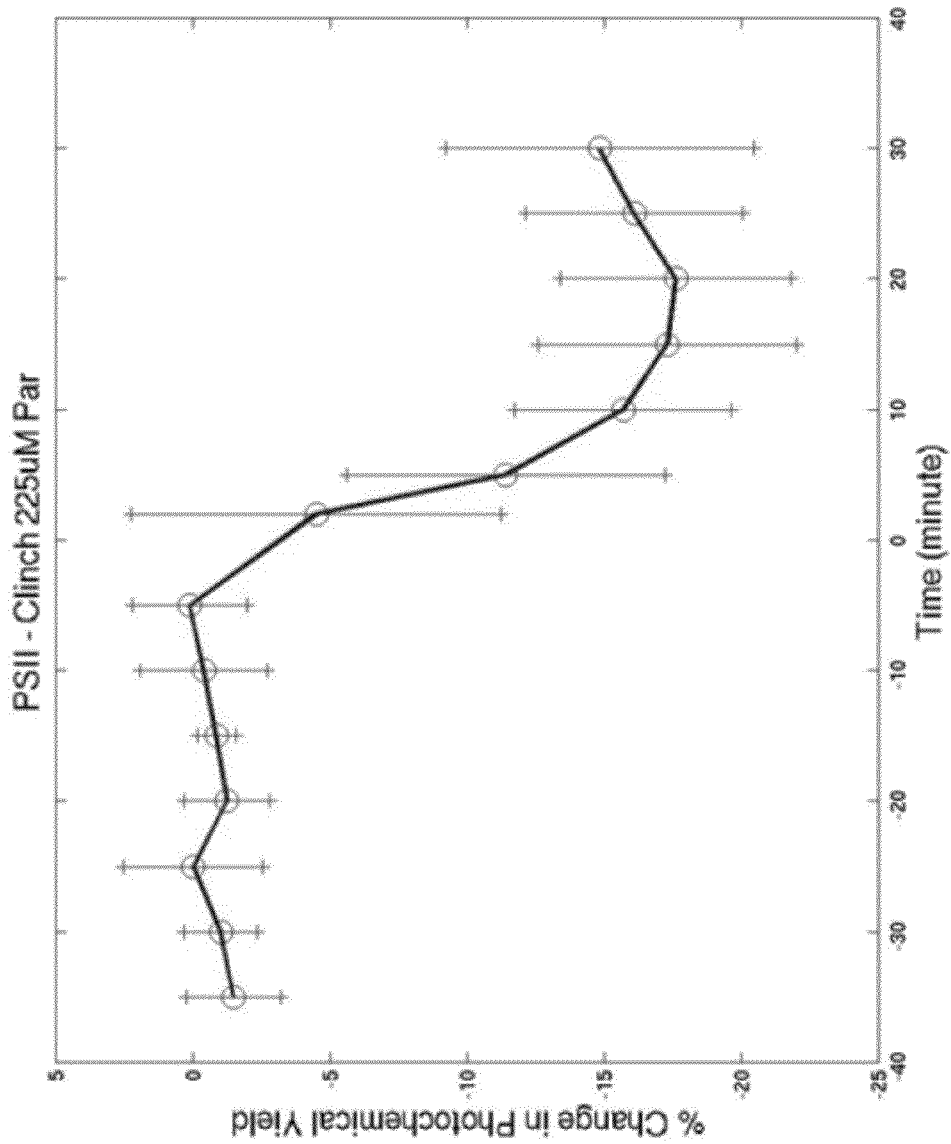
FIG. 18(a)-(h) shows the extracted features of 225 μM Paraquat in the Clinch River samples as functions of time. The toxic agent is added into the samples at time 0.
Figure 18:
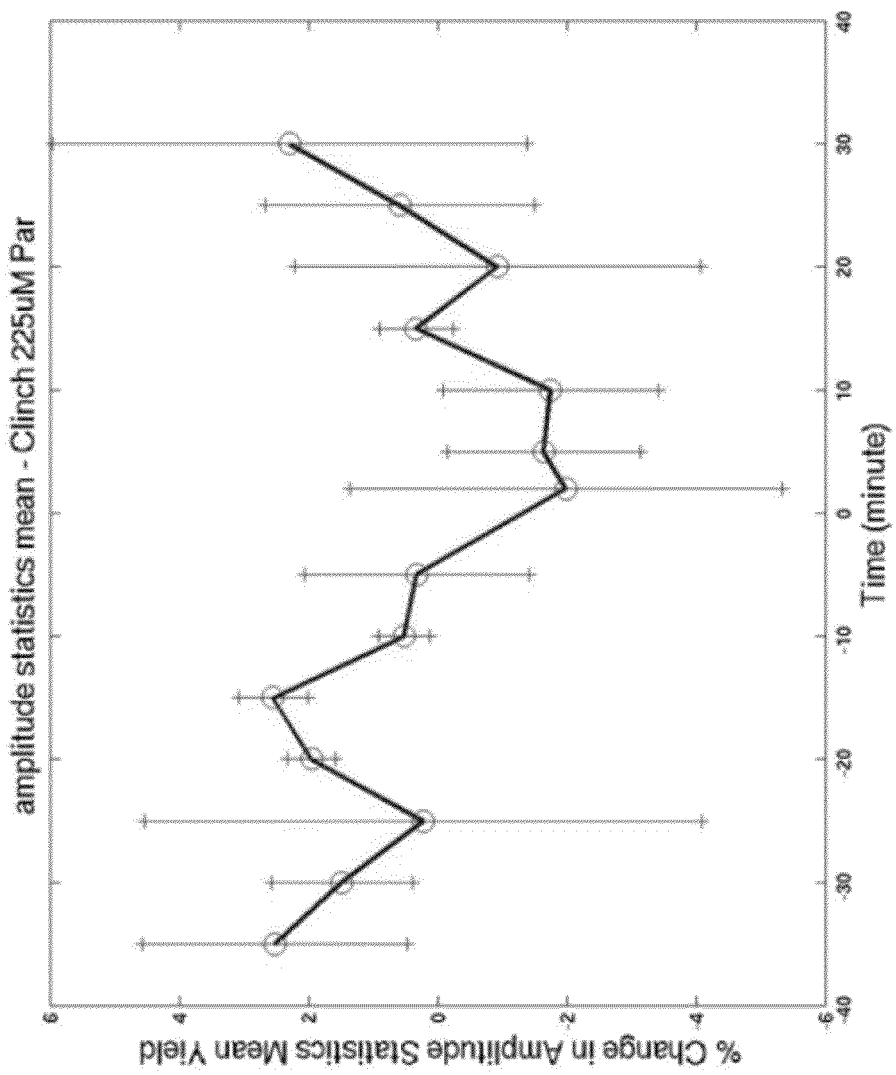
Figure 18:
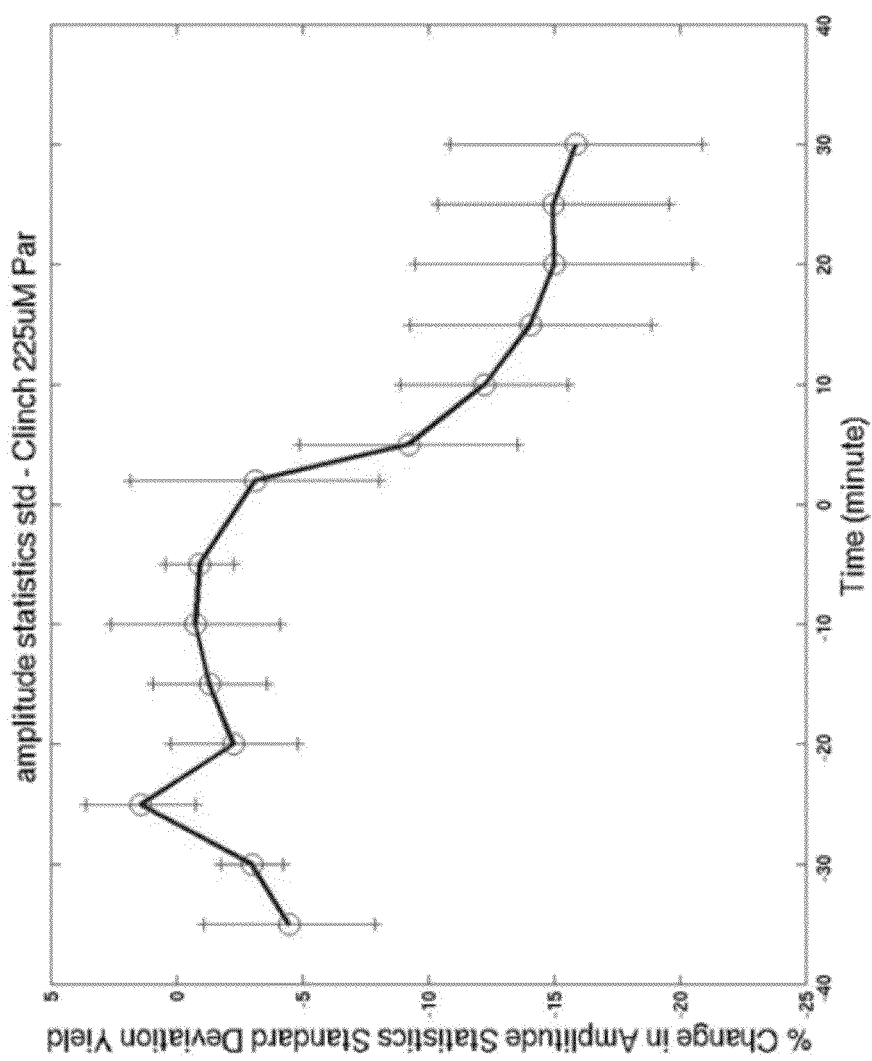
Figure 18:
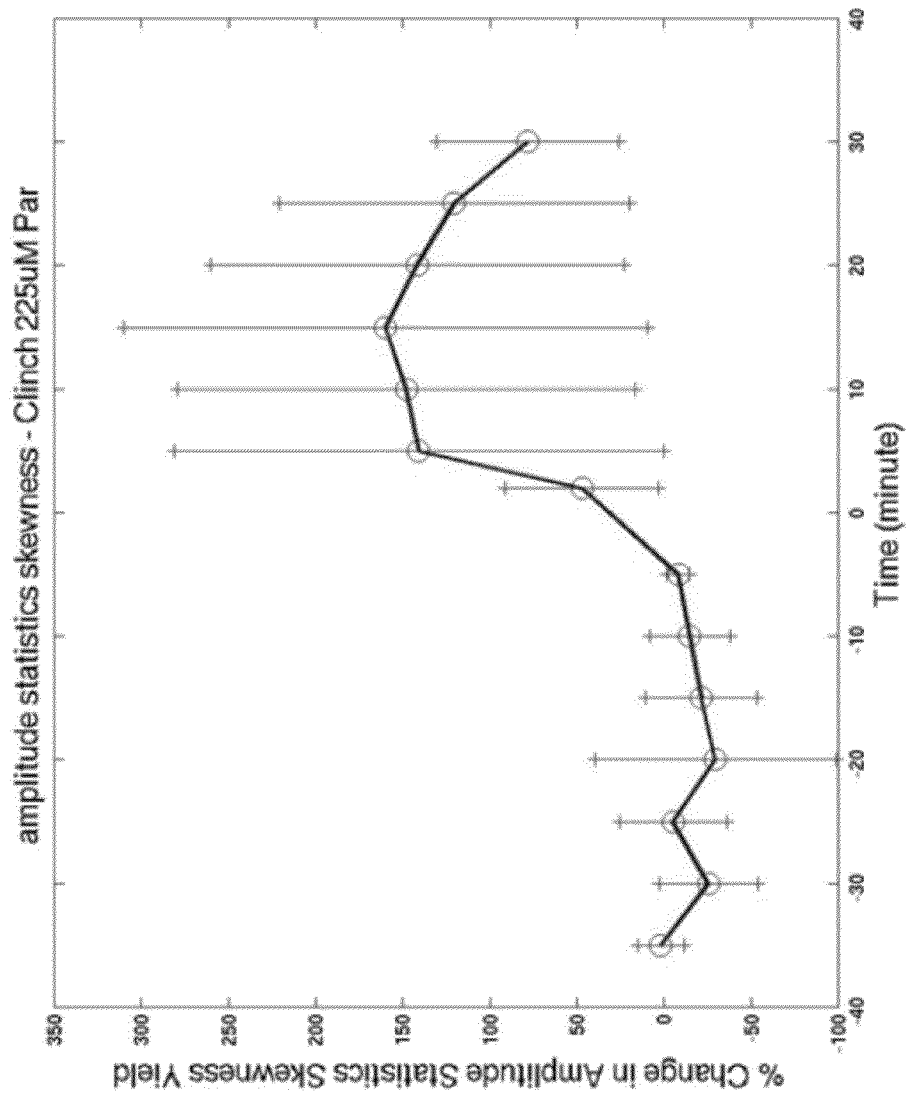
Figure 18:
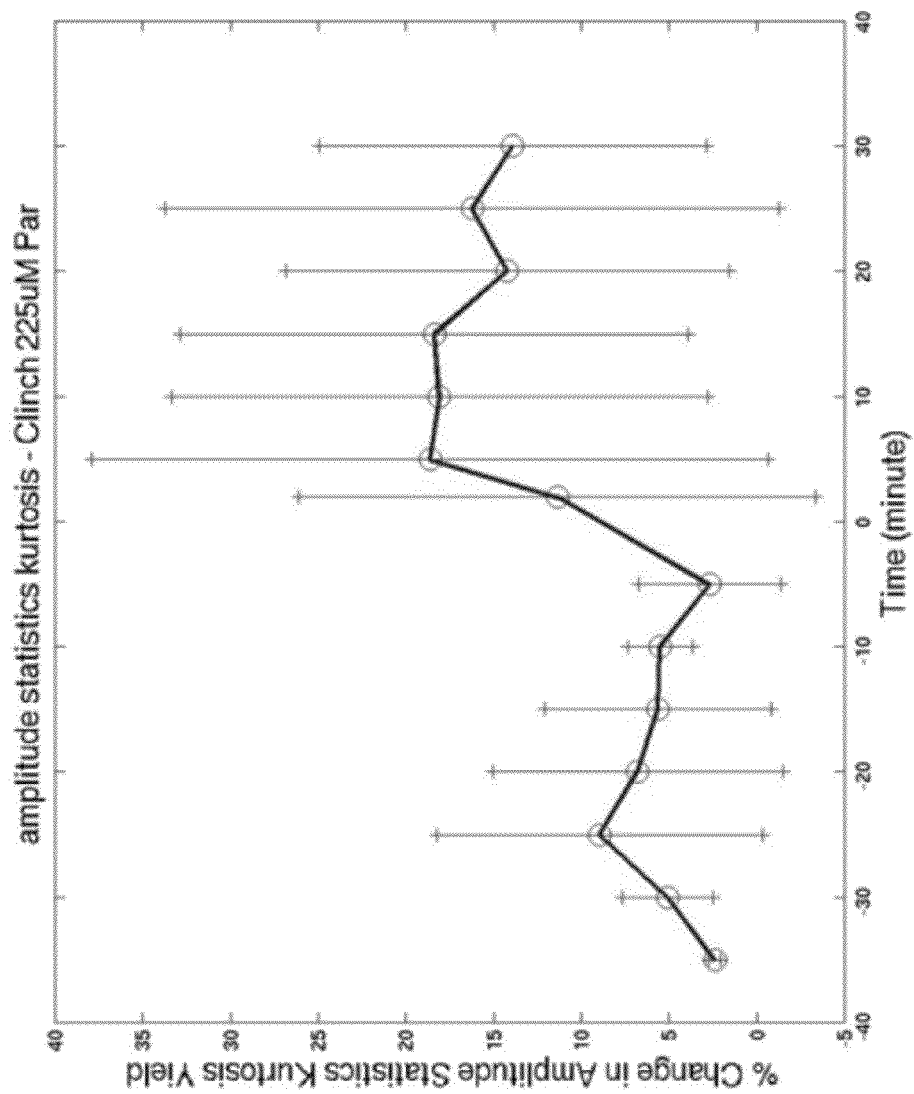
Figure 18:
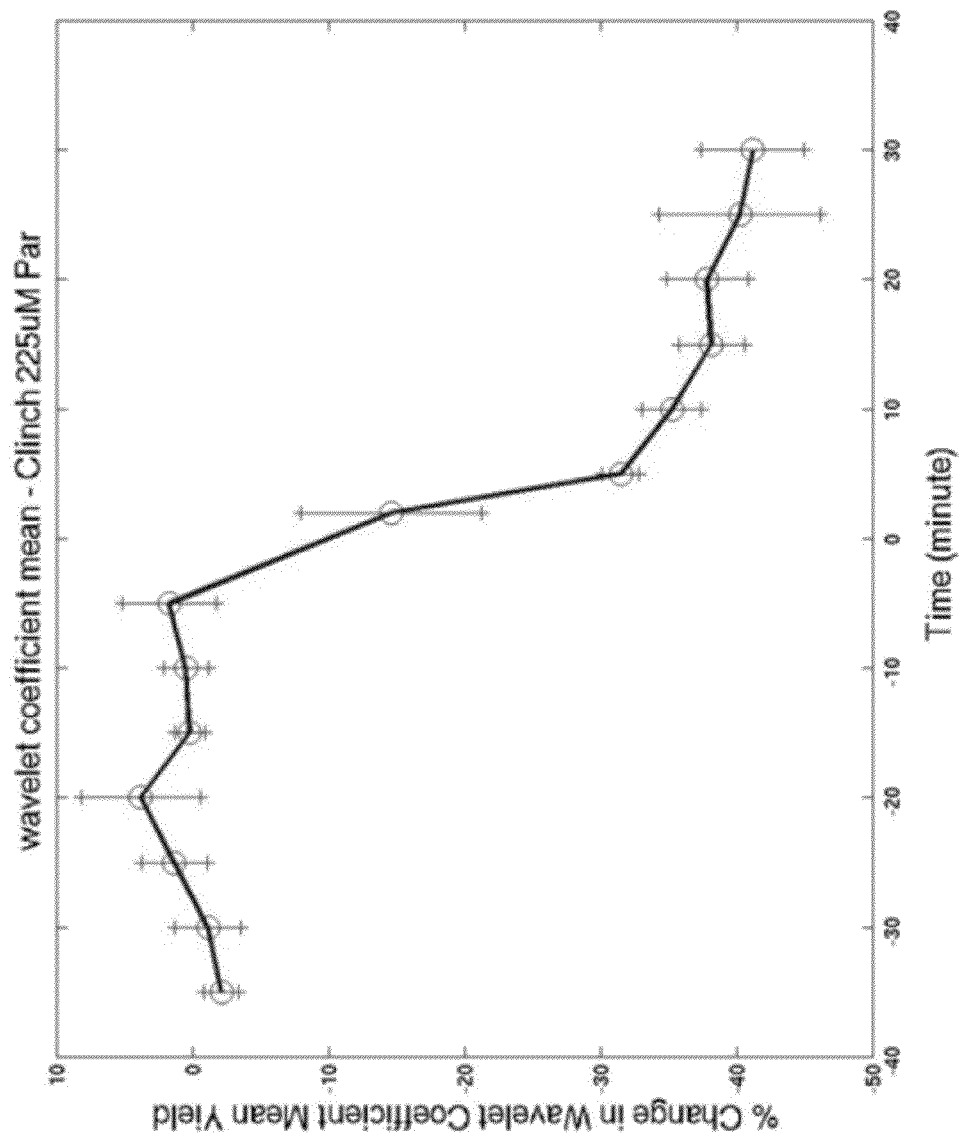
Figure 18:
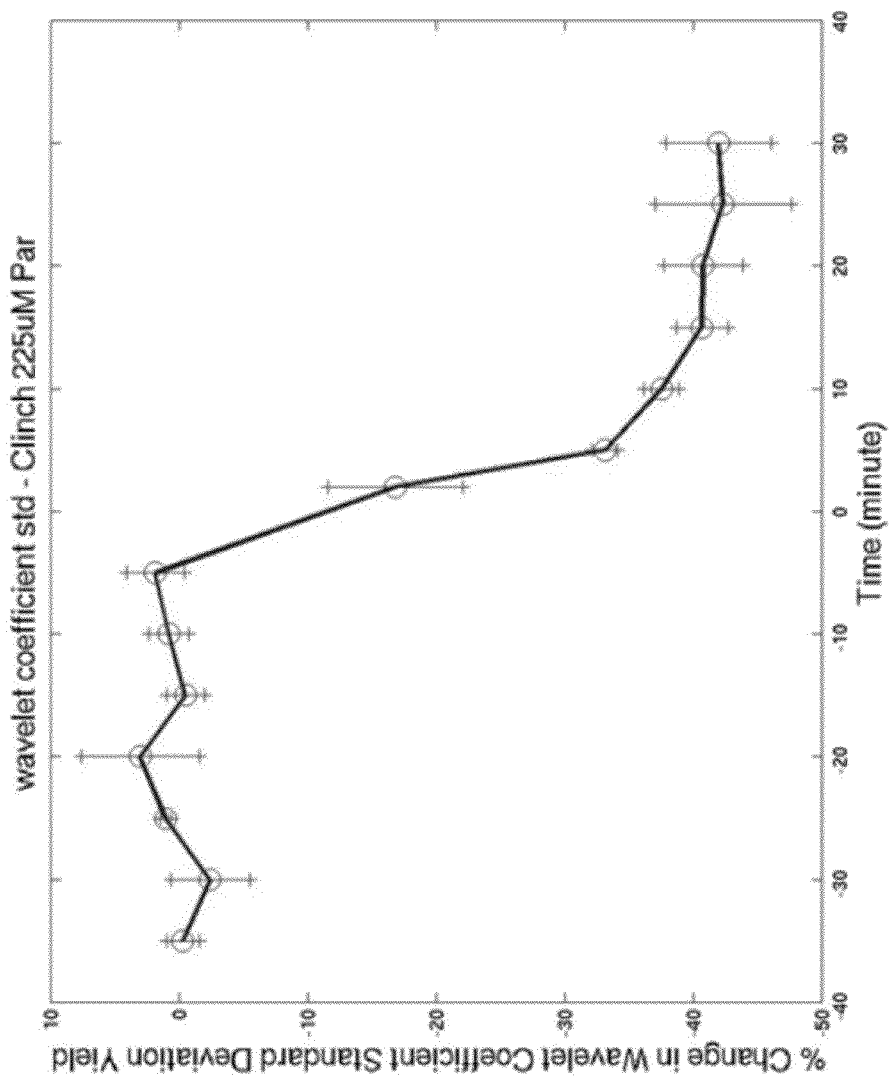
Figure 18:
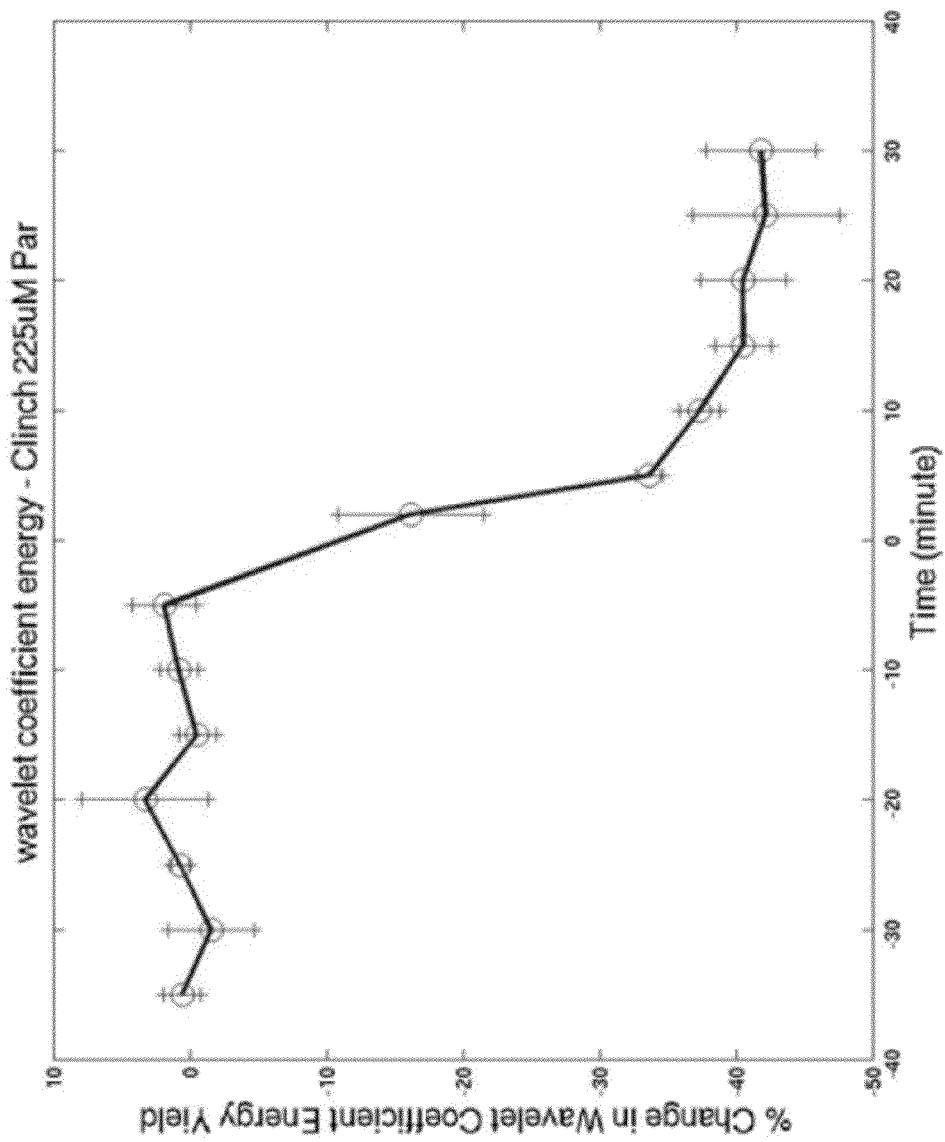
Figure 19:
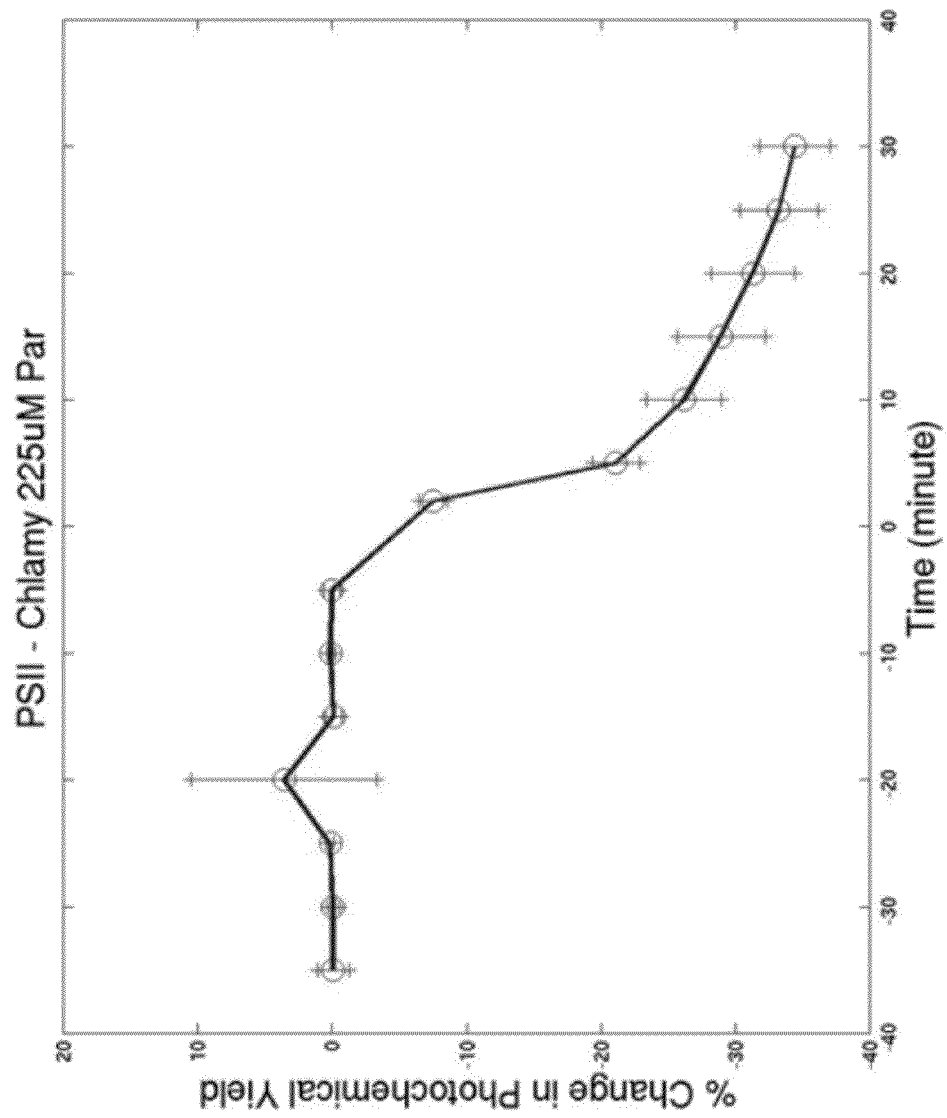
FIG. 19(a)-(h) shows the extracted features of 225 μM Paraquat in the *Chlamydonomas* samples as functions of time. The toxic agent is added into the samples at time 0.
Figure 19:
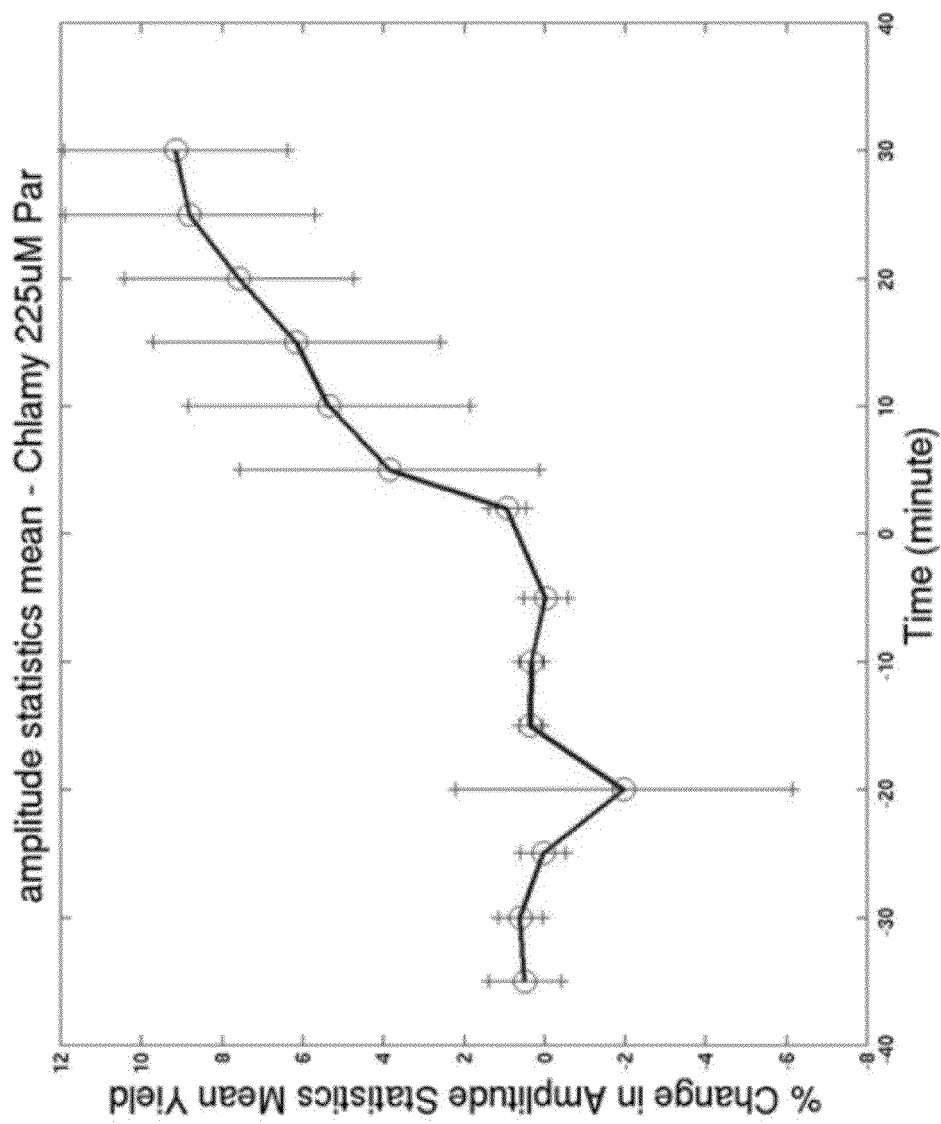
Figure 19:
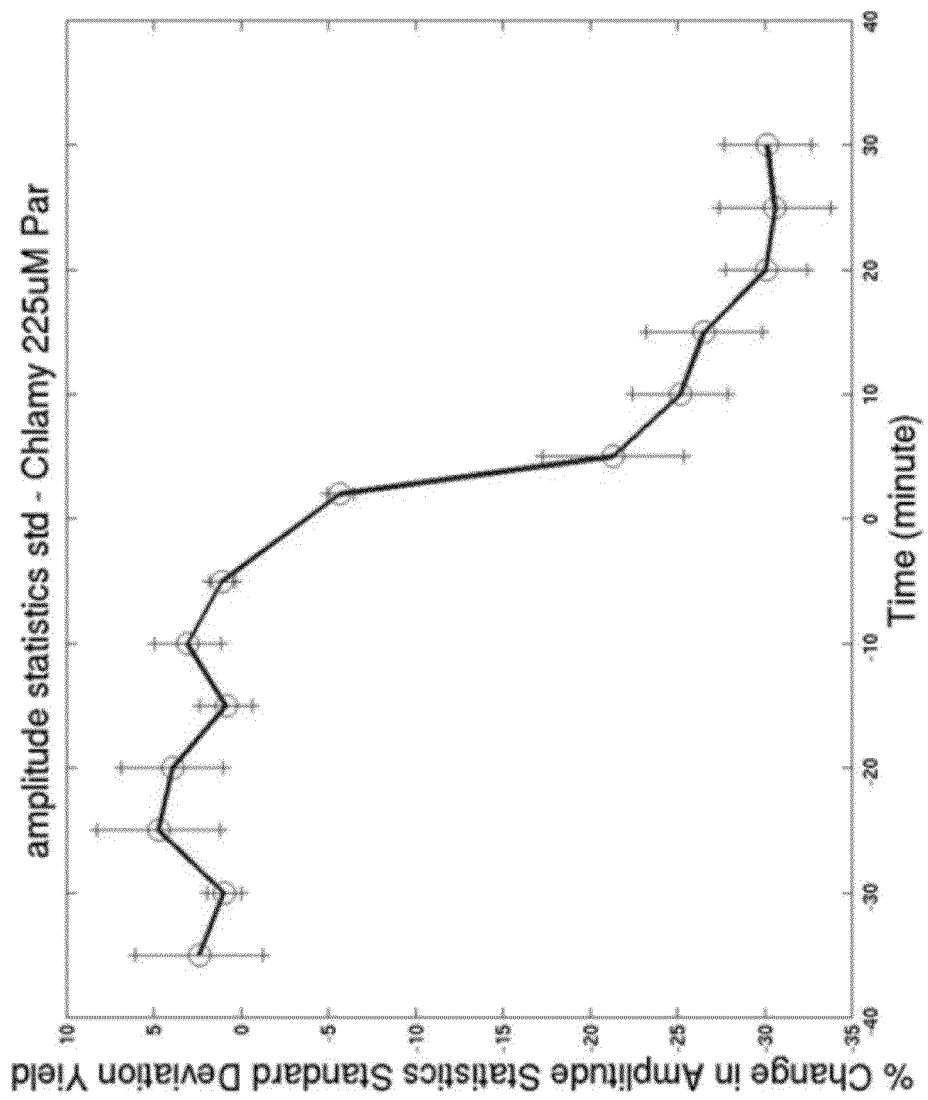
Figure 19:
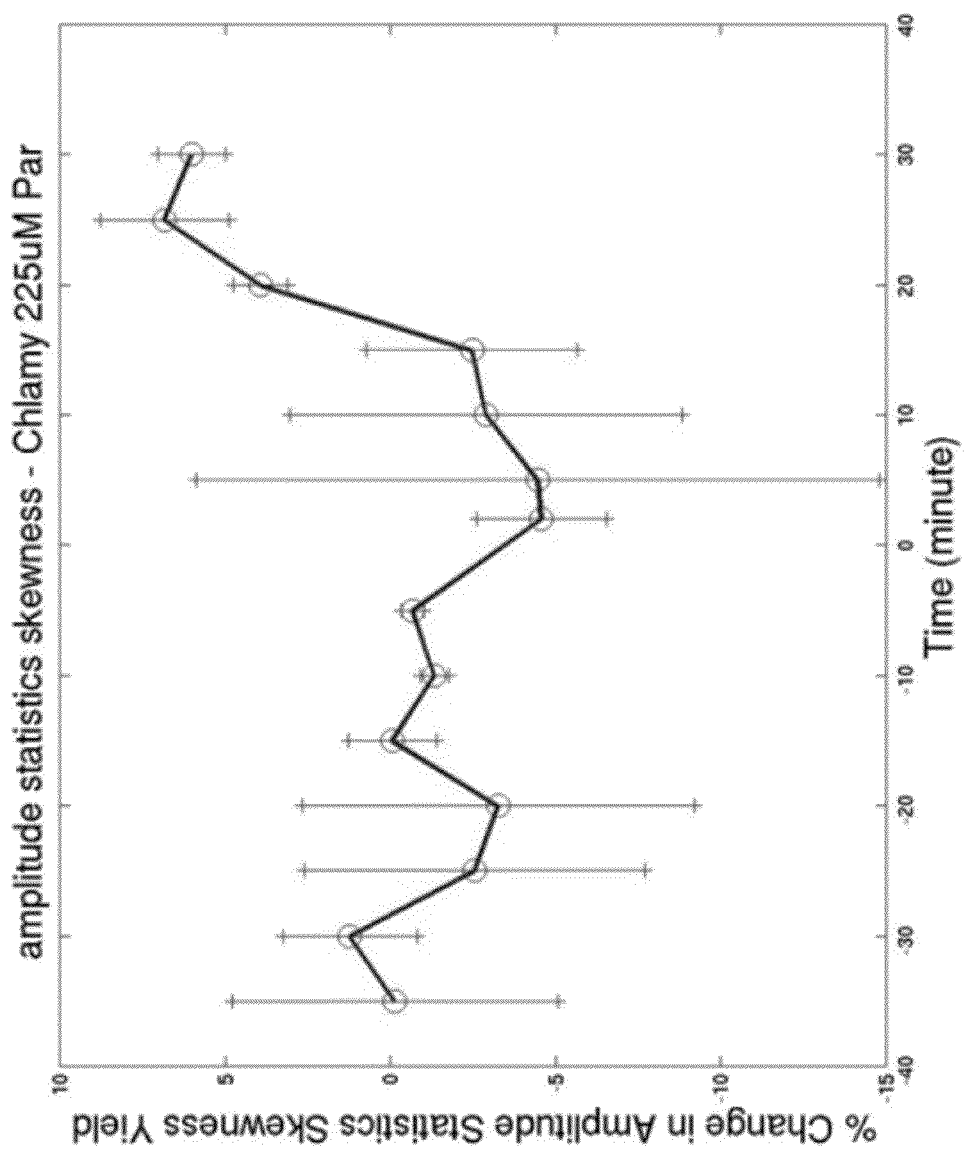
Figure 19:
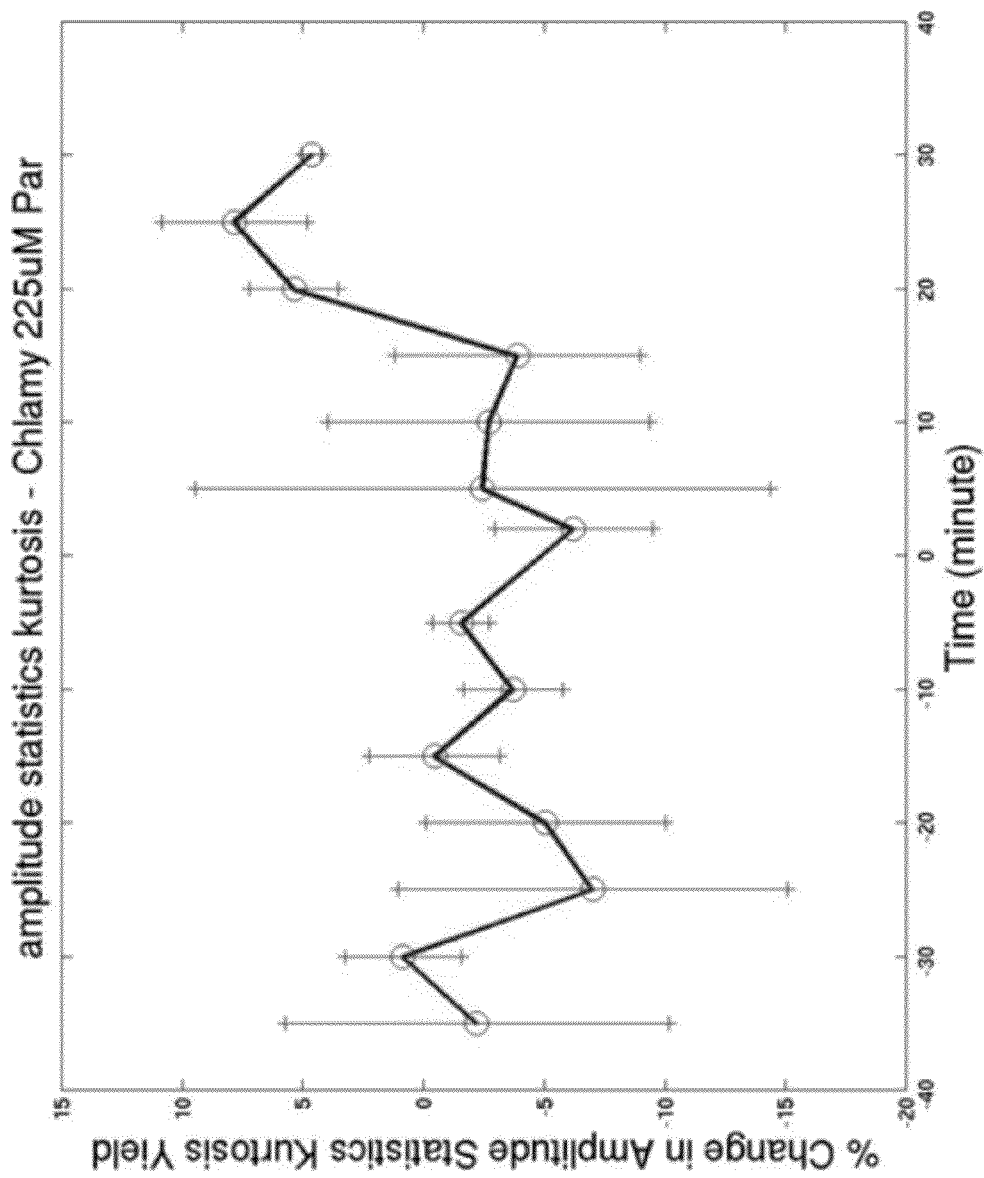
Figure 19:
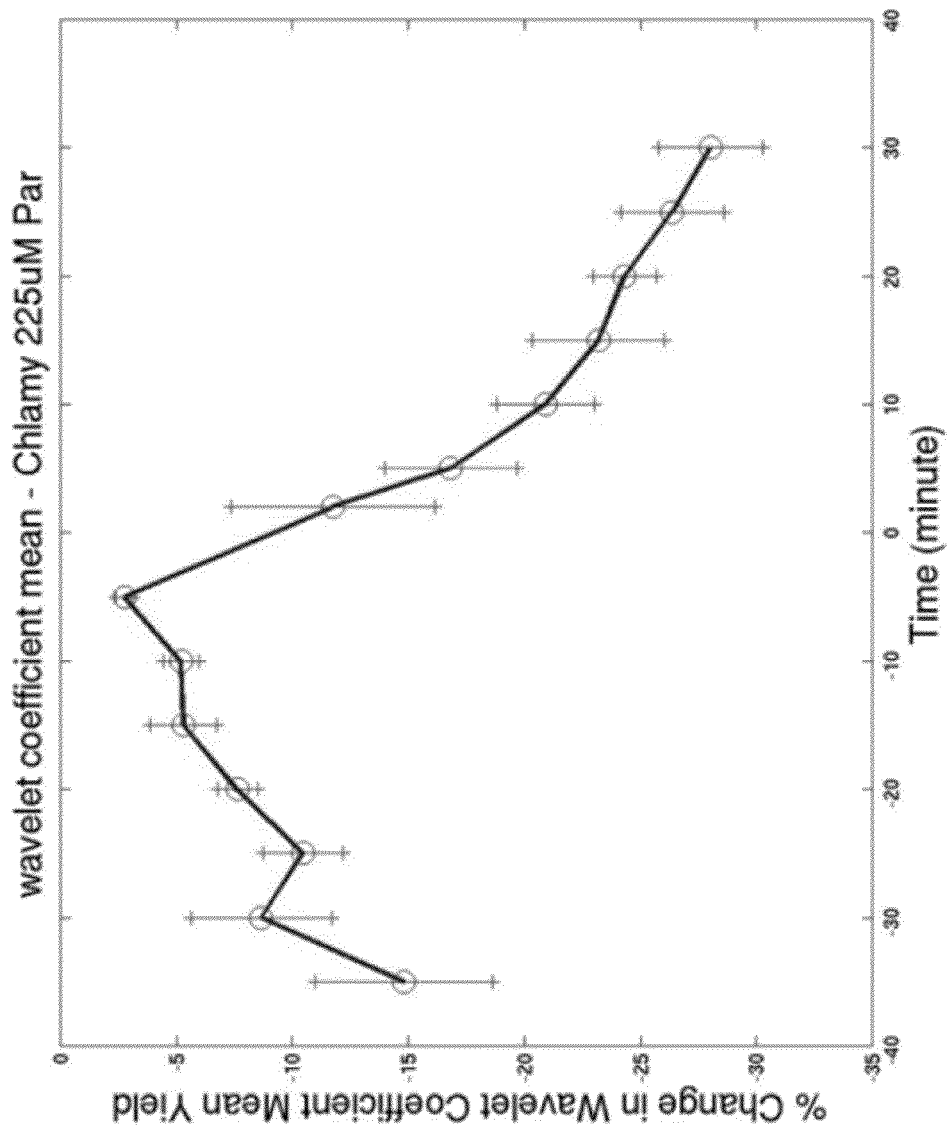
Figure 19:
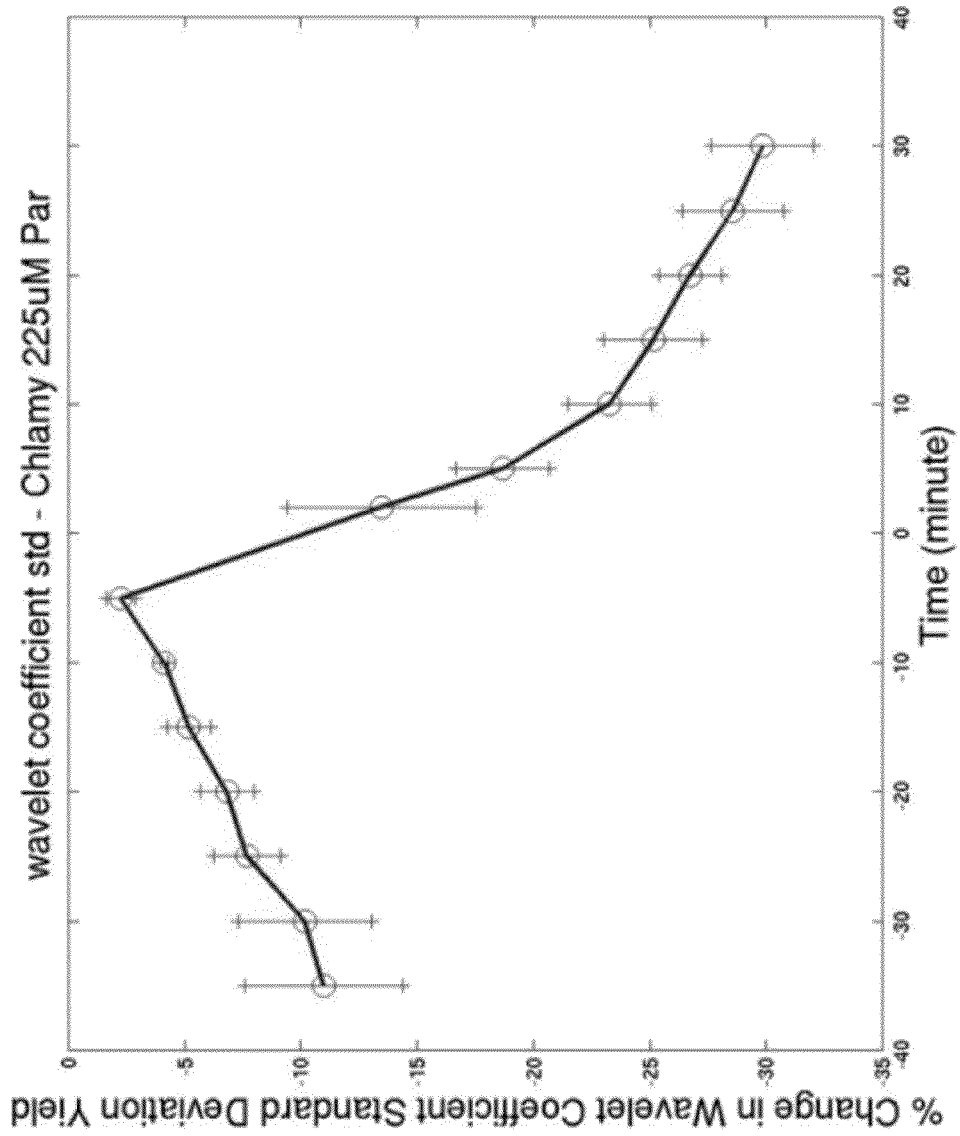
Figure 19:
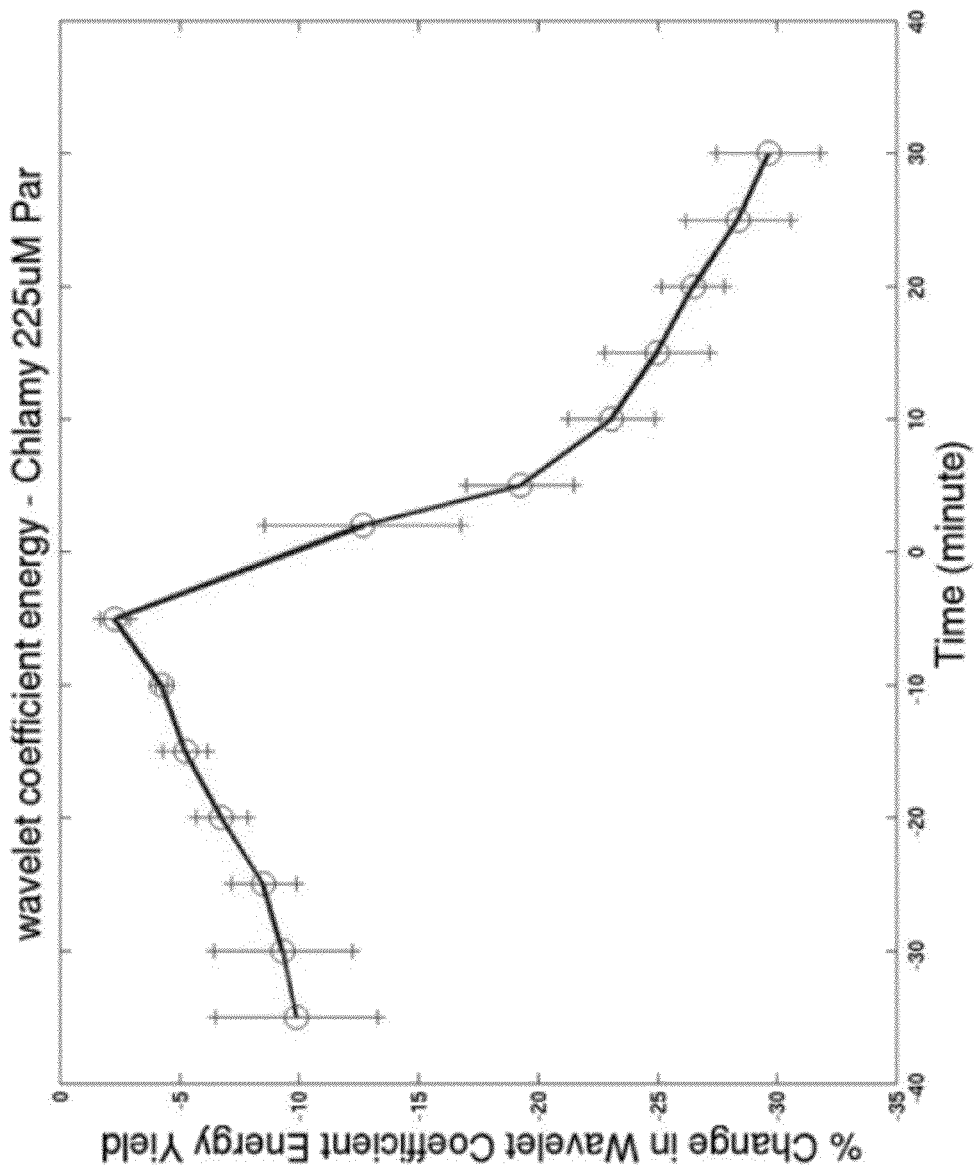
Figure 20:
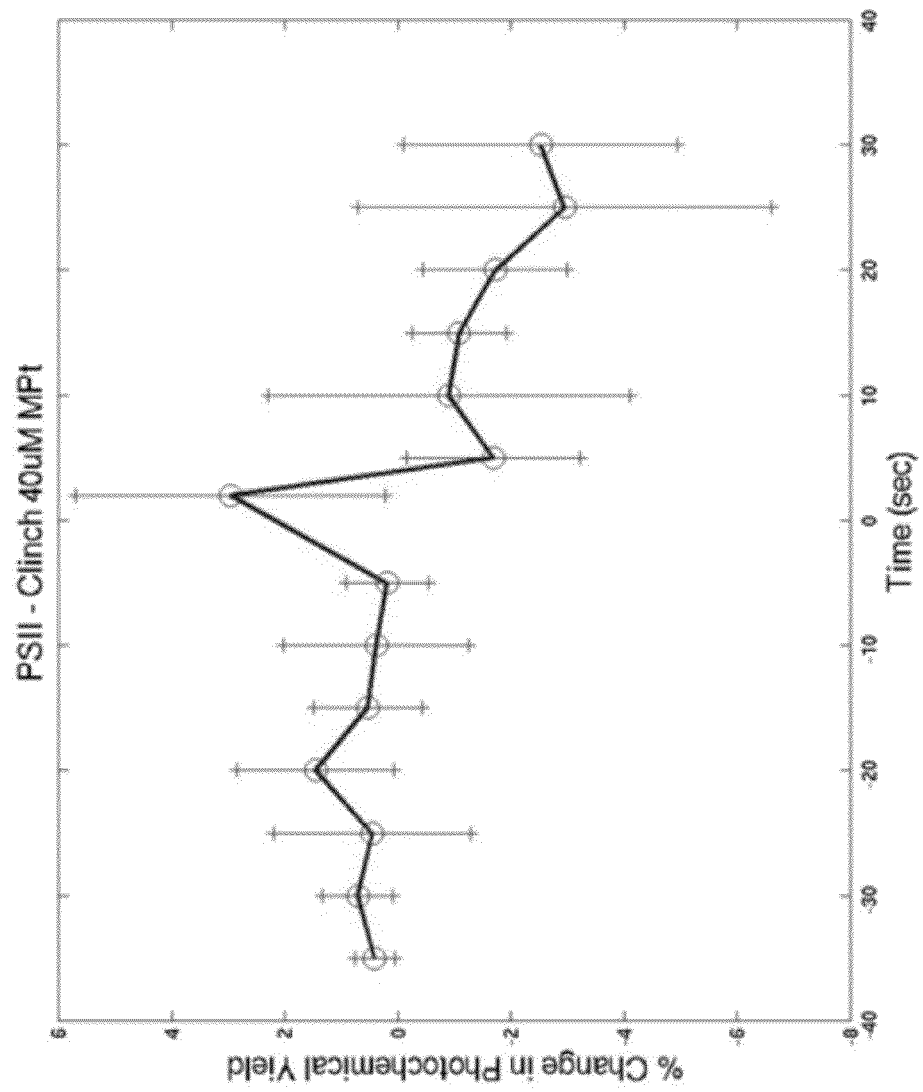
FIG. 20(a)-(h) shows the extracted features of 40 μMPt in the Clinch River samples as functions of time. The toxic agent is added into the samples at time 0.
Figure 20:
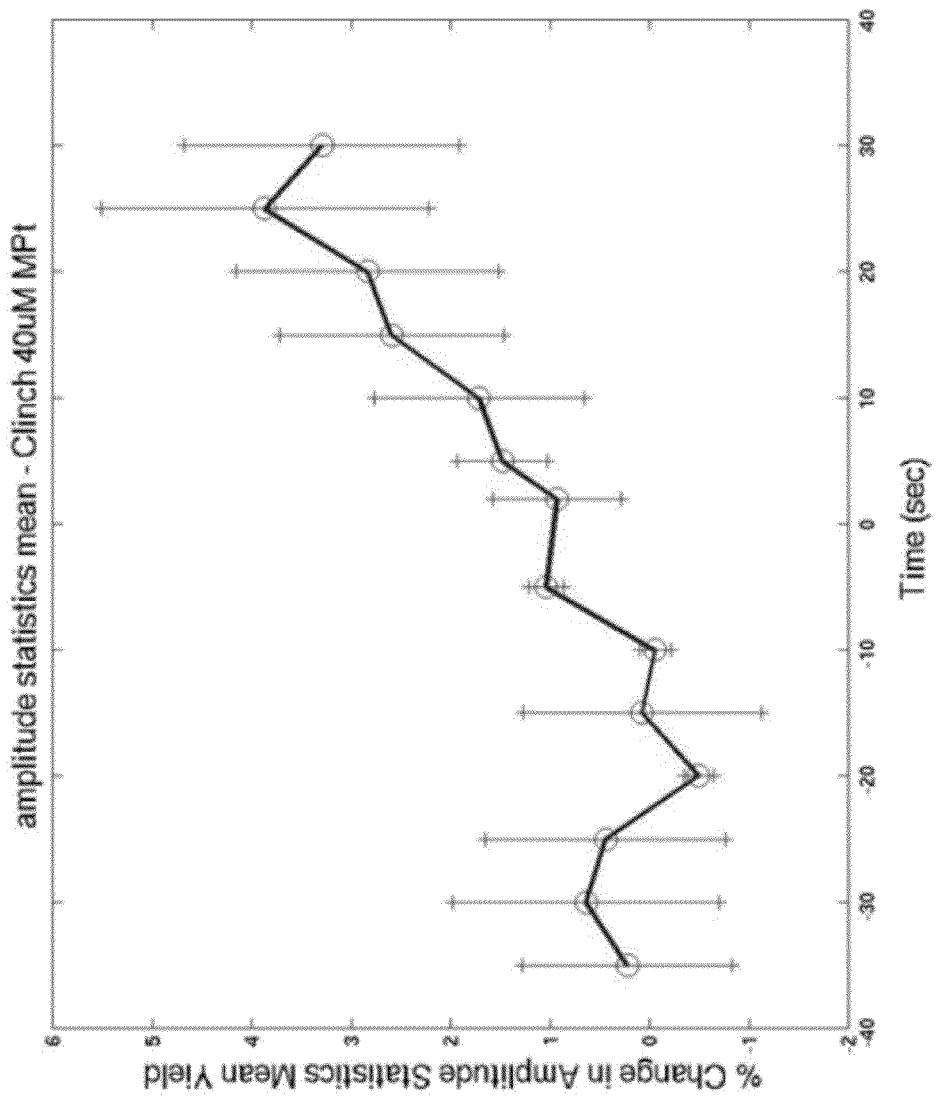
Figure 20:
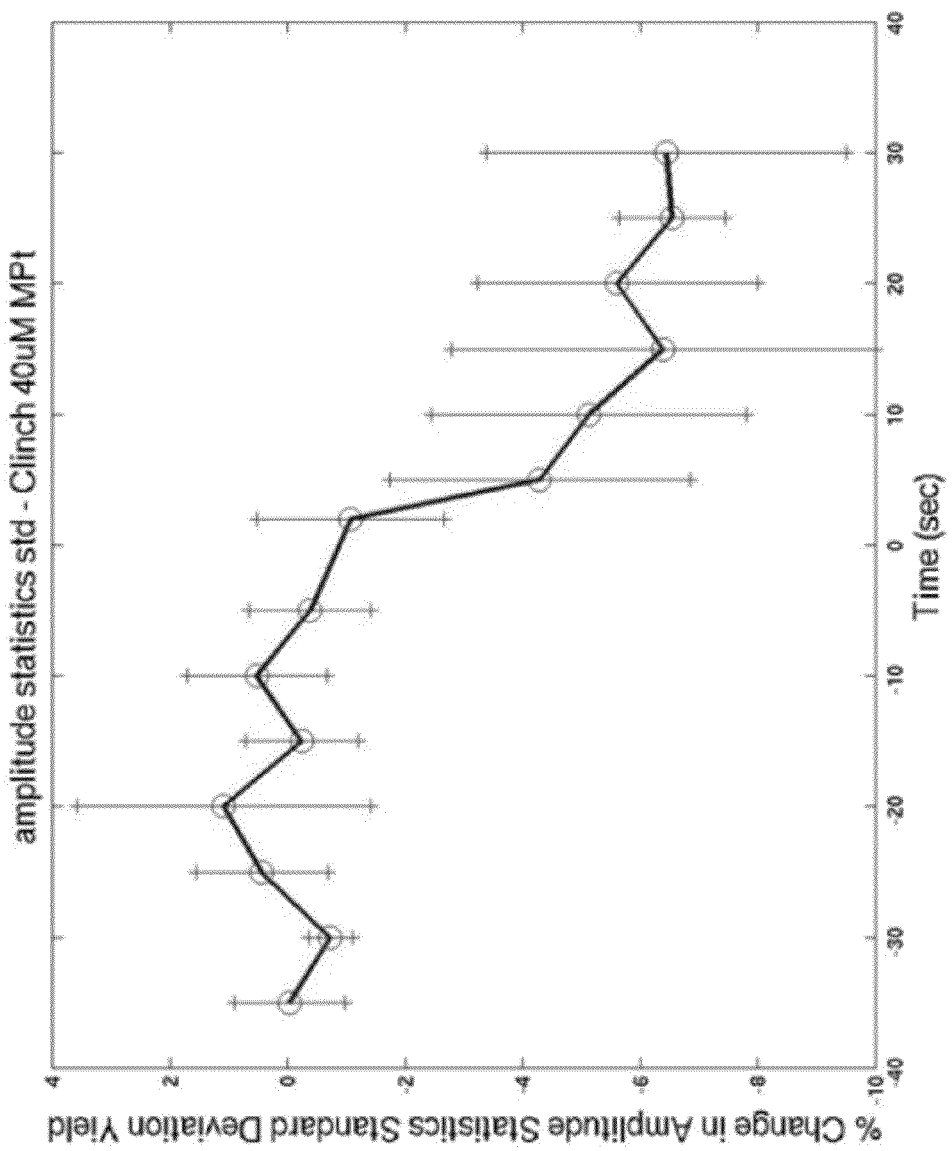
Figure 20:
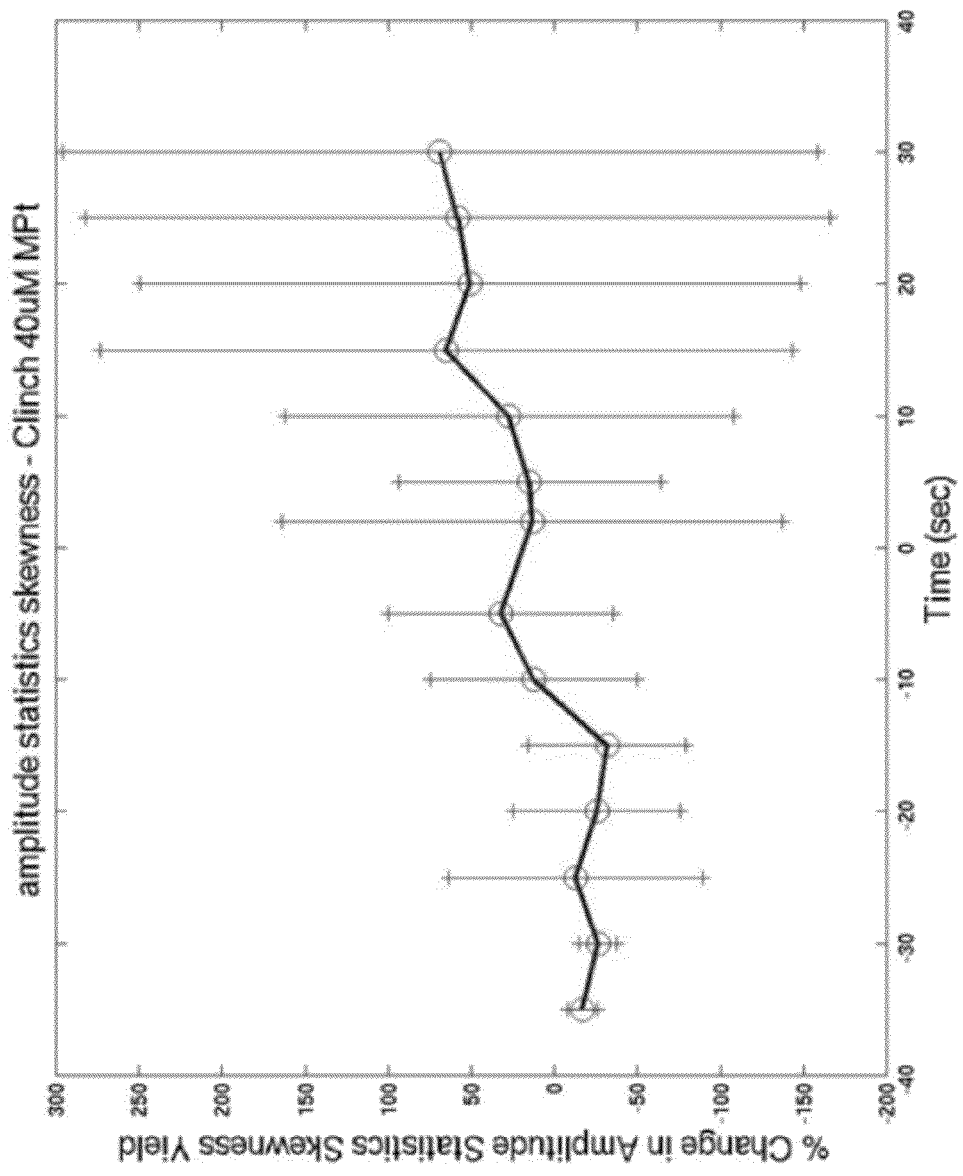
Figure 20:
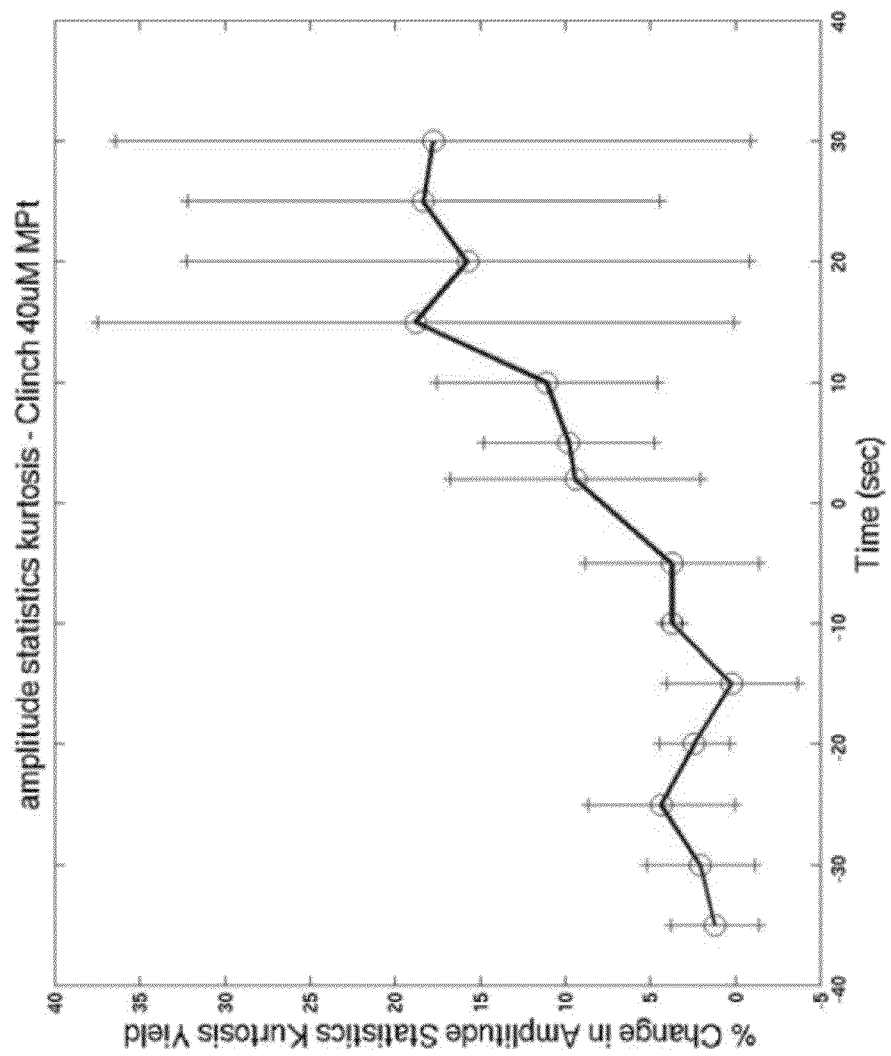
Figure 20:
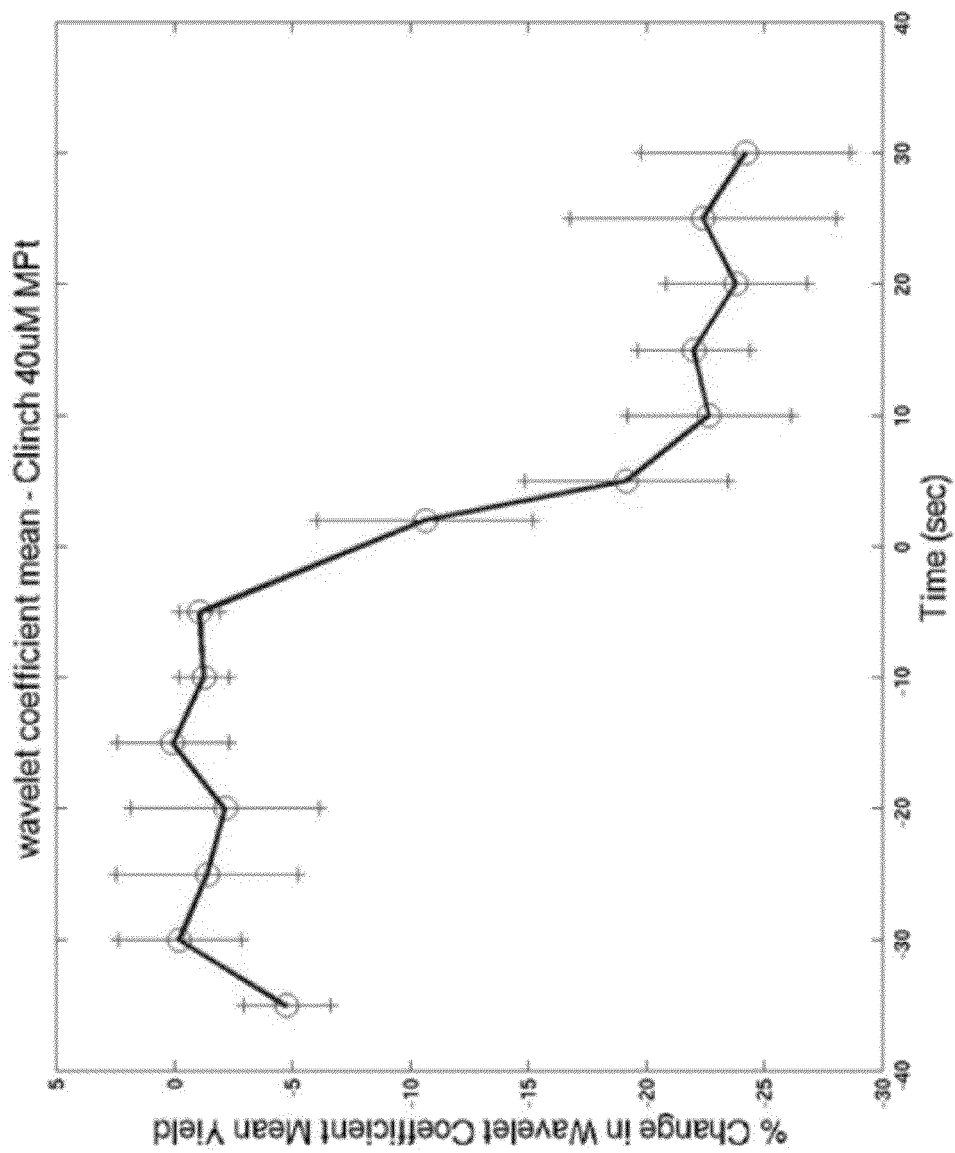
Figure 20:
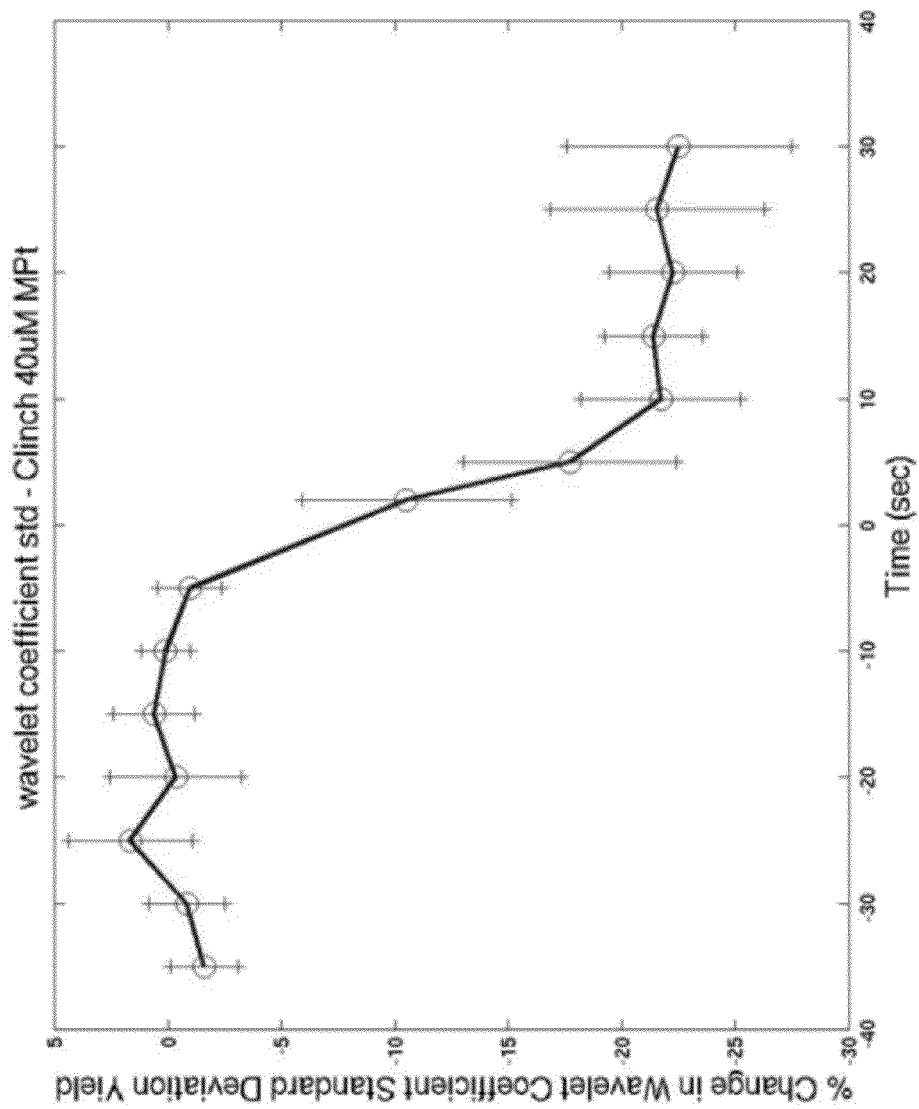
Figure 20:
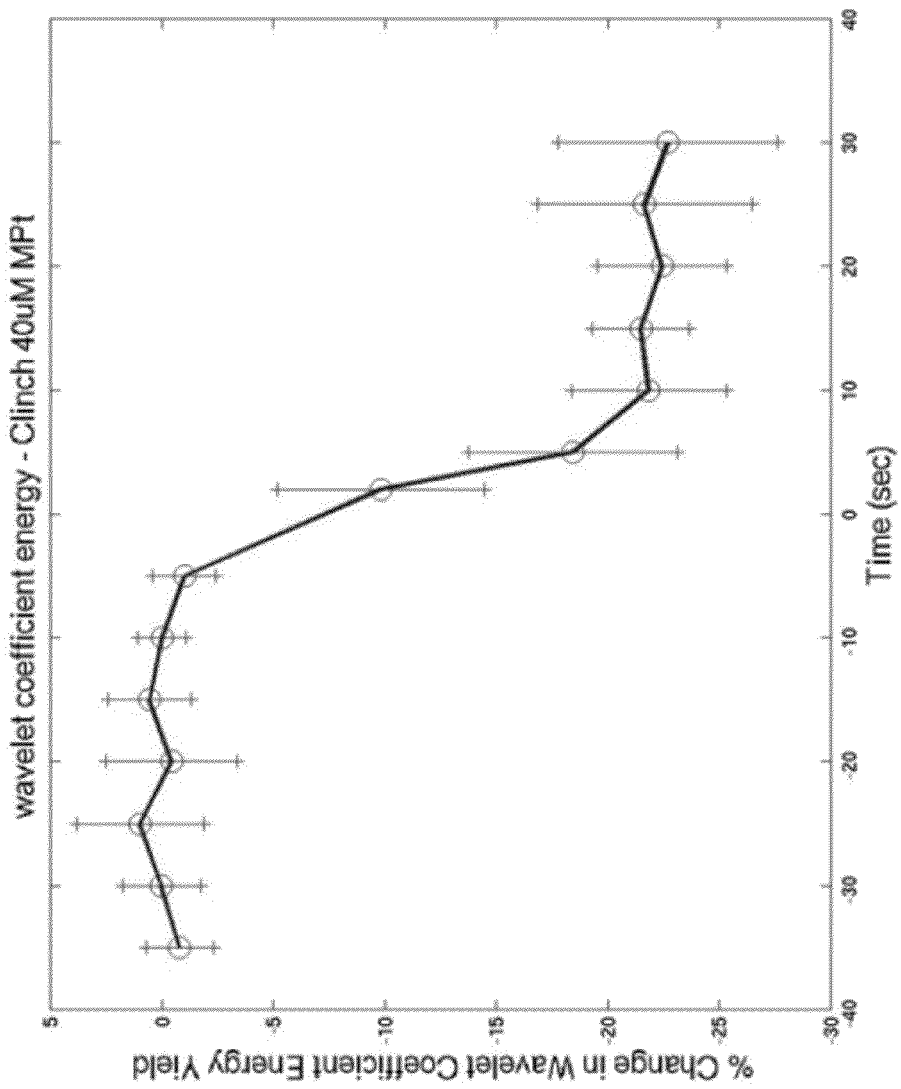
Figure 21:
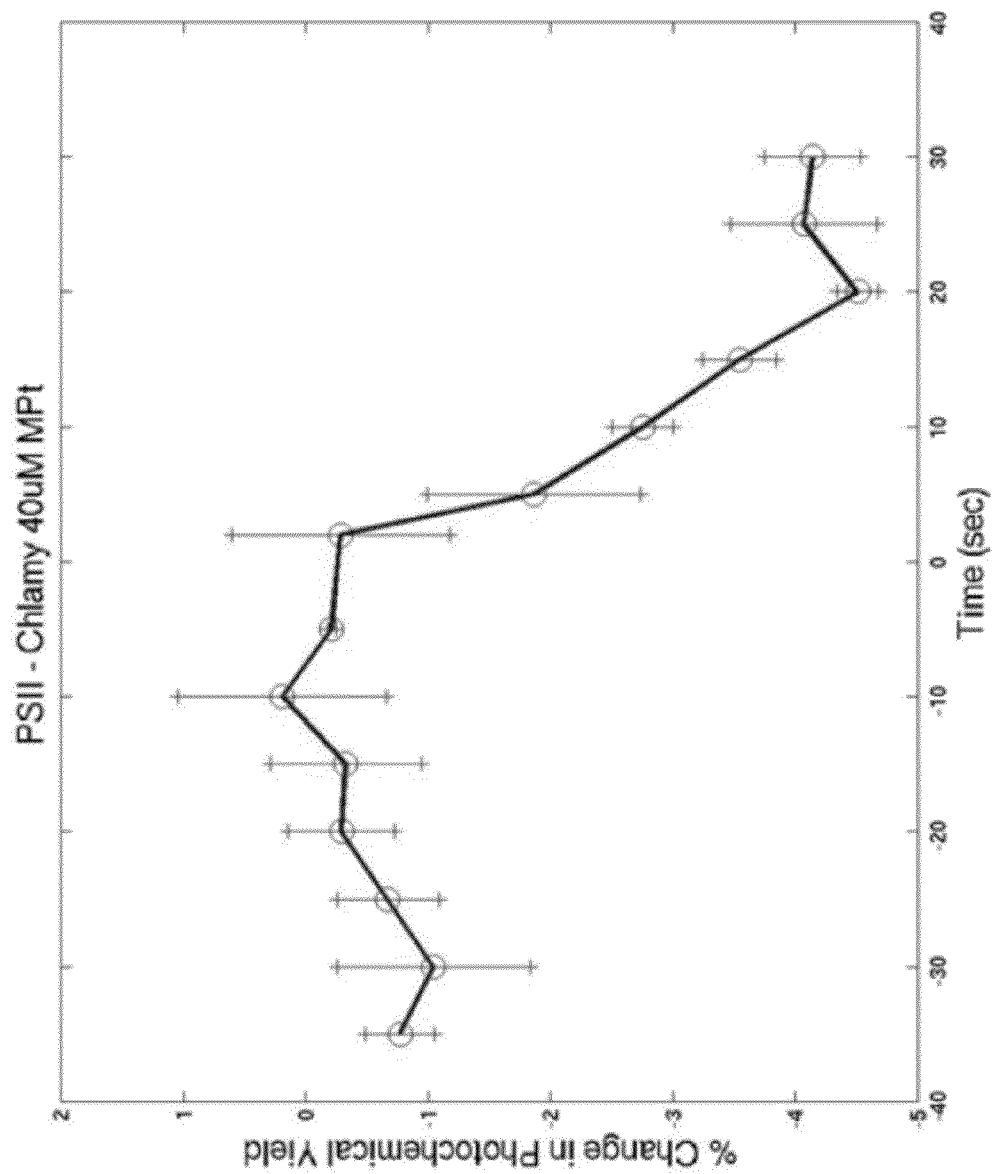
FIG. 21(a)-(h) shows the extracted features of 40 μMPt in the *Chlamydonomas* samples as functions of time. The toxic agent is added into the samples at time 0.
Figure 21:
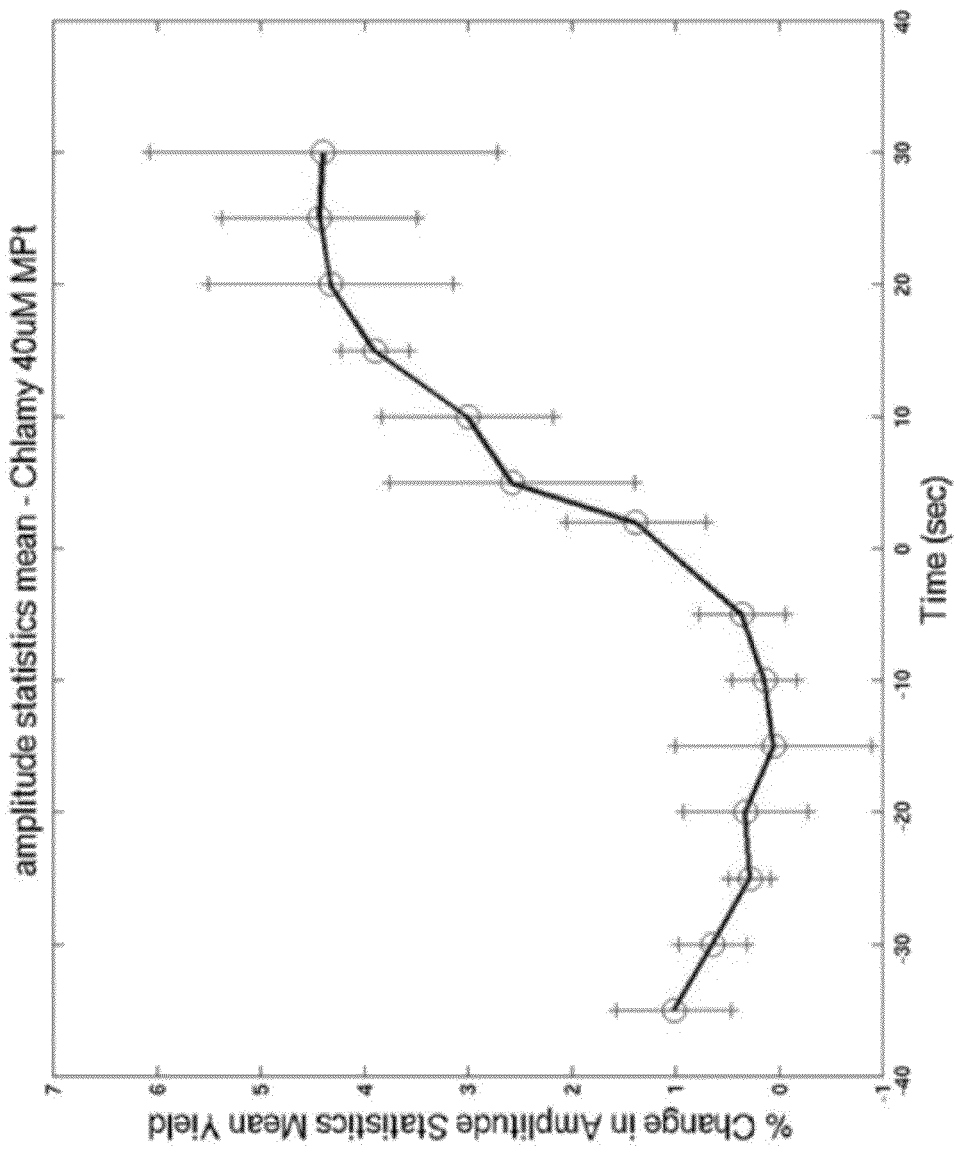
Figure 21:
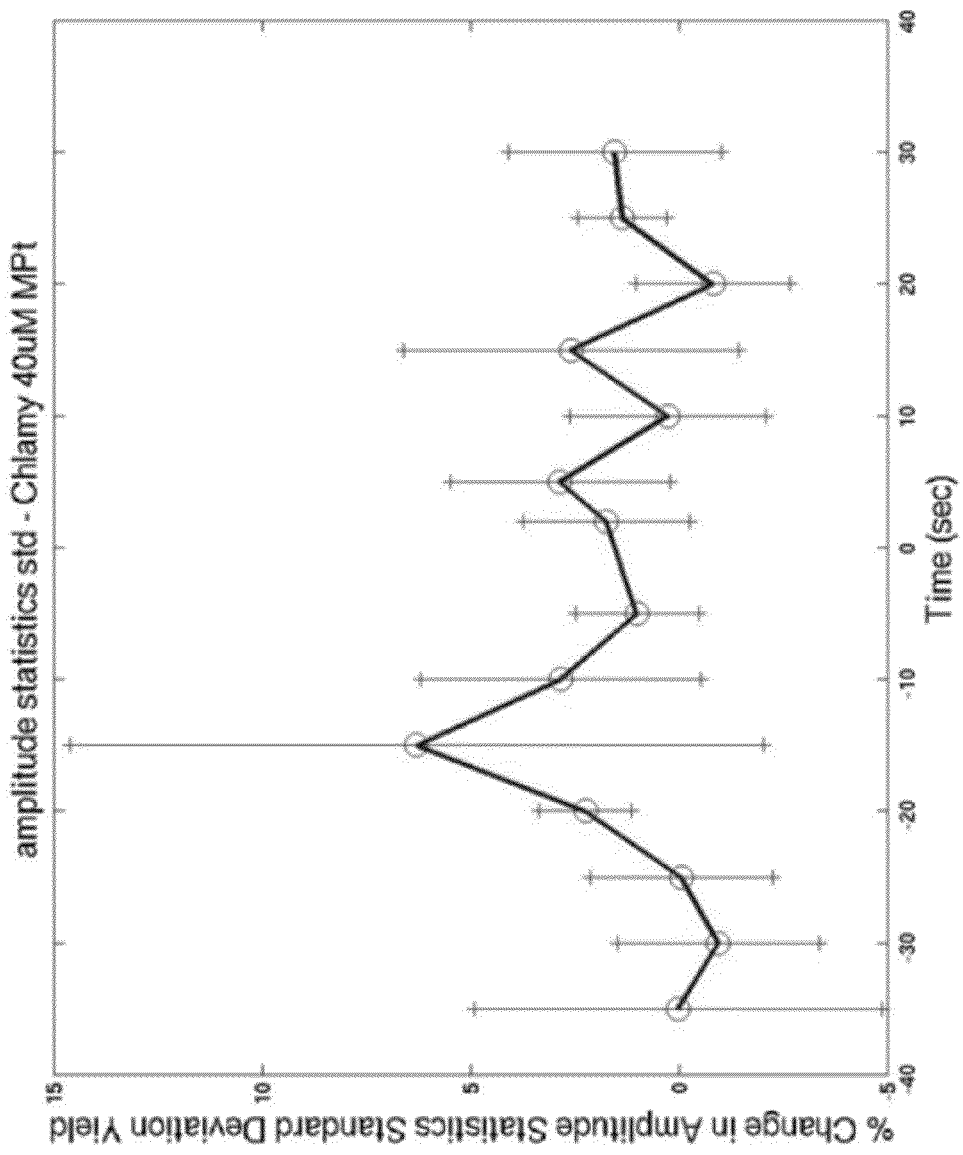
Figure 21:
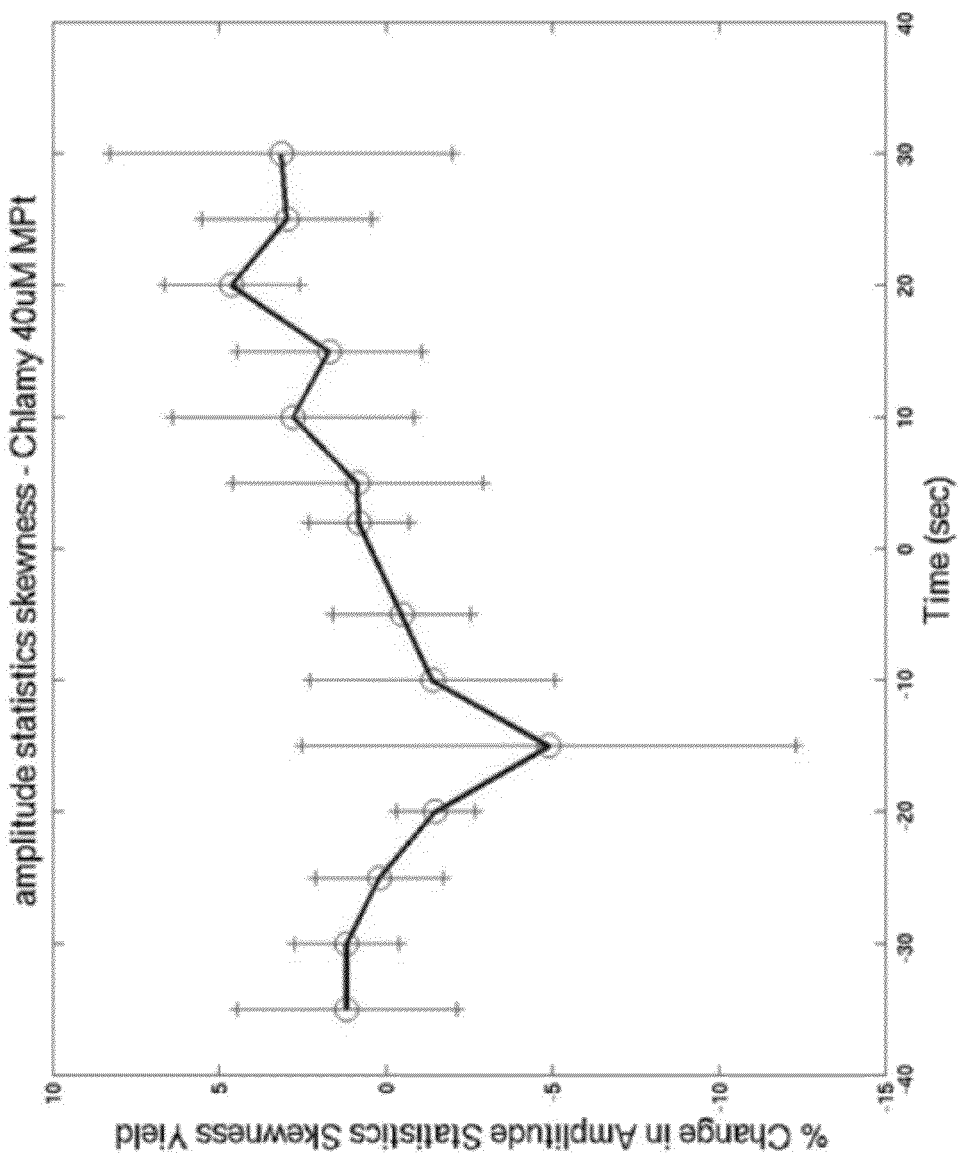
Figure 21:
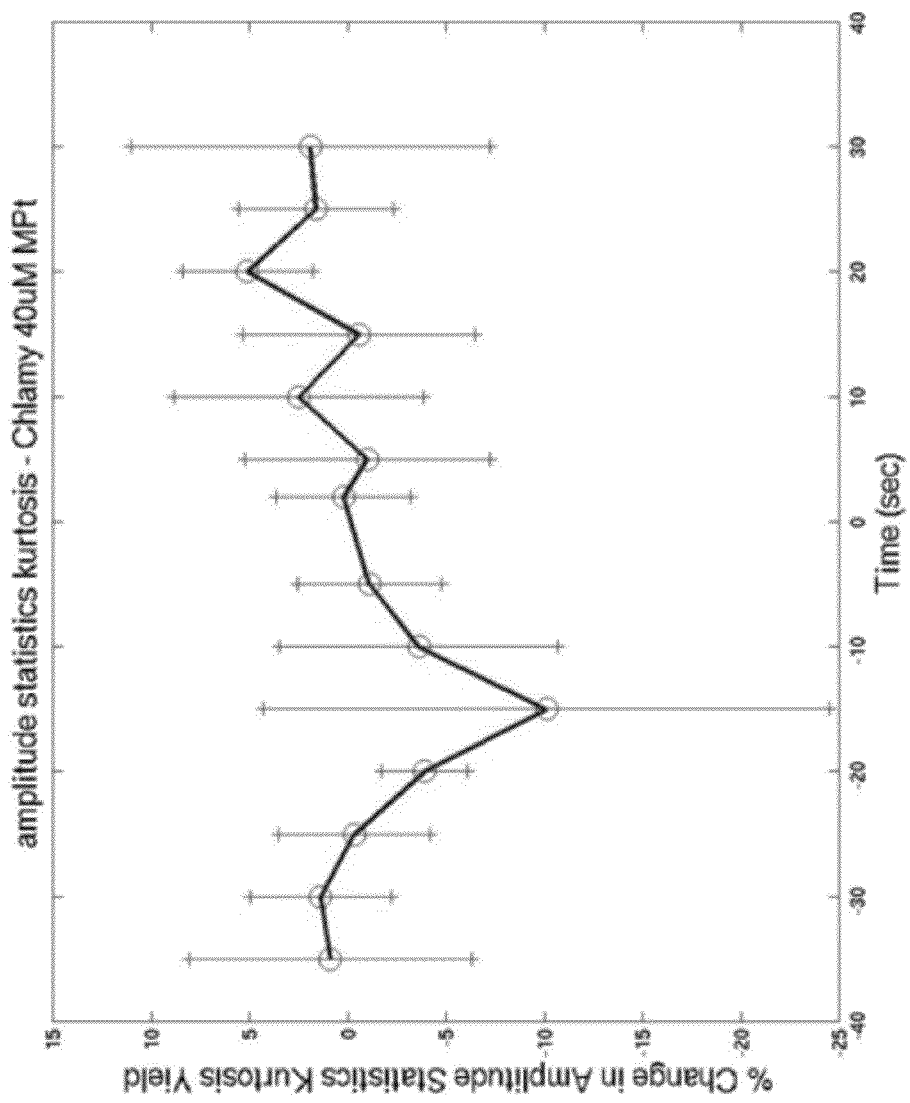
Figure 21:
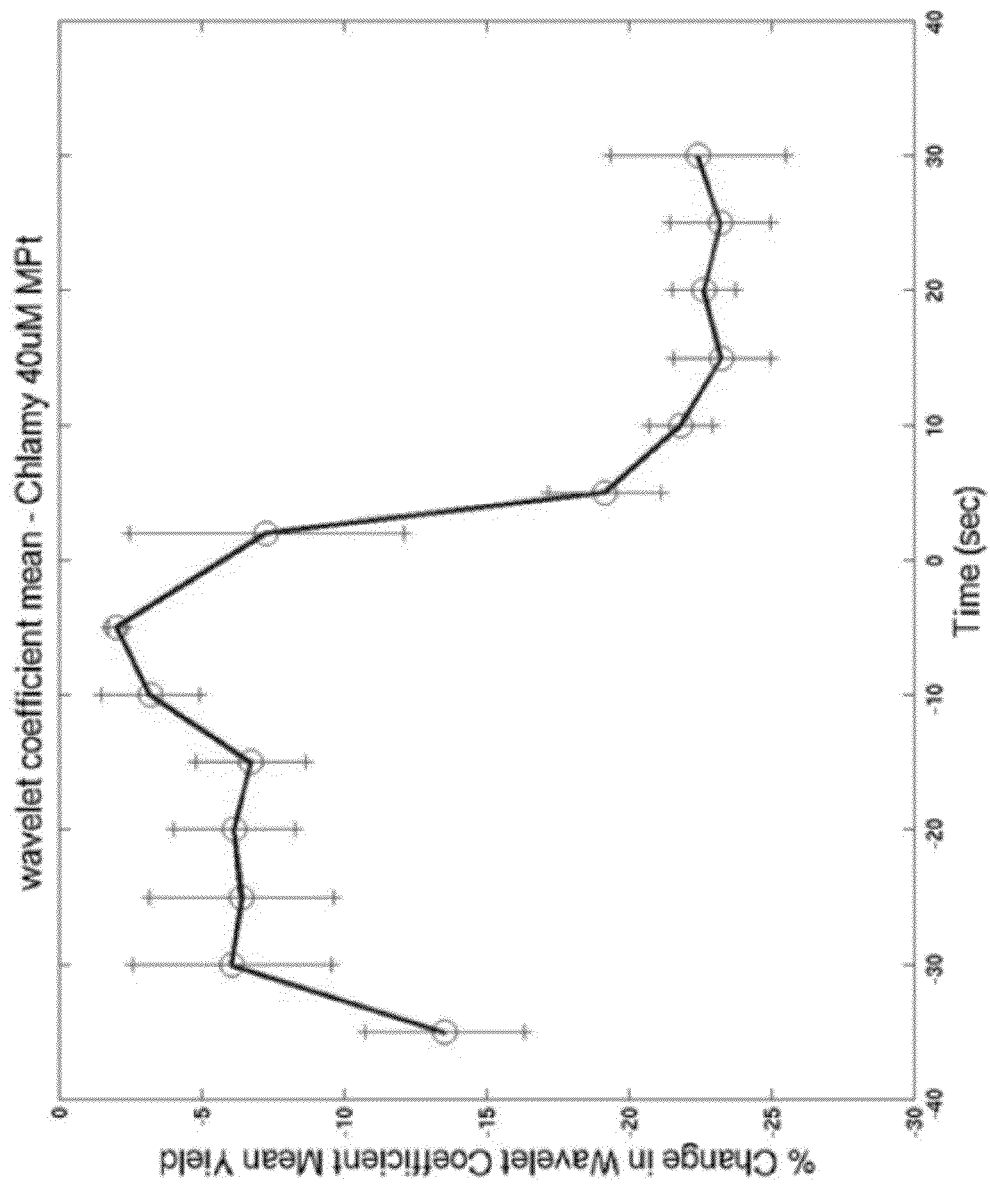
Figure 21:
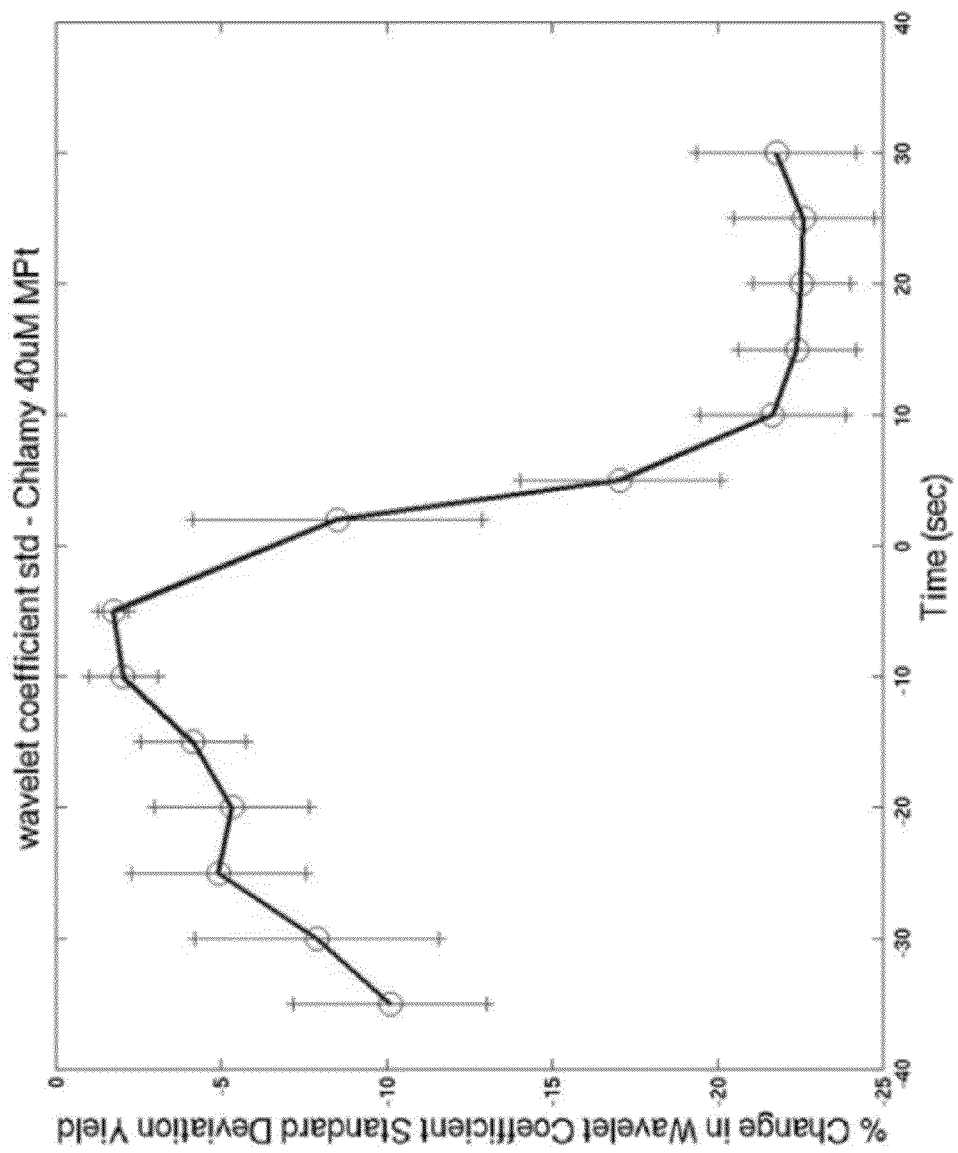
Figure 21:
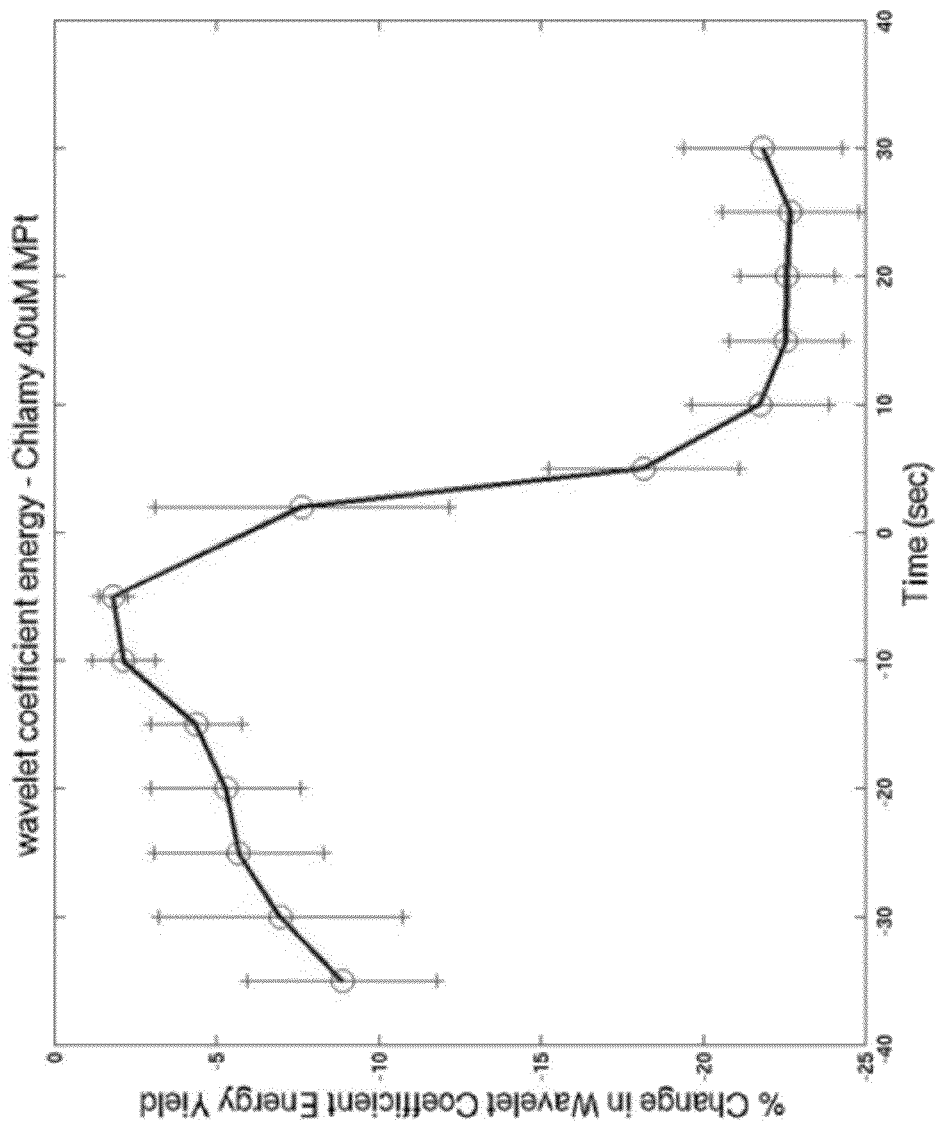
Figure 22:
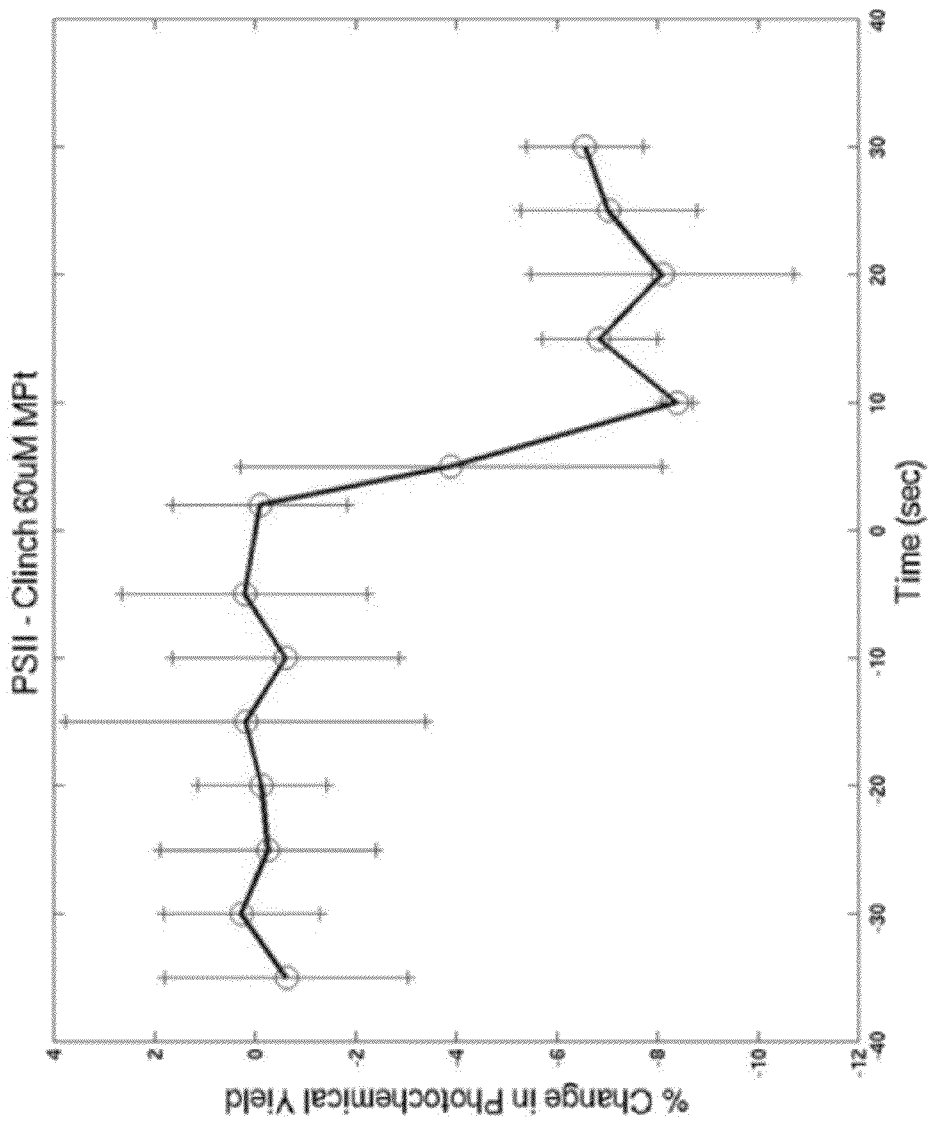
FIG. 22(a)-(h) shows the extracted features of 60 μMPt in the Clinch River samples as functions of time. The toxic agent is added into the samples at time 0.
Figure 22:
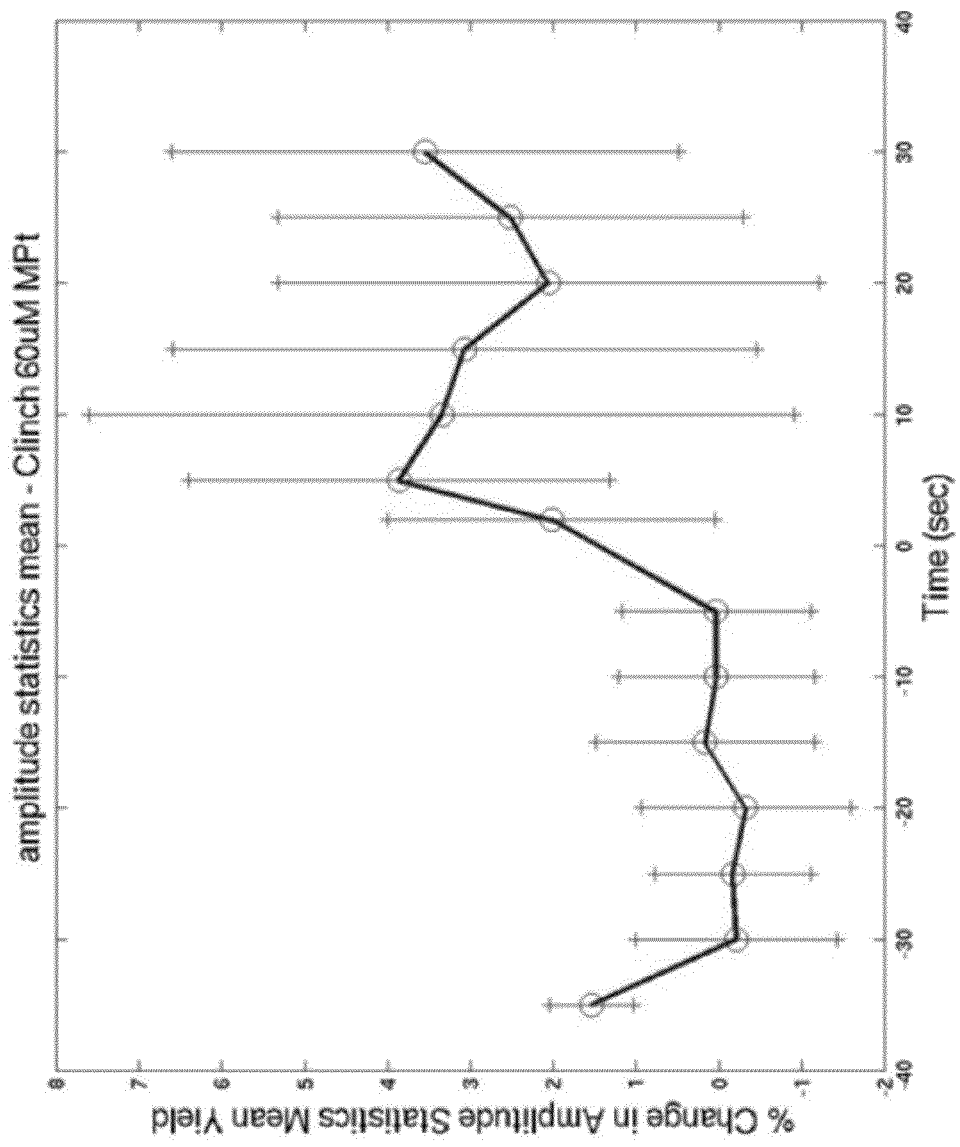
Figure 22:
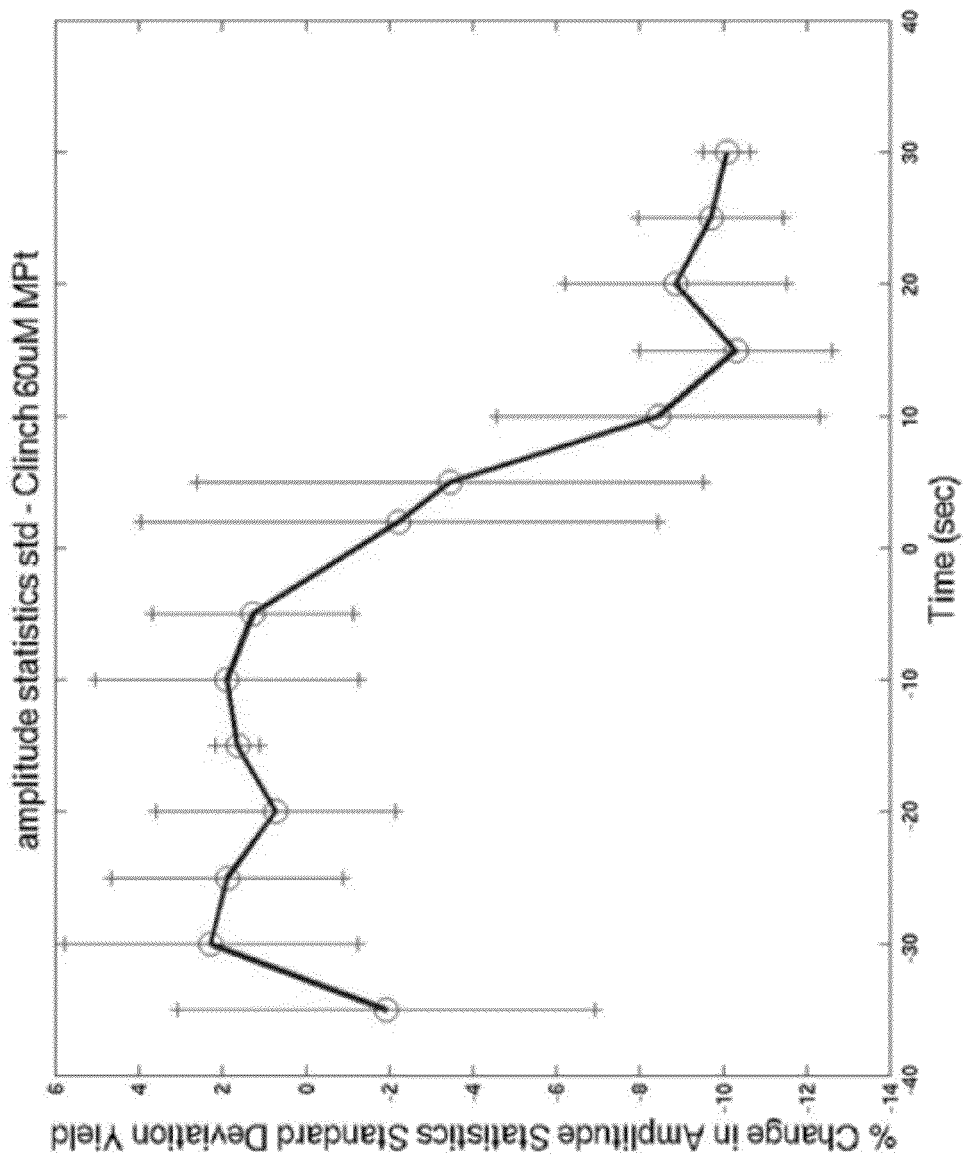
Figure 22:
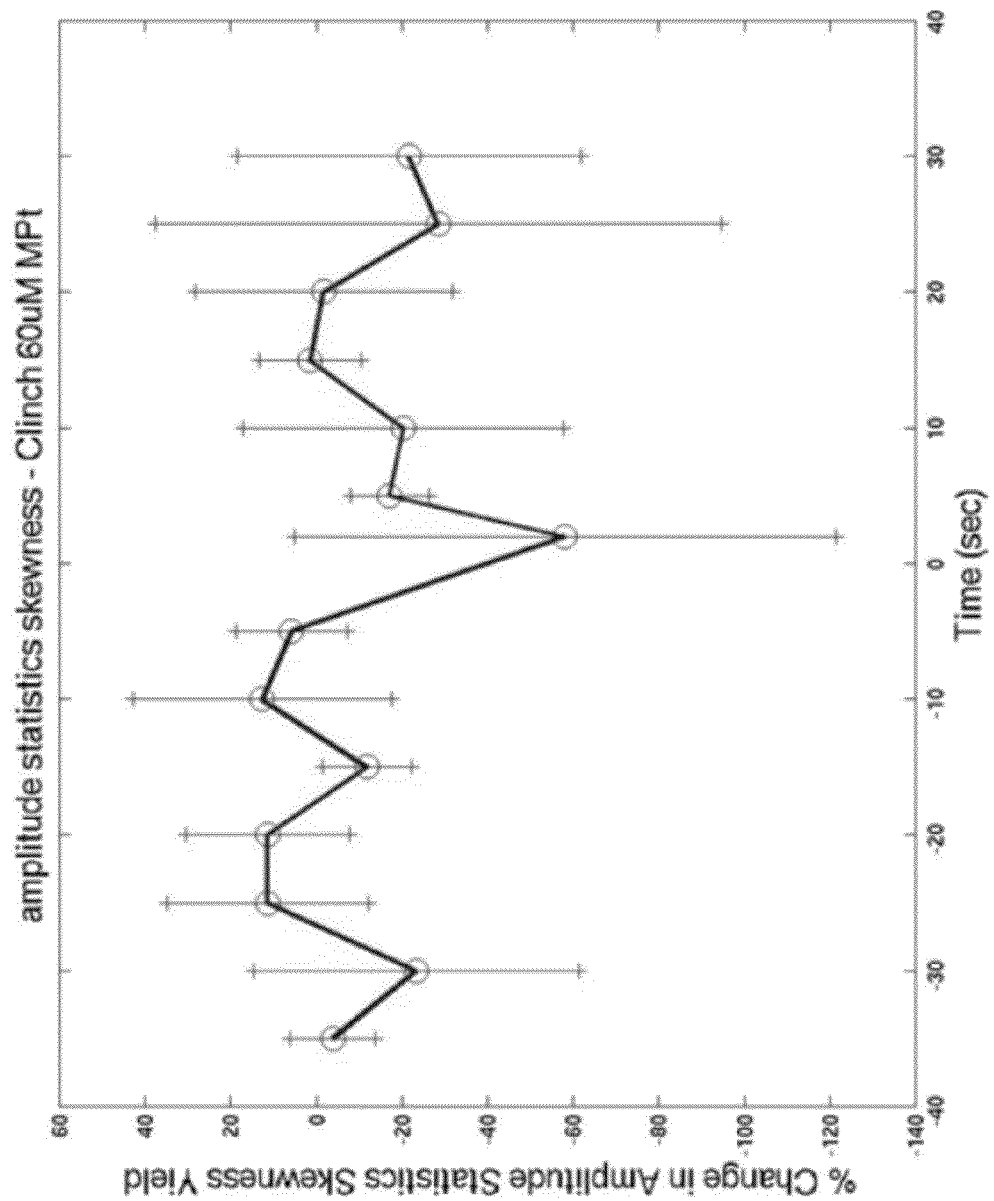
Figure 22:
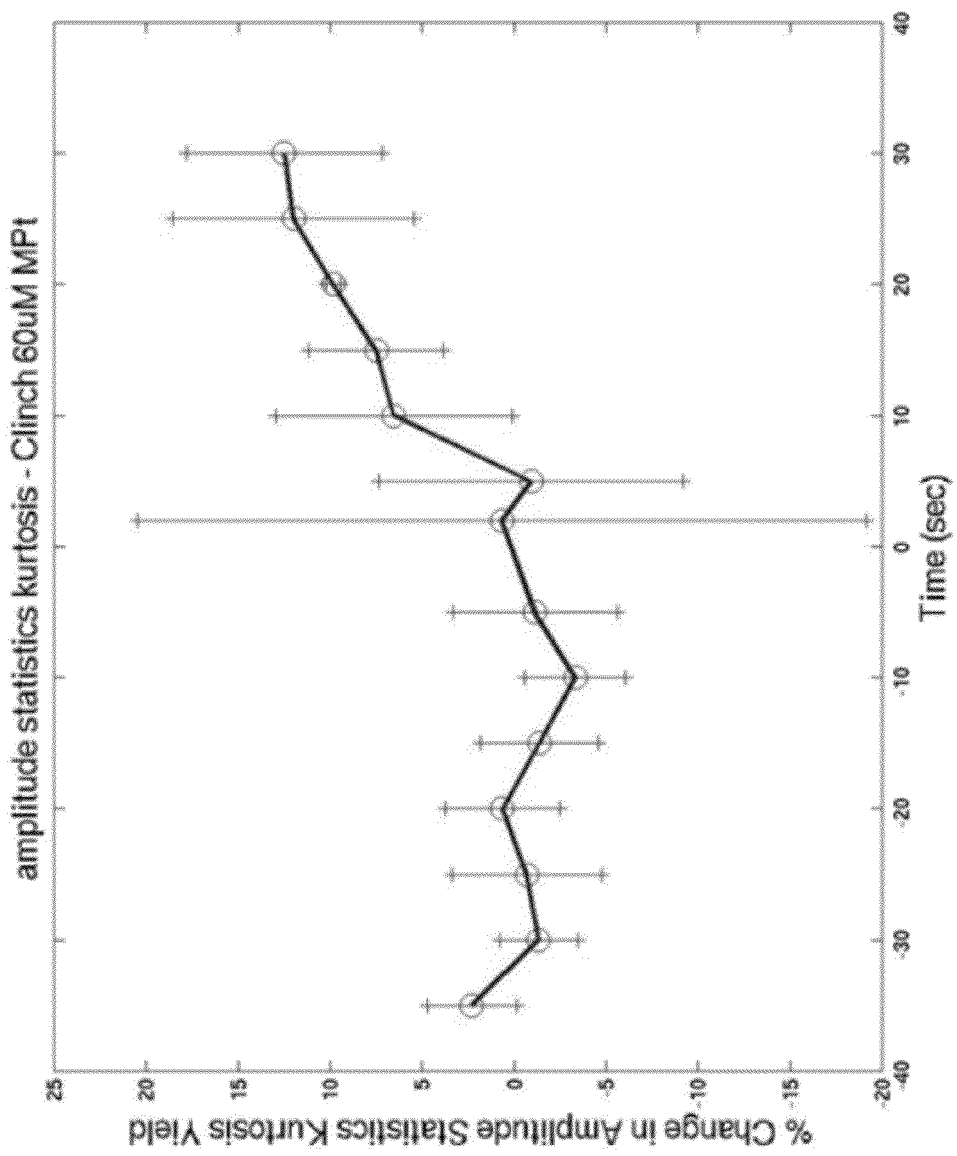
Figure 22:
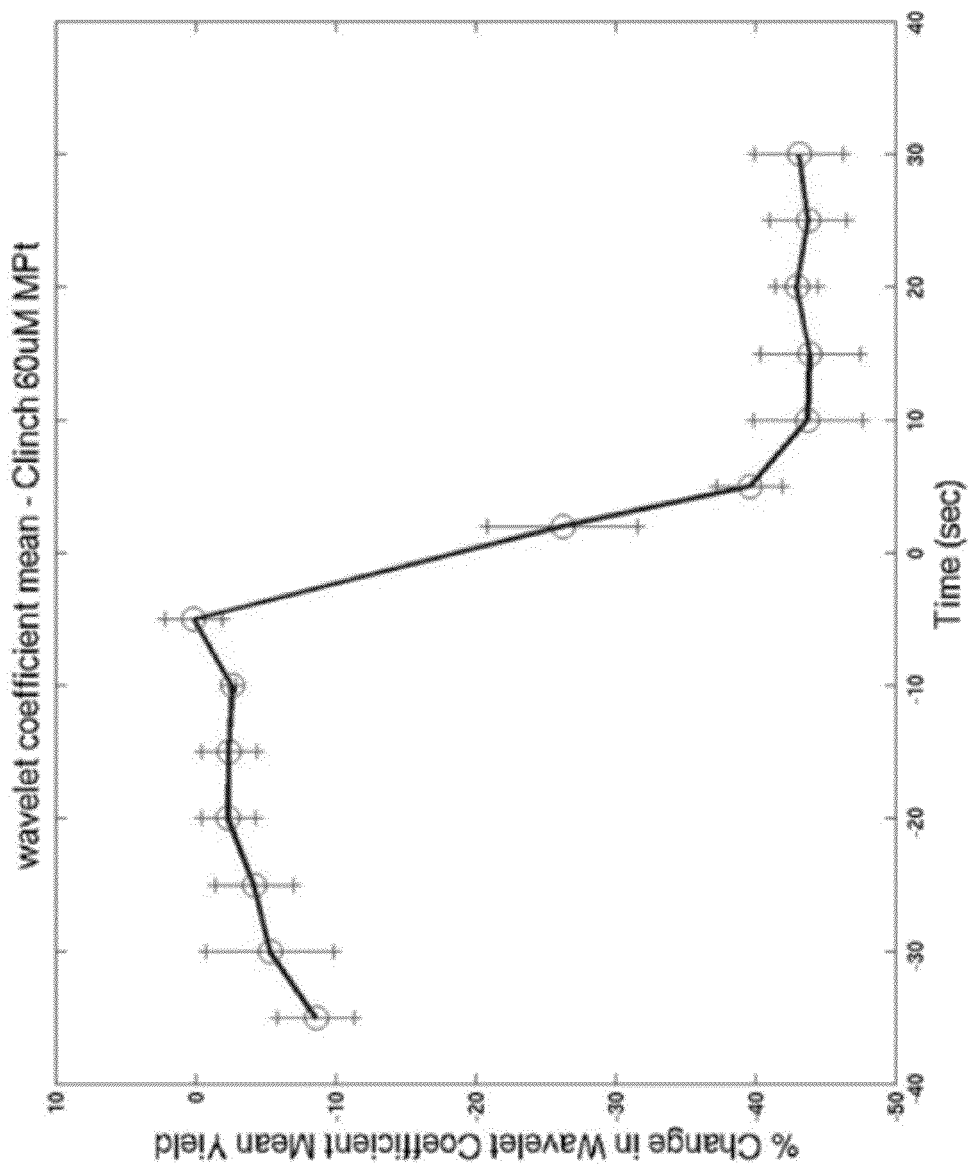
Figure 22:
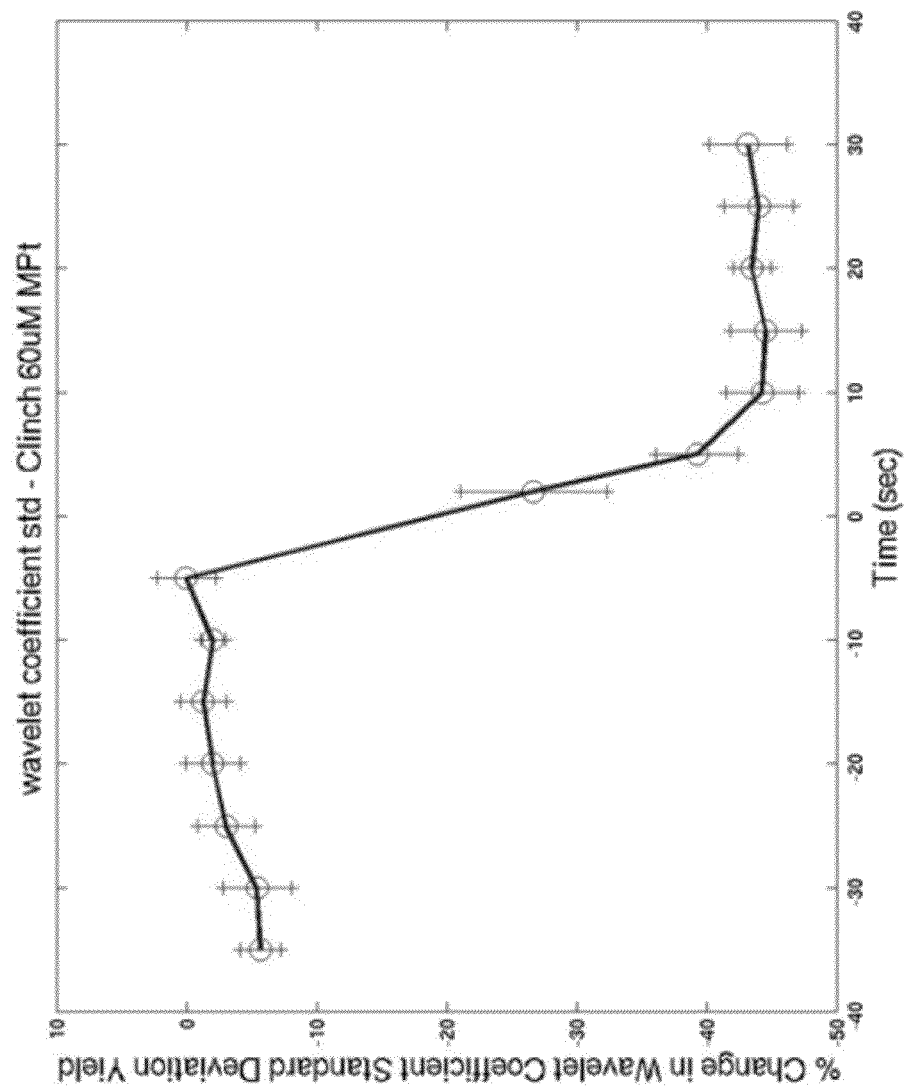
Figure 22:
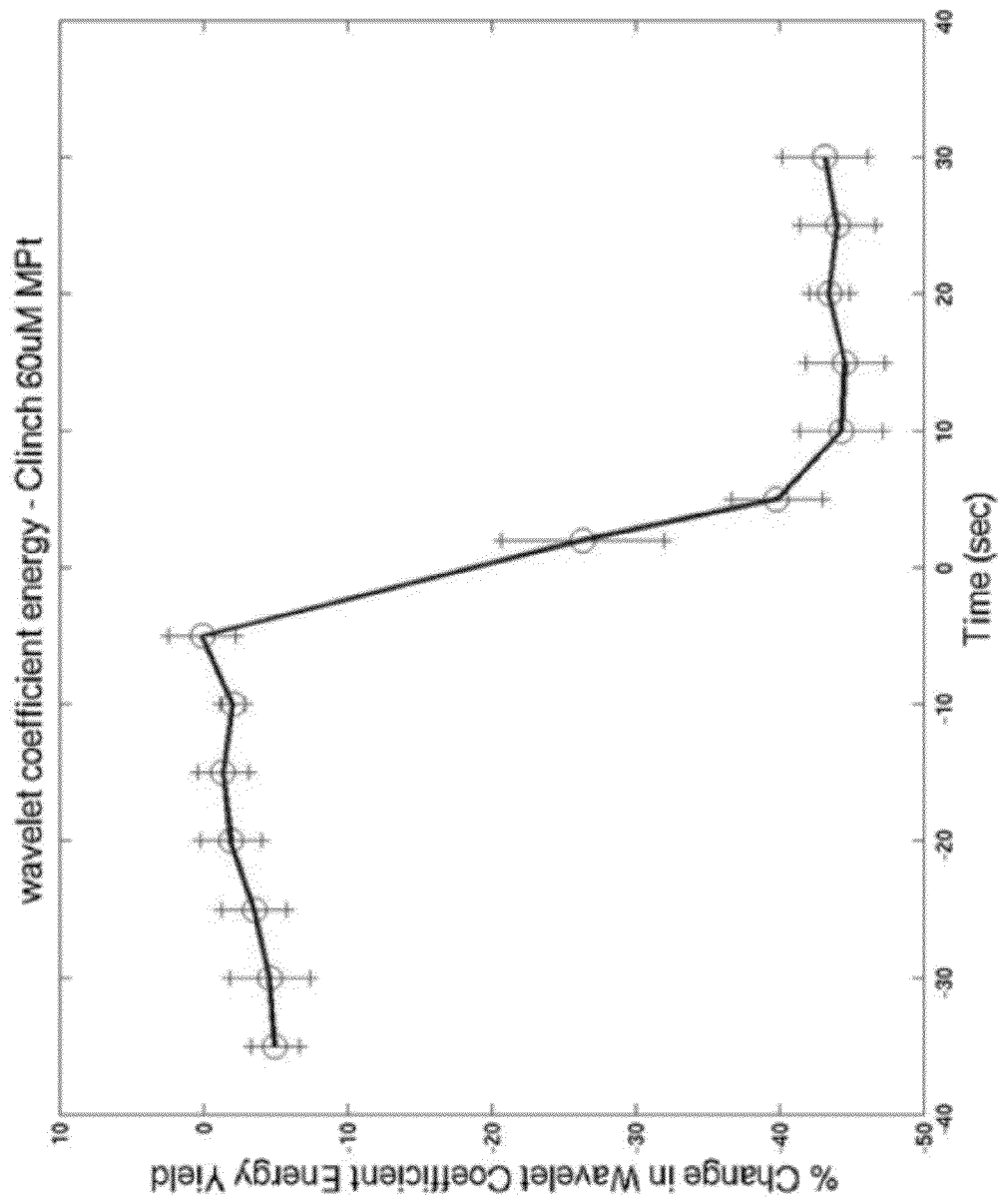
Figure 23:
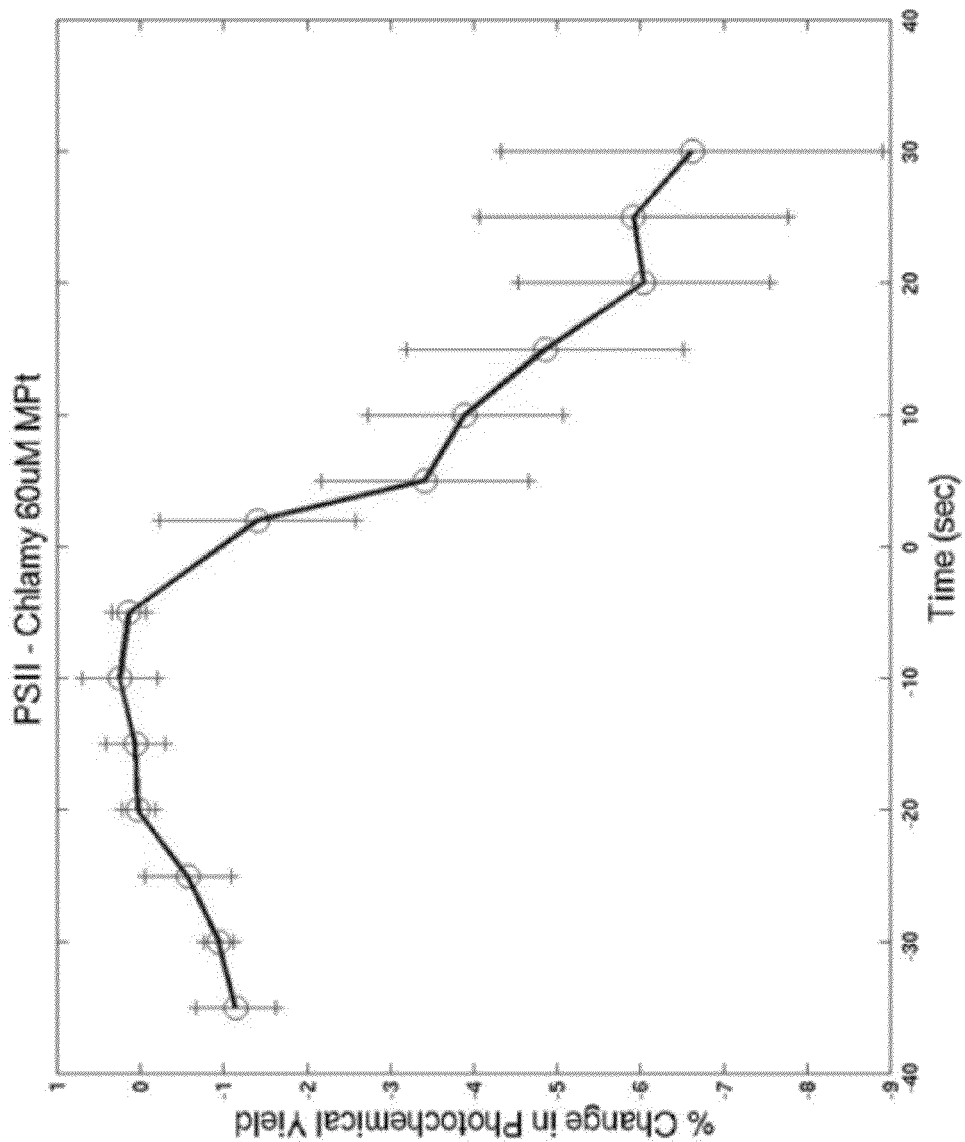
FIG. 23(a)-(h) shows the extracted features of 60 μMPt in the *Chlamydonomas* samples as functions of time. The toxic agent is added into the samples at time 0.
Figure 23:
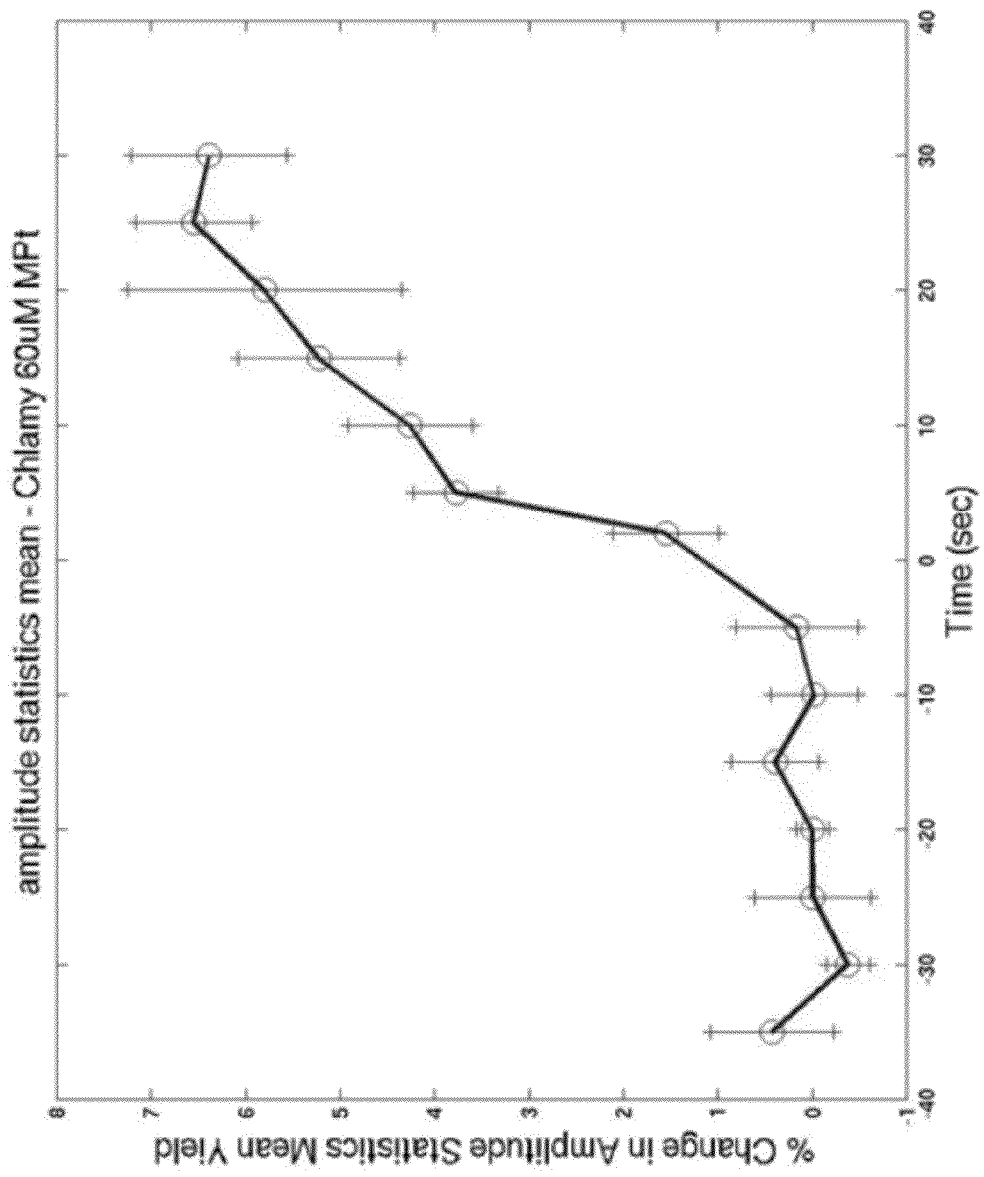
Figure 23:
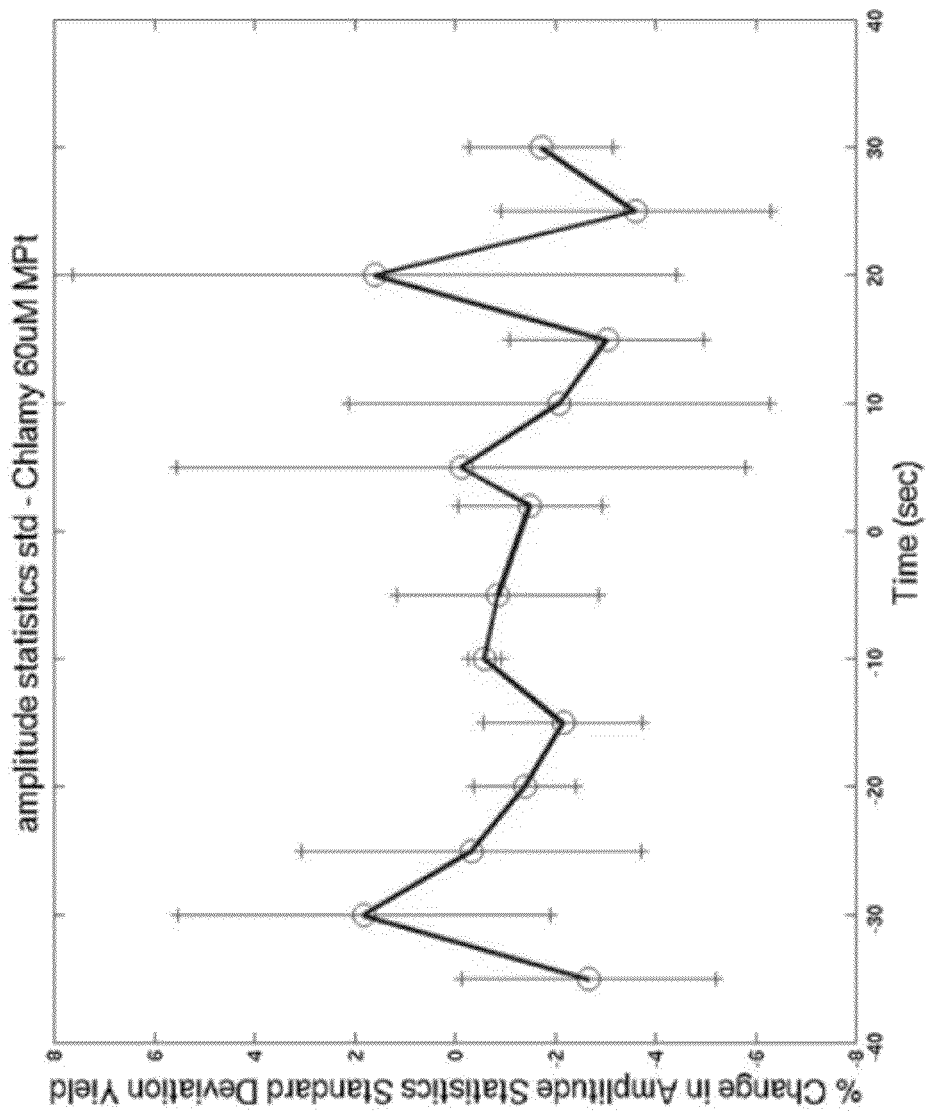
Figure 23:
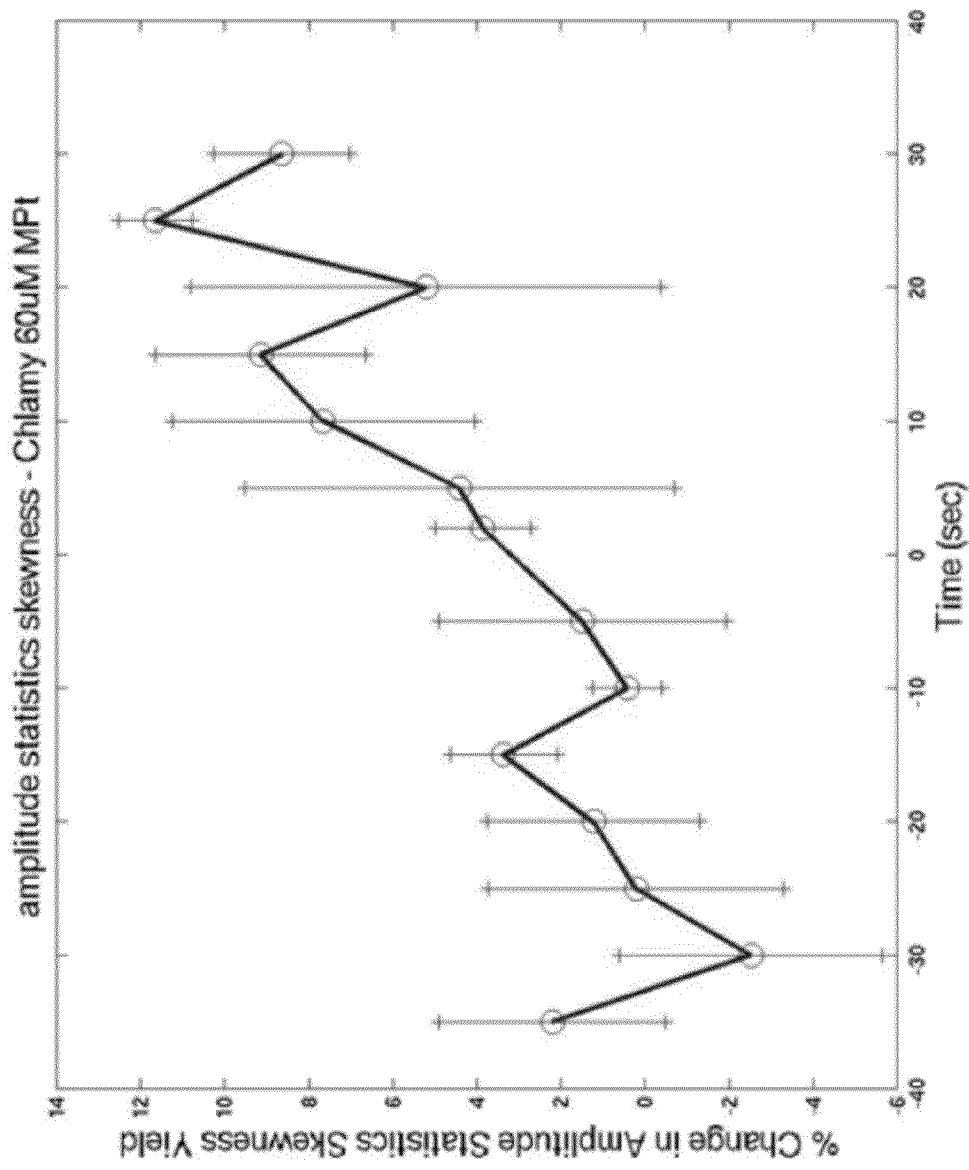
Figure 23:
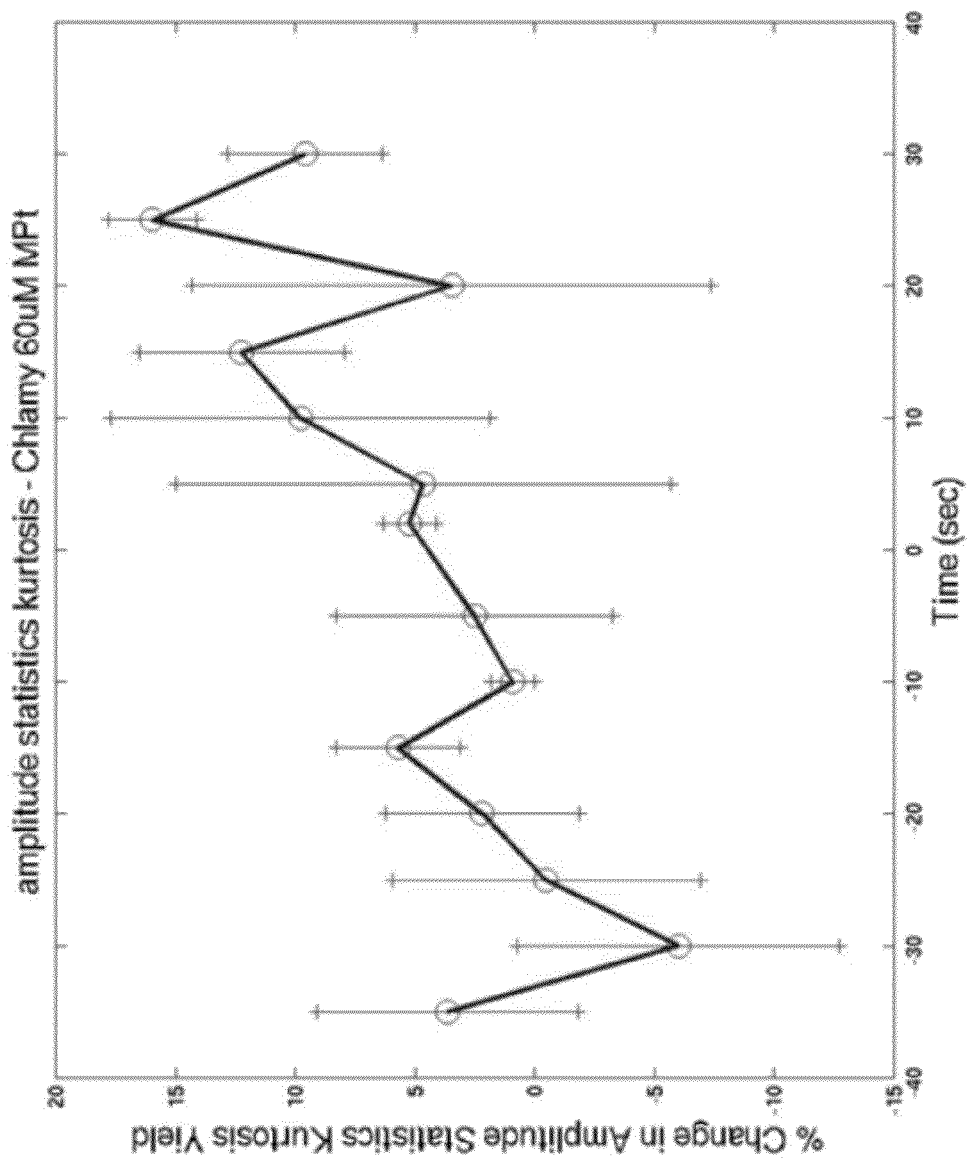
Figure 23:
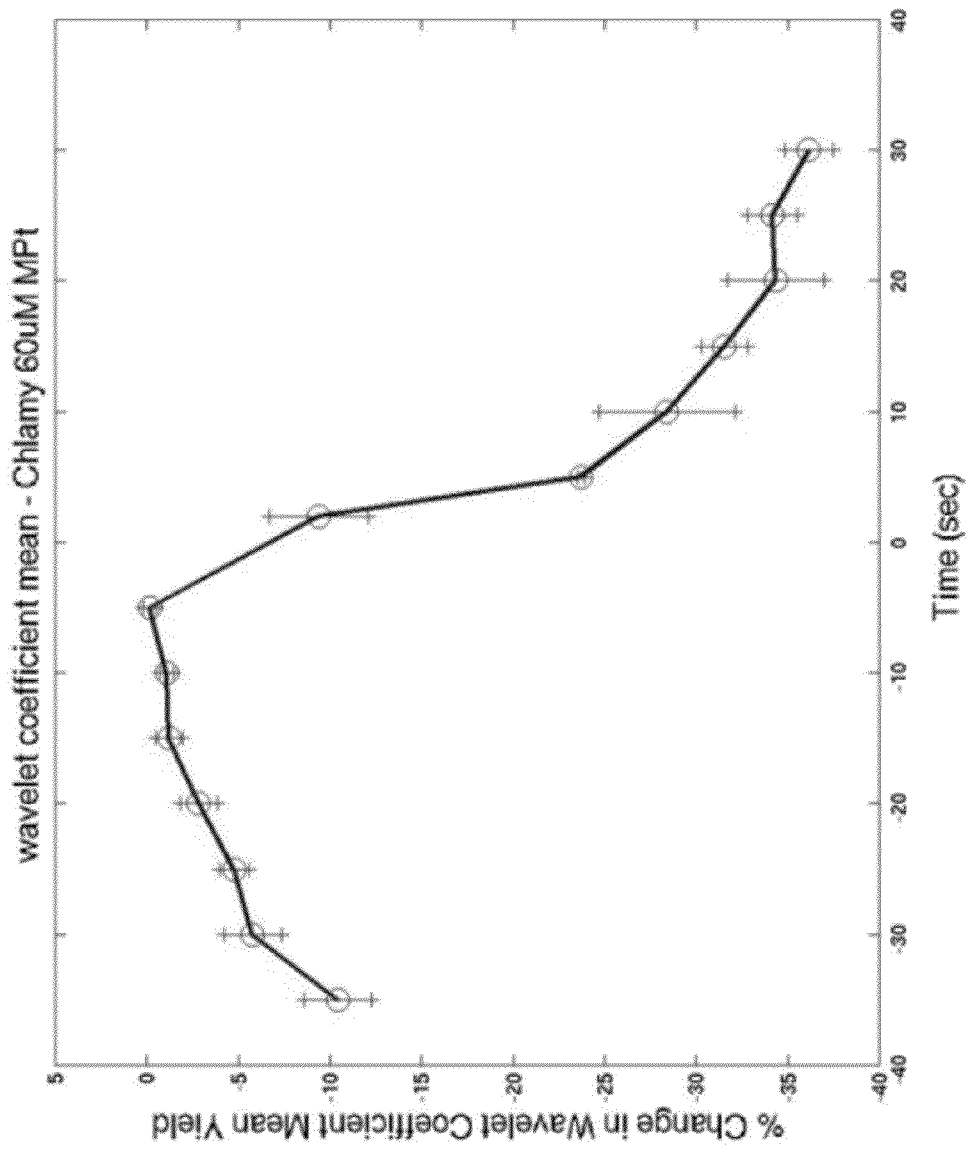
Figure 23:
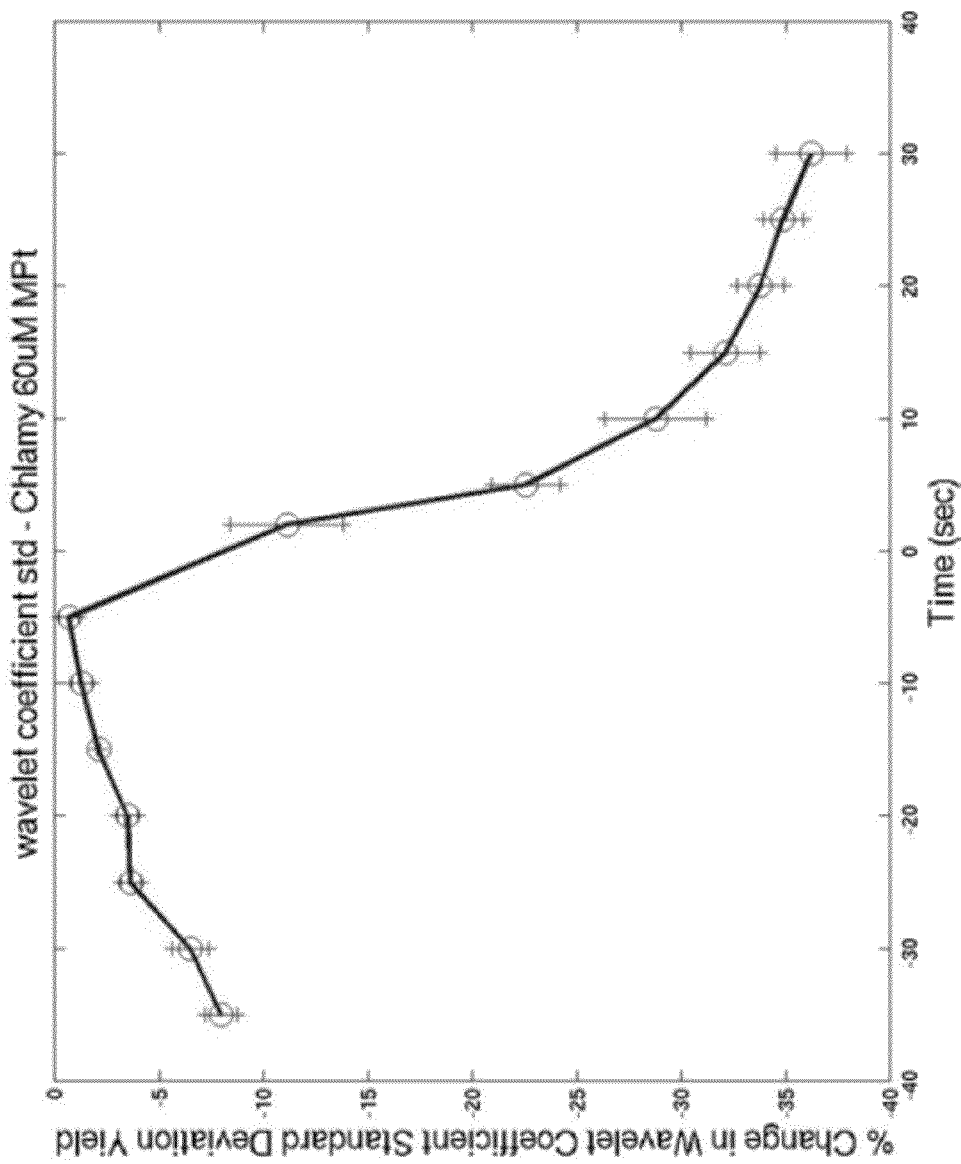
Figure 23:
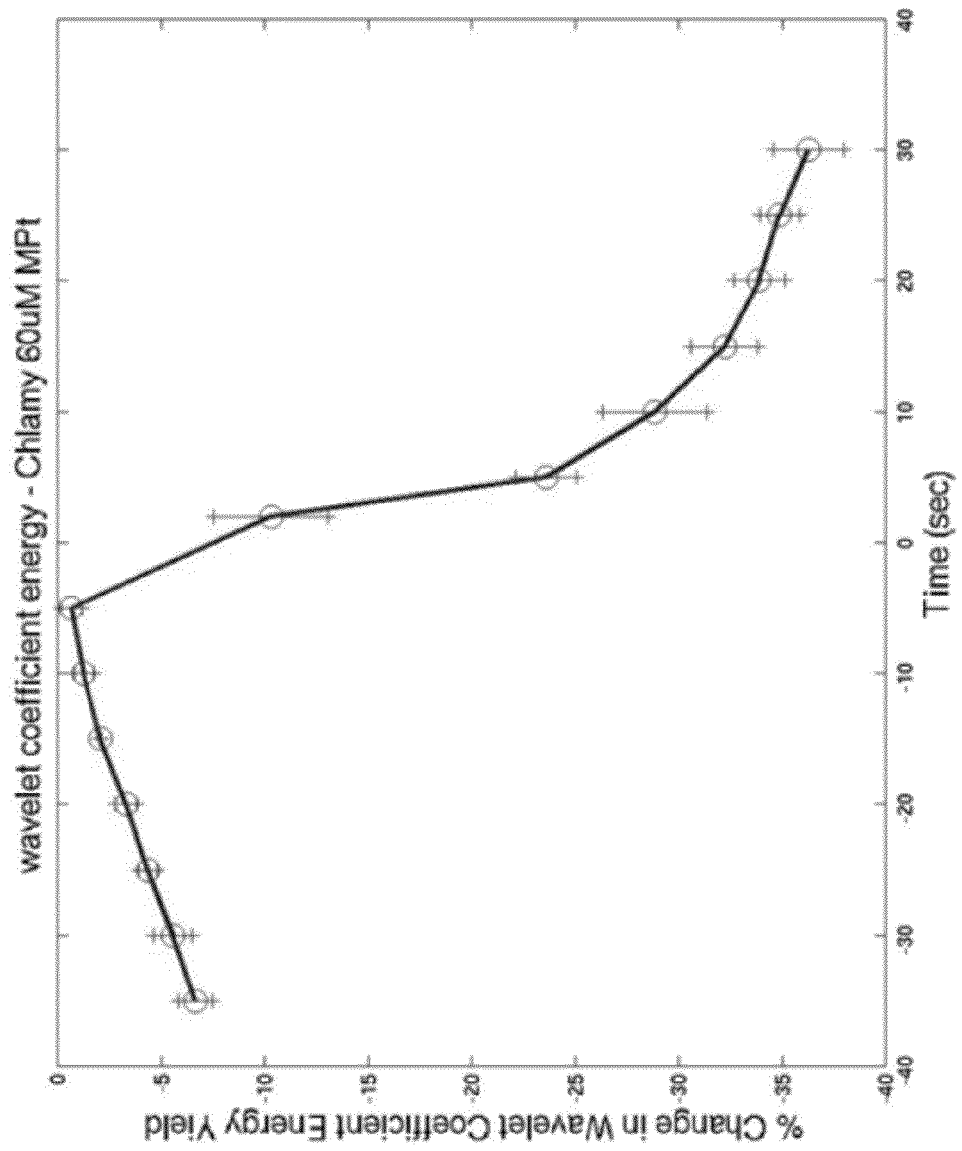

An automated biosensor system 10 for carrying out the method of present invention is shown schematically in FIG. 11. A fluorometer 12 is attached to a cell 14 so that a cell window 16 faces the fluorometer input 18. The cell has an inlet 20 having an optional particulate filter 36 and an outlet 26 for passing water therethrough. A pump 24 draws water from the outlet 26 and expels same through an exit 28. The cell 14 could have a displacement pump which draws water into the cell and expels same through a common inlet/outlet opening (analogous to 20), obviating outlet 26 and exit 28. Any means for introducing water into the cell and discharging water from the cell is suitable for carrying out the present invention.

The fluorometer 12 must be of sufficient sensitivity for measuring photosynthetic activity of naturally-occurring, free-living, indigenous photosynthetic organisms drawn into the cell 14 with sample water. Applicants have used a Walz XE-PAM pulse-amplitude-modulation fluorometer available from Heinz Walz GmbH•Eichenring 6•D-91090 Effeltrich•GERMANY Phone: +49-(0)9133/7765-0•Telefax: +49-(0)9133/5395•E-Mail: info@mail.walz.com. The Walz XE-PAM fluorometer is described in detail at the following Internet web site: http://www.walz.com/pamzta.htm.

The fluorometer is electrically connected by a connector 32 to an electronics package 30, which includes a power supply, systems for operating the fluorometer 12 and pump 24, data processing electronics, and a transmitter that transmits a signal through an antenna 34. The electronics package 30 contains commonly used devices that are well known in the art. The particular components that are used therein, and the particular method of gathering and transmitting data are not critical to the operation of the present invention. The processor preferably implementing both amplitude statistics and a time-frequency analysis can be co-located with electronics package 30, or at a remote site having antenna 24.

Operation of the biosensor 10 can be constant sampling or intermittent sampling. Intermittent operation can be random sampling or timed sampling. The pump 24 is operated to cause water to flow through the cell 14. The fluorometer 12 is activated to measure fluorescence in the water flowing through the cell 14. In a preferred embodiment, the electronics package 30 implements a processor running both amplitude statistics and a time-frequency analysis for analyzing raw data from the fluorometer 12, and emits a signal through the antenna 34 indicating the presence and/or absence of chemical warfare agent(s) in the water, as well as the identity of the agent(s). The signal is received by equipment that indicates and/or records the data.

EXAMPLES

It should be understood that the Examples described below are provided for illustrative purposes only and do not in any way define the scope of the invention.

Performance Evaluation Based on Fluorescence Induction using Amplitude Statistics and Time-Frequency Analysis Through three designed experiments, the superior efficiency of the inventive methodology was demonstrated for the detection of toxic agents, the classification of multi-type toxic agents, as well as the immunity to photo-inhibition. Fluorescence induction data set of normal primary-source drinking water samples as well as samples exposed to four different toxic agents at different concentrations were collected. The control and toxic-agent-exposed fluorescence induction data were taken every 5 minutes after the dark adaptation for 15 minutes.

20 µM DCMU, 5 mM/10 mM KCN,

40 µM/60 µM MPt, and

225 µM Paraquat.

Experiment 1—Toxic Agent Detection

The objective of the first experiment performed was to evaluate the performance of the inventive methodology in detecting the presence of toxic agents. FIGS. 12-23 show the extracted features (including PSII, amplitude statistics, and wavelet coefficient statistical features) of each specific toxic agent as functions of time. The toxic agents were added into the samples at time 0, therefore, the signals with negative time index correspond to the control data and the signals during the positive time period are the agent-exposed data collected from either the Clinch River samples or the lab-grown *Chlamydomonas reinhardtii* samples. At each time moment, three samples were collected and feature values calculated. The mean and standard deviation of these three values are used to illustrate the performance curve at that time moment. To examine the change of feature values over time, the signal collected at time 0 as reference was chosen and yield at each time moment calculated (feature at time t–feature at time 0)/feature at time 0. The following notations are used to describe these performance curves:

$\mu_c(t)$, $\sigma_c(t)$: the mean and the standard deviation of the feature values derived from the three control samples collected at moment t (with a negative time index)

$\mu_e(t)$, $\sigma_e(t)$: the mean and the standard deviation of the feature values derived from the three exposure samples collected at moment t (with a positive time index)

$$\mu_c = \frac{1}{T}\sum_{t=1}^{T}\mu_c(t), \sigma_c = \frac{1}{T-1}\sqrt{\sum_{t=1}^{T}(\mu_c(t)-\mu_c)^2}:$$

the mean and the standard deviation of the mean feature value for the control signal $$\mu_e = \frac{1}{T}\sum_{t=1}^{T}\mu_e(t), \sigma_e = \frac{1}{T-1}\sqrt{\sum_{t=1}^{T}(\mu_e(t)-\mu_e)^2}:$$

the mean and the standard deviation of the mean feature value for the exposure signal $$p_c = \frac{1}{T}\sum_{t=1}^{T}\sigma_c(t):$$

the average standard deviation for the control signals. This metric refers to the degree of error for the measurements in the three experiments.

$$p_e = \frac{1}{T}\sum_{t=1}^{T}\sigma_e(t):$$

the average standard deviation for the exposure signals.

In order to quantitatively evaluate the effectiveness of each feature in differentiating between the control and the exposure signals of different toxic agents, two metrics are introduced: the Fisher criterion and the average confidence level. The Fisher criterion originates from pattern classification (Duda, et al., 2001) where a linear projection is pursued in order to best separate two classes. In this work, the definition of Fisher criterion is used to quantify different performance curves in differentiating between the control and the exposure signals. In general, the Fisher criterion looks for the feature that maximizes the difference between the mean value of feature derived from the control and the exposed signal while minimizing the variance among them, as formulated below:

$$M_1 = \frac{|\mu_c - \mu_e|^2}{\sigma_c^2 + \sigma_e^2}$$

Table 1 lists the value of the Fisher criterion to evaluate the effect of using different features for agent detection. In both Table 1 and Table 2 "Clinch" refers to Clinch River samples and "Chlamy" to lab-grown *Chlamydomonas reinhardtii* samples. It can be seen from Table 1 below that the first-order amplitude statistics (mean) gives the best metric evaluation for most of the toxic agents, while the wavelet analysis, the standard deviation and the skewness in amplitude statistics also contribute to the differentiation between control and exposure signals in some cases.

TABLE 1

Metric to evaluate the difference between the control and the exposure signals of a specific toxic agent.

| | Clinch 5 mM KCN | Chlamy 5 mM KCN | Clinch 10 mM KCN | Chlamy 10 mM KCN | Clinch 20 µM DCMU | Chlamy 20 µM DCMU | Clinch 225 µM Paraquat | Chlamy 225 µM Paraquat | Clinch 40 µM MPt | Chlamy 40 µM MPt | Clinch 60 µM MPt | Chlamy 60 µM MPt |
|---|---|---|---|---|---|---|---|---|---|---|---|---|
| PSII | 17.7130 | 5.0371 | 22.7318 | 5.5293 | 62.8073 | 63.9 | 40.3550 | 33.4259 | 7.1502 | 7.8844 | 16.4704 | 11.7760 |
| Amplitude Statistics Mean | 35.5863 | 36.0766 | 45.5246 | 67.4501 | 356.4241 | 2111.9 | 0.6992 | 9.2416 | 5.1574 | 15.3435 | 9.9401 | 20.3104 |
| Amplitude Statistics Standard Deviation | 28.6817 | 0.9657 | 36.6538 | 1.2782 | 62.5213 | 2.3 | 14.8945 | 55.4867 | 28.2660 | 0.0137 | 10.6912 | 0.0643 |
| Amplitude Statistics Skewness | 0.8372 | 95.4071 | 0.5331 | 161.6205 | 64.7360 | 835.9 | 21.8997 | 0.1661 | 3.2165 | 2.0009 | 0.6709 | 4.4742 |
| Amplitude Statistics Kurtosis | 6.3546 | 55.1439 | 5.5483 | 40.3244 | 71.3140 | 242.9 | 13.0980 | 0.5380 | 9.3028 | 0.7696 | 2.7010 | 1.8269 |

TABLE 1-continued

Metric to evaluate the difference between the control and the exposure signals of a specific toxic agent.

| | Clinch 5 mM KCN | Chlamy 5 mM KCN | Clinch 10 mM KCN | Chlamy 10 mM KCN | Clinch 20 µM DCMU | Chlamy 20 µM DCMU | Clinch 225 µM Paraquat | Chlamy 225 µM Paraquat | Clinch 40 µM MPt | Chlamy 40 µM MPt | Clinch 60 µM MPt | Chlamy 60 µM MPt |
|---|---|---|---|---|---|---|---|---|---|---|---|---|
| Wavelet Coefficient Mean | 2.0168 | 6.4232 | 5.1258 | 10.1957 | 37.3350 | 5.3 | 88.1866 | 7.4516 | 75.2339 | 15.7935 | 148.3582 | 22.2547 |
| Wavelet Coefficient Standard Deviation | 2.1605 | 5.4072 | 7.6813 | 9.5367 | 88.0769 | 7.8 | 103.1261 | 13.2129 | 102.9558 | 19.1866 | 196.7953 | 23.6347 |
| Wavelet Coefficient Energy | 2.4914 | 6.9769 | 8.8526 | 13.0129 | 93.8024 | 8.2 | 121.8164 | 15.7150 | 159.3636 | 29.3503 | 258.6794 | 29.5307 |

The second metric is to measure the average standard deviations corresponding to the control and the exposure signals respectively. Since three experiments are conducted at each time index, a standard deviation can be calculated which in turn shows the degree of error of the measurement. Then the average standard deviation can be calculated over time. Table 2 shows the average standard deviation for each toxic agent experiment. The features with the smallest standard deviation for control and exposure signals are highlighted respectively, which correspond to the lowest degree of error in the measurements.

cation problem, which is to differentiate among KCN, MPt, DIMP, and Paraquat exposure signals.

A five-fold cross-validation was conducted to evaluate the performance of the designed system. The data set was randomly divided into five subsets of equal size, each of which is tested using the classifier trained on the remaining four subsets. The cross-validation accuracy is the average percentage of data that are correctly classified, which on the other hand, shows the confidence of classification.

Table 3 provides the classification accuracies when using different combinations of features within different response

TABLE 2

Average confidence levels corresponding to the control and the exposure signals for each toxic agent experiments.

| | | Clinch 5 mM KCN | Chlamy 5 mM KCN | Clinch 10 mM KCN | Chlamy 10 mM KCN | Clinch 20 µM DCMU | Chlamy 20 µM DCMU | Clinch 225 µM Paraquat | Chlamy 225 µM Paraquat | Clinch 40 µM MPt | Chlamy 40 µM MPt | Clinch 60 µM MPt | Chlamy 60 µM MPt |
|---|---|---|---|---|---|---|---|---|---|---|---|---|---|
| PSII | Control | 7.0917 | 0.5211 | 1.6890 | 0.5517 | 1.0858 | 2.0746 | 1.7486 | 1.4760 | 1.0621 | 0.4878 | 2.2364 | 0.3403 |
| | Exposure | 6.5320 | 1.7093 | 18.3632 | 1.7922 | 2.0 | 6.7009 | 4.7046 | 2.7538 | 2.1479 | 0.4307 | 1.8623 | 1.6207 |
| Amplitude Statistics Mean | Control | 5.2388 | 0.5618 | 0.8539 | 0.8812 | 1.5700 | 0.3313 | 1.4978 | 1.0451 | 0.7550 | 0.4799 | 1.0815 | 0.4611 |
| | Exposure | 0.9510 | 0.9920 | 7.9207 | 0.7628 | 5.8 | 3.8638 | 2.1024 | 3.2456 | 1.1627 | 1.0215 | 3.2440 | 0.8095 |
| Amplitude Statistics Standard Deviation | Control | 2.5006 | 3.5376 | 4.5622 | 9.6318 | 3.1649 | 4.2325 | 2.3274 | 2.1803 | 1.1564 | 3.3941 | 2.8899 | 2.0820 |
| | Exposure | 3.7121 | 2.2964 | 21.9756 | 8.8715 | 4.2 | 11.0207 | 4.5965 | 3.0236 | 2.5287 | 2.4095 | 2.8635 | 3.6592 |
| Amplitude Statistics Skewness | Control | 88.5797 | 3.3967 | 38.0090 | 6.9013 | 83.9859 | 5.5045 | 28.9698 | 2.8750 | 46.2854 | 3.0154 | 20.6112 | 2.4801 |
| | Exposure | 589.4564 | 8.5795 | 46.7603 | 5.5052 | 1828.5 | 119.9891 | 115.5963 | 3.8739 | 178.6413 | 3.3092 | 32.4242 | 3.2171 |
| Amplitude Statistics Kurtosis | Control | 14.1784 | 7.9964 | 3.9196 | 18.4167 | 5.9547 | 7.9097 | 4.6823 | 4.1893 | 3.0849 | 5.9877 | 3.1575 | 4.5517 |
| | Exposure | 30.0245 | 14.6607 | 37.0559 | 19.0062 | 186.0 | 104.7981 | 15.0406 | 4.8179 | 13.2075 | 5.8021 | 5.0936 | 6.4004 |
| Wavelet Coefficient Mean | Control | 4.4131 | 2.0694 | 4.6845 | 4.8448 | 3.9575 | 2.0216 | 2.3834 | 1.7193 | 2.3628 | 2.2244 | 2.3272 | 0.9600 |
| | Exposure | 10.0056 | 2.8299 | 8.8991 | 2.8766 | 3.5 | 6.6531 | 3.1095 | 2.2675 | 3.8647 | 1.7896 | 2.8639 | 1.7446 |
| Wavelet Coefficient Standard Deviation | Control | 4.0981 | 0.9213 | 2.3761 | 0.7798 | 3.4715 | 0.7323 | 2.0943 | 1.5047 | 1.8607 | 2.0927 | 1.9234 | 0.5228 |
| | Exposure | 11.1806 | 1.7690 | 10.5536 | 1.4078 | 4.0 | 6.0873 | 2.7939 | 1.9375 | 3.8073 | 2.1660 | 2.6258 | 1.5849 |
| Wavelet Coefficient Energy | Control | 4.1592 | 0.9518 | 2.5547 | 1.0033 | 3.5281 | 0.7846 | 2.1229 | 1.5015 | 1.9128 | 2.0593 | 1.9717 | 0.5363 |
| | Exposure | 11.1280 | 1.8272 | 10.4410 | 1.2675 | 3.8 | 6.0681 | 2.8405 | 1.9898 | 3.8230 | 2.1425 | 2.6207 | 1.5795 |

Experiment 2—Classification of Different Toxic Agents

After the detection of the presence of a toxic agent, a preferred next task is to classify among different types of toxic agents to identify the toxic agent(s) present. The second experiment was aimed at evaluating the performance of the classifier in differentiating among different toxic agents. Corresponding to the toxic agent exposure signals used in the data set acquired, this experiment deals with a four-class classifitime. In the terminology of classification, the classification accuracy is referred to as the probability of a sample to be correctly classified, which equals 1 minus the probability of error. It is observed from Table 3 that instead of a generally increasing classification accuracy over time, the conventional PSII efficiency feature actually performs worse when the response time increases. The combination of amplitude statistics and wavelet coefficient according to a preferred embodiment of the invention still continuously perform better than other features. However, in order to obtain an accuracy of above 90%, it was found to be necessary to wait till the response time passes 10 minutes. This is the trade-off between providing higher classification capabilities and being able to respond in a shorter period of time.

TABLE 3

Classification accuracy obtained from experiment 2 (4-class classification: KCN, MPt, Disopropyl Methylphosphonate (DIMP), and Paraquat)

| PSII effi-ciency | Amplitude statistics | Wavelet coeffi-cient | 5 min Classi-fication accuracy (%) | 10 min Classi-fication accuracy (%) | 15 min Classi-fication accuracy (%) |
|---|---|---|---|---|---|
| X |   |   | 54.84 | 51.61 | 51.09 |
|   | X |   | 70.97 | 88.71 | 85.87 |
|   |   | X | 67.74 | 70.97 | 72.83 |
| X | X |   | 77.42 | 87.10 | 85.87 |
| X |   | X | 61.29 | 79.03 | 86.96 |
|   | X | X | 77.42 | 91.94 | 89.13 |
| X | X | X | 80.65 | 91.94 | 86.96 |

Experiment 3—The Effect of Photo-Inhibition

The last experiment was performed to examine the effect of photo-inhibition in the classification of fluorescence inductive data sets exposed to different toxic agents. Photo-inhibition is a biological phenomenon of algae when the temperature of the primary-source drinking water samples increases. The characteristics of fluorescence induction curves during photo-inhibition are very similar to the curves of toxic agent exposed signals. Therefore, it is essential in real-world applications to eliminate the effect of photo-inhibition since the drinking water source can be exposed to a toxic agent during noon or early afternoon hours when photo-inhibition occurs.

To demonstrate the advantage of the inventive methodology in differentiating between photo-inhibition and toxic-agent-exposure, the classification on a data set including both the control signals with photo-inhibition and the signals exposed to different toxic agents was applied. Table 4 below lists the classification accuracies for three data sets that are composed of normal control signals, photo-inhibition control signals, and toxic agent exposure signals The results of all the three data sets show that the inclusion of photo-inhibition does not measurably affect the performance of classification either between control vs. exposure, or between the exposures of different toxic agents.

TABLE 4

Classification accuracy with photo-inhibition.

| Data set | Classification accuracy (%) |
|---|---|
| 4-class: Control (normal and Photo-inhibition), KCN (5 mM and 10 mM), 20 µM MPt, 30 µM Paraquat using water samples from the Clinch River | 93.94 |
| 2-class: Control (normal and Photo-inhibition), 2 mM KCN using samples tested with lab-grown *Chlamydomonas* | 100.0 |
| 2-class: Control (normal and Photo-inhibition), 300 µM Paraquat using samples tested with lab-grown *Chlamydomonas* | 97.37 |

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

The invention claimed is:

1. A water or air quality sensor system, comprising:
a biosensor in an air or water medium to be monitored or analyzed for the presence of one or more toxins selected from chemical, biological or radiological agents;
a detector proximate to said biosensor for measuring a time-dependent biosensor signal from said biosensor, and
a processor for analyzing said time-dependent biosensor signal to obtain a plurality of feature vectors using at least one of amplitude statistics and time-frequency analysis, said processor determining at least one parameter relating to toxicity of said air or water medium from said feature vectors.

2. The system of claim 1, further comprising a memory for storing at least one time-dependent control signal, wherein said processor analyzes said time-dependent biosensor signal to obtain said parameter from said feature vectors based on reference to said control signal.

3. The system of claim 1, wherein said system includes a classifier for identifying which of said toxins are present in said air or water medium.

4. The system of claim 1, further comprising a classifier that utilizes a support vector machine.

5. The system of claim 4, wherein said support vector machine is utilized to differentiate among different toxic agents.

* * * * *